(12) United States Patent
Gan et al.

(10) Patent No.: US 6,664,084 B2
(45) Date of Patent: Dec. 16, 2003

(54) ISOLATED NUCLEIC ACID MOLECULES ENCODING HUMAN GLUCURONYLTRANSFERASE PROTEINS, AND RELATED PRODUCTS AND PROCESSES

(75) Inventors: Weiniu Gan, Gaithersburg, MD (US); Chunhua Yan, Boyds, MD (US); Gennady V. Merkulov, Baltimore, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 103 days.

(21) Appl. No.: 09/816,095

(22) Filed: Mar. 26, 2001

(65) Prior Publication Data

US 2002/0137164 A1 Sep. 26, 2002

Related U.S. Application Data

(60) Provisional application No. 60/270,871, filed on Feb. 26, 2001.

(51) Int. Cl.⁷ .................................................. C12N 9/10
(52) U.S. Cl. .................. 435/193; 435/320.1; 435/252.3; 435/254.11; 435/325; 435/419; 536/23.1; 536/23.2; 536/23.5
(58) Field of Search ............................... 536/23.1, 23.2, 536/23.5, 320.1, 252.3, 254.11, 419, 325, 193; 435/320.1, 252.3, 254.11, 419, 325, 193

(56) References Cited

FOREIGN PATENT DOCUMENTS

| WO | WO 0075298 A | 12/2000 |
|---|---|---|
| WO | WO 0159063 A | 8/2001 |

OTHER PUBLICATIONS

Marcos et al. Homo spaiens UDP–glucuronyltransferase–S (GLCATS) mRNA, complete cds. GenBank Accession No. AY070019. Published Jan. 7, 2002.*

Seiki et al. Molecular Cloning and Expression of a Second Glucuronyltransferase Involved in the Biosynthesis of the HNK–1 Carbohydrate Epitope. Biochemical and Biophysical Research Communications (1999) 255:182–187.*

Hillier et al. zt98d09.r1 Soares testis_NHT Homo sapiens cDNA clone. GenBank Accession No. AA421030. Published Oct. 16, 1997.*

Shimoda Yasushi et al. "Cloning and Expression of a Novel Galactoside Betal, 3–Glucuronyltransferase Involved in the Biosynthesis of HNK–1 Epitope." Journal of Biological Chemistry. vol. 274, No. 24, Jun. 11, 1999, pp. 17115–17122.

Tracey, A. Database EMBL 'Online! Nov. 22, 2000, Accession No. AL450320.

Birren B. et al. Database EMBL 'Online! "Homo Sapiens Chromosome 6, Clone RP11–156I14." May 10, 2002. Accession No. AC068738.

Tracey A. Database SWALL 'Online! "Galactosylgalactosylxylosylprotein 3–Beta–Glucuronosyltransferase 2." Oct. 16, 2001. Accession No. Q9NPZ5.

* cited by examiner

Primary Examiner—Ponnathapu Achutamurthy
(74) Attorney, Agent, or Firm—Celera Genomics; Justin D. Karjala

(57) ABSTRACT

The present invention provides amino acid sequences of human glucuronyltransferase proteins and nucleic acid sequences encoding these glucuronyltransferase proteins. The present invention provides isolated glucuronyltransferase proteins and encoding nucleic acid molecules, vectors and host cells containing these nucleic acid molecules, and processes for producing the glucuronyltransferase proteins.

24 Claims, 47 Drawing Sheets

```
   1 GTTCTGAGAA GACAAGAGCA AGGGACTGAG AGCAGGCTTC CGCTGCGGCG
  51 CGCGAACACA GCCGGGACAC AACCCCCAGC GTCTCCACCC GCTCCTCGCC
 101 ACCCCGGCGG GAATGTGAGG AAGGAAAGCC CCCAGCGCCG CCGCCGCCC
 151 TCGAAGGCGT CCCAGAGAGC GTCCTGGGGG CCCGCGGCTG GAGCCCTTGT
 201 GCCCGCAGCA CCGCCGGACT GGAGCGGCCA GGCGCACCGG GTGCCCCTTC
 251 TCGGCTTCCA CTCTTCAGAA AGAGCGCGGT GGGGATCAGC GCCTTTCCCG
 301 CACTCGGCAC AACTCCGGGA CCGGCGGCGC GCGGCTGGAC CGAGTCCCGC
 351 TTCCCGCCAG CTCACCTGGA GTCGGGGGCA GCCCTGCCC GCCCGCCTGC
 401 ACCCCTTGTC GCTCTAGCTT GCGCGAACCT GCCGCTCCTC CACGCCCAGG
 451 TAGTGAGCCC CGCGGCTCCA GGTCTCTCCA GCGCCCTCGG CCCCATGGAC
 501 AGCGCACCCA TCACCACTCC CTAAGTGCTG GCGCCGCCGC TGTCCAAGCT
 551 GCGCACTGGG GTCCCTCGGC TCGCCCCTCT CTGGGGTGTC CGAGAGGCCA
 601 GGGAGCGTGC ACCATGAAGT CCGCGCTTTT CACCCGCTTC TTTATCCTCC
 651 TGCCCTGGAT CCTAATTGTC ATCATCATGC TCGACGTGGA CACGCGCAGG
 701 CCAGTGCCCC CGCTCACCCC GCGCCCCTAC TTCTCTCCCT ACGCGGTGGG
 751 CCGCGGGGGC GCCCGACTCC CGCTCCGCAG GGGCGGCCCG GCTCACGGGA
 801 CCCAAAAGCG CAACCAGTCT CGGCCGCAGC CACAGCCGGA GCCGCAGCTG
 851 CCCACCATCT ATGCCATCAC GCCCACCTAC AGCCGCCCGG TGCAGAAAGC
 901 GGAGCTGACC CGCCTGGCCA ACACGTTCCG CCAGGTGGCG CAGCTGCACT
 951 GGATCCTGGT GGAGGACGCG GCGGCGCGCA GCGAGCTGGT GAGCCGCTTC
1001 CTGGCGCGGG CCGGGCTGCC CAGCACTCAC CTGCACGTGC CCACGCCGCG
1051 GCGCTACAAG CGGCCCGGGC TGCCGCGCGC CACTGAGCAG CGCAACGCGG
1101 GCCTCGCCTG GCTGCGCCAG AGGCACCAGC ACCAGCGCGC GCAGCCCGGC
1151 GTGCTCTTCT TCGCTGACGA CGACAACACC TATAGTCTGG AGCTCTTCCA
1201 GGAGATGCGA ACCACCCGCA AGGTCTCCGT CTGGCCTGTG GGCCTGGTTG
1251 GTGGGCGGCG CTACGAACGT CCGCTGGTGG AAAACGGCAA AGTTGTTGGC
1301 TGGTACACCG GCTGGAGAGC AGACAGGCCT TTTGCCATCG ACATGGCAGG
1351 ATTTGCTGTA AGTCTTCAAG TCATTTTGTC CAATCCAAAA GCTGTATTTA
1401 AGCGTCGTGG ATCCCAGCCA GGGATGCAAG AATCTGACTT TCTCAAACAG
1451 ATAACAACAG TCGAAGAACT GGAACCGAAA GCAAATAACT GCACTAAGGT
1501 TCTCGTGTGG CACACTCGGA CAGAGAAGGT TAATCTAGCC AACGAGCCAA
1551 AGTACCACCT GGACACAGTG AAAATTGAGG TATAATAAAT TGAAGCAGCA
1601 ACTGGTGCAG TTTGTCCAGC CAGTGGATCC ATATGGAAGA GGATGTTTGG
1651 AGTTTAGGCT ACAGAGCATT CAGGTATTGT TTGTTTTACT TCAGTACAGC
1701 AGCCTTTCTT GTCATCTGAT GGACATCTGT TTAAATGGAG CTTGTCAGTT
1751 AACATAAGCT AATTGGATGG TTGGTACAAA ATGTATGTTT TGTCTTCATT
1801 TGTTCTGCAT GTTTTCTCTA CAACAACTAA ATTGGAAGAT TTTTTTGTAC
1851 AGTGCCGATA CTGCAAGATA CCACTCTTGA GTATATATTT TTTCTTTTTC
1901 TCCAATTTGC CCTTATAATT GGTAGACTTG AACAGGTTGG TAGACTTGAA
1951 CAGGTTTTTA AAACAGACAA GTATTTTGTC AGCTAAACGT TCCTGATGAT
2001 TCCTGACTTT GCAATACTAA GTAATTTTTG GAAGGTTAGT GGCAGTATAC
2051 ATCATAGGAA ATAAAAACCC ACAAATGAAA AGGTCTATGG AGTCATGTTT
2101 AATGTAGGGA ATAACATTT TGTCAATACT AGGCACCATA AAATGTAAAC
2151 ACAATTACTG TCATAAACCT AGATATACCT TCAAGGATTG AAGATTGAAA
2201 GTGGCTTTGT TTAGTTAGT TACCCTGTTT GCATATAGTG CAGAAAAAGG
2251 TCTTCATGTT AGCACTATGT ACATTAAGAA GAGATCCAAA TTACAAGAGA
2301 GGCAGATAAA ATTTGAATTC TTTAAGCATT CATTAAACGA AGTTTTGGAG
2351 TAACATCCAC GTTTATCTTC CTTTCACTAA TCACGTTCCC TGTTAAGCAC
2401 ATCATAACAA CAGCACAGTG AAGTGAATGA TGAAATAAGA GCATTTTGAT
2451 ACACTAGAAA ACAGTGCTCA GTGAGACATT TACATTCTAT TTATATGATT
2501 AAACATTTGA TCATACAGTA CCTTCCTACA GGATTACTGG CTAATTTTGG
2551 GGTGGGGTTT ATACTATTAG AGGTATTACT AACATGATAA CTACTTCCCT
2601 TATATGCAAA CATTAGAGCT ATAATTTTAT TGAGAGGAAA ACTGATTTTG
2651 CAAGTTGAGC AGCTTCTCAA ATAATGCAGT ACATGAAATC ATGGGAAATA
2701 TGAGCAAAGC TGCCCTTGAC ATAAAATGAT TTATCAACCT GCTTTTCACC
2751 ACATCAAATT GAATCAGTAC AGACCAACAC GGTCAATCAG ATCATTCTTA
2801 ATATGAACAA ATGGGTAAAA AGAAAAAAAA TATGCATATG AATAAACAGG
2851 GGAACTAGAT GCGTTTCAGC AAGGAATGTC AGGTGGTAGT TCTGGATGAA
2901 ACTTGTATTG CAGTTTTCAT TTCCACAGTT GTGTGCTGAG AGTCTGACCT
2951 GATGAGCTTC CAGACCATCC TGCTGTTGTG CTGGAGGGCT GGCCAAAACC
3001 TGCAGTAGGG GTTGCACTAC TGATACTCAT GCCAGCCATC TGCTGATTCA
3051 TCTGTGAAAC ATATAAAAGG CTTAGTTCAA GAGGCTTACT TCACTTTTAA
3101 TTCTTGTTTC TTTAGCCACA CAGTTGGTCA TTTTTTCATT AATGTGACAA
```

FIGURE 1, page 1 of 3

```
3151 CTAGTCCAAG CACTGGAATA AAAACAGAGT ACCATACAAA TATTTCTTAA
3201 AGCAAATAGC TACTTTGTTC CCTTCTTTAT CTACTTTCTA GATACAGTTT
3251 CCCCAAAGAT TAACCACAAC TTACTTAAAA AAAAATACCA AAGCAATCTT
3301 GGGATTTTAA TGAGTCCGCT ACTCTAACTA ACTTTCACCT ACACTAGGAT
3351 ATTGTGCTTT AACTACTAAG GAGTAAGAAA ATTTTAGGAA GTAAAATAGT
3401 CTAAAATTAT CCTATAAACT TTGTATGATA GATATTATTC TCTATTAAAA
3451 TCTTATATAC TTCCTAAATA TTTTTAAAGT GGTCATAAAG CATTTATTTC
3501 TCTCGCTGAT CTAACAACAT AAACATCTAA AATTTATTTT CATTGTATGC
3551 AATAAAGCAT AAGATTACAT GTATTTTTCT TCAAGACTGG AGTCAAATAT
3601 ATATATATAT AAGCATCTTA ACCCTGTGAT TCTCTTACTT CCAAAATTGG
3651 TGATAAGAGA AGGAAAGGCA AGATTTACCA TATAGTGAGT GGGTTTAAAA
3701 CTTACACTCA GAGTTAGACT GTGTTCTTAA TTTAATACAT TTGACTTGAC
3751 TTATTTACAG TTTCAAAGAC ACTAACATAA ACTACATCAC TAATCAGGCA
3801 TAAGTGTCTG AAGAAGCAGA TCACATCTTC ATACCTACTA AAGGACATTT
3851 TAACCACCTT GTCATTGGCC AGTAGATTGC ACTGATGGAG TGCTGGAGAA
3901 CAGCATCACC CTTCTGCATT ATCTGGAAGT AAGAGCCAGT ATTAACTCCT
3951 TCCTGGTTCA TCTAGCACCT TAACCTGAGC TGGGTGTGCT TCAGCATGTT
4001 GACCATGTGA CTGACACTTA GCACATACAA TTTTTTAGAT TCCCAGCGGG
4051 TAGAGACCAA TGTTTTACCT ATATTCTTGT AAATGGTGGT AGCAAAATTA
4101 ACTGTGATAT ATAGTGATTG TGCTAATGTT AGAAATCACT CTAGACTATT
4151 CCCTGAATGC TCTAAAGGTA AAACAAGTGA CCAAACAGAA ACCAAGATTG
4201 CCAAAATGCT GGAGGAACAT CAATGGGAAG TGTAAAAGGA AGAAGAGTGG
4251 GAGCATGAAC CTCTCTAAGA GCCTTTGTCT GTGCAGCTAG AGAAAAGTCA
4301 GAACACAGCA CCTGAAATAG AAATGTTCTA TCTCAGCTCT AACTTAGGTA
4351 GAAATAGGAT TTTATAATAT GAGGGGATGT CTGGTTCACA CCTTATGGGA
4401 ATTGAATCTT TTTGTACTCT TTTTAAACAT AAAAGTCATT ATAGGGTATG
4451 TAAAAGAAA ATACAACTTT ACAAAGGTTT CTCAACAAAA AGAATTTTTA
4501 CAGAGCCATG GGCAGTAAT CATCCGACCT GAAAATAGC CTTAGATCCC
4551 TCATAAAATA GTGCTTTGAG AATATGAGGC TAGATTTTTA TTTTCTAATA
4601 AAAGATCCTA AAATTATTAG TGAAGCTAAG TTGTCTAAGT GGACTGTAAA
4651 AATGTCCCAC CAGCAAGCTG GATAAAGCTT AGTGCTAATC TCAGAGGTGA
4701 CAGAGAGGGA GTCTCATGAT GCCTGAGATA ATTTCTGGCC ATTAGTGGTG
4751 TTCACGTTAC AGTTACATTA CAATTTGAAA TGAAAGATGT TTAACCTTTT
4801 TTTTACAGAA TACTCTAAAA TAGGGATAAT AACACATCAT TTGTCTATCT
4851 GATACAACTT CATAATATTT ATAGATACTT TTGACCCTAT AACATATTAT
4901 CCCTATTGAA TTCTTTCTGC CAGATCACTA GACTTAAAAA AAAAAAAAA
4951 AAAAAAAAAA AAAAAAAAA   (SEQ ID NO:1)
```

FEATURES:
5'UTR:         1-613
Start Codon:   614
Stop Codon:    1583
3'UTR:         1586

Homologous proteins:
Top 10 BLAST Hits

```
                                                                    Score    E
CRA|145000039337387  /altid=gi|12018284 /def=ref|NP_072131.1| ga...   598   e-170
CRA|98000043628449   /altid=gi|13016548 /def=emb|CAC29377.1|  (AL4...  409   e-113
CRA|18000005086948   /altid=gi|2217942  /def=dbj|BAA20551.1|  (D880...  299   4e-80
CRA|53000092569557   /altid=gi|12408652 /def=ref|NP_061114.1| bet...   296   3e-79
CRA|114000015335056  /altid=gi|9453799  /def=emb|CAB99368.1|  (AL1...  263   2e-69
CRA|18000005216702   /altid=gi|4530369  /def=gb|AAD22007.1|   (AF113..  250   2e-65
CRA|157000140415748  /altid=gi|13195672 /def=ref|NP_077218.1| RI...    250   2e-65
CRA|53000092570618   /altid=gi|12408654 /def=ref|NP_036332.2| bet...   250   2e-65
CRA|18000005191928   /altid=gi|4008515  /def=emb|CAA06742.1|  (AJ00...  250   2e-65
CRA|53000092569540   /altid=gi|3892640  /def=dbj|BAA34537.1|  (AB00...  247   2e-64
```

FIGURE 1, page 2 of 3

```
BLAST dbEST hits:
                                                    Score    E
gi|2099917  /dataset=dbest /taxon=9606 ...           605   e-171
gi|5637891  /dataset=dbest /taxon=9606 ...           303   5e-80
gi|5236525  /dataset=dbest /taxon=9606 ...           303   5e-80
gi|471573   /dataset=dbest /taxon=9606 /...          303   5e-80
gi|1225232  /dataset=dbest /taxon=9606 ...           303   5e-80
gi|11130812 /dataset=dbest /taxon=960...             303   5e-80
```

EXPRESSION INFORMATION FOR MODULATORY USE:
library source:
From BLAST dbEST hits:
gi|2099917    testis
gi|5637891    prostate
gi|5236525    kidney
gi|471573     brain
gi|1225232    ear
gi|11130812   lung From tissue screening panels:
fetal whole brain FIGURE 1, page 3 of 3

```
  1 MKSALFTRFF ILLPWILIVI IMLDVDTRRP VPPLTPRPYF SPYAVGRGGA
 51 RLPLRRGGPA HGTQKRNQSR PQPQPEPQLP TIYAITPTYS RPVQKAELTR
101 LANTFRQVAQ LHWILVEDAA ARSELVSRFL ARAGLPSTHL HVPTPRRYKR
151 PGLPRATEQR NAGLAWLRQR HQHQRAQPGV LFFADDDNTY SLELFQEMRT
201 TRKVSVWPVG LVGGRRYERP LVENGKVVGW YTGWRADRPF AIDMAGFAVS
251 LQVILSNPKA VFKRRGSQPG MQESDFLKQI TTVEELEPKA NNCTKVLVWH
301 TRTEKVNLAN EPKYHLDTVK IEV  (SEQ ID NO:2)
```

FEATURES:
Functional domains and key regions:
[1] PDOC00001 PS00001 ASN_GLYCOSYLATION
N-glycosylation site Number of matches: 2
    1      67-70 NQSR
    2    292-295 NCTK

[2] PDOC00004 PS00004 CAMP_PHOSPHO_SITE
cAMP- and cGMP-dependent protein kinase phosphorylation site Number of matches: 2
    1    202-205 RKVS
    2    264-267 RRGS

[3] PDOC00005 PS00005 PKC_PHOSPHO_SITE
Protein kinase C phosphorylation site

Number of matches: 9
    1      27-29 TRR
    2      35-37 TPR
    3    144-146 TPR
    4      63-65 TQK
    5    104-106 TFR
    6      35-37 TPR
    7    144-146 TPR
    8    200-202 TTR
    9    201-203 TRK

[4] PDOC00006 PS00006 CK2_PHOSPHO_SITE
Casein kinase II phosphorylation site

Number of matches: 3
    1    281-284 TTVE
    2    282-285 TVEE
    3    301-304 TRTE FIGURE 2, page 1 of 4

```
[5] PDOC00008 PS00008 MYRISTYL
N-myristoylation site

Number of matches: 5
      1    134-139   GLPSTH
      2    152-157   GLPRAT
      3    210-215   GLVGGR
      4    266-271   GSQPGM
      5    270-275   GMQESD

[6] PDOC00009 PS00009 AMIDATION
Amidation site 213-216   GGRR
```

Membrane spanning structure and domains:

| Helix | Begin | End | Score | Certainty |
|---|---|---|---|---|
| 1 | 5 | 25 | 1.850 | Certain |
| 2 | 239 | 259 | 0.881 | Putative |

FIGURE 2, page 2 of 4

```
BLAST Alignment to Top Hit:
>CRA|145000039337387 /altid=gi|12018284 /def=ref|NP_072131.1|
         galactoside beta-1,3-glucuronyltransferase [Rattus
         norvegicus] /org=Rattus norvegicus /taxon=10116
         /dataset=nraa /length=324
         Length = 324

Score =  598 bits (1525), Expect = e-170
 Identities = 291/324 (89%), Positives = 301/324 (92%), Gaps = 1/324 (0%)
 Frame = +1

Query: 1    MKSALFTRFFILLPWILIVIIMLDVDTRRPVPPLTPRPYFSPYAVGRGGARLPLRRGGPA  180
            MKSAL  RFFILLPWILIVIIMLDVD RRP P LT RPYFSP+ VG GG+R+PLRR  P
Sbjct: 1    MKSALCNRFFILLPWILIVIIMLDVDPRRPAPQLTSRPYFSPHTVGCGGSRVPLRRSSPG  60

Query: 181  H-GTQKRNQSRPQPQPEPQLPTIYAITPTYSRPVQKAELTRLANTFRQVAQLHWILVEDA  357
                +KRN+SRPQ QPEP+LPTIYAITPTYSRPVQKAELTRLANTFRQVAQLHWILVED
Sbjct: 61   RDAAEKRNESRPQLQPEPRLPTIYAITPTYSRPVQKAELTRLANTFRQVAQLHWILVEDR  120

Query: 358  AARSELVSRFLARAGLPSTHLHVPTPRRYKRPGLPRATEQRNAGLAWLRQRHQHQRAQPG  537
            A RSELVS FLARAGLP+THLHVPTPRRYKRP LPRATEQRNAGLAWLRQRHQHQ AQPG
Sbjct: 121  ATRSELVSSFLARAGLPNTHLHVPTPRRYKRPWLPRATEQRNAGLAWLRQRHQHQSAQPG  180

Query: 538  VLFFADDDNTYSLELFQEMRTTRKVSVWPVGLVGGRRYERPLVENGKVVGWYTGWRADRP  717
            VLFFADDDNTYSLELFQEMRTTRKVSVWPVGLVGGRRYERPLV+NGKVVGWYTGWR DRP
Sbjct: 181  VLFFADDDNTYSLELFQEMRTTRKVSVWPVGLVGGRRYERPLVKNGKVVGWYTGWREDRP  240

Query: 718  FAIDMAGFAVSLQVILSNPKAVFKRRGSQPGMQESDFLKQITTVEELEPKANNCTKVLVW  897
            FAIDMAGFAVSLQVILSNPKAVFKRRGSQPGMQESDFLKQITTV+ELEPKANNCTKVLVW
Sbjct: 241  FAIDMAGFAVSLQVILSNPKAVFKRRGSQPGMQESDFLKQITTVDELEPKANNCTKVLVW  300

Query: 898  HTRTEKVNLANEPKYHLDTVKIEV  969
            HTRTEKVNLANEPKYH+DTV IEV
Sbjct: 301  HTRTEKVNLANEPKYHMDTVNIEV  324    (SEQ ID NO:4)

>CRA|98000043628449 /altid=gi|13016548 /def=emb|CAC29377.1|
         (AL450320) bA156I14.1 (UDP-glucuronyltransferase-S)
         [Homo sapiens] /org=Homo sapiens /taxon=9606
         /dataset=nraa /length=197
         Length = 197

Score =  409 bits (1039), Expect = e-113
 Identities = 197/197 (100%), Positives = 197/197 (100%)
 Frame = +1

Query: 1    MKSALFTRFFILLPWILIVIIMLDVDTRRPVPPLTPRPYFSPYAVGRGGARLPLRRGGPA  180
            MKSALFTRFFILLPWILIVIIMLDVDTRRPVPPLTPRPYFSPYAVGRGGARLPLRRGGPA
Sbjct: 1    MKSALFTRFFILLPWILIVIIMLDVDTRRPVPPLTPRPYFSPYAVGRGGARLPLRRGGPA  60

Query: 181  HGTQKRNQSRPQPQPEPQLPTIYAITPTYSRPVQKAELTRLANTFRQVAQLHWILVEDAA  360
            HGTQKRNQSRPQPQPEPQLPTIYAITPTYSRPVQKAELTRLANTFRQVAQLHWILVEDAA
Sbjct: 61   HGTQKRNQSRPQPQPEPQLPTIYAITPTYSRPVQKAELTRLANTFRQVAQLHWILVEDAA  120

Query: 361  ARSELVSRFLARAGLPSTHLHVPTPRRYKRPGLPRATEQRNAGLAWLRQRHQHQRAQPGV  540
            ARSELVSRFLARAGLPSTHLHVPTPRRYKRPGLPRATEQRNAGLAWLRQRHQHQRAQPGV
Sbjct: 121  ARSELVSRFLARAGLPSTHLHVPTPRRYKRPGLPRATEQRNAGLAWLRQRHQHQRAQPGV  180

Query: 541  LFFADDDNTYSLELFQE  591
            LFFADDDNTYSLELFQE
Sbjct: 181  LFFADDDNTYSLELFQE  197    (SEQ ID NO:5)
```

FIGURE 2, page 3 of 4

```
Hmmer search results (Pfam):
Model    Description                              Score    E-value  N
PF00561  alpha/beta hydrolase fold                 2.6       8.2    1

Parsed for domains:
Model    Domain  seq-f  seq-t    hmm-f  hmm-t    score  E-value
PF00561   1/1     112    130 ..   216    233 .]   2.6     8.2
```

FIGURE 2, page 4 of 4

```
   1 CACAGTGTTT CATCTCTGAA TAGCCTTGGT TCCTGGAGAG GATGTAATAG
  51 CAAATAGGTT TTATGGCATA GTTGGACCAA CCAAAAGTTC CCCACTAACA
 101 AAGGTTAGTG ATGTTTTTAG TACAATTCAG TAACAACATG AATTTTATTC
 151 CAGCAAACAC AAGGCATTTT AACCAAATTT AAAATTTCCA ACAGCATGAA
 201 CCAGACTTCA GTAACTTAGG GGAGAGGGGT GCACTGCTTC CTAAGAAAAA
 251 CCTTTTCTTA AAGGGAGGCC TTGACTTCTT TCCTCTTCCC CATCCTGGCA
 301 TGATGCTGGT GCAGAATACA TTTCCAAGGT TGTGTTATAT TCAGAGGCAC
 351 ATTAGGCTAT TCGAAGAAT GGGAAGAGGT CTAATGGCTT CGTTGTTTTC
 401 TATGTTTAGG ATGCACTAAT CTGCAGAGTT TAATGTATGA GTTGTGGATG
 451 GCACAGGGAA GTTGGGACAG AAGGCTAGCT CTAGGGAGTT GTTGGGGTGG
 501 CTGGGTGTTA GTCTGAAATT TCACTCTCAC GTTTCAGAAT CTGAAGAGGA
 551 AGTTAGGGAA ATTCACAGAT GAGCCAATGC CTTTTAACAG GTGGGCGGTT
 601 CAGGGGTAGG ACTGGGAGAA GAGGAGCTGT CAGAAAAGCT GGAGAGCCAT
 651 TCGCCCCAGA GCTCTCAGTT GCACCAGAAC GCACAGTCGG AGAGAGATTT
 701 ATTTGTGAAC AAGCCCGAGA AAGGCAGACA ACCCAGACAA GATGGGCTCA
 751 GAAATTATTT ATCATAGGCT AGGGCAGAAC AGTCTGGAGC TTTCCTTCTG
 801 CTTTGCAAGC ACTTCCCTGG GACCTGCCTG GGAAGCACAG CCCTTCTTCC
 851 TGGTAAGTTA CAGAAGGTCA GGCACTCAGC TAGTAGGCCA GCTAGACAAC
 901 AAAAAGTGTC TAAACTAAGT GCCAACTGTT TACTTGGGGT CTTCCAGACC
 951 CTATCATGGT TCTATTCGTC ATGGTACACT CTGTTTGATT TCAATCGCAC
1001 CATCTTTATA TGTAGGAAGG CCAAACCGGC CCGGCTGTGT TGGGTGGGAT
1051 TTCTGCAGGC CATGCAGTGA GGACGCCACT AGCTATAGAC ACACGCAGGA
1101 GACCCACGTT CTATTTCCAT ATGCCACTTG CCACTGACCT CAGAGAAATC
1151 ATTTTAAACC CTGAACCTCA GCTTCCTTAT CCTGAAAATG AAGGCCATTC
1201 TACTTCTTAG GCCTTCTTGA CAGGAGCCTT GGGAGAGCCA AACGGAGTAA
1251 TTCCGGTGAC AGCGAAGAAC TGGGAGGGAC CGTGACTCCA AATTACTGAA
1301 GAAAAATAAG TTAAACATGC TCGGCTGGAG TTTTAGGAAT TCCACCCGCC
1351 CCCACCCGCC ATGATCAAAC TGCAGTCAGG CAGCAGCCCT CCGAATTGAT
1401 TCTTTCTTAT GGACTGTCTC ACATGCCAAA CACCTATGTG CAGCACCCCT
1451 CCATCTCCGT GGGCTCCTAT TGATGTCTGC CTTGCAGTGA AAGCGCTTTT
1501 TGTTGCCGCT GTTCGATACA CCCCAGCACA TCAACGCAGC AGCTGGGAGC
1551 AGGAGGAGGA ATCCCTTCGC TTTCTCCCCT CCTTTCACTC CGAACCCTAG
1601 GCATCAGCAG CAACGCGCGT AGCCCGGCAA ATTTCCGCAC GTGAATGGAT
1651 TTTCCTGGCT CATCTCCAAA GACCTTGCGG TATTTCACAA AGCTGAAGAG
1701 AGGTGAACGA GCATCACCCC CTCCAGGAGG TCGTGCAGCC CCGCGGGGAC
1751 GCTCCTCCCG CTCCTCCACC CGCGGTGCAG CGGCCGCCTC CCGAGCTTGC
1801 TCGCGGGGCC GTTAGCGCCA GACCCGGCGG AGAGCCAAGG GGTCCTCCG
1851 CGCCTCCCTC TCGCAGCCCC TCTCCACCAG TAGCAGCGCT GCTGTCTTCC
1901 CACAGGAGGA CTTGGGAGGA CGCTGGATTC TGCAGCGCCC CCGCCCCCTC
1951 GCTTTTTCTT TCTTTCCTTG CTTTGGGATC TTGCTGCTGG ATCCGGAGAG
2001 GTTCTGAGAA GACAAGAGCA AGGGACTGAG AGCAGGCTTC CGCTGCGGCG
2051 CGCGAACACA GCCGGGACAC AACCCCCAGC GTCTCCACCC GCTCCTCGCC
2101 ACCCCGGCGG GAATGTGAGG AAGGAAAGCC CCCAGCGCCG CCGCCCGCCC
2151 TCGAAGGCGT CCCAGAGAGC GTCCTGGGGG CCCGCGGCTG GAGCCCTTGT
2201 GCCCGCAGCA CCGCCGGACT GGAGCGGCGA GGCGCACCGG GTGCCGCTTC
2251 TCGGCTTCCA CTCTTCAGAA AGAGCGCGGT GGGGATCAGC GCCTTTCCCG
2301 CACTCGGCAC AACTCCGGGA CCGGCGGCGC GCGGCTGGAC CGAGTCCCGC
2351 TTCCCGCCAG CTCACCTGGA GTCGGGGGCA GCCCCTGCCC GCCCGCCTGC
2401 ACCCCTTGTC GCTCTAGCTT GCGCGAACCT GCCGCTCCTC CACGCCCAGG
2451 TAGTGAGCCC CGCGGCTCCA GGTCTCTGCA GCGCCCTCGG CCCCATGGAC
2501 AGCGCACCCA TCACCACTCC CTAAGTGCTG GCGCCGCCGC TGTCCAAGCT
2551 GCGCACTGGG GTCCCTCGGC TCGCCCCTCT CTGGGGTGTC CGAGAGGCCA
2601 GGGAGCGTGC ACCATGAAGT CCGCGCTTTT CACCCGCTTC TTTATCCTCC
2651 TGCCCTGGAT CCTAATTGTC ATCATCATGC TCGACGTGGA CACGCGCAGG
2701 CCAGTGCCCC CGCTCACCCC GCGCCCCTAC TTCTCTCCCT ACGCGGTGGG
2751 CCGCGGGGGC GCCCGACTCC CGCTCCGCAG GGGCGGCCCG GCTCACGGGA
2801 CCCAAAAGCG CAACCAGTCT CGGCCGCAGC CACAGCCGGA GCCGCAGCTG
2851 CCCACCATCT ATGCCATCAC GCCCACCTAC AGCCGCCCGG TGCAGAAAGC
2901 GGAGCTGACC CGCCTGGCCA ACACGTTCCG CCAGGTGGCG CAGCTGCACT
2951 GGATCCTGGT GGAGGACGCG GCGGCGCGCA GCGAGCTGGT GAGCCGCTTC
3001 CTGGCGCGGG CCGGGCTGCC CAGCACTCAC CTGCACGTGC CCACGCCGCG
3051 GCGCTACAAG CGGCCCGGGC TGCCGCGCGC CACTGAGCAG CGCAACGCGG
3101 GCCTCGCCTG GCTGCGCCAG AGGCACCAGC ACCAGCGCGC GCAGCCCGGC
```

FIGURE 3, page 1 of 40

```
3151 GTGCTCTTCT TCGCTGACGA CGACAACACC TATAGTCTGG AGCTCTTCCA
3201 GGAGGTAAAG GCCAGCCTGC CCCGCTGGGT GGGCGAGGGC GGGAGTGGGC
3251 CTCCGGGCCG GCCGGGCTGC AGTCACACGC CCCTTGCACT CCGGGTGCAC
3301 TTTTGAGTTC TCAGTTCTCC GTGCGCGCAT TCGGGCACC GAGTGGAGCC
3351 GCTCCTTGCT GGCACTCCGC AGCCTCCGCT GGCCGTGGGG GTGGAGGGGC
3401 TGTGTGTGAG AGGATCACTG TGGCTTAAGG GGCGGGAGTC TGCCCTGGGG
3451 CTTTTCTGTG TGGAGATTGT GTCAAGAGAA TAGCACAGGT GTGAGGCGCG
3501 GGAATGATTT CCAGGGGCCA GGCTCCTGAC GACCTGAGGA TGGAGCTTAG
3551 ACCTGCAGGC GCTGGCTGCG ATAGGAGATC AGGGAGGGAC CTGCACCGTA
3601 GCGGGTGGCG GTGGAGGGGT GGGGGTGGTG GGGACGGGTA GGCTAGGTGT
3651 TACTCGAGGC TTTTCAGTGC CTACAGGTGT GATTCTCAGT CTAGGACCAT
3701 ATAGGGAGAA AGGTGGAGAT AGCCTAGAGA GAAATTTGAC TATTGCGGCC
3751 CACTGGCACG GAAATGGTTG TTAGAAGAAA CACTGACTTC TATGGAGGTC
3801 CTTCCTCTCT TTCCCACACC TCACAAAAGT CTTTTCTGAC CCTCAAGATT
3851 ACTTTTTTTT TTTTTTTGCA AGAAAACCCT TTCTGGAAAA TAAACTGTTC
3901 TGCCCTGTGG TTACGTCTTT TTTGCAGCCC AAGGTAAACA TCTGGGCTGC
3951 CTGATCCCTT TTCACAACCT TTCTCTAAGG CCTCTTTTTG GCGAGTTAGC
4001 CAGGACACAT TTGGCGGGGC CTTTTGCGTC TTTCTGGTGC AGCCAGGTCC
4051 TGAGTGCATC CGGGCTCCCT GCTGTTGAGA TGGCCCATGA GTTCCCTGGG
4101 ATGCCCACGC GCGCACACGC CCCCCCCGCC GCCCCGGCA GGCACAGGGT
4151 TAGAACAGGT GTTCTTCCTT GAGGCTGGTA TCTTGCGGTG TGTGTGTGTG
4201 TAGCCTGCAA ATGAGACTGA GTGGCATGGG TTTTCTCAGT TTTCTTCTGT
4251 CTACGCAATT ACAGCCAAAG AAAATCTTCT TGATTGATTT GACGCCCTGT
4301 GAGACTGTTG CCTTCCTCCA CCTGAAATTT CTTGACGTCC TGCTTCAGAG
4351 ACTCCCCCTC AATTCCCCTT CTCCCAAGTA AACTGGACAT TGGGAAAATA
4401 CTATGTGTGA GTTGGACACT GAACTGCTAA ATAATCTGT GTGTCTGGTC
4451 ATCAGATACC CTAACTGCTT CCCACACTTT CATCCTCATC TCTGGGTTGC
4501 TTTCTTAACC CCAGGGCAGA GCTATTCTGT ACTCTTCCAG TTTAATTTTT
4551 CTGTGTGGCT TTAAAAAAAT TTTCTTAAAG GTAATTGCCG CCTTCATTTC
4601 TATTCATCCT CTCTTTCATG AATAAAAGGC ACAGTAATTG TCCTTCATCT
4651 TTTCTTTTCC ATCCTTTCAC TGTAGAGGGC TTTCTTTCCA CGTTTCTCCA
4701 AATGAATAAA TAAGCTTGGC ATTGTATAGT ATGGTCCTTA CTCAACCCAA
4751 GATTAGAGAT ACCATCTGAC GTTTTTAACT GGGCTTTTAA TCCTGCATCA
4801 GTGCTCCCCC CTCCAAAAGA AAAAGTGGC TTGCATCTGA AGCAAAGACT
4851 GTACATTTCA ATGCACCACA ATTTTTAAAC CGCAAGGTCT TTTTATTTTC
4901 TTCTACAACT TCGAAGTTGC CTCGTCTGTG ACAATATGTG GTCTTGTTGA
4951 AGTAAAATAG TGCACATTAC TGTTAATGAA CACTGTAGGA GGCTAGATTG
5001 TGAAGGAGGA ATGATTTAGT TTATTCCGAG CTTCTAGCCT CTTGGTGTGA
5051 GGTGTTAGAA GAATTGGCAC ACGCAGGCAG TGAAATGATT CAGGACACAG
5101 CCTTCCTTTG ATGCTTCCCA AACTGAAAGG AGGGTTTGTT GGTGGGGGAT
5151 ATTAAGCATC AGGAGAAAAT TCCAGTAGGT TTTTCATTAG TCCATATGGG
5201 GGAAAATATA AAATGAGGAG AGGGTAAGGA GAAAAAATA GTGTTGTCAG
5251 AGAGGACATT ATAAAGGAAA AACGCAAAAC TTTCAAGACA CTAAACTTTT
5301 GTACAATTGG AAGTAATGCA ATAAAATAAA ATAAGAGCAT ATGCAACATT
5351 TTTTAATGGT GAGGTGCCAC ATATACAAAA AATACAACAG GTTTATTGTT
5401 TCTGTTGTCA TTTTAAGCAT AATAGGCATG ACATACTTAG AATTTAAGTT
5451 TTCTATCTCC TGGAGGTCAC TCCCAGACAG TAATTTTATG ACTAGTACCT
5501 TTCTCTACCA CTCCCCCACC AGCATTGTTT TTGGACAGAT TAGGCCTTTG
5551 TTTGACATAT ATGTATGCTG ATACATTCAG TTTTCTTTAT TATAACATTT
5601 TCCATGCATG GCAAACATTA TTGAATTCCA TCATTAGGCT AGTGGAATTT
5651 ATGAATTCTT AGTCTTGTGC ATTTTCCAGA ATTTGGAAAT CCGTAGGTTT
5701 ATTTGTGAGA CAGCCTACCA TACACCCGTT CTCAGATTAA TGATTCCGTG
5751 TAAATTATAG TTTAGACATT GTTCTCTGGA GAAAACGTAG GACCAGATAA
5801 AACATTGAAA ATCTACAGCT CCTTGGGGGA AAGCAAAGAT GCTGATTAGG
5851 AATGCTATAG GGCTGAGGCA TATATCTCAG CCCTTTATAT TGTGCATGCA
5901 CACCAATTAG TTTTTCAGTA ATTCACAGTA CTTAAGGAAA GAATACCCCA
5951 AGTCAGGTTT CATCTTTTAT TCATGGTGCT TCTAATTTCC ATGGTTGATG
6001 TTAAAGTGGA TAAGATAAAA GGAGGAAAAT GAACCACGTA CAAATTAGCT
6051 CCGTAAGTAT TGGCTGCAAA TGAAGGAAAG CAAAGGATGA AAGGTCTCCA
6101 AATTAAATTA AAGACGCAAC AGGCAATCTG TGTTCAATTA TTCCTCCCTG
6151 GTAACTGGAA ATGGTGCTTT GTCATCTCAT ACAGCTAACT AATTTTCAGC
6201 CTTTCCTTTC AACTGATCTG CATTGCCAGG AAAGAAATAT TTGCATTGAA
6251 TACTCTTATG TTAACAGCCA AATCCATTTG CAAATGAAGT TTAGTGTGAA
```

FIGURE 3, page 2 of 40

```
6301 TCTTAGCTAC AGAAATGGGC CTGTTCATTG GAGAAGGAGG TGGTGGGGTT
6351 TTTCAGGTTT CAAAAATCTC AACAGCTACT CCTCTTCTTC CTGTGGCATT
6401 GATGGGGTTT TGCACTGTGG ATCACAGGTA ATCCTGCCTC CCTGTGCATC
6451 CTATCCATCT CCCTCTCTGG AAAAGCTTAC TTGCAAAGGA TTTAAGCTGC
6501 TTTAATAAAA GCCACAACTA CAGATAAATG TGACTTTATT TTTAGTCATG
6551 TTTTCAATAA CACTATTGAT CAGATTTCTG TTTTTCACCA GAAAACCTTC
6601 AAAGCTTTCT TAAATTTAAA ACAGATGCTT TTCAGGTGAA GTTGGTTTCA
6651 CCTCTGGAAA TCAATTGAAT TGAAATACTA AAAAAAAATA GCACTTTCCA
6701 AGCAAGAAAA AAAAAAACTT TAGAAATTTT GAAGTTAATG AAATAAGACT
6751 GGAAGACAGG CTGGCTCTCA GACACTTAAG GGGTTATCAA AGGAGTCAGT
6801 GACTGAGATT GCATCTAGAA GATGTTCTG GAAAGCAATG AACTAAAGAA
6851 GCCCCTTGCT TGAATCTTTT GTTGGGTGCT ATTCAGCTAT TTGTGTACTA
6901 GGCAGATAAA GGAGTTTTGA GGATTAATTC TGTCTTGCTT TTTTTTCAGA
6951 AGTATTTGTG TGCTTTCCCT CTTTACCTGC TGCTTATTGG AGTCATAATC
7001 TGAAGGATAT ACGAGTTTAC AATGTTGGC CCTTTCCCCC CTAAATAGTA
7051 CTTCTATTTA TGTTCCTGA AAGGAAACAT GAGATTTACC TTTTACCCTT
7101 GGTACATTTA CTTTATTTAG GGTAATTCTT TTTAAAGTGA AGGAACCTAG
7151 AAGATTTTCT TGGGTGGAAC ATTAAAAGAC CATTTTACCT GAAATGTGCC
7201 CCTTGTATTT TATTTCTTTC CCTCTGAAAG CTATTAAGAG TCATGCCATA
7251 GGTCTGATAA AATGTGAGAA TTTTATAGAA ATGTATATAT GAAACTACAG
7301 CCAATTTTCT TAGGCTATAA ATGTTAGGTT TTCTTTATTC TCCCTGGGTG
7351 TACAGTATTT GAATTATGGT TCGTTTTTGA TAAGAGTTTT CTTTGGAGAC
7401 CAGTAGTTTT CATTTGGATG TTGATATTTT AATGGACCAG AAATAACAAT
7451 TTGGGCCTAA AGATGTTCTC CCTTCTGCCT CTTCCTATTG TCTTTTTCCA
7501 TCATTCTTCC TCTCTCAACC TACTTTTCAC TGATGATTCT GTCTCGTGAA
7551 TAGACATGAA AACATGTTCG GATTATTGCT TGGTGCAATG AATGTTGTAT
7601 CTTTTAAACA TTTAGGCTGT TGCTGCTTCT TGGAAACCAT TGTGGGTGGC
7651 TCCCTTTTTT CTGTCTACTC TGCTTGCCTC TAAATTACAA GCTGGTAAAT
7701 TTTCTCTTGT GTGAACAGTA ATGGAATAGT AATTGCTTTT AAGGCATGCT
7751 GCAAAAGCAA AATAGAAAAT CCAAAGTCAA TGGTCTTATT TATTAACTAT
7801 TTCAGGTGGT ATTCAAGTAG TGGTAGGTTT TTTGTTGTCG TCATTGTTTT
7851 TTGCACAGAA TTCAATATTG TACAGATATG TCTATTTAAA TGTTTTGGAC
7901 TCTGGAATAT TCAGCCTGTG TAAGTTAACA CATATATATT TGATTCACAG
7951 TGCTTGTGAA GCATGAAATT TAAGTTTTGC ATGGAGCTCA AATTCTCCCA
8001 CCAAAATACA AATAAAATTG TTATACCAGT ACATAGATAG ATGCATAGGT
8051 AGGTTTAGAA TACATCTCCA AAGCACAGAA ATAAAACTAA GATAATTTGT
8101 TGTTCATGCC TGGTAATTTT TGCATACAAT TTTAATAAA TGTTAATACC
8151 CTATATCATG GATACAAGCA AAATATAGTT GACATAAATT GAGCATTTAC
8201 TATAGGCAAA GAAGTACCCT TAGGGTTTTA CGTGTATTAT TTAATCTTCA
8251 TAACACCCTG AGGTAGGTAA TAGTACTGTC TCTGTTTGTT TGCTGTTTTA
8301 ATACTAATGC TAATATTTAG TTATGGACGC AGTCCCTTGG TGAGTACAGA
8351 GGACTTAAAC AAATGCAACC TGACGGTAAT ATAGTTGTTT ACCTCTGATC
8401 TATATAATCA GTATCCCCGT TTTTAACAGA AGCACTAGGA AGTAACTTGA
8451 AAATGTCATG TAGCTGTTAT GTGGCAGAGA TAGAATTTTG AACCCAGGTG
8501 CCCTGGTTCT AGCGCCTGCA TTGTTGACTG TCCTGAAACT CATGTCATTT
8551 AACACATGAA AATATGTCAT CATTATAATA AGTAAAGCAC CTGATTAGCA
8601 GGAGCCTTGT GATATTATTA CTGTCTTCTG CCATTTTGA ATTCAGGTCT
8651 TTCTTCTTGG TTATGTCAAC TCTTAGCTTT CTCCTTTGAC CTTTTGTTAC
8701 TTTTTTCCTT TTTGTTGTTA ATGTATTACA TTGAAAAATA AATTTTTTT
8751 TTTTTGCAAG AAAATGTACT TTATTAGCTT TCTTTGTTCT GTGGGTTGAT
8801 CTTCCTGGAT ATTTCTTTAT TTTATTTATT TTTATTATTA TTATACTTTA
8851 AGTTTTAGGG TACATGTGCA CAATGTGCAG GTTAGTTACA TATGTATACA
8901 TGTGCCATGC TGGTGTGCTG CACCCATTAA CTCGTCTTTT AGCATTAGGT
8951 ATATCTCCTA ATGCTCTCCC TCCCCCCAAC CCCACCCCA CAACAGTCCC
9001 CAGAGTGTGA TGTTCCCCTT CCTGTGTCCA TGTGTTCTCA TTGTNNNNNN
9051 NNNNNNNNNN NNNNNNNNNN NNNNNNNNNN NNNNNNNNNN NNNNNNNNNN
9101 NNNNNNNNNN NNNNNNNNNN NNNNNNNNNN NNNNNNNNNN NNNNNNNNNN
9151 NNNNNNNNNN NNNNNNNNNN NNNNNNNNNN NNNNNNNNNN NNNNNNNNNN
9201 NNNNNNNNNN NNNNNNNNNN NNNNNNNNNN NNNNNNNNNN NNNNNNNNNN
9251 NNNNNNNNNN NNNNNNNNNN NNNNNNNNNN NNNNNNNNNN NNNNNNNNNN
9301 NNNNNNNNNN NNNNNNNNNN NNNNNNNNNN NNNNNNNNNN NNNNNNNNNN
9351 NNNNNNNNNN NNNNNNNNNN NNNNNNNNNN NNNNNNNNNN NNNNNNNNNN
9401 NNNNNNNNNN NNNNNNNNNN NNNNNNNNNN NNNNNNNNNN NNNNNNNNNN
```

FIGURE 3, page 3 of 40

```
 9451 NNNNNNNNNN NNNNNNNNNN NNNNNNNNNN NNNNNNNNNN NNNNNNNNNN
 9501 NNNNNNNNNN NNNNNNNNNN NNNNNNNNNN NNNNNNNNNN NNNNNNNNNN
 9551 NNNNNNNNNN NNNNNNNNNN NNNNNNNNNN NNNNNNNNNN NNNNNNNNNN
 9601 NNNNNNNNNN NNNNNNNNNN NNNNNNNNNN NNNNNNNNNN NNNNNNNNNN
 9651 NNNNNNNNNN NNNNNNNNNN NNNNNNNNNN NNNNNNNNNN NNNNNNNNNN
 9701 NNNNNNNNNN NNNNNNNNNN NNNNNNNNNN NNNNNNNNNN NNNNNNNNNN
 9751 NNNNNNNNNN NNNNNNNNNN NNNNNNNNNN NNNNNNNNNN NNNNNNNNNN
 9801 NNNNNNNNNN NNNNNNNNNN NNNNNNNNNN NNNNNNNNNN NNNNNNNNNN
 9851 NNNNNNNNNN NNNNNNNNNN NNNNNNNNNN NNNNNNNNNN NNNNNNNNNN
 9901 NNNNNNNNNN NNNNNNNNNN NNNNNNNNNN NNNNNNNNNN NNNNNNNNNN
 9951 NNNNNNNNNN NNNNNNNNNN NNNNNNNNNN NNNNNNNNNN NNNNNNNNNN
10001 NNNNNNNNNN NNNNNNNNNN NNNNNNNNNN NNNNNNNNNN NNNNNNNNNN
10051 NNNNNNNNNN NNNNNNNNNN NNNNNNNNNN NNNNNNNNNN NNNNNNNNNN
10101 NNNNNNNNNN NNNNNNNNNN NNNNNNNNNN NNNNNNNNNN NNNNNNNNNN
10151 NNNNNNNNNN NNNNNNNNNN NNNNNNNNNN NNNNNNNNNN NNNNNNNNNN
10201 NNNNNNNNNN NNNNNNNNNN NNNNNNNNNN NNNNNNNNNN NNNNNNNNNN
10251 NNNNNNNNNN NNNNNNNNNN NNNNNNNNNN NNNNNNNNNN NNNNNNNNNN
10301 NNNNNNNNNN NNNNNNNNNN NNNNNNNNNN NNNNNNNNNN NNNNNNNNNN
10351 NNNNNNNNNN NNNNNNNNNN NNNNNNNNNN NNNNNNNNNN NNNNNNNNNN
10401 NNNNNNNNNN NNNNNNNNNN NNNNNNNNNN NNNNNNNNNN NNNNNNNNNN
10451 NNNNNNNNNN NNNNNNNNNN NNNNNNNNNN NNNNNNNNNN NNNNNNNNNN
10501 NNNNNNNNNN NNNNNNNNNN NNNNNNNNNN NNNNNNNNNN NNNNNNNNNN
10551 NNNNNNNNNN NNNNNNNNNN NNNNNNNNNN NNNNNNNNNN NNNNNNNNNN
10601 NNNNNNNNNN NNNNNNNNNN NNNNNNNNNN NNNNNNNNNN NNNNNNNNNN
10651 NNNNNNNNNN NNNNNNNNNN NNNNNNNNNN NNNNNNNNNN NNNNNNNNNN
10701 NNNNNNNNNN NNNNNNNNNN NNNNNNNNNN NNNNNNNNNN NNNNNNNNNN
10751 NNNNNNNNNN NNNNNNNNNN NNNNNNNNNN NNNNNNNNNN NNNNNNNNNN
10801 NNNNNNNNNN NNNNNNNNNN NNNNNNNNNN NNNNNNNNNN NNNNNNNNNN
10851 NNNNNNNNNN NNNNNNNNNN NNNNNNNNNN NNNNNNNNNN NNNNNNNNNN
10901 NNNNNNNNNN NNNNNNNNNN NNNNNNNNNN NNNNNNNNNN NNNNNNNNNN
10951 NNNNNNNNNN NNNNNNNNNN NNNNNNNNNN NNNNNNNNNN NNNNNNNNNN
11001 NNNNNNNNNN NNNNNNNNNN NNNNNNNNNN NNNNNNNNNN NNNNNNNNNN
11051 NNNNNNNNNN NNNNNNNNNN NNNNNNNNNN NNNNNNNNNN NNNNNNNNNN
11101 NNNNNNNNNN NNNNNNNNNN NNNNNNNNNN NNNNNNNNNN NNNNNNNNNN
11151 NNNNNNNNNN NNNNNNNNNN NNNNNNNNNN NNNNNNNNNN NNNNNNNNNN
11201 NNNNNNNNNN NNNNNNNNNN NNNNNNNNNN NNNNNNNNNN NNNNNNNNNN
11251 NNNNNNNNNN NNNNNNNNNN NNNNNNNNNN NNNNNNNNNN NNNNNNNNNN
11301 NNNNNNNNNN NNNNNNNNNN NNNNNNNNNN NNNNNNNNNN NNNNNNNNNN
11351 NNNNNNNNNN NNNNNNNNNN NNNNNNNNNN NNNNNNNNNN NNNNNNNNNN
11401 NNNNNNNNNN NNNNNNNNNN NNNNNNNNNN NNNNNNNNNN NNNNNNNNNN
11451 NNNNNNNNNN NNNNNNNNNN NNNNNNNNNN NNNNNNNNNN NNNNNNNNNN
11501 NNNNNNNNNN NNNNNNNNNN NNNNNNNNNN NNNNNNNNNN NNNNNNNNNN
11551 NNNNNNNNNN NNNNNNNNNN NNNNNNNNNN NNNNNNNNNN NNNNNNNNNN
11601 NNNNNNNNNN NNNNNNNNNN NNNNNNNNNN NNNNNNNNNN NNNNNNNNNN
11651 NNNNNNNNNN NNNNNNNNNN NNNNNNNNNN NNNNNNNNNN NNNNNNNNNN
11701 NNNNNNNNNN NNNNNNNNNN NNNNNNNNNN NNNNNNNNNN NNNNNNNNNN
11751 NNNNNNNNNN NNNNNNNNNN NNNNNNNNNN NNNNNNNNNN NNNNNNNNNN
11801 NNNNNNNNNN NNNNNNNNNN NNNNNNNNNN NNNNNNNNNN NNNNNNNNNN
11851 NNNNNNNNNN NNNNNNNNNN NNNNNNNNNN NNNNNNNNNN NNNNNNNNNN
11901 NNNNNNNNNN NNNNNNNNNN NNNNNNNNNN NNNNNNNNNN NNNNNNNNNN
11951 NNNNNNNNNN NNNNNNNNNN NNNNNNNNNN NNNNNNNNNN NNNNNNNNNN
12001 NNNNNNNNNN NNNNNNNNNN NNNNNNNNNN NNNNNNNNNN NNNNNNNNNN
12051 NNNNNNNNNN NNNNNNNNNN NNNNNNNNNN NNNNNNNNNN NNNNNNNNNN
12101 NNNNNNNNNN NNNNNNNNNN NNNNNNNNNN NNNNNNNNNN NNNNNNNNNN
12151 NNNNNNNNNN NNNNNNNNNN NNNNNNNNNN NNNNNNNNNN NNNNNNNNNN
12201 NNNNNNNNNN NNNNNNNNNN NNNNNNNNNN NNNNNNNNNN NNNNNNNNNN
12251 NNNNNNNNNN NNNNNNNNNN NNNNNNNNNN NNNNNNNNNN NNNNNNNNNN
12301 NNNNNNNNNN NNNNNNNNNN NNNNNNNNNN NNNNNNNNNN NNNNNNNNNN
12351 NNNNNNNNNN NNNNNNNNNN NNNNNNNNNN NNNNNNNNNN NNNNNNNNNN
12401 NNNNNNNNNN NNNNNNNNNN NNNNNNNNNN NNNNNNNNNN NNNNNNNNNN
12451 NNNNNNNNNN NNNNNNNNNN NNNNNNNNNN NNNNNNNNNN NNNNNNNNNN
12501 NNNNNNNNNN NNNNNNNNNN NNNNNNNNNN NNNNNNNNNN NNNNNNNNNN
12551 NNNNNNNNNN NNNNNNNNNN NNNNNNNNNN NNNNNNNNNN NNNNNNNNNN
```

FIGURE 3, page 4 of 40

```
12601 NNNNNNNNNN NNNNNNNNNN NNNNNNNNNN NNNNNNNNNN NNNNNNNNNN
12651 NNNNNNNNNN NNNNNNNNNN NNNNNNNNNN NNNNNNNNNN NNNNNNNNNN
12701 NNNNNNNNNN NNNNNNNNNN NNNNNNNNNN NNNNNNNNNN NNNNNNNNNN
12751 NNNNNNNNNN NNNNNNNNNN NNNNNNNNNN NNNNNNNNNN NNNNNNNNNN
12801 NNNNNNNNNN NNNNNNNNNN NNNNNNNNNN NNNNNNNNNN NNNNNNNNNN
12851 NNNNNNNNNN NNNNNNNNNN NNNNNNNNNN NNNNNNNNNN NNNNNNNNNN
12901 NNNNNNNNNN NNNNNNNNNN NNNNNNNNNN NNNNNNNNNN NNNNNNNNNN
12951 NNNNNNNNNN NNNNNNNNNN NNNNNNNNNN NNNNNNNNNN NNNNNNNNNN
13001 NNNNNNNNNN NNNNNNNNNN NNNNNNNNNN NNNNNNNNNN NNNNNNNNNN
13051 NNNNNNNNNN NNNNNNNNNN NNNNNNNNNN NNNNNNNNNN NNNNNNNNNN
13101 NNNNNNNNNN NNNNNNNNNN NNNNNNNNNN NNNNNNNNNN NNNNNNNNNN
13151 NNNNNNNNNN NNNNNNNNNN NNNNNNNNNN NNNNNNNNNN NNNNNNNNNN
13201 NNNNNNNNNN NNNNNNNNNN NNNNNNNNNN NNNNNNNNNN NNNNNNNNNN
13251 NNNNNNNNNN NNNNNNNNNN NNNNNNNNNN NNNNNNNNNN NNNNNNNNNN
13301 NNNNNNNNNN NNNNNNNNNN NNNNNNNNNN NNNNNNNNNN NNNNNNNNNN
13351 NNNNNNNNNN NNNNNNNNNN NNNNNNNNNN NNNNNNNNNN NNNNNNNNNN
13401 NNNNNNNNNN NNNNNNNNNN NNNNNNNNNN NNNNNNNNNN NNNNNNNNNN
13451 NNNNNNNNNN NNNNNNNNNN NNNNNNNNNN NNNNNNNNNN NNNNNNNNNN
13501 NNNNNNNNNN NNNNNNNNNN NNNNNNNNNN NNNNNNNNNN NNNNNNNNNN
13551 NNNNNNNNNN NNNNNNNNNN NNNNNNNNNN NNNNNNNNNN NNNNNNNNNN
13601 NNNNNNNNNN NNNNNNNNNN NNNNNNNNNN NNNNNNNNNN NNNNNNNNNN
13651 NNNNNNNNNN NNNNNNNNNN NNNNNNNNNN NNNNNNNNNN NNNNNNNNNN
13701 NNNNNNNNNN NNNNNNNNNN NNNNNNNNNN NNNNNNNNNN NNNNNNNNNN
13751 NNNNNNNNNN NNNNNNNNNN NNNNNNNNNN NNNNNNNNNN NNNNNNNNNN
13801 NNNNNNNNNN NNNNNNNNNN NNNNNNNNNN NNNNNNNNNN NNNNNNNNNN
13851 NNNNNNNNNN NNNNNNNNNN NNNNNNNNNN NNNNNNNNNN NNNNNNNNNN
13901 NNNNNNNNNN NNNNNNNNNN NNNNNNNNNN NNNNNNNNNN NNNNNNNNNN
13951 NNNNNNNNNN NNNNNNNNNN NNNNNNNNNN NNNNNNNNNN NNNNNNNNNN
14001 NNNNNNNNNN NNNNNNNNNN NNNNNNNNNN NNNNNNNNNN NNNNNNNNNN
14051 NNNNNNNNNN NNNNNNNNNN NNNNNNNNNN NNNNNNNNNN NNNNNNNNNN
14101 NNNNNNNNNN NNNNNNNNNN NNNNNNNNNN NNNNNNNNNN NNNNNNNNNN
14151 NNNNNNNTGT GGGATATAAT CTCCTGGTGC GCCGTTTTTT AAGCCTGTCA
14201 GAAAAGTGCA GTATTAGGGT GGGAGTGACC TGATTTTCCA GGTGCCCTCT
14251 GTCACCCCTT TCTTTGACTA GGAAAGGGAA CTCCCTGACC CCTTGCGCTT
14301 CCCGAGTGAG GCAATGCCTC GCCCTGCTTT CGCTTGGGCA CGGTGTGCTG
14351 CACCCACTGT CCTGCGCCCA CTGTCTGGCA CTCCCTAGTG AGATGAACCC
14401 GGTACCTCAG ATGGAAATGC AGAAATCACC CATCTTCTGC GTCGCTCACG
14451 CTGGGAGCTG TAGACCGGAG CTGTTCCTAT TTGGCCATCG TGGCTGCCAG
14501 CTCAAAATTA TATGTTAATA TATTTGTTGT GTAGACTATA ATGTTTGAT
14551 ATAGGGATAC ATTGTGGAAT TACTAAAGCT AATTAATATA TTCATTACCT
14601 TACAATTTTA TCATTTTTTG TGTGTGTGGT GAAACATTT AAAATCTCCT
14651 CAGCAGTTTG CAGGTGTACA ATACATTGTT AATAACTATA GTCACCAATT
14701 TGTGTTGCAG TTGATCTTCT AAATGTATTC TTTCTAACTG AAATTTGTA
14751 TCCTTTGACC AAACATTTCC CCAATTCCTA CCCCTACCTT TTTTCTCCTG
14801 ATAATATTTC GTCTTGTGAA AATTTTATCT CATCTCTCAC TATCTCTGAT
14851 TTATAGACCA TTTGATATTT ATTTTTACAA GCTAGATAAA AACTGCCAAG
14901 TTAGTATATA AACTGTAGTC TTTTATTTTT TAAACTACGT ATTCTTGTGA
14951 ATAAGAATTG ATAACTTCTA TAGATATTAA AATTAAGTTT TTCCTCATTT
15001 GCTATGTATA CATCAACAAC TCTGTCTCCT AGGCGTGTAT CATGTCAGGG
15051 CAGGCAGAAC TGAACGGAAG AATAATTTTC AGGGTAGAAT GGGAGAAAAT
15101 ACAGAATTAT GTGAAGCAGG CTCAGGGGTT TATTATTGAA ACAGAGGAGA
15151 GGAGCTGGGG GCCTGAGCCA ATTTGCGCTG AAGCCAATGT GGCTGAGATG
15201 GCTCCTTCTG GGAACAGAGA TGTGCTTGGA GGAGCCTTGG TTCTCCTCAC
15251 CAATATACCC CTTATGTTGG CTGCTGCAGG CAGCACTACC AGGTTCATTT
15301 GACTGCTCAC TTGTTGGTAG AAGGTTTGTT AATTTTCTTG TCCGATTTCT
15351 TCTGAGATTA GGAATTTCCT TGGATTAAAA ACAAAATAAA TCATTGGTTG
15401 AGTCTTTTTC CAGGTTAAAA AAAACAAGAA AACTTGGAGG TGGATTGCT
15451 GAGGAGGACA GCCATGTTCT CTACCAGAAG TCAGATTGGG TCTTTTTCCT
15501 AAAACAACTA AAAACGCAGT AGTTTGTTTA CTTTTTAAAA TCCGTCTCCT
15551 CCACCTGTGG AAAGAGAACT TTAAACACTA TTTATGTTAC ATGCTGAATC
15601 TAAGACTGTT GTTCCTTCAG CTTGAACTGC AGATATTCCT AAATTGTACC
15651 TGCATCTCTA GTGAAAGCTG AGTGTGCTAA ATGCTGACCA TTCTCCATTA
15701 ACTGAGATTT CAGTTATCTA AGAGATTTGC ATCTTAGCAG TACTACTGTA
```

FIGURE 3, page 5 of 40

```
15751 TTACTCTGTA AGATTCCTTC TACCTACCTG AGCTCAAACT TCATCCTATT
15801 CAGAAGATGT TTTAATATAA CAACTCAGTA GGCCTTCTCT ACCACTTAAC
15851 AAATATTAAT TGAGCACCTA CTGTGTACAA GGCACTGTGC TTAATTAAGT
15901 CAGGGAGTAT TTCAGCTCCC TGAAACAGAG AGCATCTCAG CCCTCCCAGA
15951 TTGATTCTCT GGACTAAATA TGCATGGTAG CTTCAGTGCC TGTTGAGAGA
16001 AATGAATGTG TCTGGGAGTG TAAAGCAGAG GTCCCTAATG GAGTTGTTGA
16051 TTGTAGGAGT AATTGTGGAG GAAGTGACAT TTGAGCTGAG AAGTAAAGAA
16101 CAACAGGGCC TAGTGGGTGA TGGGACAGGG ATGAAGGAGC CCTCCAGAGA
16151 GAGAAAACCA TATTTGTGGA CCTGAATACT CACAGACCTG AAGGATGTTC
16201 TTGATGGCAA GAGGCTGGGT GGTGAGAAGA TGAGGTGGAG AAATAGGCAG
16251 CCACTTTTCC ATCTTCTGCA TGTCAAAGTG CTGTTCTCAT CTTTGAGAGA
16301 AGCTGTCCTG TAAAGAACTC TTCAGGTTCT GTGTATTTGG AAGTGGCATC
16351 TAAATCATGC CCATTGGAAT CTTCTTCCTG GATACTATCA TGTCTTTATG
16401 TAAACTTGTG AATTTAAAAG TATACATAGC AGTGTCGGAG CAGGCTTTCC
16451 TTTTTATTTT TTTGCATCTG GTTTTCAGAA TGCCCATTAG GCAAATTTTT
16501 GACCTTTAAC TTTTTCAATA GGCCTTGGAT AAGGTGGGTG GTAAATTGAT
16551 AGGAAAACTA TAGATAAGTA TTTGTCCATC TAGTTGTACC AAAGAAGTGG
16601 TAATATAGAC TTTTGTGGAT CCTTTAGAGC ACCTGATATC ACATTAAATA
16651 ATATGATACC TGAATATGTA TTTCAGTTGT TTCTCCCACT AGAATACCAG
16701 GGTAGGAATT TTCTTTTGTT TACTGTTGTA TCTGTAGTGT CCAGAGCAGT
16751 GCCTAGCATG CAGTGAATGC TTATTAAATA TTTTTTGAAT GAATGAATTA
16801 TAAGACACTT GGAAGCTGAG GGAATTTATT ATAAACAGAG TTTAATCCCT
16851 GAAAGGAGTC CTGCACAGAG ATTGTCAATC AAATCATAGT TTTGAAGTCT
16901 GTGTTGTATG TCTAAGATTG TATTGAGCCC TTTAAATAGA AACTGGAAGA
16951 TAAACGTGGT CCCTACTCTG ATTCTAAGAG CTTTTATACT AAAAGGAAAG
17001 AGAATGTCAT GAGCATTTAT GTATATAGCA AGGCATTACC ATCAACAGCC
17051 ATTAAAAGGG GAGGTTTGTC AAGGTGGTCG TGAGTCAGTT GAGTATTTGG
17101 CCTCTTCACA CGTGTGAGAG GCTGGAGGCT GGTGGGGAGC TCACATAGGC
17151 GTAACAGCCC ATGTTCAAAT CCAGCTTCAC TGCTTAGTGT TTGCATTACA
17201 TTGGCAAGGG TTGACTGCCT CCACTGATTG TTTTAAGTGC TCTAGGCAAG
17251 TAATAAATAT TAGTTCTTTT TGCCTTGTTC TTTCCACTAT GGGTGACTGC
17301 CCTAATTGAG GGTATACCAG ATAATTGCAC TGTCTTGATT TGTTAAGTGC
17351 CTCTAAATGT TCTTCTCCTG ACATCTGGAC TATGTTTCTA GAGGCCTAGG
17401 GGGAGGAGGA GGTAAAGGCA CTTGACTTTC CCAAATTAGT CTGTACCCAA
17451 GTGGAACTGC ATAAATTGGG TACCTTAATT ACACCATTGG GTATTACTAG
17501 GGTGATTACA GGGACAAGAG TTAAATAGGG CTTGTCTACA AAGAGTCCTG
17551 GGAGGAAGTG AGATGTGAGA GAACTAAAAG CATCTAAAGG ACATTTTAGA
17601 TGGAGAGGAG GTGAAGGGTG TTCTCCTGTG GGTTCTGACT TCTGATGCTA
17651 ACTCCTAACG GTGAAAGCTA GGAAGTTGAC TTACATGTAG CTCAGAGGAG
17701 GATGCTAACC TGGCTCACTG CAACTTCCAC CTCCTGGATT GAAGCGATTC
17751 CCCTGCTTCA GCCTCCTGAG TAGCTAGGAT TACAGGTGCA AGCCATCATG
17801 CCTGGCTAAT TTTTGTATTT TTAGTAAAGG TGGGGTTTCA ACATGTTGGC
17851 CAGGTTGGTC TCAAACTCCT GACCTCAGGT GATGCACCCA CCTCGGTTTC
17901 CCAAAGTGCT GGGATTACAG GTGTGAGCCA CGGTGCCTGG CCCTAGGTGT
17951 GGTTTTTAAT TACTATGTAA TCCCAGGGCC CAGTGTGGAC CTAGGACATA
18001 GTTACTACAT GATACAGTGA TTATCGTTGG CACAAATGAA TGAATCAAAG
18051 AGATAGTATG TTACAAAGGA GAGGGCACGA AATAGATTTT TTTTTTGAGC
18101 ACATGATTAG AAGCAGTATT TTAAGGTCAT TTCCTGGGCT GGGAAGGTTA
18151 GGAATATTCT TCTGACCAGC ACCTGTTGGA GGAGGTGGAA AGGATCCCAG
18201 ATGCCAGCCT TCTCTGTGTC CACCCTTCTC CCAGCCTTGC CTGGGGACAC
18251 TGAGCCCCTT GCTGGGCTTC AAGTGCCTGA TGCTTTTTTG GGAAGCCCCA
18301 TAAGCTTGCT TCTCTTTTTG CAAACATTGC TTAAGTTTTC ATTAATAAAA
18351 ACATTCTAAA GCTTATTTAG TCCAGAATGA GGAAAATGTA GGAGAGAGAG
18401 AGGGTGTGGG TGTGTGTGTG GGGCGAGGGG GTGTCTGTGT GTGGTTTTAC
18451 CTACCTATGT GGTTGCCCCT TCTTACCTGT GAATGCAGTG GCTGCTTTCC
18501 TTGTTCCTTC TCCACAGACC CTGTACCCTC CATTTCAGTT TCTGGCAAGA
18551 ATTGTGGCCA GACCCAGGGA TGCTGATGCA GTGGTCCCCA ACATTTTCTG
18601 GTCACATAAT TTCTAAAAGA ATTTTGTAAC ATTAACCCTC TGGGATATTT
18651 TTTAATTGAC ATCTACATTT TATTTTTTTT ATTATTTTAT TATTATTATA
18701 CTTAAGTTTT AGGGTACATG TGCACAATGT GCAGGTTAGT TACATATGTA
18751 TACATGTGCC ATGCTGGTGT GCTGCACCCA TTAACTAGTC TTTTAGCATT
18801 AGGTATATCT CCTAATGCTA TCCCTCCCCC CAACCCCCAC CCCACAACAG
18851 TCCCCAGAGT GTGATGTTCC CCTTCCTGTG TCTGTGTTCT CATTGTTCAA
```

```
18901 TTCCCATCTA TGAGTGAGAA CATGCGGTGT TGGTTTTTTG TCCTTGCAAT
18951 AGTTTACTGA GAATGATGAT TTCCAATTTC ATCCATGTCC CTGCAAAGGA
19001 CATGAACTCA TCATTTTTTA TGGCTGCATA GTATTCCATG GTGTATATAT
19051 GCCACATTTT CTTAATCCAG TCTATCATTG TTGGACATTT GGGTTGGTTC
19101 CAAGTCTTTG CTATTGTGAA TAGTGCTGCA ATAAACATAC ATGTGCATGT
19151 GTCTTTATAG CAGCATGATT TATAGTCCTT TGGGTATATA CCCAGTAATG
19201 GGATGGCTGG ATCAAATGGT ATTTCTAGTT CTAGATCCCT GAGGAATCGC
19251 CGCACTGACT TCCACAATGG TTTTACTAGT TTACAGTCCC ACCAACAGTG
19301 TAAAAGTGTT CCTATTTCTC CACATCCTCT CCAGCACCTG TTGTTTCCTG
19351 ACTTTTTAAT GATCACCATT CTAACTGGTG TGAGATGGTA TCTCATTGTG
19401 GTTTTGATTT GCATTTCTCT GATGGCCAGT GATGAGCGTT TTTTCATATG
19451 TCTTTTGGCT GCATAAATGT CTTCTTTTGA GAAGTGTCTA TTCATGTCCT
19501 TCGCCCACTT GTTGATGGGG TTGGTTGGTT TTTTCTTGTA AATTTGTTTG
19551 AGTTCATTGT AGATTCTGGA TATTAGCCCT TTGTCAGATG AGTAGGTTGC
19601 GAATATTTTC TCCCATTTTG TAGGTTGCCT GTTCACTCTG ATGGTAGTTT
19651 CTTTTGCTGT GCAGAAGCTC TTTAGTTTAA TTAGATCCCA TTTGTCAATT
19701 TTGGCTTTTG TTGCCAATGC TTTTGGTGTT TTAGACATGA AGTCCTTGCC
19751 CATGCCTATG TCCTGAATGG TAATGCCTAG GTTTTCTTCT AGGGTTTTTA
19801 TGGTTTTAGG TCTAACGTTT AAGTTTCCAT CTTGAATTAA TTTTTGTATA
19851 AGGTGTAAGG AAGGGATCCA GTTTCAGCTT TCTACATATG GCTAGCCAGT
19901 TTTCCCAGCA CTATTTATTA AATAGGGAAT CCTTTCCCCA TTGCTTGTTT
19951 TTCTCAGGTT TGTCAAAGAT CAGATAGTTG TAGATATGCA GCGTTATTTC
20001 TGAGGGCTCT GTTCTGTTCC ATTGATCTAT ATCTCTGTTT TGGTACCAGT
20051 ACCATGCTGT TTTGGTTACT GTAGCCTTGT AGTATAGTTT GAAGTCAGGT
20101 AGTGTGATGC CTCCAGCTTT GTTCTTTTGG CTTAGGATTG ACTTGACGAT
20151 GTGGGCTCTT TTATGGTTCC ATATAAACTT TAAAGTAGTT TTTTCCAATT
20201 CTGTGAAGAA AGTCATTGGT AGCTTGATGG GGATGGCATT GAATCTATAA
20251 ATTACCTTGG GCAGTATGGC CATTTTCACA ATATTGATTC TTCCTACCCA
20301 TGAGCATGGA ATGTTCTTCC ATTTGTTTGT ATCCTCTTTT ATTTCATTGA
20351 GCAGTGGTTT GTAGTTCTCC TTGAAGAGGT CCTTCACGTC CCTTGTAAGT
20401 TGGATTCCTA AGTATTTTAT TATCTTTGAA GCAATTGTGC ATGGGAGTTC
20451 ACTCATGATT TGGCTCTCTG TTTGTCTGTT ATTGGTGTAT AAGAATGCTT
20501 GTGATTTTTG TACATTGATT TTGTATCCTG AGACTTTGCT GAAGTTGCTT
20551 ATCAGCTTAA GGAGATTTTT GGCTGAGACA ATGGGGTTTT GTAGATATAC
20601 AATCATGTCG TCTGCAAACA GGGACAATTT GACTCCCTCT TTTCCTAATT
20651 GAATACCCTT TATGTCCTTC TTCTGCCTAA TTGCCCTGGC CAGAACTTCC
20701 AACACTATGT TGAATAGGAG TGGTGAGAGA GGGCATCCCT GTCTTGTGCC
20751 CGTTTTCAAA GGGAATGCCT CCAGTTTTTG CCCATTCAGT ATGATATTGG
20801 CTGTGGGCTT GTCATAGATA GCTCTTATTA TTTTGAGATA CGTCCCATCA
20851 ATACCTAATT TATTGAGAGT TTTTAGCATG AAGCGTTGTT GAATTTTGTC
20901 AAAGGCCTTT TCTGCATCTA TTGAGATAAT CATGTGGTTT TTGTCTTTGG
20951 TTCTGTTTAT ATGCTGGATT ACATTTATTG ATTTGCATAT ATTGAACCAG
21001 CCTTGCATCC CAGGGATGAA GCCCACTTGA TCATGGTGAA TAAGCTTTTT
21051 GATGTGCTGC TGGATTCGGT TTGCCAGTAT TTTATTGAGG ATTTTTGCAT
21101 CCATGTTCAT CAAGGATATT GGTCTAAAAT TCTCTTTTTT GGCTGTGTCT
21151 CTGCCCGGCT TTGGTATCAG GATGATGCTG GCCTCATAAA ATGAGTTAGG
21201 GAGGATTCCC TCTTTTTCTA TTGATTGGAA TAGTTTCAGA AGGAATGGTA
21251 CCAGTTCCTC CTTGTACCTC TGGTAGAATT CGGCTGTGAA TCCATCTGGT
21301 CCTGGACTCT TTTTGGTTGG TAAGCTATTG ATTATTGCCA CAATTTCAGA
21351 GCCTGTTATT GGTCTATTCA GAGATTCAAC TTCTTCCTGG TTTAGTCTTG
21401 GGAGGGTGTA TGTGCCGAGG AATTTATCCA TTTCTTCTAG ATTTTCAGT
21451 TTATTTGCGT AGAGGTGTTT ATAGTATTCT CTGATGGTAG TTTCTATTTC
21501 TGTGGGATCG GTGGTGATAT CCCCTTTATC ATTTTTTTGT GTCTATTTGA
21551 TTTTTCTCTC TTTTCTTCTT TATTAGTCTT GCTAGTGGTC TATCAATTTT
21601 GTTGATCCTT TCAAATAACC AGCTCCTGGA TTCATTAATT TTTTGAAGGG
21651 TTTTTTGTGT CTCTATTTCC TTCAGTTCTG CTCTGATTTT AGTTATTTCT
21701 TGCCTTCTGC TAGCTTTTGA ATGTGTTTGC TCTTGCTTCT TTAGTTCTTT
21751 TAATTGTGAT GTTAGGGTGT CAATTTTGGA TCTTTCCTGC TTTCTCTTGT
21801 GGGCATTTAG TGCTATAAAT TTCCCTCTAC ACACTGCTTT GAATGTATCC
21851 CAGAGATTCT GGTATGTTGT GTCTTTGTTC TCGTTGGTTT CAAAGAACAT
21901 CTTTATTTCT GCCTTCATTT CGTTATGTAC CCAGTAGTCA TTCAGGAGCA
21951 GGTTGTTCAG TTTCCATGTA GCTGAGCGGT TTGAGTGAG TTTCTTAATC
22001 TTGAGTTCTA GTTTGATTGC ACTGTGGTCT GAGAGACAGT TTGTTATAAT
```

```
22051 TTCTGTTCTT TTACATTTGC TGAGGAGAGC TTTACTTCCA ACTATGTGGT
22101 CAATTTTGGA ATAGGTGTGG TGTGGTGCTG AAAAAAATGT ATTTTCTGTT
22151 GATTTGGGGT GGAGAGTTCT TTAGATGTGT ATTAGGTCCG CTTGGTGCAG
22201 AGCTGAGTTC AATTCCTGTG TATCCTTGTT AACTTTCTGT CTCGTTGATC
22251 TGTCTAATGT TCACAGTGGG GTGTTAAAGT CTCCCATTAT TATTGTTTGG
22301 GAGTCTAAGT CTCTTTGTAG GTCACTCAGG ACTTGCTTTA TGAATCTGGG
22351 TGCTCCTGTA TTGGGTGCAT TTATATTTAG GATAGTTAGC TCTTCTTGTT
22401 GAATTGATCC CTTTACCGTT ATGTAACGGC CTTCTTTGTC TCTTTTGATC
22451 TTTGTTGGTT TAAAGTCTGT TTTATCAGAG ACTAGGATTG CAACCCCTGC
22501 CTTTTTTTGT TTTCCATTTG CTTGGTAGAT CTTCCTCCAT CCTTTTATTT
22551 TGAGCCTATG TGTGTCTCTG CACGTGTAGT ATGGGTTTCC TGAATACAGC
22601 ACACTGATGG GTCTTGACTC TTTATCCAAT TTGCCAGTCT GTGTCTTTTA
22651 ATTGGAGCAT TTAGTCCATT TACATTTAAA GTTAATATTG TTATGTGTGA
22701 ATTTGATCCT GTCATTATGA TGTTAGCTGG TTATTTTGCT CGTTAGTTGA
22751 TGCAGTTTCT TCCTAGCCTT GATGGTCTTT ACGTTTTGGC ATGATTTTGC
22801 AGTGGCTGGT ACCGGTTGTG CCTTTCCATG TTTAGTGCTT CCTTCAGGAG
22851 CTCTTGTAAG GCAGGCCTGG TGGTGACAAA TTCTCTCAGC ATTTGCTTGT
22901 CTGTAGAGTA TTTTATTTCT CCTTCACTTA CATTTTAAAA ATCATTTTAA
22951 ACTGTTGCAA AACTTTTGAT TTCCAGTGCA TTATAAATGT TGACATTTGT
23001 AATGAAATTT AAATATATCC AGTAGATCTA TAAATATTGT TAACAGTTTG
23051 ATACCCACCA CCATTCATTT AATAAACATA CTTTTCAATG ACATTTGGAT
23101 GGAGATATAT ATATACACAT ATATATATTT TTTAAGTGAG ACAGGGGTCT
23151 CTCTCTGTTG CCCAAACTGG AGTGTAGTGG TGCGATCACA GCTTACTGCA
23201 GCCTCCACCT CCCTGGGTCA AGCAATTCTC CTGCCTCACC CTCCTGAGTA
23251 GCTGGGACTA CAGGCACATG CCACCATACC TGGCTAATTT TTATTTTTAT
23301 TTTTTTTTGG TAGAGACAGG GTCCTCCTAT GTTCCCTGG CTGGTCTCAA
23351 GCTCCTGGCT TCAAGCAGTC CTACCGCCTC ATCTTTCCAA AGTACTGGTA
23401 TTACTGGTGT GAGCCACCAC ACCTGGCCAC GTTTGGATAT TTTATATTGC
23451 TCTTTTTTTT TTCTATCTTC ATTCCTCCTC AGAATTTTAT CTTAGCATAA
23501 TATTTTGAGG TTCAAAGTCA TCTCCCTATT ACACATATCT ACAATGACAA
23551 AAAGAATATA GATAGAATTT AAAGTTTTAT AATCCTGTGG CTATCAGCCT
23601 CTGTCTTAGA AAAGCTTCAG GACTGACTTA CCATTACAAT TAGTATTGGT
23651 AAACAATTAA TCAAACAAC AATAAATGTT ACAGGGTTGG GTAATTAACT
23701 ATTAAACATA AAAGCTACAT TTATTAGATT TCTTAGTGAC ATGGATGGAG
23751 CATTTTGTTG TTGATTATAT ATTCTGTATT GACAAATATT ACAGATTGCT
23801 AGAGATAGAA TTTAGTATAA ATTTCATTCC TATTAGGTCA ACTTTTTTTT
23851 ACGTAAAGAA GTAATTAAGG TGGGAATCAT TTTCTTACAG CAGTGTTTCT
23901 CAGTTTTTTG AACTCTCAAG CTTTAAGCCA AAAATTACAT GGTGATCTGA
23951 CAGCAAAAAC TATTTTAATG ATTTATTAAT GATATTAGGT CACCTCCAGT
24001 TTTGTTGAAT GCAAATAGTT AGAAACCTCT GCTTGCCCCA AAGGATTTAT
24051 TACCCATTCA TTAGAGACAT TGGCTTTCTT AATAAAGATA GCAATATTTC
24101 TGATTACCTT TGTTTGGTGC CCTGGAGGTT ATATTAGGTG GGACAGTGCA
24151 TTTAATAACA ATACAGGATG GGTGAGCAGT CAGGCCCTTT GTGAAGTGGG
24201 AGAAGGGTGA TGTGAAGTGG GGTGGGGCGG GGTGGGGGG CAGAGCGAGA
24251 GAGAAGCATG GAGAACCTGC CCCTATCCAA GTGGATCAGT TTTAGGAAAG
24301 CTTATGCCGT ATGTAGGGAT GCCAAGGGTC TGGGAATTTA TTCCCTAACT
24351 TAAAGTTATC TGCATTCACA TATTCCATGG AGAGTTGTAT GCATTCAGGT
24401 ATCATGCACT CCCAGTCTGA AAAACTGCTC TTTTGGTTGA AAGAGTATAA
24451 GGACTTGGAA GATGGGGCCT CTAGGCCTGA CTGAGCCAAA GGCTCCCATG
24501 ACCTCAAGGG AACTGACTAG TGCTTTTTTC ATTTTTTACT GCGTTCTGGG
24551 TCCCACCCTT GGCATTCAGA TGTGTGCATG AGCTGCTGTT TAATTTTCAT
24601 CATCTGCTTT ACAAATGAGG AAAAGCCCTG ATATCCAGCT CCCTCATAGG
24651 ACCTGATAAT AATACATATG GTTCTGAGAA TTAAACGAGG TAATAGGTAC
24701 GTAAAGTGGG TAAACAGAGT AACTTCACTC TCTATTTGTA CGTCTCTCAG
24751 AAGTCTGGGG CAACAGGAGC TGTGGAAGGC TCCAGAAGAC AAGATGTCAC
24801 AAAGCCACCT AGCTACTGTG GCTGTACCAA TCCTGACAGT CATAGCGGCC
24851 CCAAGGTGCT GCTCTGTTGG CTGATGGGAA TGCAGATTTA CGTATGGTCC
24901 ATATATGGAC GTGTTGTTTT ACATCTAAAT AAACTTGGCA TTGCAAGATG
24951 AAAATGCCAG TATCATTTTT AAAGGTCAAG TGACAGTTTG GGAAGATTTT
25001 TATAACTTTG ATAAGTTCCT CAGCTACATC TGTTCACACT GGCAAGAGTG
25051 CTAGAGACAT TCTTGGGAAG TCTTTTCTAT CAGAGGAGCT GCAGCCTTGC
25101 TCTGCAGAAA AGTTCTGATG ACAGTCATCA GAGTATTTGG GGCTCATGCA
25151 CTAACTGTTA ATTATTTTCA TTTTTCATTA ATGAAAATTT ATTTTAATTT
```

```
25201 TTTTCATTCT TCTTTAATGA ATTTAACTAT TTGCCTCTAC CTTTGCTTCC
25251 TGCTTTGTAT ACTGATAAGA CAGGTTTTGG GGTTTTTATG TTTTCTGGTC
25301 TTGCTTTTCC CCTTTGTTTT AGGATTTAAA AAACAAAAAG GTTAAGAGGG
25351 TAGGTTGACA GTGCTTGCAG TTTCTGTTTT ACAGCAATCC CAGCTGTTCC
25401 TCTGAAAATT GGTTGATTGT CCTATAGTTT AAAATATATA GATGTTCATT
25451 TGATTGGCTC TTGTAAATCT AGTGACATTT AAAGTACAT GGCAGCTAGT
25501 CATGGTGGCT CACACTTATA ATCCCAGCAC TTTGGGAGGC TCAGGCAGGA
25551 GGATGGCTTA GCCCAGGAGT TCGAGACCAG CTTGGGTAAC ATCATGAGAC
25601 CCCAACTCTA CAAAAATTTT TAAATAGTTG TGAGTGGTGG CATGTGCCTG
25651 TACCCTCAGC TACTTGAGAG GCTGAGGTGG GAGGATTGTT TGAGACCTGG
25701 AGTTTGAGGT TGTGGTGCTC TATGATTGCA CCACTACACT CCAGCCTGGA
25751 TGATAGACTG AGACCCTGTC TCAAAAAGA AAAAGAAAAA AGTTCATGTC
25801 TATTCTGTTT TTTGTTATGT TACTTTCCTC TAAACATGAA GAAAGCAGT
25851 GAGGAGAAAC AAAAATTGAG TATTCCTGTG TTTTTTATCA TAGTAAAATA
25901 TACATTTGCC ATTTTATATT TATCCTGATA ACCTTCAGTG TTGTAAAATA
25951 CACATTCACA ATTATTCATT TAACCTGATA ACCTCTAATC TCTTTTCCAT
26001 GAATCGGACT AGGTACCTCA TATAAGTGGA ATCATACCAT ATTTATACTT
26051 TTGTGTCTGG TTTATTTCAC TTAATGTCCT TAAGGTTCAT CCACATTGTA
26101 GCATGTCTCA GAATTTAATT CCTTTTTGGG GCTGAATAAC ATTCTATTAT
26151 ATGTATATTC CACATTTTGC TTATCCATTC ATCTCTTGAT AGGAAGTTGT
26201 GTTGCTTTCA CATTTTACCT ATTGTGAATA ATACTGGTAC CAATATTAGT
26251 GTACACATAA TCTGAGTCCC TGCTTTCCGT TCTTTTGGGT ATATACACAG
26301 AAGTAAAATT GCTAGACACA ATGGTACTTC TATGTCAGTT TTTTGAAGAA
26351 CTACCCTACT GTTTTCCATA GCAGTTACAC CATTTTACAT TTCTATCACC
26401 AGACCACGAG GGTAACAATT TCTCCACACC TTAGCCACCA CTTGTTATTT
26451 TTTGTTTTTT GGGTAATAGC CATGCAAAAA AATATGAAGT AAAGTGAAAT
26501 ATCATTATGA AAGGTGTGAA GTGATATGTC TTTGTGATTT TGATTTGCAT
26551 CTCTCCTATA ATTAGTGATG TTGAACATCT TTTCATGTGC TTATTGGCCA
26601 TTTGTCTGTC TTCTTTGGGG AAATATCTCT TCAAGCCTAT TCTGCCCATT
26651 TTTGAATTGG GTTTTGTTGT TTTTAGGAAT TCTTTAGATA TTTTGGATAT
26701 TAGTCACTTA TCAGATATGT GATTTGCAAA TGAGGATGGC CTTTTTATTT
26751 TGTTGATTGT GTTCTTTGCA CAATAGTTTT TATTTTTGAT GAAATATAAT
26801 TTTCTATTTT GTGCTTTTGG TGTTATATAT CTAAGAAATC ATGCCAAATT
26851 CAATGTCATG AAGGCTTTCT CCTGTTTTCT TCTAATAGTG TGTAGTTTTA
26901 GCTCTTTTGT ACGTGGTGTT GGGTAAGGGT TCAACTTCAT CCTTTGCAT
26951 GGGAATATCC AGTTTTTTTC CCAGCTGCAT TTGTCAAAAA GACTCTTCTT
27001 TCTTCCGTTG AATGATCTCA GTGGAAGTCA CTGATCTCAT CAAAAATCAC
27051 TGACCATATG TGGGAGCATA ACCACCTGAT GGGTTCTTCT TGCCTGCTGC
27101 CCAAATAGAG CTGGTTTATC AAGATGGGAA TTGCAATAGA GAAAGAGCTT
27151 TACACATGTA CAGCTGGCTA AATGGGAGAC TGGAGCTTTA TTATTAAATA
27201 AATAAGCCTC CCCCAAAATT TGGATGCTAG GGTTTTCTCT TTTTTTTTCT
27251 TTTTTTATTA TTTATACTTTA AGTTCTAGGG TACATGTGCA CAACGTGCAG
27301 GTTTGTTACA TATGTATATA TGTGCCACGT TGGTGTGCTG CACCCATTAA
27351 CTCATCATTT ACATTAGGTA TTCTCCTAAT GCTATCCCTT CCCCCTCCCC
27401 CCAACCCACT ACAGGCCCCA GTGTGTGATG TTCCCCACCA TGTGTCCAAG
27451 TGTTCTCATT GTTCAGTTCC CACCTATGAG TGAGAACATG TGGTGTTTGG
27501 TTTTCTGTGC TTGAGATAGT TTGCTCAGAA TGATGGTTTC CAGCTTCATC
27551 CATGTCCCTA CAAAGGACAT GAACTCACTC TTTTTTATGG CTGCATAGTA
27601 TTCCATGGTG CATATGTGCC ACATTTTCTT AATCCAATCT GTCATTGATG
27651 GACATTTGGG TTGGTTCCAA GTCTTTGCTA TTGTGAATAG TGCCGCAATA
27701 AACATACGTG TGCATGTGTC TTTATAATAG CATGATTTAT AATCCTTTGG
27751 GTATATAACC AGTAATGGGA TGGCTGGGTC AAATGGTATT TCTAGTTCTA
27801 GATCCTTGAG GAATCACCAC ACTGTCTTCC ACATGGTTGA ACGAGTTTAC
27851 ACTCCCACCA ACAGTGTAAA AGTGTTCCTA TTTCTCCCAT CCTCTCCAGC
27901 ACCTGTTGTT TCCTGACTTT TTAATGATCG CCATTCTAAC TGGTGTGAGA
27951 TGGTATCTCA TTGTGGTTTT GATTTGTATT TCTCTGATGG CCGGTGATGA
28001 TGAGCATTTT TTCGTGTGTC TGTTGGCTGC ATGTCTTTTG AGAAGTGTCT
28051 GTTCATATCC TTCGCCCACT TTTTGATGGG GTTGTTGAT TTTTTCTTGT
28101 AAATTTGTTT AAGTTCTTTG TAGATTCTGG ATATTAGCCC TTTGTCAGAT
28151 GGGTAGATTG CAAAAATATT CTCCCATTCT GTGGGTTGCC TATTCACTCT
28201 GATGGTAGTT TCTTTTGCTG TGCAGAAGCT CTTTAGTTTA ATTAGATGCC
28251 ATTTGTCAAT TTTGACTTTT GTTGCCATTG CTTTTGGTGT TTTAGTCATG
28301 AAGTCCTTGC CTATGCCTAT GACCTGAATG GTATAGCCTA CGTTTTCTTC
```

FIGURE 3, page 9 of 40

```
28351 TAGGGTTCTT ATGGTTTTAG GTCTTACATT TAAGTCTTTA ATCCATCTTG
28401 AATTAATTTT TGTATAAGGT GTAAGGAAGG GATCCAGTTT CATCTTTCTA
28451 CATATGGTTA GCCAGTTTTC CCAGCACCAT TTATTAACTA GGGAATCTTT
28501 TCCCCATTTC TTGTTTTTGT CAGGTTTGTC AAAGATCAGA TGGTTGTAGA
28551 TGTGTGGTAT TATTTCTGAG GGCTCTGTTC TGTGCCATTG GTCTATATCT
28601 CTGTTTTAGT ATCAGTACCA TGCTATTTGG TTACTGTAGC CTTATAATAT
28651 AATTTCAAGT CAGGTAGCAA GATGCCTCCA GCTTTGATCT TTTTGCTTAG
28701 GATTGTCTTG GCAATGTGGG CTCTTTTTTG GTTCCATATG AACTTTAAAG
28751 TAGTTTTTTC CAATTATGTG AAGAAAGTCA TTGGTAGCTC AATGGGGATG
28801 GCAGTTAATC TATAAATTAC CTTGGGCAGT ATGGCCATTT TCACAATACT
28851 GATTCTTCCT ATCCATAAGC ATGGAATGTT CTTCCATTTG TTTGTCCTCT
28901 TTTATTTCAT TGAGCAGTGG TTTGTAGTTC TCCTTGAAGA GGTCCTTCAC
28951 ATCCCTTGTA AGTTGGATTC CTGGGTGTTT TATTCTCTTT GAAGCAATTG
29001 TGAATGGGAG TTCACTCATG ATTTGTCTCT CTGTCTGTTT TTGGTGTATA
29051 GGAAAGCTTG TGATTTTGCA CATTGATTTT GTATCCTGAG ACTTTGCTGA
29101 AGTTGCTTAT CAGCTTAAGG AGATTTTGGG CTGAGACGAT GGGGTTTTCT
29151 AAATATACAG TCATGTCATC TGCAAACAGA GACAATTTGA CTTCCTGTTT
29201 TCGTGATTGA ATAGCTTTTA TTTCTTTTTT TAAATATATA TTTTTATTAT
29251 ACTTTAAGTT CTAGGGTACA TGTGCACAAT GTGCAGGTTT TTACATATGT
29301 ATACATGTGC CATGTTGGTG TGCTGCACCC ATTAACTCGT CATTTACATT
29351 AGGTATATCT CCTAATGCTA TCCCTCCCCC CTCTCCCTAC CCTGGTGTGT
29401 GAAGTTCCCC TTCCTGTGTC CAAGTGTTCT CATTGTTCAA TTCCCACCTA
29451 TGAGTGAGAA CATGCGGTGT TTGGTTTTTT GTCCTTGCGA TAGTTTGCTG
29501 AGAATGATGG TTTCCAGCTT CATCCATGTC CTACAAAGG ACATGAACTC
29551 ATCCTTTTTT ATGGCTGCAT AGTATTCCAT GGTGTATATG TGCCATGTTT
29601 TCTTAATCCA GTCTATCATT GTTGGACATT TGGTTTGGTT CCAAGTCTTT
29651 GCTATTGTGA ATAGTGCCTC AATAAACATA CATGTGCATG TGTCTTTATA
29701 ACAGCATGAT TTATAATCCT TTGGGTATAT ACCCAGTAAT GGGATGGCTG
29751 GGTCAAATGG TATTTCTAGT TCTAGAATCA TGAGGAATCA CCACACTGTT
29801 TTATTTCTTT CTCCTGCCTG CCAGCTCCTC CTGGTACCTC TGATAGAATT
29851 CAGCTGTGAA TATGTCTGGT CTGTGGCTTT TCTTGCTTGG TACACTATTA
29901 ATTATTGCCT CAATTTCAGA GCCTGTTATT GGTCTATTCA GGGATTCAAC
29951 TTCTTCCTGG TTTAGTCTTG GGAGGTTGTA TGTGTCCAGG AATTTTTCTA
30001 TTTCTTCTAG ATTTTCTAAT TTATTTGTGT AGAAGTGTTT ATAGTATTCT
30051 CTGATGGTAG TTTGTATTTC CGTGGGATTG GTGGTGATAC CCCCTTTATC
30101 ATTCTTATTA CATCTATTTG ATTCTTCTCT CTTTTCTTCC TTATTAGTCT
30151 GCTAGTGGTC TATCAATTTT GTTGATCTTT TCAAAAAACC AATTCCTAGA
30201 TTCATTGATT TTTTGAAGTT TTTTTTTTG TGTCTCTGTC GCCTTCAGTT
30251 CTGGTCTGAT CTTAGTTATT TCTTGCGTTC TGCTAGCTTT TGAATGTGTT
30301 TGCTCTGGCT TCTCCAGTTC TTTTAATTGT GATGTTAGGG TGTCGATTTT
30351 CAGTCTTTCC TGCTTTCTCT TGTGGGCATT TAGTGCTATA AATTTCCCTC
30401 TACACACTGC TTTGAATGTG TCCCAGAGAT TCTGGTATGT TGTGTCTTTG
30451 TTCTCGTTGG TTTCAAAGAA CATCTTTATT TCTGCCTTCA TTTCATTATG
30501 TACCCAGTAG TCATTCAGGA GCAGGTTGTT CAGTTTCCAT GTAGTTGTGC
30551 AGTTTGAAT GAGTTTCTTA ATTCTGAGTT CCAATTTGAT TGCACTATGG
30601 TCTGAGAGAG TTTGTTGTGA TTTCTGTTCT TTTACATTTG CTGAGGAGTG
30651 CCTTACTTCC AACTAAGTGG TTAATTTTGG AGTAAGTGCA ATGTGGTGCT
30701 GAGAAGAAAG TATATTCTGT TAATTTTGGG TGGAGAGTTC TGTATGTGTC
30751 TATTAAGTCC ACTTGGTGCA GAGCTGAGTT CAAGTCCTGG ATATCCTTGT
30801 TAACCTTCTG TCTCATTGAT CTAATATTGA CAGTGGAGTG TTAAGGTCTC
30851 CCATTATTGT CTCCCATTAT TATTGTTTGG GAGTCTAAGT CTCTTTGTAG
30901 GTTTCTAAGG ACTCGCTTTA TGGATCTGGG TGCTCCTGTA TTGGGTGCAT
30951 ATATATTTAG GATAGTTAGC TCTTGTTGTT GAATTGATCC CTTTACCATT
31001 ATGTTAACGG CCTTCTTTGT CTCTTTTGAT CTTTGTTGGT TTAAAGTCTG
31051 TTTTAGCAGA GACTAGGATA GCAACCCCG GTTTTTTGC TTTCCATTTG
31101 CTTGGTAGAT CTTCCTCCAT CCCTTTATTT TGAGCCTATG TGTGTCTCTG
31151 CATGTGAGAT GGGTCTCCTG AATACAGCAC ACTGATGGG CTTGACTCTT
31201 TATCCAATTT GCCAGTCTGT GTCTTTTAAT TGGGGCTTTT AGCCCATTTA
31251 CATTGAAGGT TAATATTGTT ATGTGTGAAT TTGATCCTGT CATCATGATG
31301 TTAGCTGGTT ATTTTGCTCA TTAGTTGATG CAGTTTCTTC ATAGCATCGA
31351 TGGTCTTTAC AATTTGGCCT ATTTTTGCAG TGGCTGGTAC TGGTTGTTCC
31401 TTTCCATGTT TAGTTCTTCC TTCAGGAGCT CTTGTAAGGC AGGCCTGGTG
31451 GTGACAAAAT CTCTCAGCAT TTGCTTGTCT GTAAACGATT TTATTTCTCC
```

```
31501 TTCACTTATG AAGCTTAGTT TGGCTGGATA TGAAATTCTG GCTTAAAAAT
31551 TCTTTTCTTT AAGCATGTTG AATATCGGCC CCCTCTCTCT TCTGGCTTGT
31601 AGTGTTTCTG CTGAGAGATC TGCTGTTAGT CTGATGGGCT TCCCTTTGTG
31651 GGTAACCCGA CCTTTCTCTC TGGCTGCCCT TACCATTTTT TCCTTCATTT
31701 CAACCTTGGT GAATCTGACA ATTATGTGTC TTGGGATTCC CCTTCTGGAG
31751 GAGTATCTTT GTGGCGTTCT GTGTATTTCC TGAATTTGAA TGTTGGCCTG
31801 CCTTGCTAGG TTGGGGAAGT TCTCCTGCAT AATATCCTGA AGAGTGTTTT
31851 CCAACTTGGT TCCATTCTCC CCGTCACTTT CAGGTACACC AATGAAACGT
31901 AGATTTGGTC TTTTCACATA GTCCCATATT TCTTGGAGAC TTTGTTCATT
31951 TCTTTTTACT CTTTTGTCTC TAAACTTCTC TTCTCACTTC ATTTCATTCA
32001 TTTGATCTTC AATCTCTGAT ACCCTTTCTT CCAGTTGATC GAGTCAGCTA
32051 CTGAAGCTTG TGCATTCGTC ACGTATTTCT CATGCCATGG TTTTCAGCTC
32101 CATCAGGTCA TTTAAGATCT TCTCTATGCT GGTTATTGGA ATTAGCCATT
32151 TGTCTAATCG TTTTTCCAGG TTTTTAGCTT CTTTGAGATG GGTTCGAACA
32201 CCCTCCTTTA GCTCGGAGAA GTTTGGTATT ACCAATCTTC TGAAGCCTAC
32251 TTCTGTCAAC TCATTAAAGT CATTCTCCAT CCAGCTTTCT TCCTTTGCTG
32301 GCGAGGAGCT GCGATCCTTT GGAGAAGAGT CGCTCTGATT TTTAAAATTT
32351 TTGGCTTTTC TACTCTGTTT TCTCCGCATC TTTGTGGTTT TATCAAACTT
32401 TGGTCTTTGA TGATGGTGAC CTACAGATGG GGTTTTGGTG TGGATGTCCT
32451 TTTTGTTGAT GTTGATGCTA GTTTTGTTGA TGCTTTGTTA GTTTTCCTTC
32501 TAACATTCAG GACCCTCAGC TGCAGGTCTT TTGGAGTTTG CTGGAGGTCT
32551 ACTCCAGACG CTGTTTGCCT GGGTGTCACC AGCAGAGGCT GCAGAACAAC
32601 AAATATTGCA GAACGGCAAA TGTTGCTGCC TGATCCTTCC TCTGGAACCT
32651 TCATCTCAGA GGGGCACCTG GCTGTATGAC GTGTCAGTCG GCCCCTACTG
32701 GGAGGTGTCT CCCACTGGGC TACTCAGGGG TCAGGACCC ACTTGAGGAG
32751 GCAGTCTGTC CATTCCCAGA TCTCAGACTC TGTGCTGGGA GGACCACTGC
32801 TCTCTTCAAA GCTGTCAGAC AGGGACGTTT AAGTCTGCAG GTTTCTGCTG
32851 CCTTTTGTTA AGTTATGCCC TGCCCCAGA AGTGGAGTCT ACAGAGGCAG
32901 GCAGGCCTGG TTGAGCTCTG GTGGGCTCCA CCCAGTTTGA GCTTTCTGGC
32951 CGCTTCGTTT ACCTAGTCAA GCCTCAGCAA TGGCAGACGC CCCTCCCCCA
33001 GTCTTGGGGC CGTCTTGCAG TTTGATCTCG GACTGCTGTG CTAGCAGTAA
33051 GCAAGGCTCC ATAGGTGTGG GAACCGCCGA GCCAGGCACG GGTTATAATC
33101 TCCTGGTGTG CCGTTTGCTA AGACCATTGG AAAAGCGCAG TATTAGGGCG
33151 GGAGTGTCCC GAGTTTCCAG GTACCATCTG TCACGGCTTC CCTTGGCTAG
33201 GAAAGGGAAT TCCCTGACCC CTTGTGCTTC CAGGGTGAGG TGATGCCCCG
33251 CCCTACTTTG GCTCACACTC CATGGCCTGC ACCCACTGTC CAACAAGTCC
33301 CAGTAAGATG AACCCAGTAC CTTAGTTGGA AATGCAGAAA TCTCCTGTCT
33351 TCTGCGTCAC TCACGCAGAT GCATGAGCTG TAGACTAGAG CTGTTCCTCT
33401 TCGGCCATCT TGTAACGATC CTGCTAGGGT TTTTTCAAGG ATAGTTTGGC
33451 AGGGAGAGAG ATGACAAAGG AATGAGTGCT GCTGATTGGT TGGCGGTGCA
33501 ATCACAGAGG TGTGGGAAAT GATCCTTATG CTGAGTCCAC TTCTGGGCGA
33551 AGGCCGCAGG ACTGGTTGGC AGGTCAGGTG GTGCCATCTG GTTGTCAGAA
33601 TTGCAAAAGC CTGAAAAGAC ATCTCAAAAG GCCAACCTCA GGATCTATAA
33651 TAGTGATATT ACCTGCAGGA GTAATTGAGG AAGTTGCGAA TCTTGTGATT
33701 TGCAGAATAA TGACTGGTAA TTGTTCACAT CTATGTCTTA GTAGAATTGA
33751 GGCTCCTCTC ATTCTCCCAT TCTGGTGGTC TTTCATTAGT TTTACGAAAG
33801 TAGTTTAGTT TGGGGAAGG GCTATTATCA TTTAAACTAC AAACTAAATT
33851 TCTTCCAAAG TTAGCTTGAC CCAATCCCAG GAATGACTAA GGGCATTTGG
33901 AGGGTAAAGG CAAGATGCAG GCTGGTTGGA TCAGATCTCC TTCACTGTCA
33951 TAATTTTCTC ACTGTTTTAA GTTTGCAAG GGTGGTTGCA TAGGGTTTAT
34001 TTCTGGCTC TCTATTCTAG TCCATTGGTC TATATTTCTG TCTTTATGCC
34051 AGTACCACAT TGCTTGATT AATGTAGCTT TGTTATAAGT TTTGAAATTG
34101 GAAAGTGTGA CTTACTTATT CTTTCAAGA TTCTTTTGGC TATTCAGGGT
34151 GCCTTGAGAT TCCATGTGAA TTTAAGATG TATTATTATT CTGTTACTGC
34201 AAAAACATC ATTGGGATTT TGATAGAGAT TGCATTGACT CTGTAGATCT
34251 TCTTTAGTAG TTTTGACATT TAGCAATATT AACTCTTCCA ATCCATAAAT
34301 ATGGAATTTT GTTCCATTTA TCTTTGTGGT CTTTAATTTC TTTCACCAGT
34351 GTTTCATAGT TTTTAGTGTA TATGGTTTTT GCCTCCTTGG TTAAGTTTAT
34401 TTATGATTTT TTATGCTGGT AGGTTTTATT TTTAAATTT TGGGGGAAGT
34451 GTTTTATTAA TACAAATGTA TGGGTTACAA GTGCAATTTT GTTACATGTA
34501 TAGATTGTAT AGTGGTGATG TCAGGACTTT TATGGTATCC ATCACTCAAA
34551 TAACTTCCAT TGTACCCATT AAGTACACCC CACTCCCACC TGTTAAGTTT
34601 TAATAAGTTG GTTTAGTCTC TGTTCTGTCT CTGAAAAATG TCAGATACTA
```

FIGURE 3, page 11 of 40

```
34651 CTAACAGAAC TAAAAAATCC AGGACTGAGA GAAACTTTAA GTACATACAA
34701 CAATATAAAC AGATCTTAAA AATATGATAC AGCATAGAAA AATGGAAACC
34751 AAACATATTC CACAATGTCA TTCAGTACTT TTAAATTACT ACACAGAAAG
34801 TGTTATACAT TTCACAAAAA TGTATAAGAA TAGCACACAC AAATTATCAA
34851 CAAAATAATA CAGGGTTTTC TGAATTGTCT ACCTGTGAGA TGTTTCTAAG
34901 CAGGGTTTTA TTATTGATTG ATTGATTGAG ACAGGGTCTG ACTCTGTCGC
34951 CCAGATTGGA GTACAGTGGT GCAATCCTGG CTTGACCTCC TGGCTCAAGT
35001 AATCCTTCCA CCTCAGCATC CCAAGCAGCT GGGACTATAG GTTCACACAA
35051 CCATGCCTGG CTACTTCTTT AAAAAAATTT TTGTAGAGAG TCTCACTACA
35101 CTGCTCAGGT GGTCTCAAGC TCTTGGGCTC AAGCAATTCT GACACCTCAG
35151 CCTCCCAAAG TGCAGGGATT ACGGGTGTGA GCCGTTGCAC CTGGACTAAG
35201 CAGGGTTTTA AGTGACTTGG TTCTTGTTTA TGTTGACACT AAACATGCAT
35251 CAAAGATTAA CCTTCTAAAT TCTGGAACAC AGAAAGAAGG GCAGCCCTTA
35301 TTTCAGGGCT GGGCTGATGA TAGAATTTAC TTGATGCAGT TTTTCATAGA
35351 AAGTATATGTG TCTTTTTGTT TTAAACATAT AAGAAAAGAG TTTCCACTGT
35401 TTACCTGGTA CTAGGTCCCA ATGTCTAAAC CAAGTTTGGA GAATCACATC
35451 CTCTGAGCAG CCTATGTTGA TGATGATGCT GATGACAATG ATGACAGAAG
35501 ACACTTATAT GGTACTTATT TATGTAGCAG AACCATAGTC CTTTATATGT
35551 TTTAACTCAT TTAATATTCA AAACAACCCT ATGACATGGT ACATTGATGT
35601 TGTTATACCC ATTTATATGT GTGGAAATGG TCATACAGTG TCTTATTAAT
35651 TTGCCTGAGG CCACACAGCT AATTAGTGGT GGATCTGAGG TTGGATTTCT
35701 AGGAGCCAGA TTCACAAATC CAACACTGCA CTTTGCTTTT TCTCTATTGT
35751 CTATCGCTCA TTGATTTTTT TATTCTCAAT TTTATTTCCT TCCTTTATTT
35801 TTGGTTTAAT TTTCTCTTCT TTTTTTAGTT TCTTGAGATG AAAACTTAGA
35851 TCTTTGATTT TTCTACCTCT CTTCTTTTCA ATATTTATTA TGCTTAAAGC
35901 TTTACACTTC ACCCTAGGCA TTGTTTTTGT TGCATCCCAC ATATTTTGAT
35951 GCTGTATTTT TATATTCAGA ATATTTCTA ATTTATATTT ATTTGTTCAT
36001 TTTAAAAATA ATTTTACTAA ATAATATAAA ATGCTAATTT TGAAATACTT
36051 AGGATTTTCT TACATTTGGT TTTGATTTCT AATTTAATTC TATGTGGTTT
36101 TAAAATATAG TTTCACTCAA TTGAAATTTA TTGATTTACT TTATATTCCT
36151 GCATATGGTT GATACTGGTG CATGTTGCAT GTACACTTAA ATAACATTTA
36201 TTCTGCGATT GTTGGATACA GTGTTCTATA TTTGTCAATT AGATTGAGTG
36251 CTGCTCAGAT GTTCTATATT CCTACAGATA TTTCATGTGC TTATTCTATA
36301 AAATACAAAT TGTTAATGTT TCTGATTAGG ACTAGAAGAC TTTTCTTTTA
36351 CCTTTTAAAT ATATTTTTA TTTTATGTAT TTTGAAACTA TGTTATTTGG
36401 TGCCTATACA CTTAGATTTT TTCTTGAGG AATTGATCCT TTATCATTAT
36451 GAAATATCCT TCAGGCACCC CGCTCCCACA GATGTATGCA TCTTGCTGTA
36501 CCCCTGCTTC TGCTGGCACA AATGCACAGG CATGGATCCT GCTGCCACCA
36551 CCTTGATGAA GTGTGTGGCC AGCACCCCA TCAGAGTACT GTTACCAGCA
36601 TACTGGGAAT ACCTTGCCCC CAGAGTGCAG CAGCTTTCTA ACCTCTATGG
36651 GGCAGAGAAC AAAGTTGGGG GGCCCAGTAC CAGCCCATCA GCGTTACATC
36701 ACATAGCCCA TGAGTGATGA GCTGAGCCTT GGTGCCCTGA AAGCATCCAG
36751 AATGAAGCCA GTCAACTGAA CCGACATTAT ACCACAATCA AACCCTCAAG
36801 AATATCAAAG AATATAAAAG TAAAAGCCC TATCCAAAGG ATAGCAACTT
36851 CAAAGATTAA AGGAATGTCA GCCCACACAG ATGAGAAAGA ATCAATGCAA
36901 GAACTCTGGC AATTCAAAAA ACTAGAGTGC CTTCTTACCT CCAGACAACC
36951 CCACTGGTTC CCTAGCAATG GTTCTTAACA AAACTGAAAT GACAGAGATA
37001 GAATTGAGAA TCTGGATAGA AAAAAGATCA TTGAGATTCA GGAGAAAGTT
37051 GAAACCCAAT CCAAGGAATC TAAGGAATCC AATAAAACAA TACAAGAGAT
37101 GAAACGAAAT AGCCATTTTA AGAAAGAACC AAACTGAACT GATAGAGCTG
37151 AAAAACTCAC TACAAGAATT TCATAATGCA ATCACAAGCA TTGTTAACAT
37201 CAGAATAGAC TACTAACATC AGAATAGACC AAGCTGAGGA AAGAATCTCA
37251 GAGCTTGAAG ACTGGTTCCT CAAATCAACT CAGACAAAAA TAATGAACAA
37301 ATAATTAAAA AGAGTGAACA AAACCACTGA GAAATATGAG ATTAGGTAGA
37351 GACCAAATCT GTGACTCATT GACATCCCTG AAAGAGAGAG AGAAAAAGCA
37401 ATTTTTCCAG CCTTGCTAGA GAGGCCAAAA TTCAAATTCA GGAAATGCAG
37451 AAAACCCCTG TGAGATACTA TACAAGACAA CCATCCCCAA GACATGTAGG
37501 CATCAGATTC TCCAACGTCA ACATCAAAGA AAAATACTA AGGCAGCTAG
37551 AGAAAAGGGG CAGGTCACCT ACAAAGGGAT TCCGATGAGG CTAACAGAAG
37601 ACCTTTCAGC AAAAGCACTA CAAGCCAGGA GAGATTTGGA GACCTATGTT
37651 CAGCAAAAAA AATTCCAACC AAGTATTTCC TGTGCAGCAA GACTAAGCTT
37701 AATAAGCAAA GGAGAAACAA GATCCTTTTC AGACAAGCAA ATGCTAAGAG
37751 AATTCATTAC CACCAGACAT GCCTTACAAG AGGTCCTTAA GTGAGTGCCA
```

FIGURE 3, page 12 of 40

```
37801 AATATGGAAA CAAAAGACTG TTACTGGCCA CCACAAAAAT ATACTTAAGG
37851 ACTAGACCTC TGAACACTAT AAAGCAATTA CGCTATCAAG TCTGCATAAT
37901 ATCCAGCTGA CATCATGATG ACAGGATCAA ATCAACACAT ATAAGTATTA
37951 TCCTTAAAAG TAAACATGCA AAATGCCTGA CTTAAAAAGT ACAGAATGGC
38001 AAATTTGATA AAGAAATAAG ACACATGGAG AGTTGCTCCA AATGGCAGGA
38051 TAGGAACAGT TCTGGTCTAC AGCTCCCAGC AAGATCAATG CAGAAGACAG
38101 GTAATTTCTG CATTTCCAAC TGAGGTACCT GGTTCATCTC ATTGGGATTG
38151 GTTGGACAGT GGGTGCAGCC CATGGAGGGC AAGCCGAAGC AGGGCGGTGC
38201 ATCCCTCACC GAGGAAGTGC AAGGGGTCAG GGGATTTCCC TTTCCTATCC
38251 AAGGGAAGCC ATGAGTGACT GTACCTAGAG GAAAAGTACA CTCCTGCTCA
38301 AATACTGCAC TTTTCCCACG GTATTCGCAA CAGGCAGACC GGAAGATTCC
38351 CTCCCATGCC TGCTCGGTGG GTCCCACGCT CATGGTGCCT TGCTCACTGC
38401 TAGCACAGCA GTCTGAGATC GACCTGGGAT GCTGGAGCTT GGTGGGTGGG
38451 GAGCGGCGTC CACCATTGCT GAGGCTTGAG TAAGCGGTTC TATGCTCACA
38501 GCGTAAACAA AGCAGCAGGG AAGCTTGAAC TGCACCGAGC CCACTGCAGC
38551 TCAGCAAGGC CTACTGCCTC TGTAGATTCT ACCTCGGGGG CAGGGCATAT
38601 CTGAAAAAAA TGCCGCAGAC AGCTTCTGCA GACTTAAACA TCCCTGCCTG
38651 ACAGCTCTGA AGAAAGCAGT GGTTCTCCCA GCACGGGGGC GTTCAAGCTC
38701 TGATAACGGA CAGACTACCT CCTCAAGTGG GTCCCTGACC CCTGTGTAGC
38751 CTGATTGGGG GATACCTCCC AGTAGGGGCC AACAGACATC TCATACAGGC
38801 GGGTGCCCCT CTAGGACGAA GCTTCCAGAG GAAGGATCAG GCAGCAATAT
38851 CTGCTGTTCT GCAGCCTCCA TTGGTGATAC CGAGGCAAAC GGTCTGGAGT
38901 GGAACTCCAG CAAACTCCAA CAGACCTGCA GCTGAGGGGA CTGTCTGTTA
38951 GAAGGAAAAC TAACAAAGAG GAATAGCATC AACATCAGCA AAAGGACAT
39001 CCACACGAAA ACCCCATCCG TAGGTCACCA ACATCAAAGA CCAAAGGTAG
39051 ATAAAACCAC AAAGATGGGG AGAAACCAGA GAAGAAAGGC TGAAAATTCC
39101 AAAACCAGAA CGCCTTTCTT CTCCAAGGAT CACAACTCCT CGCCAGCAAG
39151 GGAACAAAAC TGGACAGAGA ATGAATTTGA TGAGTTGACA GAAGTAGGCT
39201 TCAGAAGGTC GGTAATAACA AACTTCTCCA AGCTAAAGGA GCATGTTCTA
39251 ACCAATCGCG AGGAAGCTAA AAACCTTGAA AAAATGCTAG ATGAATGGCT
39301 AACTAGAATA CAATAACCAG TGTAGAGAAG AATATAAATG ACATGATAGA
39351 GCTTAAAACC ATAGTACAAG AACTTTATGA AACATACACA AGCTTCAATA
39401 GCTGATTCAA TCAAGCGAAA GAAAGGATAT CAGTGATTGA AGATCAAATT
39451 AATGAAATAA AGCAAGAAGA CAAGATTAGA GAAAAAAGAG TGAAAAGAAA
39501 CGAATAAAGC CTCCAAGAAA TACGGGACTA TGTGAAAAGA CCAAATCTAC
39551 GTTTGATTGG TGTACCTGAA AGTGACAGGG AGAATGGAAC CAGGTTATAA
39601 AACACTTTCA GGATATTATG CAGGAGAACT TCCCCAACCT AGCAAGGCAG
39651 GCCAACATTC AAATTCAGGA AAGACAGAGA ACACCACAAA GATACTCCTC
39701 GAGAAGAGCA ACCCCAAGAC ACATAATTGT CAGATTCACC AAGGTTGAAA
39751 TGAAGGAAAA AATGTTAAGG GCAGCCAGAG AGAAAGGTCG GGTTACCCAC
39801 AAAGGGAAGC CCATCAGACT AACAGCAGAT CTCTCAGCAG AAACACTACA
39851 AGCCAGAAGA GAGAGGGGGC CGATATTCAA CATGCTTAAA GAAAAGAATT
39901 TTTAACCCAG AATTTCATAT CCAGCCAAAC TAAGCTTCAT AAGTGAAGGA
39951 GAAATAAAAT CCTTTACAGA CAAGCAAATG CTGAGAGATT TTGTCACCAC
40001 CAGGCCTGCC TTACAAAAGC TCCTGAAGGA AGAACTAAAC ATGGAAAGGA
40051 ACAACCGCTA CCAGCCACTA CAAAAACATG ACAAATTGTA AAGACCATCG
40101 ATGCTATGAA GAAACTGCAT CAATTGATGG GCAAAATAAC CAGCTAACAT
40151 CATAATGACA GGATCAAATT CACACATAAC AATATTAACC TTCAATGTAA
40201 GTGGGCTAAA TGCCCCAATT AAAAGACACA GACTGGCAAA TTGGATAAAG
40251 AGTCAAGACC CTTGACTGTA TTCAGGAGAC CTATCTCACA TGCAAAGACA
40301 CACATAGGCT CAAATAAAGT GATGGAAGAA GATCTACCAA GCAAATGGAA
40351 AGCAAAAAAA AGGGTTTGCC ATCCTGGTCT CTGATGAAAC AGACTTTAAA
40401 GCAACAAAGA TCAAAAGAGA CAAAGAAGGC CGTTAACATA TGGTAAAGG
40451 GATCAATTCA ACAAGAAGAG CTAACTATCC TAAATATATA TGCACCCAAT
40501 ACAGGAGCAC CCAGATTCAT AAAGCAAGTT CTTAGAGACT AAGTCTACAA
40551 AGAGACTTAG ACTCCCACAC AATAATAATG GGAGACTTTA ACACCCCACT
40601 GTCAATATTA GATGGATCAA CGAGACAGAA AGTTAACAAG GATATCCAGG
40651 ACTTGAACTC AGCTCTAGAG CAAGCAGAAC TAATAGACAT CTACAGAACT
40701 CTTCTTCCCA AATCAACAGA ATATACATTC TCCTCAGCCC ACATCACAC
40751 TTATTCTAAA ATTGACCACA TAATTGGAAG CAAAACACTG CTCAGCAAAT
40801 ATAAAAGAAC AGAAATTACA TCAAACTGTC TCTCAGACCG CAATGCAATC
40851 AAATTAGAAC TCAGGATTAA GAAACTCACT CAAAACTGCA CAACTGCATG
40901 GAAACTGAAC AACCTGCTCC TGAATGACTA CTGGGTAAAT AACGAAATGA
```

```
40951 AGGCATAAAT AACAATGTTC TGTGAAGCCA ATAAGAACAA AGATACAACG
41001 TTCAAGAATC TCTGAGAAAC ATTTAAAGCA GTCTGTAGAG AGAAATTTAC
41051 AGCACTAAGT GTCCACAGGA GAAAACAGGA AAGATCTAAA ATCGACACCC
41101 TAACATTGCA ATTATAAAAG AACTACAGAA GCAAGAGCAA ATGAATTCAA
41151 AAGCTAGCAG AAGACAAGAA ATAAATCAGA GCAGAACTAA AGGAGAGAGA
41201 GACACAAAAA ACCCTTAAAA AAAATCAATG AACCCAGGAG CTGGTTTTCT
41251 GAAAAGAGCA ACAAAATAAT TACATGACAA GCAAGACTAA TAAGGAAGAA
41301 AAGAGAGAAG AATCAAATAG ACGCAATAAA AAATGATAAA GGGGATATCA
41351 CCACCGATCC CACGGAAATA CAAACTATCA TCAGACAATA CTATAAACAC
41401 CTCTACGCAA ATAAAATAGA AAATCTAGAA GAAATGGAAA AATTCCTTGA
41451 CACATACACC CTCCCAAGAC TAAACCAGGA ACAAGTTGAA TCTCTAAATA
41501 GTTCAGTGAC AGCTTCTGAA ATTGAGGCAA TAATTAATAG CCAACCAACC
41551 AAAAAAGTC CAGGACCAGA CAGACTCACA GCCAAATTCT ACCAGGGGCA
41601 CAAAGAGGAG CTAGTACCAT TCCTTCTGAA ACTATTCCAA TCAATAGAAA
41651 AAGAGGGAAT CTTCCCTAAC TCATTTTATA AGGCCAACAT CATCCTGATA
41701 ACAAAGCCTC ACAGAGACAC AACAAAAAAA GATAATTTTA GGCCAACATC
41751 CCTGATGAAC ATCGATATGA AAATTTTCAA AAAAAAATAC TGGCAAACCG
41801 AATCCAGCAG CCCATCAAAA AGCTTATCCA CTACGATCAA GTCGACTTCA
41851 TCCCTGGGAT GGAAGGCTGG TTCAACATAG GCAAATCAAT AAATGTAATC
41901 CATCACATAA ACAGAACCAA CGACAAAAAC CACATGATTA TCTCAATACA
41951 TGCAGCAAAG GCCTTCAACA AAATTCAACA GCCTTTCATG CTAAAAACTC
42001 TCAATAAACT AGGTATTGAT AGAATGTATC TCAAAACAGT AAGAGTTATT
42051 TATGACACAC CCACAGCCAA TATACTGAAT GGGCAAAAAC TGGAAGCATT
42101 CCCTTTGAAA ACTGGCACAA GACAAGGATG CTCTCTCTCA CCACTCCTAT
42151 TCAACATCGT GTTGGAAGTT CTGGCCAGGG CAATAAGGCA AGAGAAATAA
42201 ATAAATGGTA TTCAATTAGG AAAAGAGGAA GTCAAATAGT CTGTTTGTAG
42251 ATGACATGAT TATATATGTA GAAAACCTCA TCGTCTCAGC TCCAAATCTC
42301 CTTAAGCTGA TAAACAACTT CAGCAAAGTA TCAGGATACA AAATCAATGT
42351 ACAAAAATCA CAAGCATTCC TATCCACCAA GAACAGACAA ACAGAGAGCC
42401 AAATCATGAG TGAACTCCCA TTCCCAACTG CCTCAAAGAG AATAAAATAC
42451 CTAGGAATCC AACTTACAAG GGATGTGAAG GACCTCTTCA AGGAGAACTA
42501 CAAACCACTG CTCAATGAAA TAAAAGAGGA TACAAACAAA TGGAAGAACA
42551 TTCCATGCTC ATGGATAGGG AGAATCACTA TCATGAAAAT GGCCATACTG
42601 CCCAAGGTAA TTTAAAGATT CAATGCTATC CCTATCAAGC TATCACTGAC
42651 TTCACAGAAT TGGAAAAAAA CTACTTTAAA GCTCATATGG AACCAAAAAA
42701 GAGCCCACAT AGCCAAGACA ATCCTGGGCA AAAAGAACAA AGCTGGAGGC
42751 ATCACACTAC CTGACTTCAA ACTACACTAC AAGGCTACAG TAACCAAAAC
42801 AGCATGTTAC TGGTACCAAA ACAGACATGT AGACCAACGG AATAGAACAG
42851 AGGCCTCAGA AATAACACCA CACATCTACA ACCATCTGAT ATTTGACAAA
42901 CCTGACAAAA ACAAATCGGG AAAGGATTCC CTATTTAATA AATGGTGCTG
42951 GGAAAACAGG CTAGCCATAT GTAGAAAGCT GAAACTGGAT CCCTTCCTTA
43001 CACCTTATAC AAAAATTAAC TCAAGATGGA TAAAAGACTT GAATGTAATA
43051 CCTAAAACCA TAAAAACCCT ACAAAAAAAC CTAGGCAATA CCCTTCAGTG
43101 CATAGGCATG GGCAAAGACT TTATGACTAA AACACCAAAA GCAGTGGCAA
43151 CAAAAGCCAA AATTGACAAA TGGCATCTAA TTAAACTAAA CAGCTTCTGC
43201 ACAGCAAAAT AAACTACCAT CAGAGTGAAT AGGCAACCTA CAGAATGGGA
43251 GAAAAATTTT TCAATCTATC CATCTGACAA AGGGCTAATA TTCAGAATGT
43301 ACAAAGAACC TAAACAAATT TACAAGAAAA AAAAAACCAC TGCATCAAAA
43351 AGTGGGCAAA GGATATGAAC AGACACTTCT CAAAGAAGA CAGTTATGCA
43401 GCCAACAGAC ATATGAAAAA ATGTCCATCA TCACTGGTCA TCAGAGAAAT
43451 GCAAGTCAAA ACCACAATGA GATACCATCT CATGCCACTT AGAATGGCGA
43501 TCATTAAAAA GCCAGGAAAC CACAGATGCT GGAGAGGATG TGGAGAAATA
43551 GGAACACTTT TACACTGTTG GTGGGAGTGT AAATTAGTGC AACCATTGTG
43601 GAAGACAGTG TGGCGATTCC TCAAGGATCT ACAACTATAA ATACCATTTG
43651 ACCCAGCAAT CCCATTTGTG GGTATATACC CAAAGGATTA TAAAGCATTC
43701 TACTATAAGG ACACATGCAC ACATATGTTT ATTGCAGCAC TATTTACAAT
43751 AGCAAAGACT TGGAACCAAC CCAGATGTCC ATCAATAATA GACTGGATAT
43801 ATAGTATTCT ATGTCTGGTT AAAAAAAAG TTATTCAATT TTATGGATTT
43851 GGATTAGGAT CATTCCCATT TCTGTAAATA TTTACACCTA TAAGGATATC
43901 AAGAAGGAAT GTCAGGCAGT TTACTAGTAA CTTTTCAAAG TCTTAGAAAA
43951 GTTGCATTTT TTGCTGGCAC CAAGAGGGGA AACATCATA AAAATAGTTT
44001 CAAAATCTAC AATCAATGCT TTCTCCAAAA TAAATGTCTT TGTTAAAAAA
44051 AATAATAATA ATAGACTGGA TAAAGAAAAT GTGGCACATA TATACCATGG
```

```
44101 AATACTATGC AGCCATAAAA AAGGATGAGT TCATATCCTT TGTAGGTACA
44151 TGGATGAAGC TGGAAATCAT CGTTCTCAGC AAACTATCAC AAGGACAGAA
44201 AACCAAACAC CGCATGTTCT CACTCATAAG TGGGAGCTGA ACTATGGGAA
44251 CACGTGGACA CAGAGAGGGG AACATCACAC ACCGGGGCCT GTCAGAGGGT
44301 GGGGGACTGG GGGAGAGGTA GTGTTAGGAG AAATACCTAA TGTAAATGAC
44351 GAGTTGATGG GTGCAGCATA CCAGCATGGC ACATGTATAA CCACGTAACA
44401 AACCTGCATG TTGTGCACAT GTACCCTTGA ATTTAAAGTA TAATTTAAAA
44451 AAAGAAGAAG AAATAAGTCA CAATTGTATG CTGTCTTCAA CACACCCATC
44501 TCATGCAGAG CTACCCATAG GCTCAAAATA AAGGTTTAAA GAAAAATCTA
44551 CCAAGTAAAT GGGAAAAGAA AACAGGAGTT ACTATTCTAA TTTTAGACAA
44601 AGCAGACTTT AAAGCAACAA TGATCAAAAA AGACAAGCGC ATGACATAAT
44651 CATAAAGGGT TCAATTCAAC AAGAAGACTT AAATATCCTA AATATATGTA
44701 CCCAACACAG GAGCTTGCAG ATTCATAGAA CAAATTCTTA GAGACCTACA
44751 AAGAGACATG GATAACCACA CGGTAATATT GGGAGACTTC AGCACCCCAC
44801 TAACAGTATT CAATCATCAA GGCAGAACAC TAACAAAGAT ACTTGGGACC
44851 TGAACTCAGT ATTTGACTAA ATGGACCCAA CAGACATCTA CAGAACTCTG
44901 CACTCCAAAA CAACAGAATA TACATTCTTC TCATCGCCAC ATGGCACATA
44951 CTCTAAAGTC GACCACACAA TCGGCCATAA GTCAATTCTT AGCAAATTAA
45001 AAACACAAGA ATCACACTAA CCACACTCTT GGACCATGGC GCAACAAAAG
45051 TAGAAATCAG CCCCAAGAAG ATCATTCAAA ACATACAGCT ACATGCAAAT
45101 CAAACAACCT GCTCCTGAAT GACTTTTGGG TAAACAATGA AATTAAGGCA
45151 GAAATCAAGA CATTTTTTGA AACTATTGAA AATAAAGATA AAATATACGA
45201 AAATATCTGA GACACAGCTA AAATAAAGAT AAAATATACC AAAATCTCTG
45251 CGACACAGCT AAAGCAGTAT TAAGAGGGAA GTTTATAGCA CTAAACACCC
45301 CTATCAAAAA GTTAGAAAGA TCTCAAATTA ACAGCCTAAC ATTGCACCTA
45351 GAGGAACTAG AAAAACAAGA GCAAACCAAC TGCAAAGCTA GCAGAAGAAA
45401 AGAACCAAAA CAAGAACTGA ACTGAATGAA ATTGAGACAG GAAAATGATA
45451 TAAAAGACCA GTGAAACCAG AAGCTGGTTC TTTGAAACAA TAAATAAGAT
45501 GGATAGACCA CTGATTATAC TAATCAAAAA ACAGAGCAGA TCCAAATAAA
45551 CTTAATCAGA AATGACAAAG AGGACATTAC CATCAACCCA ACAGAAATAT
45601 AAAAAACCTT AAAAGACTAT TACAAACACC TCTATGCAGA CAAACTAAAA
45651 AACCTACAAG AAACGATAAA TTCTTGGAAA CATACAGTCT CCCAAGACTG
45701 AACAAGGAAG AAATTGAAAC CCTGAACAGA CCAATAACAA GTTCCAAAAT
45751 TGAATCAGTA GTAAAAAGCC TACCAACCAA AAAAGCCCTG GACCAGATGG
45801 ATCCACAACC AAATTCTGCC AGATGTATAA AGAAGAGCTG GTACCATTCC
45851 TACTGAAACT ATTCCAAAAA ATTAAGGAGG AGGGACCCCT CCCTAACTCA
45901 TTCTATAAGG CCAGCATCAT CCTGATATAA GGCCAGCATC ATCCTGATAT
45951 AAGGCCAGCT TCATCCTGAT AACGAAAACT GGGAGAGACA ACATAAAAAG
46001 AAAACCTCAA GTCAATATCC TGGACAAACA TAGATGCAAA AATTCTCAAT
46051 AAAATACTAG CAATCTGAAT TCAGCAGCAC ATCAAAAAAC TAATCCACCA
46101 TGATCCAAGT AGGCTTTATA CTTGGCATGT GAGATTGGTT CACCATATAC
46151 AAATCAATAA ATATGATTCA TCACATGAAC AGAACTAAAA AGAAAAACCA
46201 AATGATAATC TCAATAGATG CAGATACATC TATTGAATGC AAAATTCAGT
46251 ACCCCTTCAT GTTAGAAACC CTCAACAAAC TAGGCATCAA AGGAACATAC
46301 CTCAAAATAA TAAGAGCTAT CTGTGAAAAA ATCACAGCCA GCATCATACT
46351 GAAAGAGCAA AAGCTGGAAG CATTCCCCTT GTGGAATAAG ACAAGGATGC
46401 CCACTATCAC CACTCATATT CAATATACTA CTGGAAGTCC TAGGCAGAGC
46451 AGTCAAGCAA GACAAATAAA GAAAAGGCAT CCAAATAGGA AGAGAGGAAG
46501 TCAGACAATA TGATTTTATA CCTAGAAAAT TCCATAGTGT CTGCCCAAAA
46551 GCTCCTAGAT CTGACAAACA ACTTCAGCAA AGTTGCAGTG TACAAAATCA
46601 CTGTGCAAAA ATAAGTTGCA TTCCTTTACA CTAACAACAT CCAAGCTGAG
46651 AGCCAATCAA GGACACAATC CCATTCATAA TAGCCACACA AAAAATAAAA
46701 TACCTACGCA TACAGCTAAC CAGAGAGGCA AAATATTTCT AGATTGAGAA
46751 TTACAAAACA GTGCTGAAAG AAATCAGACA ACACAAACAA ACGAGAAAAC
46801 ATTCATTCCA TGCTCGTGGA TAGGAAGAAT CAATGTTGTT AAAGTGGCCA
46851 TACTGCCCAA AGCAATTTAC AGATTCAATG CTATTCCTTT CAAACTACCA
46901 GTGATATTTT TCACAGAATT AGAAAAAACT ATTCTAAAAT TCAGGTGGAA
46951 CCAAAAAAGA GCCTGAATAG CCAAATCAAT CCTGAGCAAA AAGAACAAAA
47001 CTGGAGGCAT CACATTACCA AATTCAAAC TGTACTGCAA GCTTACAGTA
47051 ACAAAAACAG CATGGTACTT GTACAAAAAC AGACACATAA ACCAATGGAA
47101 TAGAGAGCCC AGAAATAAAG CTGTCTACTC AGAACCATCT GATCTTTGAC
47151 AAAATTGACA AAAACAAACA ATGGGAAAG GACCTGCTAG TCAATAAGTG
47201 ATTCGGGATG GATCGCTACC CATATGCAGA AGATTAAAAC TAGACCACTT
```

FIGURE 3, page 15 of 40

```
47251 CCTATCACCA TATATAAAAT CAACTCAAGG ATGTATTAAA GACTTAACTG
47301 TAAAAACTAT AAAACCCTAG AGGAAAACCT AGGAAATACC ATTCTGGACA
47351 TAGTCCCTGG CAAAGATTTC ATGATGAAGA TGCCAAAAGC AATTGCAACA
47401 AAAAAACGGC AAGTGGGACC TAATTAAAGA TCTTCTGCAC AACAAAAAGA
47451 AACTATCAAG AGAGTAAACA GACAACCTAT AGAATGGGAG AAAGTATTTG
47501 TAAAGTATGC ATCTGACAAA GGTCTAATAT CCAGAATCTA TAAGGAACTT
47551 AAACAAGTTT ACAAGAAAAA AAATTTTTA AAGTAGCTAA AGTAAATGAA
47601 CAGACACTTT TCAAAAGATG ACATACATGT GACCAACAAG CATATGAAAA
47651 AATGCCCAAC ATCACTAATC ATTAGAGAAA TACAAATTAA AACCACAGTG
47701 AGATACCATC TCACACCAGT CAGAATGGGT ATTATTAAAA AGTTATAAAA
47751 TAGCAGATGT TGACGAGGTT ATGGAGAAAA GGGAATGCCT ATACGCTGCT
47801 GGTGGAAATG TAAATTAGTT CAGCCATTGT GGAAAACAGG GTGGCAATTT
47851 CTCAAAGTAC TTAAAACAGA ACTACCATTT TACCCAGCCA TCCACTTATT
47901 GGGTATATGC CCAAAGGAAT AGAAATCATT CTACCATAAA GACACATGCA
47951 CACACACGTT CATCGCAGCA CTATTCACAG TAGGAAAGAC ATGGAACCAA
48001 CTTAAATTTC CATCACTGGT AGATTGGATA AAGAAAATGT GGTACATATA
48051 CACCATGTAA TACTACGTAA CCATAAAAAA AGAATAAGAT GATGTCCTTT
48101 GCAGCAACAT GGATAGTGCT GGAGGTCAAT ACTCTAAGCG AACTAATGTA
48151 GGAACAGAAA ACCAAATGCT GCATGTTCTA ACTTATAAGT GGAAGCTAAA
48201 CATTGAGAAC ACATGGATAC AAAGAAGGGA ATAATGGACA CTGGACCTAC
48251 TTGAGGGTGG AGGGTAGGAG GAGGATGAGG AGAGAAAAAA TGACCTAATA
48301 TGCTTATTAC CTGGGTGATG AAAATCTGTA CACCAAACCC CCACAACATG
48351 CAATTTATTG ATAACAAACC TGCACATGGA CCCCTGAACC TAAAATAAAG
48401 TCTTAAAAAA AGAAGAGGGG CCGGGCACAG TGGCTCACGC CTGTAATCCC
48451 AGCACTTTGG AAGGCTGAGG CGGGTGGATC AGGAGGTCAG GAGATTGAGA
48501 CCATCCTGGC CAACACGGTG AAACCCCATC TCTACTAAAA ATACAAAAAA
48551 TTAGCCGGGT GTGGTGGTGG GCTTTTGCAG TCCCAGCTAC TCGGGAGACT
48601 GAGGCAGGAG AATGGCATGA ACTCGGGAGG TGGAGCTTGC AGTGAGCTGA
48651 GATCATGCCA CTGCACTCCA GCCTGGGCAA CAAAGCAAGA CTCCGTCTCA
48701 AAAACAAAAG AAAAACAAAA AAACAAAGAG GAGGAAGAGG AAAATAAGGC
48751 CCATGGTGCT TAAAGTCACA CATGTGCCAA AGCCAGCTAG TAAACAAAGC
48801 AAAGATCTGA ATTCAGATAT TTGTTTAACT GCTGTGGTTC TAATTATATC
48851 ACGCACCTTG GACTCAAAGC AGGATAGAGA AGGTTGGGCA GTGGATCACA
48901 AAAGATATCA GCATAAATAC ACATCATTTA TTCTGTATTA TCTGATGCCA
48951 AGCAGTGTGC TAAGCACTTT ACATACATCA TCTTATTTGT ACATCCCAAT
49001 TACCTTCTGA TACAGCTGTC AATTCCCACT TTTATCAGGA AACTGAGGAT
49051 CAAAGAGGGT AAGTAATACA TCCAGAGTTA CAAAGCTGTT AAAAATATTA
49101 GAGGGTCTGA CTCCAGTGTA TATATTTTTA AAAGCCCCTT ATTATCTCTG
49151 GTAATCACTG TCTTGAAAAC TACTTTGTCT GATATTAATA AAGCCACAGT
49201 AGCTTTCATA CACCTTCTTG TTTACATATG ATTTCCCATA TTCTTTTATC
49251 CCATCTATGT TATTAAAATG TGTCTTGTCA ATAGTATATA GTTTGTTCTT
49301 GTTCTTTAT TCATTTTGTT TTCCTGATAC TCTTTTCCCA ATTAAGGAGG
49351 TAATAATCTG TAAGCAAAGC CTTATTTACA TAAACACTGC TGTGATCTTA
49401 TACCAAATAA ACAGCCCTAG CATGTGTGTG TGTGTGTGAG AGAGAGAGAG
49451 TGTGTGAATG TGTGTGTGTT TGGGCTTTCT GAATTAGATT TTCTTTCAAG
49501 ATCCACCTAC ATCTTTACTT TTGGCCTAAG TAATGGTTGG TCATGTTAAC
49551 TGTGTAAAAT ATTAATCTTT TTCTGAAGCT ACAAAGAGTC CATGTCTACT
49601 TACTGTTCTA GGAAAAGTTT TTTCAAATTT GGGAAGTGTC TACCTTTTAA
49651 AATATTTTCT GAGAGTGTTT AATTACTTCT ATGATCTTAA AAGGTTCTCT
49701 CCATTTTACT TTTATCCAGC TGTCACATAT TCTGAGTATG TTTTCCACCA
49751 GGAGAACCTG AGAATTTTTT TTTCTCTTAG ATTTTGAGTA TAGAGATAAG
49801 ATTTTATCCT GCATCCAGTT CCAACCTGTT AATATAATTC TATGCAAGTT
49851 TCCTCTCTTG TTGTGTTTAT TTCCCTTTAT CCTTATCCTT AGTCATCTAT
49901 TCCAATGTTT ATGCTGTGCA TTATTATATT TTCATGTATC CTTGTGAAAT
49951 GTAGAGTGCT TTATGTGCAA TATTTTAAAT GTACATAAAT GGCATTATAG
50001 ATTAAAACAT TTTTTCATGT TGTACCATGT TTTTGAGGTT TATTTATATT
50051 GCTATGTATA CCTCAGTCT ACTGCTTCTA ACTGTGAAAC ATTTTTTTCA
50101 AATTCAAATT CTCATAAATG CTGTACTTAT TTTGGAAATT AGAATTCAGC
50151 ACAAGGTACT TCTCTGTATT CAACACCATA GCATTTTAGC GCTTTACTAA
50201 TGGGTGGAAA AATTAAACTT CAGTCCTACT GTTCAAGAG CCTATTTACT
50251 CAAAGATGGC CAAGATGGAA AGCTTCCACT TTCCTGTGAG TCAGGTCCTA
50301 GTAAATGTGA ATCTTACACA GAGATGATTA GTTATAGCTC CTAGCACTAA
50351 CTCCCTGGAG GCAATGTCCT TGGTGCCCCT GACTCTCTTC CATTTAGGCA
```

FIGURE 3, page 16 of 40

```
50401 CTCATCTTTG TTAGATGCCT TAGGTTTATT TACGTAAAAT CATGCTGCAC
50451 TTCTCCCTGA TACTGTGGTT AAAGTTTTTA TGGCCTTGCA CCAAACCAAC
50501 AGCCCAGAAT AGCTACATGC CAGGGAGATA TTGTCAGCAA GGTTTGGGCA
50551 TTAATATGAA GAATCTTGTA TATTGTTGAA ACTTCTGGTC AACAGAATG
50601 GAAAGTGTGC CAAATAGGAA GCTTTTGGGT ACAGGTGACA AAAACCCCAA
50651 CTCAAACTGG CTTCAACGCT AAGCACATAT ATTATCTCAC TATATTAGCA
50701 GAATAACTAA ATATTGGCAG CTGCAGAGGC AAACCCTGAC TACTGAGAGG
50751 CTTGATACAG TAAAAGCTTA TTGCTTGGTC TCACAAAGTT TGCCAGGGGT
50801 TGGTGACTCT CCTGGGCAGT TAGTGACTCA GATATGTCGC TTTATAAGCA
50851 ACACATGACT TGTAAAGTCA CCCCTGCAAG GGAAGAGGAC TGGTGGATCA
50901 CATAGATTGT TTTTAAGGAC CAGGCTGGAA ATTGACTTAT ATGAATTTTG
50951 CCCATGCTCC AGTGTGCATA AATCCGTCAT CAGTCATATG ACCCCATCCT
51001 AACTGCAAAG GATGCAGAAA CATGGAGTCT TCCTGTGAAC TTAGGAAGAG
51051 GAAAAGTGTT GAGCAAGAAG CCACATTCCA TAACAGGAAG TCCAGATATA
51101 CAGCAGGTTT TAGGGATGGA TGACTTAGTG ACTCAGTGGT GTCATCACCG
51151 TCCTGAAGTC TTTCCAATGC TCTCCACCCT GCCGTCCTCA CAATGTCAGC
51201 TTTGTCTTCA GGCTGGTTCT CTTCCTGGTT GCAAGGTGGC TGCTGTAGTT
51251 CAGCCATCAC AACCAGACAT GGCAATGTGC TGGGACAGAA AGGGACCATC
51301 CTTAGGAGTG AGGGCACTTT TCCCAGAAGC AGCCCAGCAC ACTTCCTCTG
51351 ATGGCCAGGA CTGCCAGGCC CAAACTAATC ACTGACAACT CAAGATTTAT
51401 CCCTGGCATT GAGAGACCAT CACCCTCTTG GCAGTCATGT GGGGGAAGGG
51451 CTGGTTACCA TTTGAACCAA AATGAAGCTT AGCCAATAAG GAAGAGAAGA
51501 AAGTAGATGT TGAGTAGGCA ACGAACAGTA TCTGCTATAG CCCATCCCTG
51551 GACTCGCTGA GGTTTCATGG TAAAGTTTGT GGTTTTCATC ATGTTCCTGC
51601 ACCATTCTCA GTAAGTTGAT GCCTAGCATT GCATATTTTC TTTTGCTATT
51651 GTAATGCTGT TTCATGATA GTTGCTTGTG TATAGGATTG TCATTGATTT
51701 TTCACTCACC TTTGTTCAGT TTTCTTTTAT CTATGTGTCT GTGTAATTGC
51751 CTTAAATTCT TTTTTCAAGC AGTATTAGAT GTTAATTAGA GACTGAGAAA
51801 CCCAGAGGTG GAAGGATCTT AAGTGGAGCA GGGGATCGGA TTAAAGAATA
51851 AGAAAGCAAA GAATACTGTA TTTCATTTCT GTGAAAAGAG AGGTTACATT
51901 TCCTTGCATG AGGAAAAAGT AGGAGTGTGT GCTTTTCTCA AAACTTGCTA
51951 TAAGGCTGGG TGCAGTGGCT CATGCCTATA ATCAGCACTT TAGGTGGCCA
52001 AGGCAGGAGG ATTGCTTGAG CCCAGGAGTT TGAGACCAGC CTGGGAAATC
52051 TAGTAAAGCC CTGTATCTAC AAAAAATAAA AAATTAGCTG AGAGTGGTGG
52101 TGCACGCCTG CAGTCCCCAG CTAGCTGGGA GGCTGAGGCA GGAGGATTGC
52151 TTGAGCCCAG GAGGAGGTCA AGCTTGCAGT GAGCTGTGAT CATGCCACTG
52201 AACTCCAGTC TGGGTGACAG AGTGAGACTC TGTCTTAAAA AAAAATTGCT
52251 ATGAGAGAAT GCTCTAGGTA TGTGTGTGGT CGTGGTAGAG TATAGGGGTG
52301 TACGATCACT GTAATGTGCT GGAATAGTAC CTAATTTTGA AACTGCATGG
52351 TTAATAACAT CTTTTAAGAA TGTCTAAGTG CTTTAGAGAC TTCTTTTCCC
52401 CCATTCTCCG TGAGAAGAAT AGGAGATAGA TCGTTGGTTT TCGTGTGGAA
52451 AAATTAAGAA AGAGAAATGA AGCAGTTTAA ATTTCCTCAC ATTATCATGG
52501 TATTAAGTAA ACTAGAGCAG AGGTCTTTGG GTTAGAACTC ATTTGGGAAA
52551 ATAGATTGAG TGTGGCCAAG GCAACCATTC CTGTAGTGAA CTCAGCTCCC
52601 TTTTATGTAG TGAAGATAAA TAGTTGAACA ATCCAATACA TGCCCCAGTC
52651 CCTCTCTCTC TACACACACT GCACACACAC ACACATACAC ACACACACAC
52701 ACACAGTGCC AGGAGACATT CCGGGACCAT ATTTTTTTAA GAAGAAAAAG
52751 TATTATTATG CTTTCAAGTC AGTATTGTTA ATTTATTCCT TTTTTGAGAT
52801 GTAGAGTAGC TCCTTTGTAT CTGAGTTTGC CTATTACATG AAAAGACTAG
52851 TGGATAATGA TACCAGCTAT CCTATGTTAC AAAAAGCTGC AGATCCCCAT
52901 GCCAAGTGGA CTATACAGCT ACACAAACCT TCTGTTACCT GTTGGACACA
52951 CTGCCACAGA GGCGAGCAAC ATGCTGTCTG CCATTAAAGA ACTCGGGACC
53001 CTTGAAACCC ATTTTGGGGA ATATATGTAG CAAATAATCC AATTTTAAAA
53051 GGGGCAAAAA CGTAGGTTAT CGGAGTACAT TAGACATGCT AATCTGCAGC
53101 AGTTTTGTGC AAACCTAAGT ATAATTTAAT TTGTATTAA GTTTTCCTTT
53151 TGATATCCAG ATAAGATTA ACATAGTCAT TGGCAATTAT ATTTGTATTT
53201 TCAATAAACA TCACATTTTA CTGAAGTATA CAGATCTATG CAAGGGATAG
53251 TGAAATAGAC AAAGCTCATT TGACTTTTCC AGAAGGAATG CATTTTAACA
53301 TTGGTGGCTC CTGTGGTTAG GGGGACTTCC AAAGCAGTAA CTCTTGCGTT
53351 TCCTCAGCAG CATCATCATA ATTACACCAC TATACACAAT AATTATACTC
53401 CTAGCTGTGG TTCTATTCTA CAGCAGTTGC TGCTTTCCTG GAAACCTTGG
53451 GGAAAATAGA AATTTAAATA GCTCATAGAT TTGGCTATGA TAAGTTCACA
53501 CAAAGACAAA ATTGCATTTG GCAGTTTAGT TTCCCCAACC TTTATTTGTT
```

```
53551 TCCTGATAAC TATATTTAGT CTGAACCTCT TTGTCAAGGA CACCACATAG
53601 GTTATATTGT CTTCCTCTTT GCATCCAATG AAGCAGCATA TATTGCCAGG
53651 TCATTTTTTT TTATGGTGAT GCCAAACTTG ACCACTTGGC CAAGGGAGTG
53701 ACTGCCATAC CTCTTATTGT GAAGGCACAT TTTCCTCCTG TAATTAACAA
53751 GTAACCCCAG GGGTGATACC TTGAGACAAT GAGAATATTT TGTTTTCCAA
53801 TAACTTTTAC CCAAGAATAG CTACACACAC CCCCTGTAAT TATAGACTTA
53851 TGGGTCAGTT TTTCTCACCA TGTGTTTTAA TCCATCGATG TCATTCTTTC
53901 TGATATTTAA AATCGTTCAC AGATTGGCCA GGAACCCTTC AGACCAGCTT
53951 CTGTCTTCAT TGAACTTGTC CTTGTTAGC TTTGAGCACT TCTTGGCGTT
54001 TTTGGCCCAA GATATCTTAG GCTTATCTCG TACTTTCAGT ACTCTGGACG
54051 TGTGTCAGAC CTGAAATCAG CCTCTTCTCC AAGGAGACCT GTTTCCCTTT
54101 AGTGGAAAAT AATATTTACA AACCAAGAGT TGGGTGTTTG TGTTTTACTG
54151 CTACTGGGGT GTTAATTTTT CTAGGCTCTT TAATCGTGAG TTCATATTCA
54201 AACCACCTAA TTATTTTGTT TTTATTTTGA ATTACCTTTC TTGAGGTATA
54251 GTTTACCTAA ACGAAAGTGT ACTCATTTGA AGTGCTGAGT TTGCTTCATG
54301 TTAGCAAATT CATATACCCT GAACTGTCAC CCTGTCACCT ATGACCTTTT
54351 GCAGTCAGCC CTCTTTCAGC CTCTGACCTG CTTTGTGTCA CTGTAGATTA
54401 GTGTACCTAT TCTAGAATTT CATGTAAGTG GAATAACACT ATATGAGGCC
54451 TTTTCTCTGG CTACTTTTAC TCAGCATTAT GTTTGGAAA TTGGTACATG
54501 GTATTATGCA TACCAATTAT TCATTACTGT CTCTTACTGA ATAGCAGTCC
54551 ATTGTATGTA TGTTTTGCTT ATCTATTTGT TTATCTATTT ACAAGTTGAT
54601 GAACATTTGG ACCATTTCCA GCTTATGGAT ATTATGAGTG AAACTGTTTG
54651 AACATTCAGG CACAAGGTTT TGTATGGACA TGAGCTTTCA TTTCTCTGCA
54701 GTAAATACCT AGGAAAGGAA TTGCTGTGTC ATGTTTTTTA ACTTTATAGG
54751 AAACTACCAA TTTTTTTTCC CAAGTAGTTG TTACCATTTT TTACTACCAC
54801 CAAGAATGTA TATGAGACCT AATTATTCCA CATTGTCATC AGCTCTTGGT
54851 ATTGCCAATC TTTTCATTTT AGCCATTCTG GTGGGTCAGT AGTGGCTTTA
54901 ATTTCTGTTT TTTAATTTTG TTTAATTTCT GAAATTTTAA TTTTATTGTG
54951 GTTTTAATTT CCATTTCTGT AATGGGTGAT GACACAGAGC ATCTTTTTGT
55001 GTGATAATTG GTCATTCATA TATCTTGATG AAATGTCCAT TCATATCTTT
55051 CACTGACTTT TTTAATTGGG TTGTCTTTTT TCTTGAGCTA TGAAGTTCTA
55101 TGCATTCTGA ATACTAGTGT TTTGTCAGAT GTATGTATTA GGATATGTTC
55151 TCCCAGTCTA CAGATTACTT TAAAAATTTT CCTAATAGTA TCTTTTGGAG
55201 AGTAGAAAAT TTTAATTTTG ATGAAGTCCA ATTTATAGAT TTATTTAAGG
55251 TTCCTATTAT TTATGTCGTG TTTAAGGAAG TTTTGCCTAC CCTAAGACCT
55301 CAAAGATTTT CTCCTGTATT TTCTTCTAGA AGTTTGTAAA CTAAAAAACT
55351 TTAGCTTTTG TGTTTGGGTT CATGGTCCCA TTTTAATTTA ATTTTTATGA
55401 ATTTTGTGAG ATATAGGTGT TGTTCTTTTT CTTTCTTTTT TAATTTTTTA
55451 GTTAATAAAA ATGGTATATA TTTATATTGT ATAACATGAT GATTTGATAC
55501 ATGTATACAT TGTGGAATAC ATATTACCTC ACATGGTTAT CATTTTTTTG
55551 TGATAAGAAC ACTTAAAAAT CTGTCTCAGC AATTTTTAAC TATATAATAT
55601 ATTAACTATA GTCACCATGA TATACAATAG ATCTCTTGAA CTTATTCCTT
55651 CTAAGTAAAA ATTTGTCCTT TGACCACCAG CCCCCCTGCC ACCCCTCACT
55701 CCCTGTCCAA CCTCTGATAC CACCATTTTA CTTTCTGTTT CTATGAGTTT
55751 GACTTTTTAA GATTCCATTT ATCAGTGAGA CCATTGGTAT TTGTGTTTCT
55801 TAGCCTGGTG AATTTTACTT AGCATAATGT CTTCCCAGTT TTTTTATGTT
55851 GTTGCAAATT ACAGGATTTC CTTCTTTTCT AAGGCAGAAT AGTACCCTAT
55901 TGTGTTTATG TGTATATATA TATATGTGTG TGTGTGTGTG TGTGTGTGTG
55951 TGTATATATA TATATATATA TCCCATTTTC TTAATCCATT CATCTGTTGA
56001 TAGGCACTTA GGTTGATTTT GTATCTTGGC TATTGTGAAT AGTGCTGCAA
56051 TAAACATGGG CATTCTCTTT GACATACTGA TTTCATATCC TTTGGATATA
56101 TATGTTCAAT AATGGAATTG CTGCATCATT TGGTAGCTCT ATTTTTAATA
56151 TTTTGAAGAG CCTCCATACT GTTCTCTACA ATGGCTATGC CAATTTACAT
56201 TTCTACCAAC CATGTACAAG GGTCCCTCTT TCTCCACATC TACTTTTTTT
56251 TTTTAGCATG GATGTCCATT CATTCCAGCC CTGATTGCTG AAGAGACTGT
56301 CCTTTTCCCC CATTGAACTG CCTTGGCATC TTAGCCAGAA ATCGACTGAC
56351 TATATGTAGG AGGAACTATT TCTAAATTCT CTAGTCTCTT CCATTTATCT
56401 ATGTATTTAT CCTTACACTA ATGCCACATT GTCTTGATTT ATATAGCTTT
56451 ATAATAAGCA GAGCCCAGTC AGGCCCCTCC TAGACAGTCC ATACCAGAAT
56501 TCACAAATAC ATATGACCTA AAGCAAGTAA CATAATTAAG TGAAGCTGTT
56551 CTTGTATAAG CAGTATTACT TTATTTATAT TAAAATCTAA CGGGCTAAAA
56601 TTTCAACGTG GTTCATTTTC ATTTATTAAT GTTTTGAGTC ATGTCCCTTT
56651 CTCACATGTC TCATGGTTCT TATTATGGTT TATTTCTAAT GATATCTTTA
```

```
56701 TACACATACT TTTCACACTA AATATTTAGG AACATTCCCT GTTTTCATAC
56751 ATAGAACAAT ACTGCCTCCA TACATTTTTG AAATGCGTGG CCCATTTGAT
56801 CTGTTTTTCA GTTTCCCACT TCAAAGAGAG GAATACAGTA TCTCCCATGA
56851 CAGCATCAGC TGGTTAATGA ATGGTGATTG GCATGCAGAC TCAGCATTGA
56901 GACTGCAGTG GGGAATGATG GGGACACTGT GGCAAACGGG GGAGGGCTGG
56951 CACTGCTGAG AGGGGCACAG CCACTCTACG CCACTTTCAT AACATCATGT
57001 CAAATGTACA CAAATTCACC ATTATTTATT TTGTTGCTCA AATTATTCCA
57051 GCTTTGTCCA CTAGGAGCTG TTTCAATTGG CTATGTCCCT TTGACACACA
57101 CACCAATGTG GGTTTGTTCG GTTTTTTGTC TTATTTGAAT GCTTCTTTCC
57151 TTTCTGGCTC CTCCAGGCTT ATCTTGTGTA TTTCCCATCC CAGTCCTAGA
57201 ATCAGCCATT TCTCTAAGAA TCCCTGGTTT CTTTTATAAG AGAATGGCAT
57251 TAGAAAATGC CACAGAGGTT AAGTGTCATT CCCATACAT CATAGCAAGG
57301 GTACATACTA TCAACACGAT TTATGACTAT CGATGTTACC CTTAATCATC
57351 TAGCCAAGAT GGATGGTGAA ATCATTAGGA GGGGGATGCA ATAAAGAGGA
57401 AGAAAAGCAG ACTTTATGTT CATTTTCAAG CTTGTTCCAA AGGAAAGTTA
57451 TAGGTGTATT TGATCATATA AATATCGTTT TGTTTGGAA AATCACGTTT
57501 AGGGACAATA AAATTGGAAA GAATCCTTGC TTCCAAATCA CCTCTGTGTT
57551 CAAATCTTCA TCATATTTGC ACTGCCCTTT CCTTTGTGTT CTTAGTTCAT
57601 GGGTCCCATT GGATTTGATG GGTTTCGTTT ACTTTTTGCT ACTGAAATTG
57651 TTAGTTTAAA AAAACAGGAT ACAGAGTGTC ACATTTTTA TTGTAACTCC
57701 ACTTTCTTGA AGTTGCCTAT AGCATTTTAA ATTTCAGAAG ATCGATAACT
57751 TTATTCATTT CCCTTTGGAA AAAATAAAAC AAGATTTTAA CTAGTGGCAT
57801 GTCTTCAAGG AAGCTAAAGA CATTTAACTT TTTCTGTTTT GCTCTAAGGG
57851 CATTCTGATG ATTGCCTGAA TGTGATCTTC TGAGTGTTCC AGTCCCTGGA
57901 GCTGGCTGTT AGCCATCTCC CAAGGAGGGT CGAAAAGAAC GTAGCAGAAA
57951 GCTGCAGAAA GAAAAGCTGG CTAAAGAAAC AGGAGCTGCC AGCCAGGGCA
58001 ACATAGTGAG ACCCCAACTC TATAGAAAAT TTAAAAAGCT GTCCTGGCAT
58051 GGCATGCCTG TAATCTTAGC TACTCAGAAG GCTGAGGTGG GAGGATCACT
58101 TGATCCCAGG AGTTGGGGGC TGCAGTGAGT ACTTCCAGCC TGGGTGACAG
58151 AGGAGACCCT GACTCAAAAA AAAAAAAAAG AGCCGGTTGT TGTTAAGGGC
58201 CACCAGACTG GAGTGCATGG TAGTCACCTG CCTCCCTCCT TTCCTGGAGA
58251 AGATGACAAC GTGATGAACA AGCACCACTA CCCTGGAATA GTTTAAATGG
58301 CATTCAGCCT GGAGGAGTGT GCACATGCAC CAAATATATC TTGTGTGTCC
58351 TTTGTAGCCA TTGGGTCTAT GGAGATTACT CTGGCTGTGA GTTTGGTTGA
58401 TTAACATTGC TATGCAAGCC CTGTCCATTT AGCTGGAGGT TATCACAGGA
58451 GGAATAAACC ACAGAATATG ACTTTGGCAT TGAATAAATG GGAAGAGAGT
58501 GCTTTTGGGG GCCAGAACTG TTTGTAATAT TATAACTCCT ATAAATACAT
58551 GAATTGCTGC CCCTTTATCA TAATATCCAT TGCTTTAATG CTCTGTTTTA
58601 GATTGGAGTT CACACCAGAC ACCTGAGATT GTGTTTGTTA TGTAACTGCT
58651 ATTTCATGTT GAGAAAGTAG CAAAGCTTTT AAATACTGAG AATATTTTAG
58701 TTACATGAAG ATACTTTTAG TAGTCACTGT TGTTGTTACA TTCCCCCTAC
58751 CCCTCAGAAA ATAACAGGGC TGTTAAGGAA TCCTCAAAGA GCATAGATTG
58801 AGTGAAAATG ACACAGAACA AAGGACAGAT CCCAGGAGTG AAATGAAGAA
58851 GTTCTGTAAA TAGCTGTGCC GTTTTCCTTT GAAATGTCTG GCACACTCTA
58901 TATAGTATAG TGGTCGAGGA TAGAGGGGCT AATTCTGTGA TGAAGCATTC
58951 TGCATGGAAT TTCAGCAGGG CATAGATGGT GAGGGCATCT GGATCTGTTT
59001 GAGTTTTTAA ACTAATTATA TGACAAACTT TTTAAAATGT AGCATACCTG
59051 GAAACATCAT CCCGCCACGT CATCTGCATT TAAATAATCA TTGCCTCACC
59101 TTTAACACCC AGCCTCTAGA AAAATAAAGC ATGAACAAAT GTTAGCTCTG
59151 AGCTGCTCTC AGTAATTTGG AGTGTGCTAA GCAAAACCTA CATTTTCTAG
59201 CATGAAATTG GCACAGGAAT GCATGCAAAG TTTTGCTTCT TTGATTCATC
59251 TGGTTACCTA GAACCTGAGG CCATTCTGTA TTCTGTGGAC AAAACCCTAT
59301 ATACCTTTCA TGACCCAGCT TAAATGAAAA GTCTAATGCA AAACATGCTG
59351 AATTTCTGTG GCCATATTTA ATTGTTCTAG TGGTCCCACA GGTATAGTTT
59401 ATTATTCTTT TTAATTCCCC TTTAATGGCA ATTTCTCTTT TCCTTTTTTA
59451 AAAATGTCTT TTGCCTTCTG TTCATTTATT ACCTGTCTCC CTTTTTTATT
59501 GTGAGCATGT CTCTTGCACA GCACAGACAC ATAGTGATTT CTTGTTACAT
59551 GTGGGCCCAC ATTTATTTTT TATTTCTATT TGTTTTTCAT TCCTATTTAT
59601 TTATTTATTT ATTTATTTAT TTATTTTGAG CCAGGGTCTT GCTTCATTGT
59651 CCAGGCCAGA GTGCAGTGGT GCAATCACAT CTCACTGCAA CCTCTACTTC
59701 CCGGGCTCAA GCAATCCTCC CGCCTCAGCC TCCCAAGTAG CTGGAACTAC
59751 AGGCACACAC CACCAACCAC ACCTGGCTAA TGGGCCCATA TGTAAATGAC
59801 TAATTAGTAT TTAAACACTT GCCAAGAGTT GTTAATACC TGCTGTGTGC
```

```
59851 AGGGCACAAT CTTATACATT CTTAAGGGAG CACAGAGGTG TCAGATGGGG
59901 TCTGCCCACC AGTTTTTCAC AGATTTGAAT ATTTAGCGTT CTGGGCAAAA
59951 GCAGTTTAGG AGCTGAAAAA TCATGGCCAT TTTAAGAAGA TTATCTTACC
60001 CAAAAACCCA CAGTACTATT GTTATTGCCT TATATATAAA GCCATTCTGT
60051 TAATTTTTTA AAAGTATGTA TTAGGTTTAA CCTGGTTTCT CTGTGTTTGC
60101 CATGTTTAAC ATCTAAGGCC AAAAATTTGA AATATTTTTA CTTTCTGAGT
60151 ATGTCAGGAA AGAGGAGTCT GAAGCTGGAG TGAGTTGGGG AGGTGGGGGG
60201 GACTATATTT TTATGAAAAT TTTAGTAAAT TTCCTGGGTT TTTGTCCCAC
60251 CTATGGGAA GATCTAGGAT ACAAAAGCAT TAAATGTTAA TATTGATTCA
60301 AGAATTAAAT CATCAAAACA TTGCTGGGAG AAATTAAAGA CCTAAATAAA
60351 TGTAGAGAGA TCATGTTTAT GGGCTAGAAA ACTCAATATT GTTAAGATGT
60401 CACCAAATTA ATATATAGAT TCAATGCAAT CTCTATCGGA ATTGCTGAA
60451 ATTGACCAAC TGACTCTGAA ATTCATGTGG AAATAAAAAG GATCTATAAC
60501 AGTCAAAACA ACCTTGAAAA TGAAGGATAA AGTTGGAGGA GTAATACTAT
60551 CTGATTATAA GACTTATTAT AAAGCTATGG TAAATCAGGA TATTGTGGCA
60601 TTGGTATTAA GATCACTGAA GAGACCAATG GACCAGATTA GAGCATCCAG
60651 AAATAAACCC ATACATATAT GCATAGCTGA TTTTTGAAAA AGTTGTAATG
60701 GCGGCTCAGT TGTTCCAGGA CAATTAGATA TAGTTGGAAC AATTAGTTAT
60751 CCATATACAA AAAAAGAAAA GAACTTCAAT CAGTTCCTCA TACCATATAT
60801 AAAAATTAAC TGAAAATGGA TCATAGTCTA AATATATTAC CTAAAACTAT
60851 AATACTTGTA GAAAGGAGGA GAAAACCCTT GTAACCTTGA ATTAGGCAAA
60901 TATATATATA TATATTTTTT TTTTTTCAA GCAGTTCTCA TGCCTCACCC
60951 TCCTGAATAG CTGTTGTTAC AGGTGTTCCC CACCACACCT GGCTAATTTT
61001 TGTATTTTTA GTAGAGACGG GGTTTCACCA TGTTGGCCAG GCTGGTCTCG
61051 AACTCCTGAC CTCAAGTGAT CCGCCCACCT CGACCTCCCA AAGTGTGCTG
61101 GAATTACAGG CATGAGCCAC CGTGCAGAGC CACAAAAATA TTTTAAGTAG
61151 AACATCAAAA GCATGATCCA TAAAATAACA AATAGATGAA TTGGACTTCA
61201 TTAAGATTAA AACTTCTGTT TTTCAAAAGA CACTGTTATA AGAATGAAAA
61251 GATGAGCCAC GGAGTGGGAG AAAATATTTA TACATCATAT AAAAGATTTG
61301 TGTGCAGAAT ATATAAATAA CTCTCAAAAG TCAATGTAAG AAAACCTTTT
61351 TTTTTTTGAA TGTGCGAAAG ATTTGAACTG ACTTTTTGCC AAGGAAGAGA
61401 TACAGATAGC AGTAAGCATA TTAGTCATTA AAATAATGCA AATTAAAACT
61451 ATAATGGGAT ACCACTATTA GTAGTATGTA TTAGAATTAC TGAAATTGAA
61501 GATCGACAAT ACCAAGTGTT GGTGAGGATG TGGAGGAACT AGACGTCTCT
61551 TACACTGCTG ATGAGAATGT AAAATGGCAG AAGCACTTTG GAAAATAATC
61601 TGACAGTTTC TGAAAAAGTT AAATGTATAC CTAGTGCATG ATCCAGCCAT
61651 TCCACTTCTA TGTATTTATC TTAAAAAAAA GAGAAAGAAA TTCGCATAAA
61701 CTTGTAAACA CGTATTTAGT TTGTAGCAGC TTCATCTGTA ATAGCCAAAA
61751 GCTTGAAACA ACCCAAATGT CCCTCAGCAG GTGAATGTGT AAACTGTGGT
61801 ATGAACTACG CAATAGAATA CCATCCAGTA AAATAAAGGA GGGAACTATT
61851 AATGTACATT ACAAGTAGAT GAATCTCTTT ATAACTATGC CAAATGAAAG
61901 AAGCTATATT TACACATACA CACATTCACA TACACCCCAC ATGCTGAATT
61951 ATTACATTCA TACAAATTC TAGAGGATGC AAACTAATGT ATAGTTATAG
62001 AAAGGAGATT GGGGTTTCCT GGCGATGGGT GATATAAAAA GGGATTGGAG
62051 AAATGGATTA AAAGCACAAG GAAATTTTTG GGGGTGCTGG GTGTGTTAAT
62101 TATATTCATT GTGGTGATGG CTTCATGGCT ATATACATAT GTCAAAATGT
62151 GTCTAATTTT AGACTTTAAA AAGCGCATTT TATTCTATAT TAGTATTTCA
62201 GGGATCCCAA GACAACCCTG TTTGGTGGTT TACTAGGACC TGTAGCACTC
62251 AGCATATAGT CGTTCTTAGG GCTAAGACTT ATTACACTGA CGTAGAAGGA
62301 TACACAGGTG GATCAGTAAG GGGAAATGAC ATCAGGCAGG GTCCAGAGGA
62351 ATCCATGTGT GGGTTTTCTG TGTTCCCTCC CTCCCTCTGA GATCACACAC
62401 AGCATACCAC CTCTCCAGTA GTGAAAATGT AGTCACAGCC GTACAATGAT
62451 TATACCCAGG GAAACCCACT TAAGATTCAA GAGTTCAGGG TTTTTGTTCA
62501 GGGCTTGTCA CATAGGCACT CTTGCCCACC AATATTTCAT ATTCCTGAAA
62551 GGAAAGCAGT TGTTCAGTGC CCCAGACAGA TAAAATAACC TTATAAGGGT
62601 AGGAAATGTT TCAAAGCTG TGTTCCCGGA CACTAGCCAA GGGCAAGCCT
62651 TGCAAGCAGA CCTTTCTAAA GATAAGGCTT TAGATAAAGT CTCAGCTTG
62701 TTAACACTTT TCTGCAGTCA CTTATACCTC AGCTTGTTAA AAAAAAAAAA
62751 AGTTGTAAAA GTTAGTGTGA GTTAGCACAA GACAGTTGCA GTTCATTTAT
62801 TGAAAAAATG ATAAGAGATT ATAAAAAATA GTAACTTTAG ATTTGAGGCA
62851 GACCAATGCA GTGAGAACCT CATTACCTGG AATGCTTCAT ACCCTTAAAT
62901 CCCCTCTTTG GAATTAGCCA GGAGTGTTGG TGGGTGGCTG TAATCGAGCT
62951 ACTCAGGAGG CTGAGGCAGG AGAATTACTT GAACCCGGGA GGCAGAGATT
```

FIGURE 3, page 20 of 40

```
63001 GCAGTGAGCC AAGATCACAC CACTGCACTC CAGCCTGGGC AACAGAGTGA
63051 GACTCTGACT CCAAAAAAAA AAAAAAAAA AAAAAAAAAT CCCCTTTTTG
63101 GAACAAGGTA GGATAATAAT AAGTAAAACC AGGAAGCTTG GCTAATGGGA
63151 GCTTCTAATT ATTTTTACTC TTTAATATTG TGACTTTCAT TTCTATTGTA
63201 TTTGAAAATC TTTCCAAGGT ATATCATTTT TTTCCTTTCA TAAAAATTC
63251 CTTGGTTGAT GTTCATTATT TAACCACTGG TTAACTGATT ATGACCCAGT
63301 TCAGTTCTAT AGCAAATAAA AGATAAAGCA CTGCTGTTGA AATTATAATT
63351 ACCTCAACAA CAAGACCACC TCATGCAGTT GTGCAGGTTA TACCTCGTCC
63401 AAGGCACACC CAGCTGTGAG GGTGCGTGGA GCTTAAGTCC AGCTTGTACT
63451 TTGCCAAGCT ATGGGCTCCA GCATGGGGTG TGTCTGCCCG AGAAAGGGC
63501 ACCTTTTTCT AGTTTATGCT AAGATGCCTT TTGAGCTGTT CAGCATGAGC
63551 CCTGGAAAAA GGTGGTGGTA GCGATTTTCT CCTACAGTGC TGCCTAATAT
63601 CAGCAAGCTT TCTTGTGGGC ATCTCTTTCC CCTTAAAGAA ATCCAGCTAG
63651 TAACTTTCAG TTGAGCGTCA TGTTTAACCA GGATTCCACT GTGTGTAACA
63701 AGGACAAGCG ATTCCAACGG TCTCTAGTTT GGCCCAATTG CCCTTAAAAG
63751 GCAGGCAAAT GTTAGGGTA TGTGTTTCTT TTTATCACTC TGGAAGAAGC
63801 CAGGTCAGG TCTGTATCTG GATCCCATTA TTAATGTCCC CAGCCAAGAA
63851 TTCTGTGTAT GTATAGCAAT AGAAAAGTCA GAGAAAGGAC GCTCCTGTGA
63901 CTTCTCTGAA GTTTTGTTC TTCCTAGTA ATGAAGTTC CTAAAGGGA
63951 ATTAAACTTT CTCACCTCGG AAGATAGAAG TATTGTTTAA AGATTCAACT
64001 TTGAAACAAA TAGGAAAATA TCTGATAGTT GCAACTTAGC TTCAAATCAG
64051 CGATGTCCAG ATATTGACAA CCATTTTATT TCTCCTAAAC CTTGAGCCCT
64101 AGCCCAATTT ATGACCGAGT AGAGATCATG GCACAGCAGC CAGCCTAACA
64151 GATGGGGGCC ATACTCTAGC AGCAGAAGGA TTCTGTTTTG AAACCTTCAG
64201 CTTTTGAAAT CTTACACCAC TACCAGCCCT ACTTCTTCTA CATAGATCAC
64251 ATTCATTTCC TCCCTCTTTT TCCTAAGGAA ACTTAAAACA CATGTCTTTT
64301 CCCTTTTTAT AGATGCGAAC CACCCGCAAG GTCTCCGTCT GGCCTGTGGG
64351 CCTGGTTGGT GGGCGGCGCT ACGAACGTCC GCTGGTGGAA AACGGCAAAG
64401 TTGTTGGCTG GTACACCGGC TGGAGAGCAG ACAGGCCTTT TGCCATCGAC
64451 ATGGCAGGTG AGCAGTGTGG GTGATGACAT TGTTCCTGC TGGACTGTTC
64501 TTATGCTCTT GTTTATAACG ATGCACTAGA TGAAGGAAGC TTTAAAGAC
64551 AAATTTGGAT AAAACCCTAC ATCATATCAT ATTCAGGAGA TGAAATATTT
64601 AAACCTTCAA AATAGGCTCT TTGGTTAGAT CAAGTGGAAA TTGATTTGGA
64651 GGGTGATTAG AAAATGCCCT TTCTGTTCCA TTTTGTCCCC TGTCTGTGCC
64701 TTTATCCCAC AAGCGTCTAC ATGGCAGCTA CTGGGTTGGC CACTGGGGAT
64751 TCGGTGGTGA GAGCTAGACC TGGCTCCTGC CTTCCAGGGG TCTGTTAGCT
64801 GGAACCTTTT GACTCCCTTT TCTAGAAGAC TGATATATTA AAATATATCA
64851 TGTTTATTGA TAAATTTAAC AATGATATAA AAATTGACAA GTCATTTTAA
64901 TGCTTATTGA TAGGTTTAGT GCTTTATTGA TATATTTAAT ACTAAAATAT
64951 AAACTTAGAT TTCTGGTATT TCAAGAATTT ATTGAGTATA ACTGTCTTAA
65001 AGTTTTTATT CCCTGAACAA CCAACTGAAT TGAATTAGCC CTGCAGTAGG
65051 ACCACACGTT CTAAAATGCT ACTTTATCAT AAAACAACTC ATTTTCTATG
65101 GGTTATAGAA AATGATGCCT GTGATAACTG TGGAAGGATG GAGTTTGAAA
65151 CATGAGGCTC AGAGGCAAAA AAAAAAAAAA TTCGGTGACA TCTATACTCT
65201 TAAAAATGAA GGCAGAAAGG CTTCAAAATT GATCTCATCA ATCTTGAGCT
65251 CTGAAGCACA GCTCTGTCGG GCTGCCAGCC TGTGCTTGCC CCATCTTCTG
65301 TGCATATTTC CCAGCCGTAG TCAAGATCTC CGCGTTCAGA ATTCTGATGG
65351 GATGGAGGCT GTCTTCTGAA CTGGATTCAT CACTTTTATT CTGACAATAC
65401 TATAAATCTG AGGGAGCCAG AGGACGAAGA ATACCAGGAG TCATCTGAGG
65451 GGCACAGCGC TCATGGACAG CTGTGTGGTG GGTCTTGTCA CATGGCATCG
65501 TGGGAGAGGA CAAATAGGAG ATTTTTACTC AACATTTAAC ACACATCTCC
65551 ACAGCACCAG CCCTCAGCCA GGCCATGTCT CAGGCCCCTG ACCTCTCCAT
65601 CCCTCTGTTA CTCCAGCTGT TTGCTTTGGT CTTCAGTTGT TGCAGCTCCA
65651 GAACTGAGCT GGCATCTCAG TCTAGGTCTC CACCTGGAGG CAGAAGGAGA
65701 GGCAGCTGAG CCATCTTGGA CGGTCCTGAG GACCCTCGAA AGAGGCCTGC
65751 CCTCGACCCG CTCAGAGTGC ATGGCCCTGA AAACATGGGG CATAGTGTAT
65801 CTTTTGAAAA TCGGGCTTCT TGCTGACCAG AAGTGTACCT TAGAGCAGAA
65851 AATTTAGACA ACATTAGGGA AAGTCCTTCT GCTTCTCTGG GATGTAGTTT
65901 TCTTGTGTAA AGTGAGGCAG CTGCCGGAGA TGACCACCAG GGCCCTCCAG
65951 TGCAGCCCTC CTTTCCTGGC CTCCCACCTT GGAACTCTCA GTAAGAGCC
66001 CAAGCTTGGG CTTCTAAGTG AGGATTGTGA CTGCTCAAGC AGCCGCAGAC
66051 AGACTTTTGC TTCAGATTTT CCCAGAGCCT TGTTTCAACA CGGACTTCCC
66101 AGACATATCT CCTTAACACG TGGGATGTCT GCCCATTTCC TTGCATGGAT
```

FIGURE 3, page 21 of 40

```
66151 CATGCAAGGT GAGGGCAACT TGGGTAACTC TTCCTGGATT TTAATCTAGG
66201 AACTTTATGT AGATGATCAC GTATCAAATA GACTTGTTGA ATATTTGCAT
66251 TGGTTCCCCT AGAATTTGGG TCACATTGAT ATTTCTAAAA TTAAAGATGT
66301 ATGTGTTTGT GCATTAGGGC TGGCCTATCT AGGACTGCCA AATTCTGTGG
66351 GAATTCTTTT TTCCATGACA AGACCAATGT TTGGATTTTT CTAAGCATTT
66401 CAGTATATTT TCAAAGCATA TTAAAAACAC CCATCATAAT AAGATATGAA
66451 TTATTTCCTT GCTCTGTATT CATTATCATG GTTTTAAAAT AGGAATAAAG
66501 TGTCTCTAAG GAGACAACTT TTGTCACACT AAATAATTTT TTTCACTTCA
66551 CACATGAACT TGCTTTGCAT CTTAGCTTTC AGTAAATTAT TGATATTTTT
66601 GGAAGTCTTT AAGTGTAAGT AATTTGGTCG ATAGGATAGT TATTCTGTTT
66651 TTGAGGCAGT TTGTTCTAAT TCTAACTTAA AAATTTGTGG CTTTGTTTAG
66701 ATTCCACATA CAATTCATTT ATTCTCTGGG AAGAGGGAAA AGACCTTTTA
66751 GGCCTTCATG TTCAATTGGT GCTTCCCGCC TCATTTCCAA GTTACATGTA
66801 CACACACACA CACACACACA CACACACACA CACACAATCT GAGCTCTGAG
66851 GAGCTCTACT TTGAAAATGC TCTGTGATAG TCAAGTGAGA GCACCATATT
66901 GGAGCCTGGG TCTGTCTTGC ATTTGCAAAG CGGATTAAGA GCCCAAATGG
66951 AACATTTGTG GGTTTGAGCA CATTCAGTAG AAGCCCCTCA GAGCCTGTCC
67001 TGTTTGTATC TCTGTGAGGT CATCACATAG CCCATCACTG GAAACTCATT
67051 TGAGTATCAA ACATTGAAAC TGCGATGTTT CATGTCATTC TAGTAGTTCT
67101 TACACTGTCA TTTTATTGCC ATGTTGAACT TGCCTGATAC TGAAATTTTG
67151 CTCTCAGGTG ACATGAAACA TTGTTCTTGA AATAATCTTA TGTTTACAAC
67201 CATAATGGCA GAATTAAGAT TATTTCTGTT CCATTGGAGG ATATTTTTTA
67251 AATAATGAT TACTACTTAA AAAAATTAAT ATGCCTGCCC ACAAGATGGA
67301 AAGAAAACAC TGGAGGCAGC CCCACTGGTG GTGTGCAGTT GGCTTCAAAG
67351 CTGACCAGTA GCCACATAGC TCTGCCAAGC CAGTGAGGCC CTGGGGGGTT
67401 TCTACTGTTC TGTGCCTCAG AATTCAATTC TTACACCTCA GGAATCTGAG
67451 GATTGGCTAA AAGTGAGGAA GTCCACCAAA GGTTTTAGCT CTGTTTTGAA
67501 GGGAGGCAGT TAATTTCAAG TGACAGACTC ACTTCAGCCA CTTCCAGGGA
67551 GGTGTCAGTA AGAACGACTG CTTGAAAGAA CTGAGCTTAA ATCAATCTTC
67601 ACCCTCACCA GGAGGTGTAG ATTTGTTCAA GTTGAGAACT TAAAACAGAT
67651 ATTTATTAGG AATTTTCAAC ATTGGCATGT GCCTTATTAT TAATTCTAGG
67701 ATGTGGCCCG TGGGACACGG TGCTCCATTA ATGACAGTAT ATGCAGTTCC
67751 CAGTTGAGTT GCTGGCACAC AGTAGGTACT TTATTCTGCT AAAAACACAA
67801 CTAGGTGTAC TGCAATTAGA TTCTGACACC ACCTGGAGTT GGTGCAGACC
67851 CCACAGGTTA GAGGGCACAG TCTCCAACAA GACTGCCCTT ATTTCACATG
67901 CCCCCCACGC GCTGGAGAGT CCCAGGCCAC CTGCACTTCT GATCAACTGA
67951 CTGCACTGGA TGTTTCCCAC AATCTCCTCA GGTTTGCTAA TTTGCTAGAA
68001 TGACTCACAG AACTCAGGAG AGTGCTGTAA TTATACAAAT TATCATTGTA
68051 ATCAGTGTTA TAAAGAATAC AAGTCAGGAC CAGCCAAATG AAGTGACACA
68101 CAGGCCAGCA GAGCCAGGTG GAAGGAGCAG GCTGGGAGCA TACAGGTCTT
68151 CTGTGCCTTT TCCTCATACA GGTGAAGTCT AGGAAAGCTT AGTTTTCTGG
68201 TCTGGAGTCC TGTGGACCAG GGTGTGTCGA AGCCCTGGGG ATGGATGTGC
68251 TCCCACAGGG AGACTCTGTG GCAGCCTCGG ATTGCATCCT GGGGGCAGGC
68301 ATTTAAAGTG ACTGCAGGGG GGCAGCCAGG GAAAGAGACA AGGCCCAGCA
68351 AGAGGGTGTT AGGGTGGACA GTGGCGAGGT CACTGGAGAG AAGGGGTGGA
68401 TGAATGATGA ATTCCGTTAT TGGATGTGGG AAGAGGAGGA CCCTTGCTGA
68451 GTATGGGAGA AAGACCGCTG GAAGCAGAAT GGTCTGAGCA AAGTTAGGTT
68501 TCTGGACGGG CATGGTAGCT AACACCTATA ATCTCGGCAC TTTGGGAGGC
68551 TGAGGCAGGT GAATCACCTG AGGTCAGGAG TTCAAGACCA GCCTGGCCAA
68601 CATGGTGAAA CCCCGTCTCT ACTACAAATA CAAAAATTAG CTGGGCGTGG
68651 TGGCAAATGC CTATAATCCC AGCTACTCAG GAGGCTGAGA CATGAGAATC
68701 ACTTGAACCA GGAGGTGGAG GTTGCAGTGA GCCGAGATTG CACCTCTGCA
68751 CTCCAGCCTG GGAGACACAG GGAGACTGTT TCAAAAAAAA AAAAAAAATT
68801 AGGTTTCTAA TGGAGCAGAG GGGGAGAGAT TTGATCTGGG AAAGGCTTGG
68851 GGAGGTTCTG TCTTGGCTGG ACAGGGATTT GAAAGGATGT TGTGATGATG
68901 AGTGGCCAGG AGGTATGGGT TAGGAAGAGG AAGGGTGCAA TGGCCACTGA
68951 GGTCCCCTCC AACTCGAGGG TTGTGTGATT TTGACAAGTT CTGATTCTAA
69001 GGACTGAGGT TGTGTAAGGC GGTGCACCTG GTTATACTTG TCTTCTGTCG
69051 GCAGCCAACT CCTCCTCGCC TACGGCCTAT CACCAGCTTT CCAGCTGGTG
69101 GTAGTTTTAT TCAATGGAGG CTTAAAAGCC CTGACTTTTG TGGCGAGTGG
69151 GTGGACAGTG GGGTGGGGA GCATGACTAG GAGGCAGGAG GGCCAGGAGA
69201 CAACTCTTAA GAAATGCGGC AGCAAATGAG TAGGAAAGAC AGATGGTGGC
69251 AGTTTCAAGG GGTATAACAG CTTTTTCCTC TTTCTTTAAT GATGGAGGGG
```

```
69301 GAGAAATTGA AGTTTTAAGA AGTGATAAGT GTTGAAAGTC CCAAAGGAGA
69351 GGAAATGAGG GGAGATCAAG ACCTTAGATG GACAGGTTCA CCTAGATAGA
69401 GTCACCTCTG ACTCCAGAA AAAAGGTGAG ATAAGTAAGG AAGCCAAGGG
69451 CTGGGAAGGT GGAGGGGCCA GTTGTTGGAA TTGACCGTCC GCCAAATGTT
69501 AATAGAGGGA GAAGTGACAT TTGGCTGAAT TCCACACACA CTGAATGTAG
69551 CAGCCCCTCG CCTCAAGGAG TTTTGTATCT AGCAGAGAGA GAATGTCTAC
69601 AAGAGCATGG CAGATACATC GTGGGGTCGA AAATGAGTAC AAGTGGAATG
69651 ATTGGGGGTT ACATTTAAAG AGAAAACCAC AGCCACTGGG GGAGTTTCGG
69701 GAAAGGTCTT GGGAAGAGGT GACATCTGAG AGGCACCTTC CGTGCTAGGC
69751 CCAGCCCAGG GTAGGGAGGG ATCATGGGCA GGGTGTGTTT TTGGAACAAG
69801 TTATCCCAGG GTATGTGTAG CTCTTGGGAA GGGCAAGCTG GGGTCAGATA
69851 GTGAGGACTG AGTGCTAAGA TGAGAAGTTT TTCTTCATTT CTGTGGACAT
69901 TGGAGAGTCT GACATTTTTC AAGTAGGGGA CTGATGTGAT TAGAAATACA
69951 GTTTGAGAAC CACATGTTGG CAGTGTGGGA TGAATGGGGG AGGAGGGCTG
70001 GGCCTGGAGG CTCAGGCAGC CATCTGGGTA ATGAGCCGGT AGCGGGCTGG
70051 GAGGTGAGAG GAGGTCTTAA ATACCACAGC TATTGGGGAC TTATAAAATT
70101 TTAACAGCCT TTTCAGATTA TACTCTAAAT CAGCAGACAC TTAGATCTTT
70151 TTAACACCTT TTTCTGTTGT ATGGTATGGT GATAAATGAT GTATTAAATT
70201 TAAGTTTGGT TAATTTTAAT TGGTGTAATT TGTATTATCC TTTGAGTCGT
70251 AATTTATGTG TAGAAAATAC AGTGATGTTG GGTAATTAAA ACATTCTTTT
70301 AACCAGAACA CCTATTTTGT GTAAAATAGG AGTCTGCATA TTAGGAAAAA
70351 AAAAAAAAAT CACATCACCT GACTGAAGTT TTCAAGCTCA GGATTCACTG
70401 TGGGTGTGTT GTCCCAGTGG AGGGTGTCGA GGCTGAAAGT GAGGAAGACA
70451 GTGATCACGC CTGGCTGGGC CTCCTGTATC CATACCTGCC CTCTCCCGTG
70501 TCCACTCCAC CTCGAAGCAG GAGGAATCTT TCAGGAATGC AAACCAGATT
70551 CTTGGCAGTC CCTTGCTCAT AGCTCTTCAG GGGCTACTCA TGCTCTTGGA
70601 ATAAACAATT CCTTGTCACT GGCACCTGCC AGGCCCTGCC CGGCCCACCC
70651 CTGCCCACCT TACTATTCTT GTTCCCCTCT ACTCAATCTT TGCGGGCAGA
70701 GATCACTTCC TCCAGCACAT TCTACCCTTC CCTTTGGGGC CTGCACTGAT
70751 GCCCCTGCCT GGAAATGCTC CTTCCTCGTT CAGCCCTACT CATCCTTCAA
70801 ATCTCAGCTT AAAGGCTGCC TTCTTGGGGA AGGTTTTGCT GATGCTTCAA
70851 TTAAGATAGC TCCTCCCGTG TTATAATGTG CTGTTCTCTC AGCCTCCCAT
70901 ACCTCTGCAC CTTGTCACAG TGGTTGTACA TCTCTCATTA TAATTGTTGA
70951 GGCTCCGCCA CCCCGACTCC CAGAATGCAT CCTTCCTGTA GGCAGAAGCC
71001 GGACTATCCT GCCCTCCACT CCTTGCCCAA TCCCAGCCCC AGGTTTCCCC
71051 TAGCCCCAGC CTGTGAGTGG GGCTGAGTGA CGGCACTATC CCAGAGCAGC
71101 TGTCCCCGCT ACAAGTTTAC CAGGCAAACC TTTAAAAAAT TATTATAAAT
71151 GATGACCATG AAACTGGAGG GGGTCGAGGG ATCACTCTGG GCAGGTTGCT
71201 GAAGCCTGCT TTCTGTGGGC TCTCTGCAGG GACATGGGAA TGACAGTTAT
71251 TCTGGGTCTC CTTCATCTCA ATGTTTGTCA ACAAGGAATT TTGCCTGGGT
71301 TAATTTATTT GGCAGACCTT TTCTCAGTAG ATAATGCTGT GATCAGCTTC
71351 AGCCCAGCCC GGATCAGATG ATCATCAAAG CCAAATGAGC AGTCAAAATT
71401 AATGACGTTT TGCTTTGCTT CATGAATATA AATACTGCAA GAAAATGGAG
71451 GGAATTGTCT TCCTGCCACT TTGGAGTCAT TCGTGATTTA AGTGTGCTGT
71501 TTTCCATGCA TGAATGTTTT CTATGAGAAC TATAAAGTTA CTGAATGTTC
71551 TCAGTAGAGT GACTTGATGT GTCATGTGGT ACCTTTTAGT GCAGGATCTA
71601 GGGACCAGCT TGGGACTTTG TCCTTGGGTT GGTACAGTGT GATTGTCACC
71651 GGGAGAGGAC TGCAGCTGCC AGGGGGTGGT AATTCTGTCC CAACAACTTA
71701 TAGAACCACA GGGACAGGTG GCAGAGTGTT GGGGCAATAG GCAGCCTGCC
71751 ACTCAGTTTT TAATCTATTT CTAGAACATG GTGCAGTCTA GAGACTTGCA
71801 GGGATTTGAT GCCCACAGTA CTGTGTCTGG TCCTGTCTGC ATGTGCTGTG
71851 GCCAGGGCTG TGCTGGGTAG AGGTGGGCGT GTGGGGCAAG GAGCACATGT
71901 GCATCTGTGT GCTCATACTC AGGGTGCTTG CTCTGGAGCA GCTGGTAGTG
71951 GGGTCAGGTG GGGTGGACGT GGAGAGGGAG GGCTCTGCAG AGGCCTTTCA
72001 GGGCTGAAGG GGAAGTGGGG AGACGGGTTT CCAGGCCTCT GTCCACCTCA
72051 ATTCTAGCAG CTCTGCATTT ACATATTGGA GATCCCCTCA AGATTTCAAT
72101 GGAATAAAAC ATTCATTCCA GGACTAAAAA TTTTGAAAAC CTGAAGTTTT
72151 CCTTTCTATC AGGATGTCCA GCAGACTCAA TAATTATATA TTGTTTGCTT
72201 AGCATTTACC AAGCATCAGG CATTTCGAAG CATTCTGTGT TCTTTCTTCA
72251 TGAATCCTCA CTTAGCTGTG CAAGGGATAT GCTAGTTTTA TTATCCCCAC
72301 TTACATATAA GGAGCCCGAG GCCTAGGTAT GCTAAGTGAG TTGTCTGGGA
72351 TTCAGAGTCA GGCCAGTGTG TCTACAGAGA TGGTCTCCAA CTCACCCACC
72401 TACAGCCAAG TCACTGAGTT CTTGGTCTCT GAGCCTGCAG AACAGTTTCT
```

FIGURE 3, page 23 of 40

```
72451 TGGTTTCTTC ATCTGCAGAA CAGGGAAAAT GAAATTTTTC ACAAAATCAG
72501 ACATCACGTG CAAAGCAGCC AGGAGTAGAA CATTGTAGAC ACTTGGTGAA
72551 TGTCACTCTT AACCAAGAAA CAAGACTGTG CCTTTGGGTT CAGCTGGCTC
72601 ACACATTTAT TTTGATGAAT TAGGTCAGTG TTTTGTTTGA TTATCACAGT
72651 GGTGAGGTCC ATGCAGGTAG CTGTAGGGTG GAAGAATCAC TCATCCTTGG
72701 GTCCTGCTCT GACACCTACA GGCTGTGCAG CCTGAAGATC TAGGGGAATA
72751 TCTGTTTCTT CCTAATACCT GTAGATTAGG GATCATTGCT TCTTCCTAAT
72801 ACCTGTAGAT TAGGGATCAT TGCACCAGCT TTCTGGGTTG TGTTGAGGTT
72851 GAAGTAAAAC GAATACATAC AGAAGTTCCT GCTGTTCTGT GAATATTTGA
72901 ATCTGCACCC ACTTGTAGCT TTGTGAGATC ACTCTTAACG GTAGTATTTA
72951 AGAACATTTG AACTCCGCTG TGGGCTCATG ATGAACTTCA TTTCTCTTCT
73001 GGCGGGTGGA CCTGTGCTCA TTATCATTCA ATGAATTGGC TCAGCATGCA
73051 GGATGGCATG CTGAGATAAA CGCTAGCCCT TACTTTAGAT TAAATACCCC
73101 CAAAAGAGAG TGATCAACAG GAGAAATCG AAGCCAAAAA AGATCATTAA
73151 AGAGTTGTTT AGGAGCAGAT ACGTGTTCAT TGTTAAAATT TCCCAGCTGA
73201 AAATCTAAAC AAACAGCACT TGAGCTTTCA GAAGAAAATG CCATTTGTAA
73251 CATTGAGATT TGCAAGGCAT TTGGTGCCAT GTGAGTGCCG CTTGCCCCTG
73301 TAGGTGAGTC TATGTAGACC ACGAGACAAG TATTCAATAT GCAAATTCCT
73351 GATGGCACAT AGGGAAGGAT TTAAAAGAAT GATTCTCATG CTTTCTAATC
73401 AAGTCACAAG GGGGCAAAAT GTCCTTTTTC ACCACCTCGA CTTTCCTAAG
73451 AGTCCCTAGG AGAGCATCTG TAGGTAATAG TTTTCATCTA GAATCTGTTA
73501 AATAGGTATT ATTTATTTTA CTCATATAAA TAGTTAGGAT TAAGGGTTGT
73551 TGCCCTGCAC TGCTAACGTG GGGGCCGGGG TGCAGACCAC TTCTCTCTTT
73601 GGCATGCAGG TTGTTTGCTG TGACTACTAC ACATTTTTCT GCACTGGCTT
73651 CAGAAGTTAA GCCTTGCAGG CATTCTTCCT GGGCTCCCTG AGCAGCTGTA
73701 ATCACCCTGA CCCCAAACAC TCTGCACATC AGTTCACCTC AATTTTAAAT
73751 CCCTCAGGCC AACCGCTGTG GTCAGTCGGC ATTGCCCTAA GCTGATGGGC
73801 CTGATTAAAC CAAGAGTGGC ACACACTGCC CTCCAGCCTA GGATATGCAA
73851 TGTCACTTTT CTTCTCACGT TTGCCTAGCT AATTTCCAGT TACTCTTCCA
73901 GACTCATTGA TGAGGCAGGA ATCGCTTTTT CTGGGAAGTT TTTCCTGATT
73951 TTCCATCACA CGTGGATGCC CCTTTCTACC TTTCCCCTAG AATGCCTTGG
74001 CTTATGCAGT TATGAATATT TCCACAAGGT GGCGCTCATG TCAGTGTCCT
74051 CCCTGCCCCT GGCCGCCTTG CTAGCCCCGG AGTACACTAG GAGGGCGCTC
74101 GGGTCTGCCT GCATCTCCAG GCCGGGCACA GTCTCTGATG GTAATAGCTT
74151 GAACAAATGT TTGCTGAATT CATGAATTTT AACATGTTTT CCTTTTCTAG
74201 TGTAAGGATT ATCAAAATTA AGATTTAAAG CTTCTCGCTT CTGAGACAAC
74251 ATTGCCATTA TTTAATGGTG GAGGTGTAAA GGGGGATGCC GAGCTGTATA
74301 CTCCAGAGCT CTCTGAGGAG GGTCTAATTC AGCGGGTCTC CCCATGGCTT
74351 CGCATCAAAA TGGCAAGGGG CTTTGAAAAA ACACCCACAC TTGAGCTCCA
74401 CCTAGGAGCA AAGAGACCAT ATAGTCTCTG AGGGTGAGGC CTGGTATTTG
74451 TGTGGTTGCG GGTTTTTTTT GTTTTTTTTT TTTTTTTGA GTCTTGAGGT
74501 GATCCCGAAG TGCACCCAGG AGTAAGAGAG GCGGGCGAAA GTGATCAGAA
74551 GCGACTCCTA TTTCCTTCCT GTGGCTCGTT ATCGTCTCTC AGTGGTCACA
74601 GTCCTTTCCC AGGCCACCCC CTGTGTCCAT CTCAGGTGGG ATAACCTCAT
74651 GACAGAGTTT GGGAACGCTC AATAGAGTCA CTTCCATAGA AAATACGTCT
74701 TCCATTGCTC AAGCAAGAAG AGAATTTGAG CATAGGACAG GAATATTTTA
74751 ATCATAATAA CTGAAAAACA CCAGCAACAA TATAAACAAA AAGATTGCCT
74801 GTATTCATTG GGAATGCAAG TTTTATCTGT GTTTTGATTG TGGTGAAATA
74851 TACGTAACAT AAAATTTACC ATTTTAACCA TTTTGAAGTG GACAGTTCAG
74901 TGGTATTCAA TTCATTCACA TTGTTGTGCA ACCATAACCA CTGTCCAACT
74951 CCACACCTTT TCCATCACTG AACCAAAATT CTATGCTCAC TAAACAATAA
75001 CTCCTGACTT GCCCCTCCCC TCAGCCCCTG GTTACCACAA TTCTACTTTC
75051 TGTCTCGATT AATTAGACTA TTCTAGGTAC CTCATATAAG TGGAATCATA
75101 TTTGTCCCTT TTTTTTTTTT TTTGCTTATT GAGCATAATA TCTTTAAGGT
75151 TCATTCATAT TATATTATGT ATCAGAATTT CATTCCTTTT TAAGGCTACT
75201 AATATTCCAT TGTTACGTAT AGTCCACATT TCGTTTATCC ATGCATACAG
75251 CCATGGACGT TTGGGTTGTT TCCACCTTTT GGCTACTGTG AATAATGTTG
75301 CTATAAACAT TGGTGCACAG ATATCTGTTC GAGTCCCTGC TTTAGATTCT
75351 TTTGGATGTC CAAAGTAGAA CTGTTGGATC ACAGGTAATT TTTTGTTTGA
75401 ATTTTTTGAA GAATCACCAT ACTATTTTCT ACAGCAGCTG CATCATTTTA
75451 CACTCTCCAC AGCAATGCAG GAAGGTTCCA GATTCTCCAT ATCCTCACTA
75501 ATACTTATTT GCTTCTGTTT TGTTGTATTA GTTTTTTTAA TAATAGCCAC
75551 CTAATGGGGA TGAAGTGGTA TCTCATTCTG GTTTTGATTT GCACTTCATG
```

```
75601 TGCTTCGTGG CCATTTGTAC TTCCTTCTTA GAGAAATGTC TATTCAAGTC
75651 CTTTATTTCT ATAAAATGTT TATGTATTTA TTTGACTTCA CCAACAGAAA
75701 TGGATTTTCT CACAGTTCTG GAGGCTGGAG GTCCAAGGTC AGGGTGTCAG
75751 CATGTGAGTT CCCTTGAGGC CTCTCCTTGC TCACAGATGG CCTTTCCTCT
75801 GCGGCATGCA TTCTCCACTC TCTCCTCTTT TTATATCAGT CATATTGGAC
75851 TTTGCCCATT TTTGAATTGA GTTGTTTGGT TTATTCTTGC TGAGCTGTAG
75901 AAATTCTTTA TATTTTGGGT ATTAATCCTT TATCAGATAT GCTATTTACA
75951 AATATTTTTC CCATTCTATG GGTTACCTTT CCCACTCTGT TAATACTGTT
76001 CTTTAATGCA CTAATGCTTT AGTTTTGGAA GAAGTCTAGT TTATCTATTT
76051 GATTTATTTA TTTTTATTTT TTATTTTTTG AGATGTAGTC TCGCTCTGTC
76101 CCCCAGGCTG GAGTGCAGTG GCATGATCTC GGCTCACTGC AAGCTCTACC
76151 TCCCGGGTTC ACACTTTTCT CCTGCCTCAG CCTCCTGAGT AGCTGGGACT
76201 ACAGGCACCC GCCACCATGC CCAGCTAATT TTTTGTATTT TTAGTAGAGA
76251 CGGGGTTTCA CCATGTTAGC CAGTATGGTC TGGATCTCCT GACCTCGTGA
76301 TCTGCCCGCC TTAACCTCCC AAAGTGCTGG GATTACAGGT GTGAGCCACC
76351 ACACCCAGCG TACCTATTTG ATCTTTTGTC GTCTGTGCTT TTGGTGTCAT
76401 ATCTAAGAAG TCACTGCTGA ATCCAATCTC ATGAAGCTTT CCTCGTTGTC
76451 TTCCAAGAGT TTTATAGTTT GAGTTCTTTA GCTTTAGTCT GCTGTTAGAG
76501 AAAGAATAAC AAACCTTCAT TTATCCAGAA TGGTTGAGGG TTGGGGGCAG
76551 AGTATGGTCT TTTTTATAAT TAACTGTAAT AAATTTTACC ATTTCTACAT
76601 TCCTCCATCC ATTAAAAGA TCAGGATTAG AAAGTAGGAA AATATCTAAA
76651 ACCATGCTGG AAAACAGAAA AGGACATGTA CAATGAAGCT TCTGGGAGAA
76701 ATGTGAGGCT AAGTTTGGAT GGACAGACAG ACAGAGGAGG GGGATCATAT
76751 GAGAAGTAAG AGGATGGTGT CCTCATGGGA GCCCCTGGAC ACCCCTATTC
76801 TCAGAGTGCA GAGATCCAGT GGGCTGAAGG GGGCCGTGCC TCAGACACAT
76851 GCCATCAAGC CCCTACACAG CTTCCTCGCA TGGCAGAGAA TGCCCCCACA
76901 TCAGGTGGGG GTTGTGTGGT AAGCTCCTGG TTCTGCCTGA CTTCTGGGCA
76951 GTTTCCTCCC ATTAACATGG AGGGAAAGGC TCTATCACAG CCCACTGGTG
77001 AAGCCGCCTC TGAAGTGTTG AGTTTCCCTG AGTAACTCCC TGGTTTTTCT
77051 GTGGAAACCG CTCAAAGTGG CCACAGGTGT ACCTAAAATA AAGCCTCTCA
77101 CAATTGCTAA CAAAGACCAA TACAAGCCAT CAATGCTGTT CAGCCTTGAC
77151 TTCTGTTTGC AAATATGAGT AGATAATTAA AAAAAGTAAA CCAAGACACA
77201 GGAGTTCCCA CTGAAAGAGT ATAGGAATCA AGAGAGGGCT TTTAAAATTT
77251 CTAGAGTTCA TTCTCAGATT TTAAAGATG TGGCATCATA AAACAAGAGC
77301 CAGCAGCTGT GAGGAAAGAG TCATTGGAGA GCAAGGATTC CTGTAAATAA
77351 AAGGCATGAC TGCTGGAATA ACCTCATGTG AGAGGGTGAC AGCATCGAGG
77401 CTCTAAGTGT CAGTGATACT GTTAGGGTTG CAATGCAGAG GAGTGGATCC
77451 CAAAGCCCTC CTGGAAGAAT CCTCCAGGAA TTCTTCCAAA ATAGGAGCAA
77501 AAGTACAAAG AAATAGAAAT GTCAGTGGAA GGAGACTTAT AAATCCAGCA
77551 TGTTCAGTAA GAGTTTCAGA ATTAGAAAAT AACTATATAT GAAATATCAA
77601 GAAAGAAACA GGGCTGGTTG TGGTGGCTCA CATCTGTAAT CCCAGCACTT
77651 TGGAAGGCGA AGGCAGGAGA ATCGTTTGAG GCCAGGAGTT TGAGACCACC
77701 AGCCTGGCCA ACATGGTAAA ACCCCATCTC TACTAAAAAT ATAAAAATTG
77751 GCTGGGCATG GTGGTGCACG CCTGTGATCC CAGTTACTCG GGAGGCTGAG
77801 GCAGGAGGAT TGTTTGAACC CGGGAGGCAG AGGTTACAGT GAGCTGAGAT
77851 CATCCCACTG CACTCCAGCC TGGGTGACAG AGCAAGACTC ACAGAGCAAG
77901 ACTCTGTTTC AAAAAAAAAA AAAATTAGC CAGCTGTGGT GGTGCACGCT
77951 GTAGTCCTAG CTACTTGGGA GGCTCAGCCA GAAGGATCAC TTGAGCCCAG
78001 GGGATTCGAG GCTATAGTCA TGCCACTGCA CTCCAGCCTG GGTGACAGAG
78051 TGAGACTCTG TCTCTAAAAA TCAGAAAGAA ACAGGATACA AGTTCCTATA
78101 ATACTTGAGT TTTGAGAGTG ATTCCATTGC CAGGTTTGAA TTTGGGCTCT
78151 GCTACTTCCT CAGAGTAAGC TTTTAAGCAA GTTACTTAGC CTCTCTGTGC
78201 CTCCATTTCT TCATTTGTAA ATTATGGTAG TAATAGTATC TACCTAGTGG
78251 GGTCACTGTG AGGATTAAGC AGGTTAATAC AGACAGAGCA CCTAGGACAA
78301 GGCCTGGTTC ACTGTGAATG TTTCCTAAAA TGTAGCTGCT GTTAAGCCAA
78351 CCGTCACTGC CACCACTACT CTTAGTTCTT AGAATGTACA GGTATGCGGC
78401 TGCCCTGTGA AAGCTTCACA GTCGGTCCGG TTTACCACTC CAGTCTCTCT
78451 CTCTACCTCC TCTGCCGCAT TGCCACCTCC ACCCCCACCC CCACCCACAC
78501 GCCCCGGCAT CTCTTACCTG GACCAGCAGT AACCTCCTAA CTAGCTCCAC
78551 AGCTTCATTT CTTATCCCCA ATAAATATGCT CCCTGACCCG TTAGGCTCCA
78601 GGTTAAAACA TTTCTGCAGC TCCCCTTGCA CTTCGTTTCT CCATGGCCTC
78651 CCAGGCCCTG CATGGTTGGG CATCCCACC CCCGAGCCTC GCTCAAGTTA
78701 TTTTCCTTGT GTTCTCTGTG CACTCAGCTT CAGTGGCTTG CTGTCCCATC
```

```
78751 TCACAATCCC GCCATCACGT GTACTTGTCT CTGCCTGGAA GGCTCTTTCC
78801 TCAACCCACC TGCCTCTCCC ACACCATCCT TCAGAGTCCA GCTTAATCAT
78851 CCTTGGTCCA CCCTGGAGGG TCAGATTTCT TCACATAGCA CCCGCACCCT
78901 TCCTTCATAG CACTCACCAC CGTGTGTGCA CCTGCACTAT TAGCCAACAT
78951 TCCACCTCCC TGACAAGCCT GCACCTGGGC TATAATGACT CTAAGATGCA
79001 GATCATGACT GATTTTGCTT ACCACCTTCT CCCCAGTCCC TGGCACTTTG
79051 CCTGGTATGT ATGTTTTGT TGAATGAATG AATGAATGAA TGAATGAATC
79101 CTAAGTTTAG AACAACTGTG CCAGGATTTA ATAATAAAAC AATCCCAAGG
79151 GTATTCACAG GGGGTCAGGG GGAAAACTGC TTCTCTATGA AGGAGGGAAA
79201 AATCAGACTA GCATCAGGTT TTTTTCTGTA ACACTGAATG ATACAGAATA
79251 ATGGAGAAAG GTGTTTAGAG TTCTGAAGAA AAGAAATGGA TCCTAGGATT
79301 TTTTGTACCC CGTGAAATCA TTATGTCTGT GTGAGGGCAA AAGAGACATT
79351 TCAAATATTT TTCTCAAAAA ACAAACAACA ACAACAACAA CAAAACAAA
79401 GTCACTTAAG GAAAGCGCTT TAGCCAAAGT GAATTAGAAT AAGAAACTAA
79451 AAAATAGGAA GATTGCTGTA CCAGATAAAA TAGTAAGCAA CAAAAGTGGC
79501 AATTTTAACA ATTAAAAGTG GATAGTAACT AACATGACTG TGAAGTTTAA
79551 AGCTGTTTGT TGGAATCTGG AAATAGGAGA AGCAAAGTGA AAATGAAGTT
79601 TTCAAATAAA AACGTTGGTA TATTTGAATG CCTGCTGGTG ACGGAGAGGA
79651 TAGGAAATGG GAGAATAGGT GCCCACTAGC AGATGTAGTC TCATTCAAAA
79701 AGGTAAGGGG GAGGGGGGGC AGAGAGAGGC TTTAATTCAT GATGATAAGA
79751 GAAATATCAG TTCCTTAAAA GCTCCTTAAA CAGTTAAAAA TATTTTAAAT
79801 AAGGAATTTT AAAGGTAACC ACAGTAGAAT ACATATAAAA CAAAACCTTT
79851 TCAACAATTA GAGGAAGAAG AGAAACCAAA ATGAATTCAA AAAGAAGAAG
79901 GAAAAAAAGC AAAAAAAAAA AAGTATGTAA TGCACCTAAG ATAAAACCAA
79951 ACATGATAAC CACACTAAGT GTGAAAAAAA TTAAATTGCT CTAAATAAAA
80001 CACAGCAGCA AAGCTATATC TCATATAAAA GACATGTAAA AATGTGATGG
80051 AGATGGACAA TAAAGAGATA AACTATAGTA TCCTAAGGAA GGACAGACAA
80101 CAAAAGAGCA GGAGTGTTCA CATTCGTGTT GAACAAGGCA GAAGTCAAGG
80151 ACAAAAATAT TGAATGAGAA GGAGAGGAAC ATTTTGTATT GACGGAAACT
80201 ATGTATACTA CAAAAGTACA GCATTCATCA GCCATTGTGT ATGAGTTATC
80251 AATGAGTCCA AAAACTAAAG GCAGACATAG ATAAAAATAG AAAATTTGAC
80301 AAAACCATAA TCATAGTAGA CATGTTTAAC ACACTTATCT AAATCTGACA
80351 GATTTAAGTA GACAAAAGGC TGTAGAAAAT GGAATATATA AAAAACTTGA
80401 TCTAATAATT ATATATAAAA CACTGTACTC AATAGACACA GAATATACCT
80451 TTATTTCAAG TGTTCATGAA ACATTTATAA AAATTGAAAC TGTATCAGGC
80501 CATAAAACCT TAAAAAAGTG CTTGTATAGG CTCAAAGCAC TACACTAGAA
80551 ACTAACAAAT AATAAATTAC ATAATAATGA TAATTAAAAA GTGGAGTTAG
80601 ATCTGTTGAC AAGTAGATGA CCAGAGGTAA ACTGACAGCA GGGCTGGAGA
80651 AGCATGGATG GTTTGATCCT TGCTCAGAAG CCTGGTCCCT GGCCAGTCTC
80701 TCCCTGTGCT TCCCCATCAG CATTTGCAGG GAGGAACACA GGATTACAAA
80751 GGTCATGGCT GGCTTATGGA AACACAAGCT GAAATTGAAT CTCAGGTATC
80801 TATGCCTTTG TACCTTAGGA CAGTGTGTTT TACCCACAGT TCTTTTTAAA
80851 GTGGGGAAGC GTGGACAGTC TTACAGGCAG GTGCCTTGAG CAGCTCCACC
80901 CCCGCCGCCA CCACATTCAT GTCAGTCTTG GCCTGAACAT ATCTTCAGGC
80951 TACACCAAGG TTCAAAGCCA ATGTAAGGTA AGATTTGGCT ACAGGATTTT
81001 GCATGCAGAA ACCATCAGCG CTGTTAGAAG CCCCTTTGAA GGAGTGAGAA
81051 GGAGAAAAAC CTGTACAGAG GAGAGCGTAC AGGTTACTCT AGGTACTTAA
81101 GACCAGGACT TGATGGTAAG AGAGCCTACA GGAAATGTCC AGGAAGAACC
81151 CATAGCTCTG CAGAAGAGGC AGAGGGTCGG GGGAAAACTG CCTGGCCATG
81201 GAGTGAGAGT TGGACCACCC CAATCCTGCT CCTTCTCTTT TGTGTCTTGG
81251 GTGAAAGAGT GAAATGCCTT CCAGGTTCTG ATGTAAGCTC CTTCTTTGTC
81301 CCAGTGTCCA GGCCTGCACT GGTGACCTTC TCCAGCACTC TCTGTACCTG
81351 TGCTGAACAC CCCCGGTGGG GCCCATCTGT CTGCTCTTAC CTGAACCATC
81401 TAGTGCAGCA GACACTTTGC TGGTCTCTCT ACCTCAGGCA GTTACCATAC
81451 TGCTGCCAGA GAAATTTTCC TAAAATTGAC TTTTGATTAC AATCTGGAGC
81501 CAAGGTTGCC TGCCACAGAG TAGGGTGCAG AGTCCTGGGC ACAAGCAACT
81551 TGACAGCCTT GTCACCCATC ATTGCTGCTC CAGCCTAAGA CTTGGCCTCA
81601 CAGGTCTCCC TTCCTCTACA TGGATGCTTC AAAGTCCCTC TCAGATTTCA
81651 GTGTCTCCAA AGCCCTTACT CATTCTAGTC AGATAGCATT TGCTTCTCCA
81701 ACTCCTGTGC TCCCAAAGCT CTCTACTTAC ACCTTTTATA GCATCTGTGG
81751 CACAGCTGTG CCCATATCTG TTCTTCTAAT TAAACTAGGA GTTGCCAGAG
81801 GGCAGAGACC ACATTCAGTA TTGTGTTACC AATACTGAAA ACCAGCAATG
81851 GGCCCCTAAA GAGCTTCTGA ATGAGTGAAT AATATCAAAA GGAAGATGAA
```

```
81901 AAATGAAAGA TAACATCCTT TAGATTGGTG AATAAGAATG CTCTTTTTA
81951 ATGATTATGC TTAACAAAGA ATGCTTACTA TGTTTCCAGG TAAATATTTG
82001 TTTACATATA TTCATTTAAG ATTTACAATA ACCGTATAAG ATGATAGCTA
82051 TCTGCATTTT ACATTTGTGT AAACCAAGGC ACAGAACAGT GAAAGTACCT
82101 TCCTGAGTCA CTTTAATAGT AGATGGCAGA GTAAGGATTT GAATTCAAGC
82151 CCTCCAAGTT ACAAGCCTTT ACTCAACTAC CGTCCTTCCC CGCCACACTA
82201 TTTCATTAAA ATAGGTCTTT AGGAAACTCT GAAGATTTCC AGTCAGAAAC
82251 CAACATAGCT TCCATGTGAA ACTAGGAGGT GATGTAATAG CTTCATTAGT
82301 GAATCCCTGA AGAGCTACCA TTTAAAAAAT TATTTCACTA GGATTGGGGA
82351 ATAAGTACCT TCTTCACCAT GCTCTGCTAT ATTTTCTGGG TTGGACTAGA
82401 GTGGCTTAGT TTGACCAATT CAGTAGTACC ATGGCCTCTT ACCCAGGCCA
82451 TGTCAAGCAT GTTGACTCTG CCATGCCCAG CATATACAAG TAAACTCTGA
82501 AGGGTTTATT TCCCATCAGA GTCTTTTGG TTCTAAACTT CAGTGTTAGT
82551 TGTGCCCACT AAAAAATAAT TCATGGATAT TTTCCGTATT CAGTTAATTA
82601 AACCCCTTTA TATTATGTTT GGTTATTAGG ATCAGATTTT CCATCCTTGC
82651 TCAGCATCCT GATTGTTTCC TTAGAAGATT CAGTTTTCTA TGATGGTTTT
82701 TTCAGAGTAG AGATTTAAAT GAATTGTTTA TAGATTAAAT AAAGAACACT
82751 TCTTGGAAAT GCAGAGTGTT TCACTTTTTT CCATGGAAAA TAATGACTGC
82801 TAAATACCTT TGAGGAATT TTTAAAATTA GACTTTTACT TAAGTTTCAC
82851 CTTGAAGCAA TTATAAAGTT TCAGTCAGTA GTCAGCAGAT TAACAGACCT
82901 GTTTAACAAC CAAGGCATGC TTTTTCATTC TTCTTCCACA CCAGAAGAAA
82951 ATAATTCTAA ATTATAATTG GAAGTAAATG CGGGAAGCTA TGGTTCTGTT
83001 TACTCAGTAG GAAAGGGTAG ATTTGGAAGA AAATCTATCA TGGCTGTGAA
83051 AGAACACTTC ATGACATATG AGCATTCAGT CTTAGAGCCA TGAAAATTAT
83101 AAAGGAACAC TTGCAGGAAA CAGTGGCAAT TTGGGATAGT AAATAAGCAA
83151 AGGAAACATT CCTTTATATA GCCTTCTTTT CTGCTTTCTA TATTTGATTT
83201 AAATCTAGTG GAAATGATTC CTAAATCAAT TTTACTAACA CATTTGTTTC
83251 TCACTTGGAT AGTTTTGAGA TGCCAGGGCT GGAAAGTACA GGGCCAGGGG
83301 AAAAAAAAGT AGTTAAGTAG CAGTTTTCTG TTTTCAATCA TCAAACCCTA
83351 CATTACAGTA TTTTGTTTTT CTTCTATACT TACCTATAAT GTGGTACTGG
83401 GATTTGGGGT TGCAAAAAGA GTAATGTCAT TGGGAATGAC AGAGTAAGGA
83451 CTTCTGAATA TTCTCATCCA TAAAAACAGT GAGAACACTG GCAAAATTTG
83501 TCAAAGTCAA CTTCTTAAGA ACTATGGAAA TTAGCTAAAA GTATGCAAGA
83551 ATCTGGGGAG TTTTGTTTTT TTTTTTTAAA AAAAGGCTAA ATCTTGGTAA
83601 GAGCAGTATT GTAGTATATC AATTTGCCCT ATTTCCATCC CCTTCTCTCC
83651 ATTTCCTCCA TGGTAGCTTT GAAAACCAAC AGCCCTGTAA TTGTGGTGAA
83701 AACCAGCAGC ATAGCAGTTA CTAGAAGGGC AGAACAGGGT TGGAACTCAT
83751 TCAGAGCTCC ATTTTAAGAG AATTGTCATT ATGTGATCTG TCCAGCAATT
83801 CCCTAGAAAA CCCTGTTCAC AAGGCTTGTC TTTATTTGAC CTCATTCACT
83851 AGAGCAAACA GGCTTTTCCC TGGGGGCGTT TGTCAAAAAC AGCTTGTGGT
83901 GATTGTTTAC CATCACAGCT CCCTGAGGCA ATAACAGTTG TGGCAAACAA
83951 GCTAAGCAAA AAACTTCATT CCGTAGGGGC ATTTGAAAAG CTCTGACATA
84001 TTTCTGGAAG GCCTTGTGGA TGTGTAGGAC TATATGCATG CCCAGGGCTA
84051 TGTGCTTGTT CAAGAAAATC CTTACAAGT CCTCAGTCCT CCCCCTCTTA
84101 GTACTGTGAG CCCCTGTGCA ATCAAGAAGT GAAAACTAAA GCAGTTGTAC
84151 ATTGCCTGGC TGAGTGTTGA AAGCATGCCC AAATGGACAC AGAGCATCTT
84201 GGCAAAGACT GAGAGACTCT GGTTCCAGGC ATTTAAGGAA ATCTGTGTCC
84251 AATATTTAGT TGACCTCTTA AGCTAACTGA ACACAGACTT CATTGCCCAC
84301 ACTCAGCAAA GAACACAGAC TTTACAAAGT TAGTTCAAGG AAGTCACTAA
84351 AACGATAATG ACAACAATAA AAGAACAACT AACCTTAGAG CATCTGATTT
84401 CCAGAGTTGT CACATTATAT TATTTCAAAT GTTCAGTTTT CAGCAAAAGA
84451 GTACAAGACA TGCAAATAAA CAAGAAAGCA TAACCAATAC ACAAAAAAGA
84501 AAGCAGTTGA TAGAAACTGT CCCTGAAAAT GTCTGGACAT TATATTTGGT
84551 AGGTAAAAAC TTTAAATCAG ATATTTTAAA TATATGGAGT CCACTAAAGA
84601 TAACCATGTC TAAATAGCTA AAGAAAAATG GGAGAATGAT GTCTCACAAA
84651 TAGAGATCAA TAAAGAGATA GAAATTATAT ATTTTTAAAA AGAACCAAA
84701 TAGAAATGCT GGAGTTGAAA TGTACACTAA TAAAACAAA AAATTCAATA
84751 GAGGGGCTCA AGCAGTTTC AGCAGGCAGA AGAATTAGTG AATTTGAAAC
84801 ATAGATAAAT TGATATGATC CAGTTTAAGG AACAGAAAAA AGAATGACGA
84851 AAAATGAACA GGACCTCATA GTCTTATTAT TCACATATAC TAATATACAT
84901 ATTATGAGTC GTAGAAAAAG AGAGAAAAG GGACAAAAAG AATATTTGAA
84951 AAAAAATGTT AGAACTTCCC AAATCTGTAT GAAAACATT AAACATCGAG
85001 GAAGCTCAGT GGATTCCAAG TAGGATAAAC TCAGAGATTC ATACCTAGAC
```

```
85051 ACATCATAAT CAGTTGAAAA CCAAACATGA AGAGAATCTT GAGAGTAACA
85101 AAAGAAAACT GAATATGATT AACAAAGGCT CTTTAATAAG CCATTGTTTA
85151 TTAACAAAGA CTGATTTCTT ATCAGAAACC ACAGAAGCTA GAAGGCAGTG
85201 GGATGACAGA TTCAAAGTAC TGGAAGGAAA AAAAGAAAGA TCAACCAAGA
85251 ATTCTGTATC CAGCAAAACT ATCCTTCAAA AATGAAGGAG AAATGAAAAT
85301 ATTCCCAATT AACAAACACC ATGAAAATTC ATTGCTAGCA CATGTGCCCT
85351 ACAAGAAATA CTCAAAGGAG TCCTTTAGGC AAAAGTGAAA GGATGCTAGA
85401 CGGGAACTGT AATCCACATG AACAAATAAG AACACTAGTA AAAGTAACTA
85451 CATAGGTAAT TTTGAAAGGC AGTATAAATG TAATCTTTAT AGCTCTTTTC
85501 TCCTGTTTTG AAAAACAGCT ACATAAACCA GTCATCAGAA ATCTGGTTTG
85551 AGGAGCACAA AATGTATAAA GATATAATTT TTATGACAAT AATAGCCCAA
85601 ATGAGGGGCA AAGAATGGAT CTGTGTAGGG GCAAAGTTTT TTTATCCTGT
85651 TGAAATTAAG TTGGTATTAA TCTGAACTAA ACTGTTAGAA ATTGAAATGT
85701 TAATTATAAT CCCCATGGCA ACCTCTAAGA AAATAACTCA AATGATAAAT
85751 GACAAGAGAA TTAAATCAT ACACTAGGAA ATATTTGTTT AATAATAAAG
85801 AAGGCAGTAA TAGAGAAATA GAGGAATAAA ATAACATTAG ACATGTAGAA
85851 AACAAACTTC AAAAAGACAA ATGTAAATCA ATTTATTGGT AATTACATTA
85901 AACGTAACTG GATAAAAAAC CCAATCAAAA GGCAGATGGA CAGGATGTAT
85951 AAAAATGATC CAACTATATG CTGTCTACAA GACAAACATG TTAGATTCAA
86001 AGACACAAAT AAATTGAAAG CAAGAGAAGA GAAAAAGTA TATATCATGC
86051 TAACAGGAAC CAAAAAAAAA AAAAAAAGA ACGGGAATGA TTATATGAAC
86101 ACCAGACAAA ATAGACTTTA AGACGAACTG TTACTAGAGA CCAAAAAAAA
86151 GTTATAATGA GAAAAGGGTC ACTCTGTCAA GAAGATATAA CTATAAACAT
86201 ATACGTGACT TACAGCAGAG CTCCAAAATA CACAAAGTAA AAATGACAAA
86251 ACTGAAGGAA AAAATAATTC ATCAATAATC ATTGCAACTA TCAACATCCC
86301 ACTTTCAATA CTAGACAGAA CAACTAGATA GATCAACTGG GATAGAAGAC
86351 TTGAAAAACA CTGTAAATCA ATTAGATGTA ACAAACATCT ATAGAACACT
86401 CCACCCAACA AGAATGGAAT ACGCTTTCTT CTCAAAGGCA CAATGGAACA
86451 TTCTCCAAGA TTATATACCA TCTTAGGCCA TAAAGCAGGA CACAATTTAA
86501 AATAACTAAA ATTACACAAA GTATGGTCTT GGTTTATACT GGAATAAAAT
86551 CAGAAATTAA TACCAGAAAG GAGTTTGTGA AATTCACAAA TATATGGAAA
86601 TTATACACAC ACTCCTAAAA AAAATCAATT TGTTAAGAAA TCACAGGGAA
86651 AATTGGGAAA TATTTTGAAG AGAATGAAAA TGGAAAAACA ACATATGAAA
86701 ACCTATGGGG GTACAGCCAG AGTAGTGCTT AGCAGGACAT TTATAGCTTC
86751 ACATACCTCC ATTAAAAAGA AGAAGATCT CAAATCAATA ACCTAACCTT
86801 CTGCCATAAA AAAACAGAAA AAGAAGAGTA AACTCAAAAT AAGCAGAAGG
86851 AAGTTATTAG ATTAGAGAAA AATACAGAAT ATAAAAACAA TATAAGAAAA
86901 TCCATAAAAA TGTTTTTTAA AAACCAACAA ATTGGGAAAC CTTTACTTAG
86951 ACTGTCAAGA AAAAGGAGAG AAGCCTCACA TTACTAAAAT CAGGAATGAA
87001 AGCACGAATA TTAATACCAA CCTTACATAA ATTTTATGAG AATACTTTAA
87051 AAAATTGTAT TGCAACAAAT TAGATAACCT ATATGAAAAT GGACAAATTA
87101 TTGGAATGAC TATTAAAACT GTCTCAAAAA AATCTAAATA GGCCTATAAC
87151 AGAGAGATTG AATAATAAT CAACAAAACT TCCCTCAGAG AAAAGCCCAT
87201 TTTCAGATGG CTTTACTTGG GACTTCTACC AAACATTTAA AGAATTACCA
87251 ATTCTTCACA AATCCTCCAA AAAATAGAAG GGAACACTTT TGAAGGAATT
87301 CTACCAAGCC AATGTTACCC TGATACCAAA ACCAAAGACA TCACGAAGAA
87351 AAAAAAAAAA AAAAAAAACA GACAGACCTA TATCCCTTTT GAATACAGAT
87401 GCAAAAATCC TTAAAAAAAA AATACTAGTA AAGTGAATTG AGCAACATAT
87451 AGAAGGATT ATACACCATG AGCAGGTAAG ATTTATCCCT GGAATATAAG
87501 ATTATTTCAA ATATAAAAGT AAATCAATGT AACACACCAT ATCAATACAA
87551 TAAAGAACAA AAGCTGCACA ATTATATCAG TAGATGCAGA AAAAGCACCT
87601 GACAAAATTC AGCATTCTTT CATGATAAAA ACACTAGAGA GAACATCAAT
87651 AAACTAGGAA TAGGAGGGAA CTTCATTTAT TTGATAAAGC ATATCTATGA
87701 AAAATTCACA GCTAACATTT TTAATAGTTG AATGCCGAAA GCTTTTTCCC
87751 TAAGATCAAG AATAAGACAA GATGACCCCT CTACCCATTT GTATACACCA
87801 TTGCACTATA GCTTATAAAA GGCATCCAGA TTGTAAAGGC ATTAGTAAAA
87851 CTATCTCCAT TTATCAATGA CATGATCTTT TACATAGAAA AATCCTAAGG
87901 AACACACACA CATAACTGTT TTTTTGTTTG TTTGTTTGTT TGTTTTTAAG
87951 AGATTTCTT GAGGGTTTAT TTACATGGCT GTTTGGACAT CTCTGTTGAA
88001 AAGGAAAACT CTTTTTTTTT CTTTTTTTTA TTATTATTAT ACTTTAAGTT
88051 TTAGGGTACA TGTGCACAAC GTGCAGGTTT GTTACATATG TATACATGTG
88101 CCATGCTGGT GTGCTGCACC CATTAACTCG TCATTTAGCA TTAGGGTATA
88151 TCTCCTAAAT GCTATCCCTC CCCCCTCCCC CCACCCCACA ACAGTCCCTG
```

```
88201 GTGTGTGATG TTCCCCTTCC TGTGTCCATG TGTTCTCATC GTTCAATTCC
88251 CACCTATGAG TGAGAACATG CGGTGTTTGG TTCTTTGTCC TTGCGATAGT
88301 TTGCTGAGTA ATGATGGTTT CCAGCTTCAT CCATGTCCCT ACAAAGGACA
88351 TGAACTCATC ATTTTTGATG GCTGCATAGT ATTCCATGGT GTATATGTGC
88401 CACATTTTCT TAATCCAGTC TATCGTTGTT GGATATTTGG GTTGGTTCCA
88451 AGTCTTTGCT ATTGTAATA GTGCCGCAAT AAACATACGT GTGCATGTGT
88501 CTTTCTAGCA GCATGATTTA TAATCCTTTG GGTATATACC CAGTAATGGG
88551 ATGGCTGGGT CAAATGGTAT TTCTAGTTCT AGATCCCTGA GGAATCGCCA
88601 CACTGACTTC CACAATGGTT TTACTAGTTT ACAGTCCCAC CAACAGTGTA
88651 AAAGTGTTCC TATTTCTCCA CATCCTCTCC AGCACCTGTT GTTTCCTGAC
88701 TTTTTAATGA TCACCATTCT AACTGGTGTG AGATGGTATC TCATTGTGGT
88751 TTTGATTTGC ATTTCTCTGA TGGCCAGTGA TGAACACACA CAACTGTTAA
88801 TGCTAATTAA ATGAGTTTAG CAAGACTGCA TTGATACAAA ATCAATATAT
88851 GAAAATCAAT TGTATTTATA TACACTAGCA ATGAACAATC TGAAAATTAA
88901 ACTAAGAAAA TTTCATTCAC AATAGTGTCA GAAATAATAA AATGCTTAGT
88951 AATAAAGTAT GACTTACACA GGAAACTATA AAATATCACT GAAATGAAGA
89001 ACTAAATAAG TGGAAAGATA TGTTCATGGA TTAGAAGACT TAATATTGTT
89051 ATGGGTCAGA AGACTTAATA TTGCTAAAAT GGCAATATTC CCCCAATTAA
89101 TCTACAGATT CAATGCAATC TTTATCAAAA TTCTGGCTGC CCTTTTTGTA
89151 AAAATTGACA AGGTATTTGT TTCTAAAATT GATATGGAAA GTGATGAACT
89201 CAGAAAGAAG TTAGGGGATT TATACTTCCC AATTTGAAAA CTTATAAAAC
89251 TACAATAATG CCATCACCAG ATGGAGCGAC ATGCACCTTA TAGTCCCAGC
89301 TACTCAGGAG GCTGAGGCAG GAGCATCCCT CGAGCCCAGG AGTTTGAGAC
89351 CAGCCTGGAC AACATAGGAA GACCCTGTCT CAACTTAAAG AAAGCAAACT
89401 ACAGTAATAC AGTGTGGTAC TGACATAAGG ATAGCCATAT AGATTAATGA
89451 AATAGAACTG ACAGTGTAGA AATAAATCAT TTATGGTCAG TTGATTTTTG
89501 CCAAAGGTTC TAAGACAGTT CAATGGGAAA AAAAGTCTTC TCAAAAATTG
89551 GTTCCCAGAG TTATGAATAT GCTAAAACCG CCCTTAATCA TACCATATAA
89601 AAGGACAAGT TTTAATATAT GTGAATTATA TCTCAATAAG GAGGGGTGGT
89651 GGGCAGGAAA GGTGGAAACA CACAACATTC AAAAGGCAG TGTATGCTTT
89701 GCTGGGAAGA GGTATGAAAG GAGAGTTGGC CGGCTCAGAA TTAGAGGAGG
89751 TCCCACACAT ATCTTTCTTT CTCCAGCAAG TTCCATGACT GCACTGTGTG
89801 TATATACTTT TTAATATGAA AGTTGAAATC TCTTTTTCTT ATTGTTTAAC
89851 GTGGGGGGGG AAAGAGAGGC TTTTGAAATT ACCTGATAGC TATTGGTAAC
89901 ACTAAACATG TGTCAAGAGC CCAATACTCT AGGACAACTA CCCAGAGTGA
89951 TTATTACACA GAAAAAGCTG TTAGTATCTT TCTTGTGGCC AAACTATAAA
90001 AGTCTTGTTG CCAAAAGTCA TCGTTTAGAA ACTGGAACTA GTTCTTATTT
90051 GTAACAGCCT TGCTGAGATT AGATGATGTA TAGTTGGAGA AGAGAGAATG
90101 TGGCAGTGGG ATGAGCCTAT GGAGGTGAGG CTAAATTGAT ACTTACACAA
90151 TAGAAGAACT GAGAAGCACT ATTGATACTG TTAACTGTGG CTGAAGGAAG
90201 AAGAGGAGGC TTGCTGTACT TCTTCCTTTC CAATATTTCT GCCTTTTTTG
90251 TGGGGGTGGG AGCCTTATTT AAATGGCCAG GATCTCCAGG ACTTTGTTGA
90301 ATAAAGTCA AGAGCAGCCA TCCTTGCCTC ATTCCAATCT TCAGGGATTT
90351 AACACTCAGT CTTTCACCAA TTAAGTATAA TGTTGGCATT AGGTATTTTT
90401 GTAGATGCCC TTATTAAGTT GAGAAAGTTC ACTTCTAGTC TTAGTTTGCT
90451 GAGAGGCTTT TATTTCTTCT TTTCATTATT ACTAGATGTT AGATTTTGTC
90501 AAAGCATTTT CTCCAGCTAT TGTGATAGTC AGATTTTTTT TTTTAGTCTG
90551 CTAATATGGT GAATTACATT GATTGATTTT GAAATTTTAA ACCAACATTG
90601 CAATCTGGAG ATAATCCTCA AGTGGTCATG ATTTATTGTC TTTTTATTGT
90651 TGAATTTGAT TTGCTAAAAT TTTGAGAATT TTTCTGTGAT CATGAGGATT
90701 ATTAGTCTGT AGTTTTCTTG TAATGTTTTT GTCTGGTTTT GGTATCAGGG
90751 CAATGCTGGT CTTACAGGAT AACTTGAGAA AGATTTCCTC CTTTTCTATT
90801 TTCTAGAAAA ATTCATGTAG AATTGCTGTC ATTTCTTCCT TAAATGCTTG
90851 GTAGAATTTA CCAGTGAAGC TCTCTGGTCC TGGAGGGTTG TGTGTATGTG
90901 TGTGGAAGAT TTTAATTATA AACTTAATTT ATTTGATACA GGGCTATTTC
90951 ACATTATCTA TTTCTTCATG AGTGAGCCTT GTAGCTTGTC TTTCAAGGAC
91001 TTTTTCTATT TTGATCTAAG TTGTCAAATT TACTATCATA AAAAGTTGCT
91051 TATAATAGCC CCATATTATC ATTTTAAGGT TTGTAGAACC TATCTCTTTC
91101 ATTTCTGAGG CTGGTAATTT ATATCTTCTC TTTTTCCTGA TAAGCATGGG
91151 TAGAGTTTAT CAATTTTATT AACTTTTTTT TCCTAAATGA CTAGGTTTTT
91201 ATTTCACTTA TCTTCTCAAT TGTTTTCTAT TTCTACTTTA GTCGTTTCTG
91251 CTCTCATATC TATTAGTATA GTCGTTTTCT CCATTTACTT TGGGCTTCAT
91301 TTGCTTTCTT TTTCTAATTT ATAAAGGTAG GAGCTTAGGT TATTGAATTC
```

```
91351 AGACCTTTCT TATCCAGTAA GTGCTTAATG TTTTCTAAAA ACTAGTTTCC
91401 CATCTAAACA CTCCTTTAGA TGTATCCTAC ACATTTTGAT ATGTCTTGTT
91451 TTCATTTTCA TTCAGTTAAC CACTTTATCA TTTCCCTTTT GATTTCTTCT
91501 TTGGTTTGTA TTTTGCTTAG AATTATATTG TTTAGTTTCC AAATATTTGG
91551 GATATTTTCC AGGTATCTTT GTATTTACTG ATATCTATTT TAATTCCACT
91601 GTAGTCAGAA AACATATTTT GTACAATTTA AATTATTTTA AATGTATTGA
91651 GACAGATTTA TGGCCCAGAC TATGGTCTAA CTATCGTGAT AATGTTCCCA
91701 TGTGTACTTT AAAAGATTGT ATTCTGCTGT TGTTGGGTGG AGTGTTCTAT
91751 AAATGTCATT TAGGTGTAGT TGAAAATGTT ATTTAAGTCT TACATATCTT
91801 TCCTGAGTTT TCAAGTTTGT AAATTTTTCA GTCGTCATTT CTTCAAATTT
91851 TTTTCCCTGT CTCCCTCATT CATTCACCTT TGACTCTGTT CCTGTGACTC
91901 TGTACGGTGT GTGTGTGTTG GTCTTGCCTT TTCTGTTTCA TTTTGGTAGT
91951 TTCTGTCATT ATGTGTTCGA GTTACTCAA CTTTTATTCT GCAGTGTCTC
92001 CTCTGCTGCT AATCCCATCC AATGTATTTT TCATCTCAGA CATTGTATTT
92051 TTCATCACTG AGGTGTCTTG GGCATCAGGC ATTTTGAATT TTATGTTGCT
92101 AGATACTGGA TGAGAGAGAC ATATATGTAT ACACACAACC ATACATAAAA
92151 ACACATATAT ATGTAATGTT ATACTATATT ATAAATACAT ATGTATTCTT
92201 GAGCTTTGTA CTGGGACACA ACTGAGTTAA CTTGGAAACA TTTTGATCCT
92251 TTCCAGGCTT GCTTTTGAAG TTTGTTAGGC AAAACCATCT CAGCCTCTAG
92301 TTTAGGGCTA ATCAATTTGA CCTTACAACA GGCACGATAA CCTTCCAAGT
92351 TCTCCTCCAG GTGCTCCAGC TGTTACTAGG TAGCTCCACT CTGGCTACTG
92401 AGAATGGGAA CTAGTCCCCT CCAGTAATTG ATTCACCTGC TCCTTGCCAG
92451 TGGTTCTGTA CCTGGCCTGA GGTAGTTGTG TGAGCATTTG CTCTTCATAC
92501 TCAGTTGAAG AGTTGAGGAG AGCTGTCTAC AGATCAGCAG AGTTCTTCCT
92551 TCTCTAGTAC TCCACCCTGC ATATCCTAGT TGTCTTGGCC TCCTCAAATT
92601 CTCAGTTGTT TCCTCAATTC AAGGGGACTG CAGAGCTTTC CGGGTTCCCC
92651 TCCCTGTGGT GTAGCCTGAA AACATACTTC AGGCAGGAAG CTGGGGCAGT
92701 TGTAGGGGTC ACATTTCTCT TTTCTCAGAG ATCTCTGTCT CATGTGCCTC
92751 TTTTCCAATG TCTGGAAACT TTTTTCAATC ATTTTGTCTG CCTTTTCGTT
92801 ATTTAAAACA AGTGAGGAAA AACCAGTCCC TATTGCAATT TTGTCCAGAA
92851 ATGTAAATAG CTTGTTGGAC TTTTAAAGTC TTACAAATTT TCTACTCAGT
92901 AATCAGTAAT CATATATGGA GGTAGGCCCT ATCCCTCTGC CTGAGAGGGA
92951 ATAGTTATTC CTGAGTATCC ATAGGGAATT GGTTTCAGGA CTGCTACTCA
93001 TACCAAAATC CATGGACGCT CAAGTCCCTG ATATAGTGTT TACATATAAC
93051 CTAGGCAGAT CCTCCTGTAT ACTTTAAATC ATCTCTAGAT TACTTACCTA
93101 ATACAATGCA AATGCCATGC AAATTGTTGT TATACTATAT AGCTTTAAAA
93151 CTTGTATTAT TTTGACTGGC TGCTGTAGCT CACGCCTGTA ATCCCAGCAC
93201 TTTAGGAGGC CGAGGGGGCA AGATAACTTG AAGTCAGGAG TTCAAGACCA
93251 GCCTGGCCGA CATAGTGAAA CCCCGTCTCT GCTAAAAATA CAAAATTAGC
93301 CAGGCCCACG TCTGTAGTCC CAGCTACTCG GGAGGCTGAG GCAGGAGAAT
93351 CACTTGAACC CAGGAGGCAG AGGTTGCAGT GAGCCGAGAT TGTGCCACTG
93401 CACTCCAGCC TGGGCAACAA GAGTGAAACT CTGTCCAAAA ACAAAAAAGC
93451 CCTATTATTT CTTGTTGTAT TGTCATTTTT TTGTTTTATT TTCAGATATT
93501 TTTAATCTGA GGTTAGTTGG ATCTGCAGAT GCATCTGCAG ATACAGAGGG
93551 TGACTGTGTA TCCTCCCCAC CTAGCTCTGC TGAAGAAGTC AGGAAATCCT
93601 GCCTTCTCAG TGAACAATCA TTTTTATTTG CATTTTTTTT TTTACTCAGC
93651 TGACCAGGGC AGAAAATCCT ACTCCCATGA CTTTCGTAAG CATCTCCAAA
93701 GTAACCAACA TCTTTAAAGA TAACGAATCT CACTAAAAAA GGAAAGATAT
93751 AATACTTGAA GTATAAATAC TTGGAATTAC CCAAGAAAAC ATCTTAGGTT
93801 GGAAATCAAT GGTTTAGGAT TCCCTTTACT GTGATTTCAG AGGGGAGAAC
93851 TCTTTAACTC TGCCCCCAGC TTCACAGCGG GTCAGATTCC CCAAAAGTAA
93901 CCCAGGGGTT GACCTAGTTA ACATGCAGTC TCTCCTGCCA GCTGTGACCT
93951 GCTTCCTTTC AAGAGATCAC TGAGCAAAGG AAATTGCGTT AGCTGATTGT
94001 GGGGCATCTG AATTGTGCTC CTCCACCCCT TTGTATTAGA GAATAGAAAA
94051 ACACTTGGGT ACTGTGGAGA GCCACAGGCT AACATGTCTC CAGGGTGCTG
94101 GCCTTCAGG TGCGCACCAT TCTCTAGTGA CACCAGGAAA GGAGACCTTG
94151 CTGCAAAATG ATGTATAGCT TCACAACTGG CTGTTAACTT TACATAAATT
94201 GTAGATTTTG CCATGTCATT CTGTGTGAAG CGCTGGAAGG ATATTCCTGT
94251 GCTAACGAAA GCAACAAAAG AATCTGAATC CTTCAGTGG CGTGATGGTT
94301 AATGTGTTAA AGTCTTAGGG GAAAATGAAG GAAATCAGAT CCAGGTGGCT
94351 CCATATCATT TCCAGAAATC ACCTCTGCAC AATTTGGATC CCATGTTTTT
94401 GAGAGAATGG GGAAATACAA CCAGTATCCT GAAGCCATGT GAAGAATGTA
94451 TCAGGAGTTT CAGTATGACT GAGAAGGGTA GGCTCTCATC TGAATTTAAA
```

FIGURE 3, page 30 of 40

```
94501 AAAAAAAAAA AAAAAAAAAG GATAAAGCTT ATTTATAAGC ATGTGGGAAA
94551 AAGCAAGAAA TCTTTTAACA CTAAAATCTG ATCTGACCTG TTGGAAAGGA
94601 CACTACGTTA TCAATTTGAA CCTCTGGCTT TTGTTGAGGT GTCTGGTGGT
94651 TGTCCTAGTT GTGTCTAAGG AAGGCTGTGG ACTTGTTACC AGAGTTGCTA
94701 TCACATGTAG GTGTCCTGGC TTTGCTACCT GGAACTTTCC CAAACCTTTT
94751 ACATCTGTCA ACCAGTATTC TTTCAGCCAT AAATGGTGGC TGGCATCACC
94801 TGCCCCTCAT GATCACACTG ACAATAGTAT TTTTATTTAT ATATTGCAGT
94851 ATCTTTTGAA CAGTGCTTTG CAGTCAGTGG AGTCTTTCCA TACCTCAATT
94901 TTTCATCAAA CATTGAGTTG AAGTGTTACA CTTCTCTCGC AAATAAGAA
94951 ATGGGGAAGT TAGAAAATCA AGAAAGGTTA AATGAGTTGG CCAGTGTCCC
95001 AGGGGCAGGG ACCTAGGCAA AAACAAAAGG CTTCTAATTC AAATCCAGT
95051 ATTCTCTGCT AAAATGTGCC ACCTCCCTCC CTTTAGGGTT GGTGGAGGTA
95101 TCGATACTGG GGCTAGTCCT ACAGCTAATG CTTTATGATT CTTTGTTCTG
95151 CTTCACTCAG CACCTGCTGT ACCATGTTAT GTTTGTAAGT GGCTTAGTGT
95201 TAACTTTTCT CCAAAAGGCA GCAGGGTCTG GAACAGGAGA CTGGCCCAGT
95251 CTGGCATCTG GAGAGGATGG TGGTTGTGGT GTTTTCACAG CTCCTCCATT
95301 ACCACCTGGT ATCATTTAGT ATTACTTTGC AAACTGAATC ATAAATCAAC
95351 TCATTTAATG TAGAGAAGGG CAAAAGTTGC TGAGAAATGT TTTGTGGGTT
95401 GGTGCCCGGA GCTTCAACTC TGGGAGGGTG CCTGACTTGA CAGTATCACC
95451 TTAGTCACTA AGGAAAAAGA GATCCAGGGC TTCAGACCTT CAAAACAATT
95501 ATTACTTGCT GAGATGGCAA AAACAATTGT AGAGTGCTTC AATGGCTGAG
95551 CTTTAAACAG TTTGTTAAAC TACAGATTAA ATACGAATGA TTCTTTTTTC
95601 TTTGAGACAG GGCCTCATTC TGTTGCCCAG GCTGGAGTTG CAGTGGCACA
95651 GTCATAGCTC ACAGCAGCCA CAACCTCATA GGCTCAGGCA ATCCTCCCAC
95701 CTCAGCCTCC TAAGTAGCTG GGACTACAGG CACGCACCAC GTGCCACAAC
95751 ACCCAGCTAA TTTTTGTATT TTTTGTAGAG ACAGGGTCTC ATTATGCTGC
95801 CCAGGCTGGT CTTGAACTCC TGGGCTCAAG AGATCCTTCT GCCTTGGCCT
95851 CCCAAAGTGC TGAGATTACA GATGTGAGAC ACTGTGCCCA GCCAGTAATG
95901 ATTTTTCGTA TGACCAAACC ATTGAAGAAA ATTTACACTT ATTTTTGGTA
95951 AATGAAATAC CAAAAAAAAA CTTTATCAGA TGATGGCCTG ATATCTCCTG
96001 CACTGATTTC TGCCCCACAT ACCCTTTTA GATTGAACCA AATTAGAAAT
96051 ATAACCAGA TGATTAAAAA TTAGGTATGA TTCATTTTCC AGCTAATCGG
96101 CTTTACTTCT GTTGCTCCCT CTTCTAAATG CAAAATGAAT CCAAGCAGTG
96151 CTGGATTTAA GGAAGCATAC ATAATTAATA TTACAGGGCA GGCAGGAGAG
96201 CTGGGCATGT GGTCTCATAC CCCACATGTA GTTAGGTAAG CATGTATGTT
96251 TTTCAGCTGC ATTTATTTCT TAGTTATTCC TAGTGGCAAA TGTGGGGGGT
96301 TGATGATCAC TGTGAAACAG CAGCTTATAA AATTCACCCT TTATTATCAA
96351 CAGACTAAAC TTCCTATTTT GCGTAGATGC TCCTGTGCAC GCCTTTATTT
96401 TACACGGAAT GTAAAATATT GTAATGACTG ATTTTCCTTT GAGACTGTAA
96451 TACAGGTAAT GTTCCTATTC AACTTTGTAA ACCAAGACCT GACACACAGT
96501 AGGTATTTTA AAAACTGTTT TGATGTGACC AAAATTATAC AGAAAAAAAG
96551 AGAAGTACAC CAGGATTTTA AAGTCTCTTT TTTTTTTTTA TTTTCACAA
96601 AGGATTTGCT GTAAGTCTTC AAGTCATTTT GTCCAATCCA AAAGCTGTAT
96651 TTAAGCGTCG TGGATCCCAG CCAGGGATGC AAGAATCTGA CTTTCTCAAA
96701 CAGATAACAA CAGTCGAAGA ACTGGAACCG AAAGCAAATA ACTGCACTAA
96751 GGTATTCATT ACACTTGTGC TGCCCGACCT CGAGTGTCAC CATGAAGAGT
96801 GCGCTACCCA AGCTATTTCC TTCCCCTTCA GGTTCTCGTG TGGCACACTC
96851 GGACAGAGAA GGTTAATCTA GCCAACGAGC CAAAGTACCA CCTGGACACA
96901 GTGAAAATTG AGGTATAAAT TGAAGCAGCA ACTGGTGCAG TTTGTCCAGC
96951 CAGTGGATCC ATATGGAAGA GGATGTTTGG AGTTTAGGCT ACAGAGCATT
97001 CAGGTATTGT TTGTTTTACT TCAGTACAGC AGCCTTTCTT GTCATCTGAT
97051 GGACATCTGT TTAAATGGAG CTTGTCAGTT AACATAAGCT AATTGGATGG
97101 TTGGTACAAA ATGTATGTTT TGTCTTCATT TGTTCTGCAT GTTTTCTCTA
97151 CAACAACTAA ATTGGAAGAT TTTTTTGTAC AGTGCCGATA CTGCAAGATA
97201 CCACTCTTGA GTATATATTT TTTCTTTTTC TCCAATTTGC CCTTATATT
97251 GGTAGACTTG AACAGGTTGG TAGACTTGAA CAGGTTTTTA AAACAGACAA
97301 GTATTTTGTC AGCTAAACGT TCCTGATGAT TCCTGACTTT GCAATACTAA
97351 GTAATTTTTG GAAGGTTAGT GGCAGTATAC ATCATAGGAA ATAAAAACCC
97401 ACAAATGAAA AGGTCTATGG AGTCATGTTT AATGTAGGGA ATAACATTT
97451 TGTCAATACT AGGCACCATA AAATGTAAAC ACAATTACTG TCATAAACCT
97501 AGATATACCT TCAAGGATTG AAGATTGAAA GTGGCTTTGT TTTAGTTAGT
97551 TACCCTGTTT GCATATAGTG CAGAAAAAGG TCTTCATGTT AGCACTATGT
97601 ACATTAAGAA GAGATCCAAA TTACAAGAGA GGCAGATAAA ATTTGAATTC
```

FIGURE 3, page 31 of 40

```
97651 TTTAAGCATT CATTAAACGA AGTTTTGGAG TAACATCCAC GTTTATCTTC
97701 CTTTCACTAA TCACGTTCCC TGTTAAGCAC ATCATAACAA CAGCACAGTG
97751 AAGTGAATGA TGAAATAAGA GCATTTGAT ACACTAGAAA ACAGTGCTCA
97801 GTGAGACATT TACATTCTAT TTATATGATT AAACATTTGA TCATACAGTA
97851 CCTTCCTACA GGATTACTGG CTAATTTTGG GGTGGGGTTT ATACTATTAG
97901 AGGTATTACT AACATGATAA CTACTTCCCT TATATGCAAA CATTAGAGCT
97951 ATAATTTTAT TGAGAGGAAA ACTGATTTTG CAAGTTGAGC AGCTTCTCAA
98001 ATAATGCAGT ACATGAAATC ATGGGAAATA TGAGCAAAGC TGCCCTTGAC
98051 ATAAAATGAT TTATCAACCT GCTTTTCACC ACATCAAATT GAATCAGTAC
98101 AGACCAACAC GGTCAATCAG ATCATTCTTA ATATGAACAA ATGGGTAAAA
98151 AGAAAAAAAA TATGCATATG AATAAACAGG GGAACTAGAT GCGTTTCAGC
98201 AAGGAATGTC AGGTGGTAGT TCTGGATGAA ACTTGTATTG CAGTTTTCAT
98251 TTCCACAGTT GTGTGCTGAG AGTCTGACCT GATGAGCTTC CAGACCATCC
98301 TGCTGTTGTG CTGGAGGGCT GGCCAAAACC TGCAGTAGGG GTTGCACTAC
98351 TGATACTCAT GCCAGCCATC TGCTGATTCA TCTGTGAAAC ATATAAAAGG
98401 CTTAGTTCAA GAGGCTTACT TCACTTTTAA TTCTTGTTTC TTTAGCCACA
98451 CAGTTGGTCA TTTTTTCATT AATGTGACAA CTAGTCCAAG CACTGGAATA
98501 AAAACAGAGT ACCATACAAA TATTTCTTAA AGCAAATAGC TACTTTGTTC
98551 CCTTCTTTAT CTACTTTCTA GATACAGTTT CCCCAAAGAT TAACCACAAC
98601 TTACTTAAAA AAAAATACCA AAGCAATCTT GGGATTTTAA TGAGTCCGCT
98651 ACTCTAACTA ACTTTCACCT ACACTAGGAT ATTGTGCTTT AACTACTAAG
98701 GAGTAAGAAA ATTTTAGGAA GTAAATAGT CTAAAATTAT CCTATAAACT
98751 TTGTATGATA GATATTATTC TCTATTAAAA TCTTATATAC TTCCTAAATA
98801 TTTTTAAAGT GGTCATAAAG CATTTATTTC TCTCGCTGAT CTAACAACAT
98851 AAACATCTAA AATTTATTTT CATTGTATGC AATAAAGCAT AAGATTACAT
98901 GTATTTTTCT TCAAGACTGG AGTCAAATAT ATATATATAT AAGCATCTTA
98951 ACCCTGTGAT TCTCTTACTT CCAAAATTGG TGATAAGAGA AGGAAAGGCA
99001 AGATTTACCA TATAGTGAGT GGGTTTAAAA CTTACACTCA GAGTTAGACT
99051 GTGTTCTTAA TTTAATACAT TTGACTTGAC TTATTTACAG TTTCAAAGAC
99101 ACTAACATAA ACTACATCAC TAATCAGGCA TAAGTGTCTG AAGAAGCAGA
99151 TCACGTCTTC ATACCTACTA AAGGACATTT TAACCACCTT GTCGTTGGCC
99201 AGTAGATTGC ACTGATGGAG TGCTGGAGAA CAGCATCACC CTTCTGCATT
99251 ATCTGGAAGT AAGAGCCAGT ATTAACTCCT TCCTGGTTCA TCTAGCACCT
99301 TAACCTGAGC TGGGTGTGCT TCAGCATGTT GACCATGTGA CTGACACTTA
99351 GCACATACAA TTTTTTAGAT TCCCAGCGGG TAGAGACCAA TGTTTTACCT
99401 ATATTCTTGT AAATGGTGGT AGCAAAATTA ACTGTGATAT ATAGTGATTG
99451 TGCTAATGTT AGAAATCACT CTAGACTATT CCCTGAATGC TCTAAAGGTA
99501 AAACAAGTGA CCAAACAGAA ACCAAGATTG CCAAAATGCT GGAGGAACAT
99551 CAATGGGAAG TGTAAAAGGA AGAAGAGTGG GAGCATGAAC CTCTCTAAGA
99601 GCCTTTGTCT GTGCAGCTAG AGAAAAGTCA GAACACAGCA CCTGAAATAG
99651 AAATGTTCTA TCTCAGCTCT AACTTAGGTA GAAATAGGAT TTTATAATAT
99701 GAGGGGATGT CTGGTTCACA CCTTATGGGA ATTGAATCTT TTTGTACTCT
99751 TTTTAAACAT AAAAGTCATT ATAGGGTATG TAAAAGAAA ATACAACTTT
99801 ACAAAGGTTT CTCAACAAAA AGAATTTTTA CAGAGCCATG GGGCAGTAAT
99851 CATCCGACCT GAAAACAGC CTTAGATCCC TCATAAAATA GTGCTTTGAG
99901 AATATGAGGC TAGATT  (SEQ ID NO:3)
```

FEATURES:
Start: 2614
Exon: 2614-3204
Intron: 3205-64312
Exon: 64313-64457
Intron: 64458-96602
Exon: 96603-96751
Intron: 96752-96831
Exon: 96832-96915
Stop: 96916

CHROMOSOME MAP POSITION:
Chromosome 6

FIGURE 3, page 32 of 40

ALLELIC VARIANTS (SNPs):

| DNA Position | Major | Minor | Domain | Protein Position | Major | Minor |
|---|---|---|---|---|---|---|
| 899 | A | G | Beyond ORF(5') | | | |
| 1196 | C | G | Beyond ORF(5') | | | |
| 2600 | A | G | Beyond ORF(5') | | | |
| 4797 | A | T | Intron | | | |
| 6461 | C | A | Intron | | | |
| 6543 | - | T | Intron | | | |
| 8419 | G | A | Intron | | | |
| 8636 | T | C | Intron | | | |
| 17222 | - | C G | Intron | | | |
| 49439 | A | T | Intron | | | |
| 49612 | G | T | Intron | | | |
| 69716 | G | A | Intron | | | |
| 69742 | G | A | Intron | | | |
| 69920 | C | T | Intron | | | |
| 70038 | C | G | Intron | | | |
| 70956 | C | T | Intron | | | |
| 71021 | A | C | Intron | | | |
| 71547 | G | C | Intron | | | |
| 71592 | C | G | Intron | | | |
| 71601 | G | A | Intron | | | |
| 72024 | C | G | Intron | | | |
| 72161 | A | G | Intron | | | |
| 72259 | C | T | Intron | | | |
| 72363 | T | C | Intron | | | |
| 72639 | G | C | Intron | | | |
| 72698 | T | C | Intron | | | |
| 72716 | C | A | Intron | | | |
| 86903 | C | A | Intron | | | |
| 89261 | C | T | Intron | | | |
| 95175 | T | C | Intron | | | |
| 96648 | T | G | Exon | 261 | V | G |
| 99242 | A | G T | Beyond ORF(3') | | | |
| 99349 | T | C | Beyond ORF(3') | | | |
| 99443 | A | G | Beyond ORF(3') | | | |
| 99867 | T | C | Beyond ORF(3') | | | |

Context:

DNA Position

899
```
TTCAGGGGTAGGACTGGGAGAAGAGGAGCTGTCAGAAAAGCTGGAGAGCCATTCGCCCCA
GAGCTCTCAGTTGCACCAGAACGCACAGTCGGAGAGAGATTTATTTGTGAACAAGCCCGA
GAAAGGCAGACAACCCAGACAAGATGGGCTCAGAAATTATTTATCATAGGCTAGGGCAGA
ACAGTCTGGAGCTTTCCTTCTGCTTTGCAAGCACTTCCCTGGGACCTGCCTGGGAAGCAC
AGCCCTTCTTCCTGGTAAGTTACAGAAGGTCAGGCACTCAGCTAGTAGGCCAGCTAGACA
[A,G]
CAAAAAGTGTCTAAACTAAGTGCCAACTGTTTACTTGGGGTCTTCCAGACCCTATCATGG
TTCTATTCGTCATGGTACACTCTGTTTGATTTCAATCGCACCATCTTTATATGTAGGAAG
GCCAAACCGGCCCGGCTGTGTTGGGTGGGATTTCTGCAGGCCATGCAGTGAGGACGCCAC
TAGCTATAGACACACGCAGGAGACCCACGTTCTATTTCCATATGCCACTTGCCACTGACC
TCAGAGAAATCATTTTAAACCCTGAACCTCAGCTTCCTTATCCTGAAAATGAAGGCCATT
```

1196
```
ACAACAAAAAGTGTCTAAACTAAGTGCCAACTGTTTACTTGGGGTCTTCCAGACCCTATC
ATGGTTCTATTCGTCATGGTACACTCTGTTTGATTTCAATCGCACCATCTTTATATGTAG
GAAGGCCAAACCGGCCCGGCTGTGTTGGGTGGGATTTCTGCAGGCCATGCAGTGAGGACG
CCACTAGCTATAGACACACGCAGGAGACCCACGTTCTATTTCCATATGCCACTTGCCACT
GACCTCAGAGAAATCATTTTAAACCCTGAACCTCAGCTTCCTTATCCTGAAAATGAAGGC
[C,G]
ATTCTACTTCTTAGGCCTTCTTGACAGGAGCCTTGGGAGAGCCAAACGGAGTAATTCCGG
```

FIGURE 3, page 33 of 40

```
         TGACAGCGAAGAACTGGGAGGGACCGTGACTCCAAATTACTGAACAAAAATAAGTTAAAC
         ATGCTCGGCTGGAGTTTTAGGAATTCCACCCGCCCCCACCCGCCATGATCAAACTGCAGT
         CAGGCAGCAGCCCTCCGAATTGATTCTTTCTTATGGACTGTCTCACATGCCAAACACCTA
         TGTGCAGCACCCCTCCATCTCCGTGGGCTCCTATTGATGTCTGCCTTGCAGTGAAAGCGC

2600     GCACTCGGCACAACTCCGGGACCGGCGGCGCGCGGCTGGACCGAGTCCCGCTTCCCGCCA
         GCTCACCTGGAGTCGGGGGCAGCCCCTGCCCGCCCGCCTGCACCCCTTGTCGCTCTAGCT
         TGCGCGAACCTGCCGCTCCTCCACGCCCAGGTAGTGAGCCCCGCGGCTCCAGGTCTCTGC
         AGCGCCCTCGGCCCCATGGACAGCGCACCCATCACCACTCCCTAAGTGCTGGCGCCGCCG
         CTGTCCAAGCTGCGCACTGGGGTCCCTCGGCTCGCCCCTCTCTGGGGTGTCCGAGAGGCC
         [A,G]
         GGGAGCGTGCACCATGAAGTCCGCGCTTTTCACCCGCTTCTTTATCCTCCTGCCCTGGAT
         CCTAATTGTCATCATCATGCTCGACGTGGACACGCGCAGGCCAGTGCCCCCGCTCACCCC
         GCGCCCCTACTTCTCTCCCTACGCGGTGGGCCGCGGGGGCGCCCGACTCCCGCTCCGCAG
         GGGCGGCCCGGCTCACGGGACCCAAAAGCGCAACCAGTCTCGGCCGCAGCCACAGCCGGA
         GCCGCAGCTGCCCACCATCTATGCCATCACGCCCACCTACAGCCGCCCGGTGCAGAAAGC

4797     TTGCTTTCTTAACCCCAGGGCAGAGCTATTCTGTACTCTTCCAGTTTAATTTTTCTGTGT
         GGCTTTAAAAAAATTTTCTTAAAGGTAATTGCCGCCTTCATTTCTATTCATCCTCTCTTT
         CATGAATAAAAGGCACAGTAATTGTCCTTCATCTTTTCTTTTCCATCCTTTCACTGTAGA
         GGGCTTTCTTTCCACGTTTCTCCAAATGAATAAATAAGCTTGGCATTGTATAGTATGGTC
         CTTACTCAACCCAAGATTAGAGATACCATCTGACGTTTTAACTGGGCTTTTAATCCTGC
         [A,T]
         TCAGTGCTCCCCCCTCCAAAAGAAAAAAGTGGCTTGCATCTGAAGCAAAGACTGTACATT
         TCAATGCACCACAATTTTTAAACCGCAAGGTCTTTTTATTTTCTTCTACAACTTCGAAGT
         TGCCTCGTCTGTGACAATATGTGGTCTTGTTGAAGTAAAATAGTGCACATTACTGTTAAT
         GAACACTGTAGGAGGCTAGATTGTGAAGGAGGAATGATTTAGTTTATTCCGAGCTTCTAG
         CCTCTTGGTGTGAGGTGTTAGAAGAATTGGCACACGCAGGCAGTGAAATGATTCAGGACA

6461     ATGGTGCTTTGTCATCTCATACAGCTAACTAATTTTCAGCCTTTCCTTTCAACTGATCTG
         CATTGCCAGGAAAGAAATATTTGCATTGAATACTCTTATGTTAACAGCCAAATCCATTTG
         CAAATGAAGTTTAGTGTGAATCTTAGCTACAGAAATGGGCCTGTTCATTGGAGAAGGAGG
         TGGTGGGGTTTTTCAGGTTTCAAAAATCTCAACAGCTACTCCTCTTCTTCCTGTGGCATT
         GATGGGGTTTTGCACTGTGGATCACAGGTAATCCTGCCTCCCTGTGCATCCTATCCATCT
         [C,A]
         CCTCTCTGGAAAAGCTTACTTGCAAAGGATTTAAGCTGCTTTAATAAAAGCCACAACTAC
         AGATAAATGTGACTTTATTTTTAGTCATGTTTTCAATAACACTATTGATCAGATTTCTGT
         TTTTCACCAGAAAACCTTCAAAGCTTTCTTAAATTTAAAACAGATGCTTTTCAGGTGAAG
         TTGGTTTCACCTCTGGAAATCAATTGAATTGAAATACTAAAAAAAAATAGCACTTTCCAA
         GCAAGAAAAAAAAAACTTTAGAAATTTTGAAGTTAATGAAATAAGACTGGAAGACAGGC

6543     GCATTGAATACTCTTATGTTAACAGCCAAATCCATTTGCAAATGAAGTTTAGTGTGAATC
         TTAGCTACAGAAATGGGCCTGTTCATTGGAGAAGGAGGTGGTGGGGTTTTTCAGGTTTCA
         AAAATCTCAACAGCTACTCCTCTTCTTCCTGTGGCATTGATGGGGTTTTGCACTGTGGAT
         CACAGGTAATCCTGCCTCCCTGTGCATCCTATCCATCTCCCTCTCTGGAAAAGCTTACTT
         GCAAAGGATTTAAGCTGCTTTAATAAAAGCCACAACTACAGATAAATGTGACTTTATTTT
         [-,T]
         AGTCATGTTTTCAATAACACTATTGATCAGATTTCTGTTTTTCACCAGAAAACCTTCAAA
         GCTTTCTTAAATTTAAAACAGATGCTTTTCAGGTGAAGTTGGTTTCACCTCTGGAAATCA
         ATTGAATTGAAATACTAAAAAAAAATAGCACTTTCCAAGCAAGAAAAAAAAAAACTTTAG
         AAATTTTGAAGTTAATGAAATAAGACTGGAAGACAGGCTGGCTCTCAGACACTTAAGGGG
         TTATCAAAGGAGTCAGTGACTGAGATTGCATCTAGAAGATGTTTCTGGAAAGCAATGAAC

8419     TTTGCATACAATTTTAAATAAATGTTAATACCCTATATCATGGATACAAGCAAAATATAG
         TTGACATAAATTGAGCATTTACTATAGGCAAAGAAGTACCCTTAGGGTTTTACGTGTATT
         ATTTAATCTTCATAACACCCTGAGGTAGGTAATAGTACTGTCTCTGTTTGTTTGCTGTTT
         TAATACTAATGCTAATATTTAGTTATGGACGCAGTCCCTTGGTGAGTACAGAGGACTTAA
         ACAAATGCAACCTGACGGTAATATAGTTGTTTACCTCTGATCTATATAATCAGTATCCCC
         [G,A]
         TTTTTAACAGAAGCACTAGGAAGTAACTTGAAAATGTCATGTAGCTGTTATGTGGCAGAG
         ATAGAATTTTGAACCCAGGTGCCCTGGTTCTAGCGCCTGCATTGTTGACTGTCCTGAAAC
         TCATGTCATTTAACACATGAAAATATGTCATCATTATAATAAGTAAAGCACCTGATTAGC
         AGGAGCCTTGTGATATTATTACTGTCTTCTGCCATTTTTGAATTCAGGTCTTTCTTCTTG
```

```
       GTTATGTCAACTCTTAGCTTTCTCCTTTGACCTTTTGTTACTTTTTTCCTTTTTGTTGTT
8636   CTTGGTGAGTACAGAGGACTTAAACAAATGCAACCTGACGGTAATATAGTTGTTTACCTC
       TGATCTATATAATCAGTATCCCCGTTTTTAACAGAAGCACTAGGAAGTAACTTGAAAATG
       TCATGTAGCTGTTATGTGGCAGAGATAGAATTTTGAACCCAGGTGCCCTGGTTCTAGCGC
       CTGCATTGTTGACTGTCCTGAAACTCATGTCATTTAACACATGAAATATGTCATCATTA
       TAATAAGTAAAGCACCTGATTAGCAGGAGCCTTGTGATATTATTACTGTCTTCTGCCATT
       [T,C]
       TTGAATTCAGGTCTTTCTTCTTGGTTATGTCAACTCTTAGCTTTCTCCTTTGACCTTTTG
       TTACTTTTTTCCTTTTTGTTGTTAATGTATTACATTGAAAAATAAAATTTTTTTTTTTG
       CAAGAAAATGTACTTTATTAGCTTTCTTTGTTCTGTGGGTTGATCTTCCTGGATATTTCT
       TTATTTTATTTTATTTTATTATTATTATACTTTAAGTTTTAGGGTACATGTGCACAATGT
       GCAGGTTAGTTACATATGTATACATGTGCCATGCTGGTGTGCTGCACCCATTAACTCGTC

17222  ATTGAGCCCTTTAAATAGAAACTGGAAGATAAACGTGGTCCCTACTCTGATTCTAAGAGC
       TTTTATACTAAAAGGAAAGAGAATGTCATGAGCATTTATGTATATAGCAAGGCATTACCA
       TCAACAGCCATTAAAAGGGGAGGTTTGTCAAGGTGGTCGTGAGTCAGTTGAGTATTTGGC
       CTCTTCACACGTGTGAGAGGCTGGAGGCTGGTGGGGAGCTCACATAGGCGTAACAGCCCA
       TGTTCAAATCCAGCTTCACTGCTTAGTGTTTGCATTACATTGGCAAGGGTTGACTGCCTC
       [-,C,G]
       AGTGATTGTTTTAAGTGCTCTAGGCAAGTAATAAATATTAGTTCTTTTTGCCTTGTTCTT
       TCCACTATGGGTGACTGCCCTAATTGAGGGTATACCAGATAATTGCACTGTCTTGATTTG
       TTAAGTGCCTCTAAATGTTCTTCTCCTGACATCTGGACTATGTTTCTAGAGGCCTAGGGG
       GAGGAGGAGGTAAAGGCACTTGACTTTCCCAAATTAGTCTGTACCCAAGTGGAACTGCAT
       AAATTGGGTACCTTAATTACACCATTGGGTATTACTAGGGTGATTACAGGGACAAGAGTT

49439  TTATTATCTCTGGTAATCACTGTCTTGAAAACTACTTTGTCTGATATTAATAAAGCCACA
       GTAGCTTTCATACACCTTCTTGTTTACATATGATTTCCCATATTCTTTTATCCCATCTAT
       GTTATTAAAATGTGTCTTGTCAATAGTATATAGTTTGTTCTTGTTTCTTTATTCATTTTG
       TTTTCCTGATACTCTTTTCCCAATTAAGGAGGTAATAATCTGTAAGCAAAGCCTTATTTA
       CATAAACACTGCTGTGATCTTATACCAAATAAACAGCCCTAGCATGTGTGTGTGTGTGTG
       [A,T]
       GAGAGAGAGAGTGTGTGAATGTGTGTGTGTTTGGGCTTTCTGAATTAGATTTTCTTTCAA
       GATCCACCTACATCTTTACTTTTGGCCTAAGTAATGGTTGGTCATGTTAACTGTGTAAAA
       TATTAATCTTTTTCTGAAGCTACAAAGAGTCCATGTCTACTTACTGTTCTAGGAAAAGTT
       TTTTCAAATTTGGGAAGTGTCTACCTTTTAAAATATTTTCTGAGAGTGTTTAATTACTTC
       TATGATCTTAAAAGGTTCTCTCCATTTTACTTTTATCCAGCTGTCACATATTCTGAGTAT

49612  CATTTTGTTTTCCTGATACTCTTTTCCCAATTAAGGAGGTAATAATCTGTAAGCAAAGCC
       TTATTTACATAAACACTGCTGTGATCTTATACCAAATAAACAGCCCTAGCATGTGTGTGT
       GTGTGTGAGAGAGAGAGTGTGTGAATGTGTGTGTGTTTGGGCTTTCTGAATTAGATTT
       TCTTTCAAGATCCACCTACATCTTTACTTTTGGCCTAAGTAATGGTTGGTCATGTTAACT
       GTGTAAAATATTAATCTTTTTCTGAAGCTACAAAGAGTCCATGTCTACTTACTGTTCTAG
       [G,T]
       AAAAGTTTTTTCAAATTTGGGAAGTGTCTACCTTTTAAAATATTTTCTGAGAGTGTTTAA
       TTACTTCTATGATCTTAAAAGGTTCTCTCCATTTTACTTTTATCCAGCTGTCACATATTC
       TGAGTATGTTTTCCACCAGGAGAACCTGAGAATTTTTTTTCTCTTAGATTTTGAGTATA
       GAGATAAGATTTATCCTGCATCCAGTTCCAACCTGTAATATAATTCTATGCAAGTTTC
       CTCTCTTGTTGTGTTTATTTCCCTTTATCCTTATCCTTAGTCATCTATTCCAATGTTTAT

69716  CAGAAAAAGGTGAGATAAGTAAGGAAGCCAAGGGCTGGGAAGGTGGAGGGGCCAGTTGT
       TGGAATTGACCGTCCGCCAAATGTTAATAGAGGGAGAAGTGACATTTGGCTGAATTCCAC
       ACACACTGAATGTAGCAGCCCCTCGCCTCAAGGAGTTTTGTATCTAGCAGAGAGAGAATG
       TCTACAAGAGCATGGCAGATACATCGTGGGGTCGAAAATGAGTACAAGTGGAATGATTGG
       GGGTTACATTTAAAGAGAAAACCACAGCCACTGGGGGAGTTTCGGGAAAGGTCTTGGGAA
       [G,A]
       AGGTGACATCTGAGAGGCACCTTCCGTGCTAGGCCCAGGCCAGGGTAGGGAGGGATCATG
       GGCAGGGTGTGTTTTGGAACAAGTTATCCCAGGGTATGTGTAGCTCTTGGGAAGGGCAA
       GCTGGGGTCAGATAGTGAGGACTGAGTGCTAAGATGAGAAGTTTTTCTTCATTTCTGTGG
       ACATTGGAGAGTCTGACATTTTTCAAGTAGGGGACTGATGTGATTAGAAATACAGTTTGA
       GAACCACATGTTGGCAGTGTGGGATGAATGGGGAGGAGGGCTGGGCCTGGAGGCTCAGG

69742  AGCCAAGGGCTGGGAAGGTGGAGGGGCCAGTTGTTGGAATTGACCGTCCGCCAAATGTTA
```

FIGURE 3, page 35 of 40

```
         ATAGAGGGAGAAGTGACATTTGGCTGAATTCCACACACACTGAATGTAGCAGCCCCTCGC
         CTCAAGGAGTTTTGTATCTAGCAGAGAGAGAATGTCTACAAGAGCATGGCAGATACATCG
         TGCGGTCGAAAATGAGTACAAGTGGAATGATTGGGGGTTACATTTAAAGAGAAAACCACA
         GCCACTGGGGGAGTTTCGGGAAAGGTCTTGGGAAGAGGTGACATCTGAGAGGCACCTTCC
         [G,A]
         TGCTAGGCCCAGGCCAGGGTAGGGAGGGATCATGGGCAGGGTGTGTTTTGGAACAAGTT
         ATCCCAGGGTATGTGTAGCTCTTGGGAAGGGCAAGCTGGGGTCAGATAGTGAGGACTGAG
         TGCTAAGATGAGAAGTTTTTCTTCATTTCTGTGGACATTGGAGAGTCTGACATTTTTCAA
         GTAGGGGACTGATGTGATTAGAAATACAGTTTGAGAACCACATGTTGGCAGTGTGGGATG
         AATGGGGGAGGAGGGCTGGGCCTGGAGGCTCAGGCAGCCATCTGGGTAATGAGCCGGTAG

69920    CGTGGGGTCGAAAATGAGTACAAGTGGAATGATTGGGGGTTACATTTAAAGAGAAAACCA
         CAGCCACTGGGGGAGTTTCGGGAAAGGTCTTGGGAAGAGGTGACATCTGAGAGGCACCTT
         CCGTGCTAGGCCCAGGCCAGGGTAGGGAGGGATCATGGGCAGGGTGTGTTTTGGAACAA
         GTTATCCCAGGGTATGTGTAGCTCTTGGGAAGGGCAAGCTGGGGTCAGATAGTGAGGACT
         GAGTGCTAAGATGAGAAGTTTTTCTTCATTTCTGTGGACATTGGAGAGTCTGACATTTTT
         [C,T]
         AAGTAGGGGACTGATGTGATTAGAAATACAGTTTGAGAACCACATGTTGGCAGTGTGGGA
         TGAATGGGGGAGGAGGGCTGGGCCTGGAGGCTCAGGCAGCCATCTGGGTAATGAGCCGGT
         AGCGGGCTGGGAGGTGAGAGGAGGTCTTAAATACCACAGCTATTGGGGACTTATAAATT
         TTAACAGCCTTTTCAGATTATACTCTAAATCAGCAGACACTTAGATCTTTTTAACACCTT
         TTTCTGTTGTATGGTATGGTGATAAATGATGTATTAAATTTAAGTTTGGTTAATTTTAAT

70038    TTCCGTGCTAGGCCCAGGCCAGGGTAGGGAGGGATCATGGGCAGGGTGTGTTTTGGAAC
         AAGTTATCCCAGGGTATGTGTAGCTCTTGGGAAGGGCAAGCTGGGGTCAGATAGTGAGGA
         CTGAGTGCTAAGATGAGAAGTTTTTCTTCATTTCTGTGGACATTGGAGAGTCTGACATTT
         TTCAAGTAGGGGACTGATGTGATTAGAAATACAGTTTGAGAACCACATGTTGGCAGTGTG
         GGATGAATGGGGGAGGAGGGCTGGGCCTGGAGGCTCAGGCAGCCATCTGGGTAATGAGCC
         [C,G]
         GTAGCGGGCTGGGAGGTGAGAGGAGGTCTTAAATACCACAGCTATTGGGGACTTATAAAA
         TTTTAACAGCCTTTTCAGATTATACTCTAAATCAGCAGACACTTAGATCTTTTTAACACC
         TTTTTCTGTTGTATGGTATGGTGATAAATGATGTATTAAATTTAAGTTTGGTTAATTTTA
         ATTGGTGTAATTTGTATTATCCTTTGAGTCGTAATTTATGTGTAGAAAATACAGTGATGT
         TGGGTAATTAAAACATTCTTTTAACCAGAACACCTATTTTGTGTAAAATAGGAGTCTGCA

70956    CACCTTACTATTCTTGTTCCCCTCTACTCAATCTTTGCGGGCAGAGATCACTTCCTCCAG
         CACATTCTACCCTTCCCTTTGGGGCCTGCACTGATGCCCCTGCCTGGAAATGCTCCTTCC
         TCGTTCAGCCCTACTCATCCTTCAAATCTCAGCTTAAAGGCTGCCTTCTTGGGGAAGGTT
         TTGCTGATGCTTCAATTAAGATAGCTCCTCCCGTGTTATAATGTGCTGTTCTCTCAGCCT
         CCCATACCTCTGCACCTTGTCACAGTGGTTGTACATCTCTCATTATAATTGTTGAGGCTC
         [C,T]
         GCCACCCCGACTCCCAGAATGCATCCTTCCTGTAGGCAGAAGCCGGACTATCCTGCCCTC
         CACTCCTTGCCCAATCCCAGCCCCAGGTTTCCCCTAGCCCCAGCCTGTGAGTGGGGCTGA
         GTGACGGCACTATCCCAGAGCAGCTGTCCCCGCTACAAGTTTACCAGGCAAACCTTTAAA
         AAATTATTATAAATGATGACCATGAAACTGGAGGGGGTCGAGGGATCACTCTGGGCAGGT
         TGCTGAAGCCTGCTTTCTGTGGGCTCTCTGCAGGGACATGGGAATGACAGTTATTCTGGG

71021    TCTACCCTTCCCTTTGGGGCCTGCACTGATGCCCCTGCCTGGAAATGCTCCTTCCTCGTT
         CAGCCCTACTCATCCTTCAAATCTCAGCTTAAAGGCTGCCTTCTTGGGGAAGGTTTTGCT
         GATGCTTCAATTAAGATAGCTCCTCCCGTGTTATAATGTGCTGTTCTCTCAGCCTCCCAT
         ACCTCTGCACCTTGTCACAGTGGTTGTACATCTCTCATTATAATTGTTGAGGCTCCGCCA
         CCCCGACTCCCAGAATGCATCCTTCCTGTAGGCAGAAGCCGGACTATCCTGCCCTCCACT
         [A,C]
         CTTGCCCAATCCCAGCCCCAGGTTTCCCCTAGCCCCAGCCTGTGAGTGGGCTGAGTGAC
         GGCACTATCCCAGAGCAGCTGTCCCCGCTACAAGTTTACCAGGCAAACCTTTAAAAAATT
         ATTATAAATGATGACCATGAAACTGGAGGGGGTCGAGGGATCACTCTGGGCAGGTTGCTG
         AAGCCTGCTTTCTGTGGGCTCTCTGCAGGGACATGGGAATGACAGTTATTCTGGGTCTCC
         TTCATCTCAATGTTTGT

71547    TTATTCTGGGTCTCCTTCATCTCAATGTTTGTCAACAAGGAATTTTGCCTGGGTTAATTT
         ATTTGGCAGACCTTTTCTCAGTAGATAATGCTGTGATCAGCTTCAGCCCAGCCCGGATCA
         GATGATCATCAAAGCCAAATGAGCAGTCAAAATTAATGACGTTTTGCTTTGCTTCATGAA
         TATAAATACTGCAAGAAAATGGAGGGAATTGTCTTCCTGCCACTTTGGAGTCATTCGTGA
```

FIGURE 3, page 36 of 40

```
            TTTAAGTGTGCTGTTTTCCATGCATGAATGTTTTCTATGAGAACTATAAAGTTACTGAAT
            [G,C]
            TTCTCAGTAGAGTGACTTGATGTGTCATGTGGTACCTTTTAGTGCAGGATCTAGGGACCA
            GCTTGGGACTTTGTCCTTGGGTTGGTACAGTGTGATTGTCACCGGGAGAGGACTGCAGCT
            GCCAGGGGGTGGTAATTCTGTCCCAACAACTTATAGAACCACAGGGACAGGTGGCAGAGT
            GTTGGGGCAATAGGCAGCCTGCCACTCAGTTTTTAATCTATTTCTAGAACATGGTGCAGT
            CTAGAGACTTGCAGGGATTTGATGCCCACAGTACTGTGTCTGGTCCTGTCTGCATGTGCT

71592    TGCCTGGGTTAATTTATTTGGCAGACCTTTTCTCAGTAGATAATGCTGTGATCAGCTTCA
            GCCCAGCCCGGATCAGATGATCATCAAAGCCAAATGAGCAGTCAAAATTAATGACGTTTT
            GCTTTGCTTCATGAATATAAATACTGCAAGAAAATGGAGGGAATTGTCTTCCTGCCACTT
            TGGAGTCATTCGTGATTTAAGTGTGCTGTTTTCCATGCATGAATGTTTTCTATGAGAACT
            ATAAAGTTACTGAATGTTCTCAGTAGAGTGACTTGATGTGTCATGTGGTACCTTTTAGTG
            [C,G]
            AGGATCTAGGGACCAGCTTGGGACTTTGTCCTTGGGTTGGTACAGTGTGATTGTCACCGG
            GAGAGGACTGCAGCTGCCAGGGGGTGGTAATTCTGTCCCAACAACTTATAGAACCACAGG
            GACAGGTGGCAGAGTGTTGGGGCAATAGGCAGCCTGCCACTCAGTTTTTAATCTATTTCT
            AGAACATGGTGCAGTCTAGAGACTTGCAGGGATTTGATGCCCACAGTACTGTGTCTGGTC
            CTGTCTGCATGTGCTGTGGCCAGGGCTGTGCTGGGTAGAGGTGGGCGTGTGGGCAAGGA

71601    TAATTTATTTGGCAGACCTTTTCTCAGTAGATAATGCTGTGATCAGCTTCAGCCCAGCCC
            GGATCAGATGATCATCAAAGCCAAATGAGCAGTCAAAATTAATGACGTTTTGCTTTGCTT
            CATGAATATAAATACTGCAAGAAAATGGAGGGAATTGTCTTCCTGCCACTTTGGAGTCAT
            TCGTGATTTAAGTGTGCTGTTTTCCATGCATGAATGTTTTCTATGAGAACTATAAAGTTA
            CTGAATGTTCTCAGTAGAGTGACTTGATGTGTCATGTGGTACCTTTTAGTGCAGGATCTA
            [G,A]
            GGACCAGCTTGGGACTTTGTCCTTGGGTTGGTACAGTGTGATTGTCACCGGGAGAGGACT
            GCAGCTGCCAGGGGGTGGTAATTCTGTCCCAACAACTTATAGAACCACAGGGACAGGTGG
            CAGAGTGTTGGGGCAATAGGCAGCCTGCCACTCAGTTTTTAATCTATTTCTAGAACATGG
            TGCAGTCTAGAGACTTGCAGGGATTTGATGCCCACAGTACTGTGTCTGGTCCTGTCTGCA
            TGTGCTGTGGCCAGGGCTGTGCTGGGTAGAGGTGGGCGTGTGGGCAAGGAGCACATGTG

72024    GAGTGTTGGGGCAATAGGCAGCCTGCCACTCAGTTTTTAATCTATTTCTAGAACATGGTG
            CAGTCTAGAGACTTGCAGGGATTTGATGCCCACAGTACTGTGTCTGGTCCTGTCTGCATG
            TGCTGTGGCCAGGGCTGTGCTGGGTAGAGGTGGGCGTGTGGGCAAGGAGCACATGTGCA
            TCTGTGTGCTCATACTCAGGGTGCTTGCTCTGGAGCAGCTGGTAGTGGGGTCAGGTGGGG
            TGGACGTGGAGAGGGAGGGCTCTGCAGAGGCCTTTCAGGGCTGAAGGGGAAGTGGGGAGA
            [C,G]
            GGGTTTCCAGGCCTCTGTCCACCTCAATTCTAGCAGCTCTGCATTTACATATTGGAGATC
            CCCTCAAGATTTCAATGGAATAAAACATTCATTCCAGGACTAAAAATTTTGAAAACCTGA
            AGTTTTCCTTTCTATCAGGATGTCCAGCAGACTCAATAATTATATATTGTTTGCTTAGCA
            TTTACCAAGCATCAGGCATTTGGAAGCATTCTGTGTTCTTTCTTCATGAATCCTCACTTA
            GCTGTGCAAGGGATATGCTAGTTTTATTATCCCCACTTACATATAAGGAGCCCGAGGCCT

72161    TGCTGGGTAGAGGTGGGCGTGTGGGCAAGGAGCACATGTGCATCTGTGTGCTCATACTC
            AGGGTGCTTGCTCTGGAGCAGCTGGTAGTGGGGTCAGGTGGGGTGGACGTGGAGAGGGAG
            GGCTCTGCAGAGGCCTTTCAGGGCTGAAGGGGAAGTGGGGAGACGGGTTTCCAGGCCTCT
            GTCCACCTCAATTCTAGCAGCTCTGCATTTACATATTGGAGATCCCCTCAAGATTTCAAT
            GGAATAAAACATTCATTCCAGGACTAAAAATTTTGAAAACCTGAAGTTTTCCTTTCTATC
            [A,G]
            GGATGTCCAGCAGACTCAATAATTATATATTGTTTGCTTAGCATTTACCAAGCATCAGGC
            ATTTGGAAGCATTCTGTGTTCTTTCTTCATGAATCCTCACTTAGCTGTGCAAGGGATATG
            CTAGTTTTATTATCCCCACTTACATATAAGGAGCCCGAGGCCTAGGTATGCTAAGTGAGT
            TGTCTGGGATTCAGAGTCAGGCCAGTGTGTCTACAGAGATGGTCTCCAACTCACCCACCT
            ACAGCCAAGTCACTGAGTTCTTGGTCTCTGAGCCTGCAGAACAGTTCTTGGTTTCTTCA

72259    TGGGGTGGACGTGGAGAGGGAGGGCTCTGCAGAGGCCTTTCAGGGCTGAACGGGAAGTGG
            GGAGACGGGTTTCCAGGCCTCTGTCCACCTCAATTCTAGCAGCTCTGCATTTACATATTG
            GAGATCCCCTCAAGATTTCAATGGAATAAAACATTCATTCCAGGACTAAAAATTTTGAAA
            ACCTGAAGTTTTCCTTTCTATCAGGATGTCCAGCAGACTCAATAATTATATATTGTTTGC
            TTAGCATTTACCAAGCATCAGGCATTTGGAAGCATTCTGTGTTCTTTCTTCATGAATCCT
            [C,T]
            ACTTAGCTGTGCAAGGGATATGCTAGTTTTATTATCCCCACTTACATATAAGGAGCCCGA
```

FIGURE 3, page 37 of 40

```
         GGCCTAGGTATGCTAAGTGAGTTGTCTGGGATTCAGAGTCAGGCCAGTGTGTCTACAGAG
         ATGGTCTCCAACTCACCCACCTACAGCCAAGTCACTGAGTTCTTGGTCTCTGAGCCTGCA
         GAACAGTTTCTTGGTTTCTTCATCTGCAGAACAGGGAAAATGAAATTTTTCACAAAATCA
         GACATCACGTGCAAAGCAGCCAGGAGTAGAACATTGTAGACACTTGGTGAATGTCACTCT

72363    CTGCATTTACATATTGGAGATCCCCTCAAGATTTCAATGGAATAAAACATTCATTCCAGG
         ACTAAAAATTTTGAAAACCTGAAGTTTTCCTTTCTATCAGGATGTCCAGCAGACTCAATA
         ATTATATATTGTTTGCTTAGCATTTACCAAGCATCAGGCATTTGGAAGCATTCTGTGTTC
         TTTCTTCATGAATCCTCACTTAGCTGTGCAAGGGATATGCTAGTTTTATTATCCCCACTT
         ACATATAAGGAGCCCGAGGCCTAGGTATGCTAAGTGAGTTGTCTGGGATTCAGAGTCAGG
         [T,C]
         CAGTGTGTCTACAGAGATGGTCTCCAACTCACCCACCTACAGCCAAGTCACTGAGTTCTT
         GGTCTCTGAGCCTGCAGAACAGTTTCTTGGTTTCTTCATCTGCAGAACAGGGAAAATGAA
         ATTTTTCACAAAATCAGACATCACGTGCAAAGCAGCCAGGAGTAGAACATTGTAGACACT
         TGGTGAATGTCACTCTTAACCAAGAAACAAGACTGTGCCTTTGGGTTCAGCTGGCTCACA
         CATTTATTTTGATGAATTAGGTCAGTGTTTTGTTTGATTATCACAGTGGTGAGGTCCATG

72639    AGTTGTCTGGGATTCAGAGTCAGGCCAGTGTGTCTACAGAGATGGTCTCCAACTCACCCA
         CCTACAGCCAAGTCACTGAGTTCTTGGTCTCTGAGCCTGCAGAACAGTTTCTTGGTTTCT
         TCATCTGCAGAACAGGGAAAATGAAATTTTTCACAAAATCAGACATCACGTGCAAAGCAG
         CCAGGAGTAGAACATTGTAGACACTTGGTGAATGTCACTCTTAACCAAGAAACAAGACTG
         TGCCTTTGGGTTCAGCTGGCTCACACATTTATTTTGATGAATTAGGTCAGTGTTTTGTTT
         [G,C]
         ATTATCACAGTGGTGAGGTCCATGCAGGTAGCTGTAGGGTGGAAGAATCACTCATCCTTG
         GGTCCTGCTCTGACACCTACAGGCTGTGCAGCCTGAAGATCTAGGGGAATATCTGTTTCT
         TCCTAATACCTGTAGATTAGGGATCATTGCTTCTTCCTAATACCTGTAGATTAGGGATCA
         TTGCACCAGCTTTCTGGGTTGTGTTGAGGTTGAAGTAAAACGAATACATACAGAAGTTCC
         TGCTGTTCTGTGAATATTTGAATCTGCACCCACTTGTAGCTTTGTGAGATCACTCTTAAC

72698    ACCTACAGCCAAGTCACTGAGTTCTTGGTCTCTGAGCCTGCAGAACAGTTTCTTGGTTTC
         TTCATCTGCAGAACAGGGAAAATGAAATTTTTCACAAAATCAGACATCACGTGCAAAGCA
         GCCAGGAGTAGAACATTGTAGACACTTGGTGAATGTCACTCTTAACCAAGAAACAAGACT
         GTGCCTTTGGGTTCAGCTGGCTCACACATTTATTTTGATGAATTAGGTCAGTGTTTTGTT
         TGATTATCACAGTGGTGAGGTCCATGCAGGTAGCTGTAGGGTGGAAGAATCACTCATCCT
         [T,C]
         GGGTCCTGCTCTGACACCTACAGGCTGTGCAGCCTGAAGATCTAGGGGAATATCTGTTTC
         TTCCTAATACCTGTAGATTAGGGATCATTGCTTCTTCCTAATACCTGTAGATTAGGGATC
         ATTGCACCAGCTTTCTGGGTTGTGTTGAGGTTGAAGTAAAACGAATACATACAGAAGTTC
         CTGCTGTTCTGTGAATATTTGAATCTGCACCCACTTGTAGCTTTGTGAGATCACTCTTAA
         CGGTAGTATTTAAGAACATTTGAACTCCGCTGTGGGCTCATGATGAACTTCATTTCTCTT

72716    GAGTTCTTGGTCTCTGAGCCTGCAGAACAGTTTCTTGGTTTCTTCATCTGCAGAACAGGG
         AAAATGAAATTTTTCACAAAATCAGACATCACGTGCAAAGCAGCCAGGAGTAGAACATTG
         TAGACACTTGGTGAATGTCACTCTTAACCAAGAAACAAGACTGTGCCTTTGGGTTCAGCT
         GGCTCACACATTTATTTTGATGAATTAGGTCAGTGTTTTGTTTGATTATCACAGTGGTGA
         GGTCCATGCAGGTAGCTGTAGGGTGGAAGAATCACTCATCCTTGGGTCCTGCTCTGACAC
         [C,A]
         TACAGGCTGTGCAGCCTGAAGATCTAGGGGAATATCTGTTTCTTCCTAATACCTGTAGAT
         TAGGGATCATTGCTTCTTCCTAATACCTGTAGATTAGGGATCATTGCACCAGCTTTCTGG
         GTTGTGTTGAGGTTGAAGTAAAACGAATACATACAGAAGTTCCTGCTGTTCTGTGAATAT
         TTGAATCTGCACCCACTTGTAGCTTTGTGAGATCACTCTTAACGGTAGTATTTAAGAACA
         TTTGAACTCCGCTGTGGGCTCATGATGAACTTCATTTCTCTTCTGGCGGGTGGACCTGTG

86903    AATTGGGAAATATTTTGAAGAGAATGAAAATGGAAAAACAACATATGAAAACCTATGGGG
         GTACAGCCAGAGTAGTGCTTAGCAGGACATTTATAGCTTCACATACCTCCATTAAAAAGA
         AGAAAGATCTCAAATCAATAACCTAACCTTCTGCCATAAAAAACAGAAAAGAAGAGTA
         AACTCAAAATAAGCAGAAGGAAGTTATTAGATTAGAGAAAAATACAGAATATAAAAACAA
         TATAAGAAAATC
         [C,A]
         ATAAAAATGTTTTTTAAAAACCAACAAATTGGGAAACCTTTACTTAGACTGTCAAGAAAA
         AGGAGAGAAGCCTCACATTACTAAAATCAGGAATGAAAGCACGAATATTAATACCAACCT
         TACATAAATTTTATGAGAATACTTTAAAAAATTGTATTGCAACAAATTAGATAACCTATA
         TGAAAATGGACAAATTATTGGAATGACTATTAAAACTGTCTCAAAAAAATCTAAATAGGC
```

FIGURE 3, page 38 of 40

```
        CTATAACAGAGA
89261   GACTTACACAGGAAACTATAAAATATCACTGAAATGAAGAACTAAATAAGTGGAAAGATA
        TGTTCATGGATTAGAAGACTTAATATTGTTATGGGTCAGAAGACTTAATATTGCTAAAAT
        GGCAATATTCCCCCAATTAATCTACAGATTCAATGCAATCTTTATCAAAATTCTGGCTGC
        CCTTTTTGTAAAAATTGACAAGGTATTTGTTTCTAAAATTGATATGGAAAGTGATGAACT
        CAGAAAGAAGTTAGGGGATTTATACTTCCCAATTTGAAAACTTATAAAACTACAATAATG
        [C,T]
        CATCACCAGATGGAGCGACATGCACCTTATAGTCCCAGCTACTCAGGAGGCTGAGGCAGG
        AGCATCCCTCGAGCCCAGGAGTTTGAGACCAGCCTGGACAACATAGGAAGACCCTGTCTC
        AACTTAAAGAAAGCAAACTACAGTAATACAGTGTGGTACTGACATAAGGATAGCCATATA
        GATTAATGAAATAGAACTGACAGTGTAGAAATAAATCATTTATGGTCAGTTGATTTTTGC
        CAAAGGTTCTAAGACAGTTCAATGGGAAAAAAAGTCTTCTCAAAAATTGGTTCCCAGAGT

95175   CAGTGGAGTCTTTCCATACCTCAATTTTTCATCAAACATTGAGTTGAAGTGTTACACTTC
        TCTCGCAAATAAAGAAATGGGGAAGTTAGAAAATCAAGAAAGGTTAAATGAGTTGGCCAG
        TGTCCCAGGGGCAGGGACCTAGGCAAAAACAAAAGGCTTCTAATTCCAAATCCAGTATTC
        TCTGCTAAAATGTGCCACCTCCCTCCCTTTAGGGTTGGTGGAGGTATCGATACTGGGGCT
        AGTCCTACAGCTAATGCTTTATGATTCTTTGTTCTGCTTCACTCAGCACCTGCTGTACCA
        [T,C]
        GTTATGTTTGTAAGTGGCTTAGTGTTAACTTTTCTCCAAAAGGCAGCAGGGTCTGGAACA
        GGAGACTGGCCCAGTCTGGCATCTGGAGAGGATGGTGGTTGTGGTGTTTCACAGCTCCT
        CCATTACCACCTGGTATCATTTAGTATTACTTTGCAAACTGAATCATAAATCAACTCATT
        TAATGTAGAGAAGGGCAAAAGTTGCTGAGAAATGTTTTGTGGGTTGGTGCCCGGAGCTTC
        AACTCTGGGAGGGTGCCTGACTTGACAGTATCACCTTAGTCACTAAGGAAAAAGAGATCC

96648   CAACAGACTAAACTTCCTATTTTGCGTAGATGCTCCTGTGCACGCCTTTATTTTACACGG
        AATGTAAAATATTGTAATGACTGATTTTCCTTTGAGACTGTAATACAGGTAATGTTCCTA
        TTCAACTTTGTAAACCAAGACCTGACACACAGTAGGTATTTTAAAAACTGTTTTGATGTG
        ACCAAAATTATACAGAAAAAAAGAGAAGTACACCAGGATTTTAAAGTCTCTTTTTTTTTT
        TTATTTTTCACAAAGGATTTGCTGTAAGTCTTCAAGTCATTTTGTCCAATCCAAAAGCTG
        [T,G]
        ATTTAAGCGTCGTGGATCCCAGCCAGGGATGCAAGAATCTGACTTTCTCAAACAGATAAC
        AACAGTCGAAGAACTGGAACCGAAAGCAAATAACTGCACTAAGGTATTCATTACACTTGT
        GCTGCCCGACCTCGAGTGTCACCATGAAGAGTGCGCTACCCAAGCTATTTCCTTCCCCTT
        CAGGTTCTCGTGTGGCACACTCGGACAGAGAAGGTTAATCTAGCCAACGAGCCAAAGTAC
        CACCTGGACACAGTGAAAATTGAGGTATAAATTGAAGCAGCAACTGGTGCAGTTTGTCCA

99242   AGCATCTTAACCCTGTGATTCTCTTACTTCCAAAATTGGTGATAAGAGAAGGAAAGGCAA
        GATTACCATATAGTGAGTGGGTTTAAAACTTACACTCAGAGTTAGACTGTGTTCTTAAT
        TTAATACATTTGACTTGACTTATTTACAGTTTCAAAGACACTAACATAAACTACATCACT
        AATCAGGCATAAGTGTCTGAAGAAGCAGATCACGTCTTCATACCTACTAAAGGACATTTT
        AACCACCTTGTCGTTGGCCAGTAGATTGCACTGATGGAGTGCTGGAGAACAGCATCACCC
        [A,G,T]
        TCTGCATTATCTGGAAGTAAGAGCCAGTATTAACTCCTTCCTGGTTCATCTAGCACCTTA
        ACCTGAGCTGGGTGTGCTTCAGCATGTTGACCATGTGACTGACACTTAGCACATACAATT
        TTTTAGATTCCCAGCGGGTAGAGACCAATGTTTTACCTATATTCTTGTAAATGGTGGTAG
        CAAAATTAACTGTGATATATAGTGATTGTGCTAATGTTAGAAATCACTCTAGACTATTCC
        CTGAATGCTCTAAAGGTAAAACAAGTGACCAAACAGAAACCAAGATTGCCAAAATGCTGG

99349   CTGTGTTCTTAATTTAATACATTTGACTTGACTTATTTACAGTTTCAAAGACACTAACAT
        AAACTACATCACTAATCAGGCATAAGTGTCTGAAGAAGCAGATCACGTCTTCATACCTAC
        TAAAGGACATTTTAACCACCTTGTCGTTGGCCAGTAGATTGCACTGATGGAGTGCTGGAG
        AACAGCATCACCCTTCTGCATTATCTGGAAGTAAGAGCCAGTATTAACTCCTTCCTGGTT
        CATCTAGCACCTTAACCTGAGCTGGGTGTGCTTCAGCATGTTGACCATGTGACTGACACT
        [T,C]
        AGCACATACAATTTTTTAGATTCCCAGCGGGTAGAGACCAATGTTTTACCTATATTCTTG
        TAAATGGTGGTAGCAAAATTAACTGTGATATATAGTGATTGTGCTAATGTTAGAAATCAC
        TCTAGACTATTCCCTGAATGCTCTAAAGGTAAAACAAGTGACCAAACAGAAACCAAGATT
        GCCAAAATGCTGGAGGAACATCAATGGGAAGTGTAAAAGGAAGAAGAGTGGAGCATGAA
        CCTCTCTAAGAGCCTTTGTCTGTGCAGCTAGAGAAAGTCAGAACACAGCACCTGAAATA

99443   GAAGCAGATCACGTCTTCATACCTACTAAAGGACATTTTAACCACCTTGTCGTTGGCCAG
```

```
        TAGATTGCACTGATGGAGTGCTGGAGAACAGCATCACCCTTCTGCATTATCTGGAAGTAA
        GAGCCAGTATTAACTCCTTCCTGGTTCATCTAGCACCTTAACCTGAGCTGGGTGTGCTTC
        AGCATGTTGACCATGTGACTGACACTTAGCACATACAATTTTTTAGATTCCCAGCGGGTA
        GAGACCAATGTTTTACCTATATTCTTGTAAATGGTGGTAGCAAAATTAACTGTGATATAT
        [A,G]
        GTGATTGTGCTAATGTTAGAAATCACTCTAGACTATTCCCTGAATGCTCTAAAGGTAAAA
        CAAGTGACCAAACAGAAACCAAGATTGCCAAAATGCTGGAGGAACATCAATGGGAAGTGT
        AAAAGGAAGAACAGTGGGAGCATGAACCTCTCTAAGAGCCTTTGTCTGTGCAGCTAGAGA
        AAAGTCAGAACACAGCACCTGAAATAGAAATGTTCTATCTCAGCTCTAACTTAGGTAGAA
        ATAGGATTTTATAATATGAGGGGATGTCTGGTTCACACCTTATGGGAATTGAATCTTTTT

99867   AGGAAGAAGAGTGGGAGCATGAACCTCTCTAAGAGCCTTTGTCTGTGCAGCTAGAGAAAA
        GTCAGAACACAGCACCTGAAATAGAAATGTTCTATCTCAGCTCTAACTTAGGTAGAAATA
        GGATTTTATAATATGAGGGGATGTCTGGTTCACACCTTATGGGAATTGAATCTTTTTGTA
        CTCTTTTTAAACATAAAAGTCATTATAGGGTATGTAAAAAGAAAATACAACTTTACAAAG
        GTTTCTCAACAAAAAGAATTTTTACAGAGCCATGGGGCAGTAATCATCCGACCTGAAAAA
        [T,C]
        AGCCTTAGATCCCTCATAAAATAGTGCTTTGAGAATATGAGGCTAGATT
```

FIGURE 3, page 40 of 40

US 6,664,084 B2

ISOLATED NUCLEIC ACID MOLECULES ENCODING HUMAN GLUCURONYLTRANSFERASE PROTEINS, AND RELATED PRODUCTS AND PROCESSES

RELATED APPLICATIONS

The present application claims priority to provisional application U.S. Ser. No. 60/270,871, filed Feb. 26, 2001.

FIELD OF THE INVENTION

The present invention is in the field of enzyme proteins that are related to the transferase enzyme subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Many human enzymes serve as targets for the action of pharmaceutically active compounds. Several classes of human enzymes that serve as such targets include helicase, steroid esterase and sulfatase, convertase, synthase, dehydrogenase, monoxygenase, transferase, kinase, glutanase, decarboxylase, isomerase and reductase. It is therefore important in developing new pharmaceutical compounds to identify target enzyme proteins that can be put into high-throughput screening formats. The present invention advances the state of the art by providing novel human drug target enzymes related to the transferase subfamily.

Transferases

The novel human protein, and encoding gene, provided by the present invention shows the greatest degree of similarity to a glucuronyltransferase cloned from a rat brain cDNA library (Seiki et al., Biochem. Biophys. Res. Commun. 255 (1), 182–187 (1999)). This glucuronyltransferase is important for the biosynthesis of the HNK-1 carbohydrate epitope of glycoproteins. It was demonstrated that transfection of glucuronyltransferase cDNA into COS-1 cells caused the HNK-1 carbohydrate epitope to be expressed on the cell surfaces and also caused the cells to undergo morphological changes. The rat glucuronyltransferase has type II transmembrane topology and the amino acid sequence shares 49% identity with rat GlcAT-P, which is another glucuronyltransferase involved in HNK-1 biosynthesis (Seiki et al., Biochem. Biophys. Res. Commun. 255 (1), 182–187 (1999); for information on GlcAT-P, see Terayama et al. (1997) Proc. Natl. Acad. Sci. USA 94, 6093–6098).

Enzyme proteins, particularly members of the transferase enzyme subfamily, are a major target for drug action and development. Accordingly, it is valuable to the field of pharmaceutical development to identify and characterize previously unknown members of this subfamily of enzyme proteins. The present invention advances the state of the art by providing previously unidentified human enzyme proteins, and the polynucleotides encoding them, that have homology to members of the transferase enzyme subfamily. These novel compositions are useful in the diagnosis, prevention and treatment of biological processes associated with human diseases.

SUMMARY OF THE INVENTION

The present invention is based in part on the identification of amino acid sequences of human enzyme peptides and proteins that are related to the transferase enzyme subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate enzyme activity in cells and tissues that express the enzyme. Experimental data as provided in FIG. 1 indicates expression in humans in testis, prostate, kidney, brain (including fetal brain), ear, and lung.

DESCRIPTION OF THE FIGURE SHEETS

FIG. 1 provides the nucleotide sequence of a cDNA molecule that encodes the enzyme protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in testis, prostate, kidney, brain (including fetal brain), ear, and lung.

FIG. 2 provides the predicted amino acid sequence of the enzyme of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the enzyme protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 35 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a enzyme protein or part of a enzyme protein and are related to the transferase enzyme subfamily. Utilizing these sequences, additional genomic sequences were assembled and transcript and/or cDNA sequences were isolated and characterized. Based on this analysis, the present invention provides amino acid sequences of human enzyme peptides and proteins that are related to the transferase enzyme subfamily, nucleic acid sequences in the form of transcript sequences, cDNA sequences and/or genomic sequences that encode these enzyme peptides and proteins, nucleic acid variation (allelic information), tissue distribution of expression, and information about the closest art known protein/peptide/domain that has structural or sequence homology to the enzyme of the present invention.

In addition to being previously unknown, the peptides that are provided in the present invention are selected based on their ability to be used for the development of commercially important products and services. Specifically, the present peptides are selected based on homology and/or structural relatedness to known enzyme proteins of the transferase enzyme subfamily and the expression pattern observed. Experimental data as provided in FIG. 1 indicates expression in humans in testis, prostate, kidney, brain (including fetal brain), ear, and lung. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known transferase family or subfamily of enzyme proteins.

Specific Embodiments

Peptide Molecules

The present invention provides nucleic acid sequences that encode protein molecules that have been identified as being members of the enzyme family of proteins and are related to the transferase enzyme subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the enzyme peptides of the present invention, enzyme peptides, or peptides/proteins of the present invention.

The present invention provides isolated peptide and protein molecules that consist of, consist essentially of, or comprise the amino acid sequences of the enzyme peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the enzyme peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated enzyme peptide can be purified from cells that naturally express it, purified from cells that have been altered to express it (recombinant), or synthesized using known protein synthesis methods. Experimental data as provided in FIG. 1 indicates expression in humans in testis, prostate, kidney, brain (including fetal brain), ear, and lung. For example, a nucleic acid molecule encoding the enzyme peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the enzyme peptides of the present invention are the naturally occurring mature proteins. A brief description of how various types of these proteins can be made/isolated is provided below.

The enzyme peptides of the present invention can be attached to heterologous sequences to form chimeric or fusion proteins. Such chimeric and fusion proteins comprise a enzyme peptide operatively linked to a heterologous protein having an amino acid sequence not substantially homologous to the enzyme peptide. "Operatively linked" indicates that the enzyme peptide and the heterologous protein are fused in-frame. The heterologous protein can be fused to the N-terminus or C-terminus of the enzyme peptide.

In some uses, the fusion protein does not affect the activity of the enzyme peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant enzyme peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). A enzyme peptide-encoding nucleic acid can be cloned into such an expression vector such that the fusion moiety is linked in-frame to the enzyme peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the enzyme peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, H. G., eds., Humana Press, New Jersey, 1994; *Sequence Analysis in Molecular Biology;* von Heinje, G., Academic Press, 1987; and *Sequence Analysis Primer,* Gribskov, M., and Devereux, J., eds., M Stockton Press, New York 1991). In a preferred embodiment, the percent identity between two amino acid sequences is determined using the Needleman and Wunsch (*J. Mol. Biol.* (48); 444–453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et. al., *Nucleic Acids Res.* 12(1):387(1984)); using a NWSgapdna, CMP matrix and a gap weight of 40, 50, 60, 70, or 80, and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0); using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the enzyme peptides of the present invention as well as being encoded by the same genetic locus as the enzyme peptide provided herein. The gene encoding the novel enzyme of the present invention is located on a genome component that has been mapped to human chromosome 6 (as indicated in FIG. 3), which is supported by multiple lines of evidence, such as STS and BAC map data.

Allelic variants of a enzyme peptide can readily be identified as being a human protein having a high degree (significant) of sequence homology/identity to at least a portion of the enzyme peptide as well as being encoded by the same genetic locus as the enzyme peptide provided herein. Genetic locus can readily be determined based on the genomic information provided in FIG. 3, such as the genomic sequence mapped to the reference human. The gene encoding the novel enzyme of the present invention is located on a genome component that has been mapped to human chromosome 6 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a enzyme peptide encoding nucleic acid molecule under stringent conditions as more fully described below.

FIG. 3 provides information on SNPs that have been found in the gene encoding the enzyme of the present invention. SNPs were identified at 35 different nucleotide positions, including a non-synonymous coding SNP at nucleotide position 96648 (protein position 261). The change in the amino acid sequence caused by this SNP is indicated in FIG. 3 and can readily be determined using the universal genetic code and the protein sequence provided in FIG. 2 as a reference. Some of these SNPs that are located outside the ORF and in introns may affect gene transcription.

Paralogs of a enzyme peptide can readily be identified as having some degree of significant sequence homology/ identity to at least a portion of the enzyme peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a enzyme peptide encoding nucleic acid molecule under moderate to stringent conditions as more fully described below.

Orthologs of a enzyme peptide can readily be identified as having some degree of significant sequence homology/ identity to at least a portion of the enzyme peptide as well as being encoded by a gene from another organism. Preferred orthologs will be isolated from mammals, preferably primates, for the development of human therapeutic targets and agents. Such orthologs will be encoded by a nucleic acid sequence that will hybridize to a enzyme peptide encoding nucleic acid molecule under moderate to stringent conditions, as more fully described below, depending on the degree of relatedness of the two organisms yielding the proteins.

Non-naturally occurring variants of the enzyme peptides of the present invention can readily be generated using recombinant techniques. Such variants include, but are not limited to deletions, additions and substitutions in the amino acid sequence of the enzyme peptide. For example, one class of substitutions are conserved amino acid substitution. Such substitutions are those that substitute a given amino acid in a enzyme peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant enzyme peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/ regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as enzyme activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the enzyme peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a enzyme peptide. Such fragments can be chosen based on the ability to retain one or more of the biological activities of the enzyme peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the enzyme peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in enzyme peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W.H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the enzyme peptides of the present invention also encompass derivatives or analogs in which a substituted amino acid residue is not one encoded by the genetic code, in which a substituent group is included, in which the mature enzyme peptide is fused with another compound, such as a compound to increase the half-life of the enzyme peptide (for example, polyethylene glycol), or in which the additional amino acids are fused to the mature enzyme peptide, such as a leader or secretory sequence or a sequence for purification of the mature enzyme peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a enzyme-effector protein interaction or enzyme-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, enzymes isolated from humans and their human/mammalian orthologs serve as targets for identifying agents for use in mammalian therapeutic applications, e.g. a human drug, particularly in modulating a biological or pathological response in a cell or tissue that expresses the enzyme. Experimental data as provided in FIG. 1 indicates that the enzymes of the present invention are expressed in humans in testis, prostate, kidney, brain, ear, and lung, as indicated by virtual northern blot analysis. In addition, PCR-based tissue screening panels indicate expression in fetal brain. A large percentage of pharmaceutical agents are being developed that modulate the activity of enzyme proteins, particularly members of the transferase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in testis, prostate, kidney, brain (including fetal brain), ear, and lung. Such uses can readily be determined using the information provided herein, that which is known in the art, and routine experimentation.

The proteins of the present invention (including variants and fragments that may have been disclosed prior to the present invention) are useful for biological assays related to enzymes that are related to members of the transferase subfamily. Such assays involve any of the known enzyme functions or activities or properties useful for diagnosis and treatment of enzyme-related conditions that are specific for the subfamily of enzymes that the one of the present invention belongs to, particularly in cells and tissues that express the enzyme. Experimental data as provided in FIG. 1 indicates that the enzymes of the present invention are expressed in humans in testis, prostate, kidney, brain, ear, and lung, as indicated by virtual northern blot analysis. In addition, PCR-based tissue screening panels indicate expression in fetal brain.

The proteins of the present invention are also useful in drug screening assays, in cell-based or cell-free systems. Cell-based systems can be native, i.e., cells that normally express the enzyme, as a biopsy or expanded in cell culture. Experimental data as provided in FIG. 1 indicates expression in humans in testis, prostate, kidney, brain (including fetal brain), ear, and lung. In an alternate embodiment, cell-based assays involve recombinant host cells expressing the enzyme protein.

The polypeptides can be used to identify compounds that modulate enzyme activity of the protein in its natural state or an altered form that causes a specific disease or pathology associated with the enzyme. Both the enzymes of the present invention and appropriate variants and fragments can be used in high-throughput screens to assay candidate compounds for the ability to bind to the enzyme. These compounds can be further screened against a functional enzyme to determine the effect of the compound on the enzyme activity. Further, these compounds can be tested in animal or invertebrate systems to determine activity/effectiveness. Compounds can be identified that activate (agonist) or inactivate (antagonist) the enzyme to a desired degree.

Further, the proteins of the present invention can be used to screen a compound for the ability to stimulate or inhibit interaction between the enzyme protein and a molecule that normally interacts with the enzyme protein, e.g. a substrate or a component of the signal pathway that the enzyme protein normally interacts (for example, another enzyme). Such assays typically include the steps of combining the enzyme protein with a candidate compound under conditions that allow the enzyme protein, or fragment, to interact with the target molecule, and to detect the formation of a complex between the protein and the target or to detect the biochemical consequence of the interaction with the enzyme protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant enzymes or appropriate fragments containing mutations that affect enzyme function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) enzyme activity. The assays typically involve an assay of events in the signal transduction pathway that indicate enzyme activity. Thus, the phosphorylation of a substrate, activation of a protein, a change in the expression of genes that are up- or down-regulated in response to the enzyme protein dependent signal cascade can be assayed.

Any of the biological or biochemical functions mediated by the enzyme can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the enzyme can be assayed. Experimental data as provided in FIG. 1 indicates that the enzymes of the present invention are expressed in humans in testis, prostate, kidney, brain, ear, and lung, as indicated by virtual northern blot analysis. In addition, PCR-based tissue screening panels indicate expression in fetal brain.

Binding and/or activating compounds can also be screened by using chimeric enzyme proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native enzyme. Accordingly, a different set of signal transduction components is available as an end-point assay for activation. This allows for assays to be performed in other than the specific host cell from which the enzyme is derived.

The proteins of the present invention are also useful in competition binding assays in methods designed to discover compounds that interact with the enzyme (e.g. binding partners and/or ligands). Thus, a compound is exposed to a enzyme polypeptide under conditions that allow the compound to bind or to otherwise interact with the polypeptide. Soluble enzyme polypeptide is also added to the mixture. If the test compound interacts with the soluble enzyme polypeptide, it decreases the amount of complex formed or activity from the enzyme target. This type of assay is particularly useful in cases in which compounds are sought that interact with specific regions of the enzyme. Thus, the soluble polypeptide that competes with the target enzyme region is designed to contain peptide sequences corresponding to the region of interest.

To perform cell free drug screening assays, it is sometimes desirable to immobilize either the enzyme protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of enzyme-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a enzyme-binding protein and a candidate compound are incubated in the enzyme protein-presenting wells and the amount of complex trapped in the well can be quantitated. Methods for detecting such complexes, in addition to those described above for the GST-immobilized complexes, include immunodetection of complexes using antibodies reactive with the enzyme protein target molecule, or which are reactive with enzyme protein and compete with the target molecule, as well as enzyme-linked assays which rely on detecting an enzymatic activity associated with the target molecule.

Agents that modulate one of the enzymes of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of enzyme protein activity identified according to these drug screening assays can be used to treat a subject with a disorder mediated by the enzyme pathway, by treating cells or tissues that express the enzyme. Experimental data as provided in FIG. 1 indicates expression in humans in testis, prostate, kidney, brain (including fetal brain), ear, and lung. These methods of treatment include the steps of administering a modulator of enzyme activity in a pharmaceutical composition to a subject in need of such treatment, the modulator being identified as described herein.

In yet another aspect of the invention, the enzyme proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the enzyme and are involved in enzyme activity. Such enzyme-binding proteins are also likely to be involved in the propagation of signals by the enzyme proteins or enzyme targets as, for example, downstream elements of a enzyme-mediated signaling pathway. Alternatively, such enzyme-binding proteins are likely to be enzyme inhibitors.

The two-hybrid system is based on the modular nature of most transcription factors, which consist of separable DNA-binding and activation domains. Briefly, the assay utilizes two different DNA constructs. In one construct, the gene that codes for a enzyme protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a enzyme-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the enzyme protein.

This invention further pertains to novel agents identified by the above-described screening assays. Accordingly, it is within the scope of this invention to further use an agent identified as described herein in an appropriate animal model. For example, an agent identified as described herein (e.g., a enzyme-modulating agent, an antisense enzyme nucleic acid molecule, a enzyme-specific antibody, or a enzyme-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The enzyme proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in testis, prostate, kidney, brain (including fetal brain), ear, and lung. The method involves contacting a biological sample with a compound capable of interacting with the enzyme protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered enzyme activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the enzyme protein in which one or more of the enzyme functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and enzyme activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in testis, prostate, kidney, brain (including fetal brain), ear, and lung. Accordingly, methods for treatment include the use of the enzyme protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the enzyme proteins. Antibodies can be prepared from any region of the peptide as described herein. However, preferred regions will include those involved in function/activity and/or enzyme/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the enzymes of the present invention are expressed in humans in testis, prostate, kidney, brain, ear, and lung, as indicated by virtual northern blot analysis. In addition, PCR-based tissue screening panels indicate expression in fetal brain. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in testis, prostate, kidney, brain (including fetal brain), ear, and lung. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in testis, prostate, kidney, brain (including fetal brain), ear, and lung. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in testis, prostate, kidney, brain (including fetal brain), ear, and lung. Thus, where a specific protein has been correlated with expression in a specific tissue, antibodies that are specific for this protein can be used to identify a tissue type.

The antibodies are also useful for inhibiting protein function, for example, blocking the binding of the enzyme peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a enzyme peptide or protein of the present invention (cDNA, transcript and genomic sequence). Such nucleic acid molecules will consist of, consist essentially of, or comprise a nucleotide sequence that encodes one of the enzyme peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the enzyme peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the enzyme proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel enzyme of the present invention is located on a genome component that has been mapped to human chromosome 6 (as indicated in FIG. 3), which is supported by multiple lines of evidence, such as STS and BAC map data.

FIG. 3 provides information on SNPs that have been found in the gene encoding the enzyme of the present invention. SNPs were identified at 35 different nucleotide positions, including a non-synonymous coding SNP at nucleotide position 96648 (protein position 261). The change in the amino acid sequence caused by this SNP is indicated in FIG. 3 and can readily be determined using the universal genetic code and the protein sequence provided in FIG. 2 as a reference. Some of these SNPs that are located outside the ORF and in introns may affect gene transcription.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45 C., followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 35 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel enzyme of the present invention is located on a genome component that has been mapped to human chromosome 6 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the enzymes of the present invention are expressed in humans in testis, prostate, kidney, brain, ear, and lung, as indicated by virtual northern blot analysis. In addition, PCR-based tissue screening panels indicate expression in fetal brain. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in enzyme protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a enzyme protein, such as by measuring a level of a enzyme-encoding nucleic acid in a sample of cells from a subject e.g., mRNA or genomic DNA, or determining if a enzyme gene has been mutated. Experimental data as provided in FIG. 1 indicates that the enzymes of the present invention are expressed in humans in testis, prostate, kidney, brain, ear, and lung, as indicated by virtual northern blot analysis. In addition, PCR-based tissue screening panels indicate expression in fetal brain.

Nucleic acid expression assays are useful for drug screening to identify compounds that modulate enzyme nucleic acid expression.

The invention thus provides a method for identifying a compound that can be used to treat a disorder associated with nucleic acid expression of the enzyme gene, particularly biological and pathological processes that are mediated by the enzyme in cells and tissues that express it. Experimental data as provided in FIG. 1 indicates expression in humans in testis, prostate, kidney, brain (including fetal brain), ear, and lung. The method typically includes assaying the ability of the compound to modulate the expression of the enzyme nucleic acid and thus identifying a compound that can be used to treat a disorder characterized by undesired enzyme nucleic acid expression. The assays can be performed in cell-based and cell-free systems. Cell-based assays include cells naturally expressing the enzyme nucleic acid or recombinant cells genetically engineered to express specific nucleic acid sequences.

The assay for enzyme nucleic acid expression can involve direct assay of nucleic acid levels, such as mRNA levels, or on collateral compounds involved in the signal pathway. Further, the expression of genes that are up- or down-regulated in response to the enzyme protein signal pathway can also be assayed. In this embodiment the regulatory regions of these genes can be operably linked to a reporter gene such as luciferase.

Thus, modulators of enzyme gene expression can be identified in a method wherein a cell is contacted with a candidate compound and the expression of mRNA determined. The level of expression of enzyme mRNA in the presence of the candidate compound is compared to the level of expression of enzyme mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate enzyme nucleic acid expression in cells and tissues that express the enzyme. Experimental data as provided in FIG. 1 indicates that the enzymes of the present invention are expressed in humans in testis, prostate, kidney, brain, ear, and lung, as indicated by virtual northern blot analysis. In addition, PCR-based tissue screening panels indicate expression in fetal brain. Modulation includes both up-regulation (i.e. activation or agonization) or down-regulation (suppression or antagonization) or nucleic acid expression.

Alternatively, a modulator for enzyme nucleic acid expression can be a small molecule or drug identified using the screening assays described herein as long as the drug or small molecule inhibits the enzyme nucleic acid expression in the cells and tissues that express the protein. Experimental data as provided in FIG. 1 indicates expression in humans in testis, prostate, kidney, brain (including fetal brain), ear, and lung.

The nucleic acid molecules are also useful for monitoring the effectiveness of modulating compounds on the expression or activity of the enzyme gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in enzyme nucleic acid expression, and particularly in qualitative changes that lead to pathology. The nucleic acid molecules can be used to detect mutations in enzyme genes and gene expression products such as mRNA. The nucleic acid molecules can be used as hybridization probes to detect naturally occurring genetic mutations in the enzyme gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the enzyme gene associated with a dysfunction provides a diagnostic tool for an active disease or susceptibility to disease when the disease results from overexpression, underexpression, or altered expression of a enzyme protein.

Individuals carrying mutations in the enzyme gene can be detected at the nucleic acid level by a variety of techniques. FIG. 3 provides information on SNPs that have been found in the gene encoding the enzyme of the present invention. SNPs were identified at 35 different nucleotide positions, including a non-synonymous coding SNP at nucleotide position 96648 (protein position 261). The change in the amino acid sequence caused by this SNP is indicated in FIG. 3 and can readily be determined using the universal genetic code and the protein sequence provided in FIG. 2 as a reference. Some of these SNPs that are located outside the ORF and in introns may affect gene transcription. The gene encoding the novel enzyme of the present invention is located on a genome component that has been mapped to human chromosome 6 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a enzyme gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant enzyme gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the enzyme gene in an individual in order to select an appropriate compound or dosage regimen for treatment. FIG. 3 provides information on SNPs that have been found in the gene encoding the enzyme of the present invention. SNPs were identified at 35 different nucleotide positions, including a non-synonymous coding SNP at nucleotide position 96648 (protein position 261). The change in the amino acid sequence caused by this SNP is indicated in FIG. 3 and can readily be determined using the universal genetic code and the protein sequence provided in FIG. 2 as a reference. Some of these SNPs that are located outside the ORF and in introns may affect gene transcription.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control enzyme gene expression in cells, tissues, and organisms. A DNA antisense nucleic acid molecule is designed to be complementary to a region of the gene involved in transcription, preventing transcription and hence production of enzyme protein. An antisense RNA or DNA nucleic acid molecule would hybridize to the mRNA and thus block translation of mRNA into enzyme protein.

Alternatively, a class of antisense molecules can be used to inactivate mRNA in order to decrease expression of enzyme nucleic acid. Accordingly, these molecules can treat a disorder characterized by abnormal or undesired enzyme nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the enzyme protein, such as substrate binding.

The nucleic acid molecules also provide vectors for gene therapy in patients containing cells that are aberrant in enzyme gene expression. Thus, recombinant cells, which include the patient's cells that have been engineered ex vivo and returned to the patient, are introduced into an individual where the cells produce the desired enzyme protein to treat the individual.

The invention also encompasses kits for detecting the presence of a enzyme nucleic acid in a biological sample. Experimental data as provided in FIG. 1 indicates that the enzymes of the present invention are expressed in humans in testis, prostate, kidney, brain, ear, and lung, as indicated by virtual northern blot analysis. In addition, PCR-based tissue screening panels indicate expression in fetal brain. For example, the kit can comprise reagents such as a labeled or labelable nucleic acid or agent capable of detecting enzyme nucleic acid in a biological sample; means for determining the amount of enzyme nucleic acid in the sample; and means for comparing the amount of enzyme nucleic acid in the sample with a standard. The compound or agent can be packaged in a suitable container. The kit can further comprise instructions for using the kit to detect enzyme protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the enzyme proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the enzyme gene of the present invention. FIG. 3 provides information on SNPs that have been found in the gene encoding the enzyme of the present invention. SNPs were identified at 35 different nucleotide positions, including a non-synonymous coding SNP at nucleotide position 96648 (protein position 261). The change in the amino acid sequence caused by this SNP is indicated in FIG. 3 and can readily be determined using the universal genetic code and the protein sequence provided in FIG. 2 as a reference. Some of these SNPs that are located outside the ORF and in introns may affect gene transcription.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology,* Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified enzyme gene of the present invention can be routinely identified using the sequence information disclosed herein can be readily incorporated into one of the established kit formats which are well known in the art, particularly expression arrays.

Vectors/host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium.* Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroenzyme. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli.* (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943 (1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed, Cold Spring Harbor Laboratory,* Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as enzymes, appropriate secretion signals are incorporated into the vector. The signal sequence can be endogenous to the peptides or heterologous to these peptides.

Where the peptide is not secreted into the medium, which is typically the case with enzymes, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a enzyme protein or peptide that can be further purified to produce desired amounts of enzyme protein or fragments. Thus, host cells containing expression vectors are useful for peptide production.

Host cells are also useful for conducting cell-based assays involving the enzyme protein or enzyme protein fragments, such as those described above as well as other formats known in the art. Thus, a recombinant host cell expressing a native enzyme protein is useful for assaying compounds that stimulate or inhibit enzyme protein function.

Host cells are also useful for identifying enzyme protein mutants in which these functions are affected. If the mutants naturally occur and give rise to a pathology, host cells containing the mutations are useful to assay compounds that have a desired effect on the mutant enzyme protein (for example, stimulating or inhibiting function) which may not be indicated by their effect on the native enzyme protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a enzyme protein and identifying and evaluating modulators of enzyme protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the enzyme protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the enzyme protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, enzyme protein activation, and signal transduction, may not be evident from in vitro cell-free or cell-based assays. Accordingly, it is useful to provide non-human transgenic animals to assay in vivo enzyme protein function, including substrate interaction, the effect of specific mutant enzyme proteins on enzyme protein function and substrate interaction, and the effect of chimeric enzyme proteins. It is also possible to assess the effect of null mutations, that is, mutations that substantially or completely eliminate one or more enzyme protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule encoding a glucuronyltransferase, wherein the nucleic acid molecule consists of a nucleotide sequence selected from the group consisting of:
   (a) a nucleotide sequence that encodes SEQ ID NO:2, except that residue 261 of SEQ ID NO:2 is glycine;
   (b) a nucleotide sequence that encodes an amino acid sequence having at least 99% sequence identity to SEQ ID NO:2;
   (c) a nucleotide sequence having at least 99% sequence identity to SEQ ID NO:1; and
   (d) a nucleotide sequence having at least 99% sequence identity to SEQ ID NO:3.

2. An isolated nucleic acid molecule consisting of a nucleotide sequence that is completely complementary to a nucleotide sequence of claim 1.

3. A nucleic acid vector comprising the nucleic acid molecule of claim 1.

4. A host cell containing the vector 3.

5. A process for producing a polypeptide comprising culturing the host cell of claim 4 under conditions sufficient for the production of the polypeptide encoded by the vector, and recovering said polypeptide.

6. The vector of claim 3, wherein said vector is selected from the group consisting of a plasmid, a virus, and a bacteriophage.

7. The vector of claim 3, wherein said isolated nucleic acid molecule is inserted into said vector in proper orientation and correct reading frame such that a polypeptide having at least 99% sequence identity to SEQ ID NO:2 may be expressed by a cell transformed with said vector.

8. The vector of claim 7, wherein said isolated nucleic acid molecule is operatively linked to a promoter sequence.

9. An isolated nucleic acid molecule comprising a nucleotide sequence selected from the group consisting of:
   (a) a cDNA sequence that encodes SEQ ID NO:2;
   (b) SEQ ID NO:1;
   (c) nucleotides 614–1582 of SEQ ID NO:1; and
   (d) a nucleotide sequence that is completely complementary to a nucleotide sequence of any of (a)–(c).

10. A nucleic acid vector comprising the nucleic acid molecule of claim 9.

11. A host cell containing the vector of claim 10.

12. A process for producing a polypeptide comprising culturing the host cell of claim 11 under conditions sufficient for the production of the polypeptide encoded by the vector and recovering said polypeptide.

13. The vector of claim 10, wherein said vector is selected from the group consisting of a plasmid, a virus, and a bacteriophage.

14. The vector of claim 10, wherein said isolated nucleic acid molecule is inserted into said vector in proper orientation and correct reading frame such that a polypeptide comprising SEQ ID NO:2 may be expressed by a cell transformed with said vector.

15. The vector of claim 14, wherein said isolated nucleic acid molecule is operatively linked to a promoter sequence.

16. An isolated nucleic acid molecule consisting of a nucleotide sequence selected from the group consisting of:
   (a) a nucleotide sequence that encodes a polypeptide comprising the amino acid sequence of SEQ ID NO:2;
   (b) a nucleotide sequence consisting of SEQ ID NO:1;
   (c) a nucleotide sequence consisting of SEQ ID NO:3; and
   (d) a nucleotide sequence that is completely complementary to a nucleotide sequence of any of (a)–(c).

17. A nucleic acid vector comprising the nucleic acid molecule of claim 16.

18. A host cell containing the vector of claim 17.

19. A process for producing a polypeptide comprising culturing the host cell of claim 18 under conditions sufficient for the production of the polypeptide encoded by the vector, and recovering said polypeptide.

20. The vector of claim 17, wherein said vector is selected from the group consisting of a plasmid, a virus, and a bacteriophage.

21. The vector of claim 17, wherein said isolated nucleic acid molecule is inserted into said vector in proper orientation and correct reading frame such that a polypeptide comprising SEQ ID NO:2 may be expressed by a cell transformed with said vector.

22. The vector of claim 21, wherein said isolated nucleic acid molecule is operatively linked to a promoter sequence.

23. An isolated polynucleotide consisting of the nucleotide sequence of SEQ ID NO:1.

24. An isolated polynucleotide consisting of the nucleotide sequence of SEQ ID NO:3.

* * * * *

SEQUENCE LISTING

<160> NUMBER OF SEQ ID NOS: 5

<210> SEQ ID NO 1
<211> LENGTH: 4970
<212> TYPE: DNA
<213> ORGANISM: Human

<400> SEQUENCE: 1

| | | | | | |
|---|---|---|---|---|---|
| gttctgagaa | gacaagagca | agggactgag | agcaggcttc | cgctgcggcg | cgcgaacaca | 60 |
| gccgggacac | aaccccccagc | gtctccaccc | gctcctcgcc | accccggcgg | gaatgtgagg | 120 |
| aaggaaagcc | cccagcgccg | ccgcccgccc | tcgaaggcgt | cccagagagc | gtcctggggg | 180 |
| cccgcggctg | gagcccttgt | gcccgcagca | ccgccggact | ggagcggcga | ggcgcaccgg | 240 |
| gtgccgcttc | tcggcttcca | ctcttcagaa | agagcgcggt | ggggatcagc | gcctttcccg | 300 |
| cactcggcac | aactccggga | ccggcggcgc | gcggctggac | cgagtcccgc | ttcccgccag | 360 |
| ctcacctgga | gtcggggggca | gccctgccc | gcccgcctgc | accccttgtc | gctctagctt | 420 |
| gcgcgaacct | gccgctcctc | cacgcccagg | tagtgagccc | cgcggctcca | ggtctctgca | 480 |
| gcgccctcgg | ccccatggac | agcgcaccca | tcaccactcc | ctaagtgctg | gcgccgccgc | 540 |
| tgtccaagct | gcgcactggg | gtccctcggc | tcgcccctct | ctggggtgtc | cgagaggcca | 600 |

-continued

| | |
|---|---|
| gggagcgtgc accatgaagt ccgcgctttt cacccgcttc tttatcctcc tgccctggat | 660 |
| cctaattgtc atcatcatgc tcgacgtgga cacgcgcagg ccagtgcccc cgctcacccc | 720 |
| gcgcccctac ttctctccct acgcggtggg ccgcgggggc gcccgactcc cgctccgcag | 780 |
| ggcggcccg gctcacggga cccaaaagcg caaccagtct cggccgcagc cacagccgga | 840 |
| gccgcagctg cccaccatct atgccatcac gcccacctac agccgcccgg tgcagaaagc | 900 |
| ggagctgacc cgcctggcca cacgttccg ccaggtggcg cagctgcact ggatcctggt | 960 |
| ggaggacgcg gcgcgcgca gcgagctggt gagccgcttc ctggcgcggg ccgggctgcc | 1020 |
| cagcactcac ctgcacgtgc ccacgccgcg gcgctacaag cggcccgggc tgccgcgcgc | 1080 |
| cactgagcag cgcaacgcgg gcctcgcctg gctgcgccag aggcaccagc accagcgcgc | 1140 |
| gcagcccggc gtgctcttct tcgctgacga cgacaacacc tatagtctgg agctcttcca | 1200 |
| ggagatgcga accaccccgca aggtctccgt ctggcctgtg ggcctggttg gtgggcggcg | 1260 |
| ctacgaacgt ccgctggtgg aaaacggcaa agttgttggc tggtacaccg gctggagagc | 1320 |
| agacaggcct tttgccatcg acatggcagg atttgctgta agtcttcaag tcattttgtc | 1380 |
| caatccaaaa gctgtatta agcgtcgtgg atcccagcca gggatgcaag aatctgactt | 1440 |
| tctcaaacag ataacaacag tcgaagaact ggaaccgaaa gcaaataact gcactaaggt | 1500 |
| tctcgtgtgg cacactcgga cagagaaggt taatctagcc aacgagccaa agtaccacct | 1560 |
| ggacacagtg aaaattgagg tataataaat tgaagcagca actggtgcag tttgtccagc | 1620 |
| cagtggatcc atatggaaga ggatgtttgg agtttaggct acagagcatt caggtattgt | 1680 |
| ttgttttact tcagtacagc agcctttctt gtcatctgat ggacatctgt ttaaatggag | 1740 |
| cttgtcagtt aacataagct aattggatgg ttggtacaaa atgtatgttt tgtcttcatt | 1800 |
| tgttctgcat gttttctcta caacaactaa attggaagat ttttttgtac agtgccgata | 1860 |
| ctgcaagata ccactcttga gtatatattt tttcttttc tccaatttgc ccttataatt | 1920 |
| ggtagacttg aacaggttgg tagacttgaa caggttttta aaacagacaa gtattttgtc | 1980 |
| agctaaacgt tcctgatgat tcctgacttt gcaatactaa gtaattttg gaaggttagt | 2040 |
| ggcagtatac atcataggaa ataaaaccc acaaatgaaa aggtctatgg agtcatgttt | 2100 |
| aatgtaggga ataacatttt tgtcaatact aggcaccata aaatgtaaac acaattactg | 2160 |
| tcataaacct agatatacct tcaaggattg aagattgaaa gtggctttgt tttagttagt | 2220 |
| taccctgttt gcatatagtg cagaaaaagg tcttcatgtt agcactatgt acattaagaa | 2280 |
| gagatccaaa ttcaagaga ggcagataaa atttgaattc tttaagcatt cattaaacga | 2340 |
| agttttggag taacatccac gtttatcttc ctttcactaa tcacgttccc tgttaagcac | 2400 |
| atcataacaa cagcacagtg aagtgaatga tgaaataaga gcattttgat acactagaaa | 2460 |
| acagtgctca gtgagacatt tacattctat ttatatgatt aaacatttga tcatacagta | 2520 |
| ccttcctaca ggattactgg ctaattttgg ggtggggttt atactattag aggtattact | 2580 |
| aacatgataa ctacttccct tatatgcaaa cattagagct ataattttat tgagaggaaa | 2640 |
| actgattttg caagttgagc agcttctcaa ataatgcagt acatgaaatc atgggaaata | 2700 |
| tgagcaaagc tgcccttgac ataaaatgat ttatcaacct gcttttcacc acatcaaatt | 2760 |
| gaatcagtac agaccaacac ggtcaatcag atcattctta atatgaacaa atgggtaaaa | 2820 |
| agaaaaaaaa tatgcatatg aataaacagg ggaactagat gcgtttcagc aaggaatgtc | 2880 |
| aggtggtagt tctggatgaa acttgtattg cagtttttcat ttccacagtt gtgtgctgag | 2940 |
| agtctgacct gatgagcttc cagaccatcc tgctgttgtg ctggagggct ggccaaaacc | 3000 |

```
tgcagtaggg gttgcactac tgatactcat gccagccatc tgctgattca tctgtgaaac    3060
atataaaagg cttagttcaa gaggcttact tcacttttaa ttcttgtttc tttagccaca    3120
cagttggtca ttttttcatt aatgtgacaa ctagtccaag cactggaata aaacagagt     3180 accatacaaa tatttcttaa agcaaatagc tactttgttc ccttctttat ctactttcta    3240
gatacagttt ccccaaagat taaccacaac ttacttaaaa aaaatacca aagcaatctt     3300 gggattttaa tgagtccgct actctaacta actttcacct acactaggat attgtgcttt    3360
aactactaag gagtaagaaa attttaggaa gtaaatagt  ctaaaattat cctataaact    3420
ttgtatgata gatattattc tctattaaaa tcttatatac ttcctaaata ttttaaagt     3480 ggtcataaag catttatttc tctcgctgat ctaacaacaa aaacatctaa aatttatttt    3540
cattgtatgc aataaagcat aagattacat gtatttttct tcaagactgg agtcaaatat    3600
atatatatat aagcatctta accctgtgat tctcttactt ccaaaattgg tgataagaga    3660
aggaaaggca agatttacca tatagtgagt gggtttaaaa cttacactca gagttagact    3720
gtgttcttaa tttaatacat ttgacttgac ttatttacag tttcaaagac actaacataa    3780
actacatcac taatcaggca taagtgtctg aagaagcaga tcacatcttc atacctacta    3840
aaggacattt taaccaccct gtcattggcc agtagattgc actgatggag tgctggagaa    3900
cagcatcacc cttctgcatt atctggaagt aagagccagt attaactcct tcctggttca    3960
tctagcacct taacctgagc tgggtgtgct tcagcatgtt gaccatgtga ctgacactta    4020
gcacatacaa ttttttagat tcccagcggg tagagaccaa tgttttacct atattcttgt    4080
aaatggtggt agcaaaatta actgtgatat atagtgattg tgctaatgtt agaaatcact    4140
ctagactatt ccctgaatgc tctaaaggta aacaagtga ccaaacagaa accaagattg      4200
ccaaaatgct ggaggaacat caatgggaag tgtaaaagga agaagagtgg gagcatgaac    4260
ctctctaaga gcctttgtct gtgcagctag agaaaagtca gaacacagca cctgaaatag    4320
aaatgttcta tctcagctct aacttaggta gaaataggta tttataatat gagggatgt     4380 ctggttcaca ccttatggga attgaatctt tttgtactct ttttaaacat aaaagtcatt    4440
atagggtatg taaaaagaaa atacaacttt acaaaggttt ctcaacaaaa agaattttta    4500
cagagccatg gggcagtaat catccgacct gaaaaatagc cttagatccc tcataaaata    4560
gtgctttgag aatatgaggc tagatttta ttttctaata aaagatccta aaattattag     4620
tgaagctaag ttgtctaagt ggactgtaaa aatgtcccac cagcaagctg ataaagctt     4680 agtgctaatc tcagaggtga cagagaggga gtctcatgat gcctgagata atttctggcc    4740
attagtggtg ttcacgttac agttacatta caatttgaaa tgaaagatgt ttaaccttt     4800 ttttacagaa tactctaaaa tagggataat aacacatcat ttgtctatct gatacaactt    4860
cataatattt atagatactt ttgacccctat aacatattat ccctattgaa ttctttctgc   4920
cagatcacta gacttaaaaa aaaaaaaaa aaaaaaaaa aaaaaaaaa                  4970
```

<210> SEQ ID NO 2
<211> LENGTH: 323
<212> TYPE: PRT
<213> ORGANISM: Human

<400> SEQUENCE: 2

```
Met Lys Ser Ala Leu Phe Thr Arg Phe Phe Ile Leu Leu Pro Trp Ile
 1               5                  10                  15

Leu Ile Val Ile Ile Met Leu Asp Val Asp Thr Arg Arg Pro Val Pro
```

```
                20                  25                  30
Pro Leu Thr Pro Arg Pro Tyr Phe Ser Pro Tyr Ala Val Gly Arg Gly
                35                  40                  45

Gly Ala Arg Leu Pro Leu Arg Arg Gly Gly Pro Ala His Gly Thr Gln
 50                  55                  60

Lys Arg Asn Gln Ser Arg Pro Gln Pro Gln Pro Glu Pro Gln Leu Pro
 65                  70                  75                  80

Thr Ile Tyr Ala Ile Thr Pro Thr Tyr Ser Arg Pro Val Gln Lys Ala
                 85                  90                  95

Glu Leu Thr Arg Leu Ala Asn Thr Phe Arg Gln Val Ala Gln Leu His
                100                 105                 110

Trp Ile Leu Val Glu Asp Ala Ala Ala Arg Ser Glu Leu Val Ser Arg
                115                 120                 125

Phe Leu Ala Arg Ala Gly Leu Pro Ser Thr His Leu His Val Pro Thr
                130                 135                 140

Pro Arg Arg Tyr Lys Arg Pro Gly Leu Pro Arg Ala Thr Glu Gln Arg
145                 150                 155                 160

Asn Ala Gly Leu Ala Trp Leu Arg Gln Arg His Gln His Gln Arg Ala
                165                 170                 175

Gln Pro Gly Val Leu Phe Phe Ala Asp Asp Asp Asn Thr Tyr Ser Leu
                180                 185                 190

Glu Leu Phe Gln Glu Met Arg Thr Thr Arg Lys Val Ser Val Trp Pro
                195                 200                 205

Val Gly Leu Val Gly Gly Arg Arg Tyr Glu Arg Pro Leu Val Glu Asn
                210                 215                 220

Gly Lys Val Val Gly Trp Tyr Thr Gly Trp Arg Ala Asp Arg Pro Phe
225                 230                 235                 240

Ala Ile Asp Met Ala Gly Phe Ala Val Ser Leu Gln Val Ile Leu Ser
                245                 250                 255

Asn Pro Lys Ala Val Phe Lys Arg Arg Gly Ser Gln Pro Gly Met Gln
                260                 265                 270

Glu Ser Asp Phe Leu Lys Gln Ile Thr Thr Val Glu Glu Leu Glu Pro
                275                 280                 285

Lys Ala Asn Asn Cys Thr Lys Val Leu Val Trp His Thr Arg Thr Glu
                290                 295                 300

Lys Val Asn Leu Ala Asn Glu Pro Lys Tyr His Leu Asp Thr Val Lys
305                 310                 315                 320

Ile Glu Val

<210> SEQ ID NO 3
<211> LENGTH: 99916
<212> TYPE: DNA
<213> ORGANISM: Human
<220> FEATURE:
<221> NAME/KEY: misc_feature
<222> LOCATION: (1)...(99916)
<223> OTHER INFORMATION: n = A,T,C or G

<400> SEQUENCE: 3
cacagtgttt catctctgaa tagccttggt tcctggagag gatgtaatag caaataggtt     60
ttatggcata gttggaccaa ccaaaagttc cccactaaca aaggttagtg atgtttttag    120
tacaattcag taacaacatg aattttattc cagcaaacac aaggcatttt aaccaaattt    180
aaaatttcca acaggatgaa ccagacttca gtaacttagg ggagagggt  gcactgcttc    240 ctaagaaaaa ccttttctta aagggaggcc ttgacttctt tcctcttccc catcctggca    300
```

-continued

```
tgatgctggt gcagaataca tttccaaggt tgtgttatat tcagaggcac attaggctat      360
tcgagagaat gggaagaggt ctaatggctt cgttgttttc tatgtttagg atgcactaat      420
ctgcagagtt taatgtatga gttgtggatg gcacagggaa gttgggacag aaggctagct      480
ctagggagtt gttggggtgg ctgggtgtta gtctgaaatt tcactctcac gtttcagaat      540
ctgaagagga agttagggaa attcacagat gagccaatgc cttttaacag gtgggggtt      600 cagggggtagg actgggagaa gaggagctgt cagaaaagct ggagagccat tcgcccaga      660 gctctcagtt gcaccagaac gcacagtcgg agagagattt atttgtgaac aagcccgaga      720
aaggcagaca acccagacaa gatgggctca gaaattattt atcataggct agggcagaac      780
agtctggagc tttccttctg ctttgcaagc acttccctgg gacctgcctg ggaagcacag      840
cccttcttcc tggtaagtta cagaaggtca ggcactcagc tagtaggcca gctagacaac      900
aaaaagtgtc taaactaagt gccaactgtt tacttgggt cttccagacc ctatcatggt       960
tctattcgtc atggtacact ctgtttgatt tcaatcgcac catctttata tgtaggaagg      1020
ccaaaccggc ccgctgtgt tgggtgggat ttctgcaggc catgcagtga ggacgccact       1080
agctatagac acacgcagga gacccacgtt ctatttccat atgccacttg ccactgacct      1140
cagagaaatc atttttaaacc ctgaacctca gcttccttat cctgaaaatg aaggccattc     1200
tacttcttag gccttcttga caggagcctt gggagagcca aacggagtaa ttccggtgac      1260
agcgaagaac tgggagggac cgtgactcca aattactgaa gaaaaataag ttaaacatgc      1320
tcggctggag ttttaggaat tccacccgcc cccacccgcc atgatcaaac tgcagtcagg      1380
cagcagccct ccgaattgat tctttcttat ggactgtctc acatgccaaa cacctatgtg      1440
cagcacccct ccatctccgt gggctcctat tgatgtctgc cttgcagtga aagcgctttt      1500 tgttccgct gttcgataca ccccagcaca tcaacgcagc agctgggagc aggaggagga      1560
atcccttcgc tttctcccct cctttcactc cgaaccctag gcatcagcag caacgcgcgt      1620
agcccggcaa atttccgcac gtgaatggat tttcctggct catctccaaa gaccttgcgg     1680
tatttcacaa agctgaagag aggtgaacga gcatcacccc ctccaggagg tcgtgcagcc    1740
ccgcggggac gctcctcccg ctcctccacc cgcggtgcag cggccgcctc ccgagcttgc    1800
tcgcggggcc gttagcgcca gaccggcgg agagccaagg ggtccctccg cgcctccctc      1860
tcgcagcccc tctccaccag tagcagcgct gctgtcttcc cacaggagga cttgggagga   1920
cgctggattc tgcagcgccc ccgcccctc gctttttctt tctttccttg ctttgggatc     1980
ttgctgctgg atccggagag gttctgagaa gacaagagca agggactgag agcaggcttc    2040
cgctgcggcg cgcgaacaca gccgggacac aaccccccagc gtctccaccc gctcctcgcc  2100
accccggcgg gaatgtgagg aaggaaagcc cccagcgccg ccgcccgccc tcgaaggcgt   2160
cccagagagc gtcctggggg cccgcggctg gagcccttgt gccccgcagca ccgccggact  2220 ggagcggcga ggcgcaccgg gtgccgcttc tcggcttcca ctcttcagaa agagcgcggt    2280
ggggatcagc gcctttcccg cactcggcac aactccggga ccggcggcgc gcggctggac  2340
cgagtcccgc ttcccgccag ctcacctgga gtcgggggca gcccctgccc gcccgcctgc   2400
accccttgtc gctctagctt gcgcgaacct gccgctcctc cacgcccagg tagtgagccc   2460
cgcggctcca ggtctctgca gcgccctcgg ccccatggac agcgcaccca tcaccactcc     2520
ctaagtgctg gcgccgccgc tgtccaagct gcgcactggg gtccctcggc tcgcccctct   2580
ctggggtgtc cgagaggcca gggagcgtgc accatgaagt ccgcgctttt cacccgcttc   2640
```

-continued

```
tttatcctcc tgccctggat cctaattgtc atcatcatgc tcgacgtgga cacgcgcagg    2700
ccagtgcccc cgctcacccc gcgcccctac ttctctccct acgcggtggg ccgcggggc    2760 gcccgactcc cgctccgcag gggcggcccg gctcacggga cccaaaagcg caaccagtct    2820
cggccgcagc cacagccgga gccgcagctg cccaccatct atgccatcac gcccacctac    2880
agccgcccgg tgcagaaagc ggagctgacc cgcctggcca cacgttccg ccaggtggcg     2940 cagctgcact ggatcctggt ggaggacgcg gcggcgcgca gcgagctggt gagccgcttc    3000
ctggcgcggg ccgggctgcc cagcactcac ctgcacgtgc ccacgccgcg gcgctacaag    3060
cggcccgggc tgccgcgcgc cactgagcag cgcaacgcgg gcctcgcctg gctgcgccag    3120
aggcaccagc accagcgcgc gcagcccggc gtgctcttct tcgctgacga cgacaacacc    3180
tatagtctgg agctcttcca ggaggtaaag gccagcctgc cccgctgggt gggcgagggc    3240
gggagtgggc ctccgggccg gccgggctgc agtcacacgc cccttgcact ccgggtgcac    3300
ttttgagttc tcagttctcc gtgcgcgcat tcggggcacc gagtggagcc gctccttgct    3360
ggcactccgc agcctccgct ggccgtgggg gtggaggggc tgtgtgtgag aggatcactg    3420
tggcttaagg ggcgggagtc tgccctgggg cttttctgtg tggagattgt gtcaagagaa    3480
tagcacaggt gtgaggcgcg ggaatgattt ccaggggcca ggctcctgac gacctgagga    3540
tggagcttag acctgcaggc gctggctgcg ataggagatc agggagggac ctgcaccgta    3600
gcgggtggcg gtgagggggt gggggtggtg gggacgggta ggctaggtgt tactcgaggc    3660
ttttcagtgc ctacaggtgt gattctcagt ctaggaccat ataggagaa aggtggagat    3720 agcctagaga gaaatttgac tattgcggcc cactggcacg gaaatggttg ttagaagaaa    3780
cactgacttc tatggaggtc cttcctctct ttcccacacc tcacaaaagt cttttctgac    3840
cctcaagatt acttttttt tttttttgca agaaaaccct ttctggaaaa taaactgttc    3900
tgccctgtgg ttacgtcttt tttgcagccc aaggtaaaca tctgggctgc ctgatccctt    3960
ttcacaacct ttctctaagg cctcttttg gcgagttagc caggacacat ttggcggggc    4020
cttttgcgtc tttctggtgc agccaggtcc tgagtgcatc cgggctccct gctgttgaga    4080
tggcccatga gttccctggg atggccacgc gcgcaccgcc cccccccgcc gccccggca    4140 ggcacagggt tagaacaggt gttcttcctt gaggctggta tcttgcggtg tgtgtgtgtg    4200
tagcctgcaa atgagactga gtggcatggg ttttctcagt ttttcttctgt ctacgcaatt    4260 acagccaaag aaaatcttct tgattgattt gacgccctgt gagactgttg ccttcctcca    4320
cctgaaattt cttgacgtcc tgcttcagag actcccctc aattccccctt ctcccaagta    4380 aactggacat tgggaaaata ctatgtgtga gttggacact gaactgctaa ataatctgt     4440 gtgtctggtc atcagatacc ctaactgctt cccacacttt catcctcatc tctgggttgc    4500
tttcttaacc ccagggcaga gctattctgt actcttccag tttaatttt ctgtgtggct     4560 ttaaaaaat tttcttaaag gtaattgccg ccttcatttc tattcatcct ctctttcatg    4620 aataaaggc acagtaattg tccttcatct tttcttttcc atccttttcac tgtagagggc    4680 tttctttcca cgtttctcca aatgaataaa taagcttggc attgtatagt atggtcctta    4740
ctcaacccaa gattagagat accatctgac gttttaact gggcttttaa tcctgcatca    4800
gtgctccccc ctccaaaaga aaaagtggc ttgcatctga agcaaagact gtacatttca    4860
atgcaccaca ttttaaaac cgcaaggtct tttattttc ttctacaact tcgaagttgc    4920
ctcgtctgtg acaatatgtg gtcttgttga agtaaaatag tgcacattac tgttaatgaa    4980
cactgtagga ggctagattg tgaaggagga atgatttagt ttattccgag cttctagcct    5040
```

```
cttggtgtga ggtgttagaa gaattggcac acgcaggcag tgaaatgatt caggacacag      5100
ccttcctttg atgcttccca aactgaaagg agggtttgtt ggtgggggat attaagcatc      5160
aggagaaaat tccagtaggt ttttcattag tccatatggg ggaaaatata aaatgaggag      5220
agggtaagga gaaaaaaata gtgttgtcag agaggacatt ataaaggaaa aacgcaaaac      5280
tttcaagaca ctaaactttt gtacaattgg aagtaatgca ataaaataaa ataagagcat      5340
atgcaacatt ttttaatggt gaggtgccac atatacaaaa aatacaacag gtttattgtt      5400
tctgttgtca ttttaagcat aataggcatg acatacttag aatttaagtt ttctatctcc      5460
tggaggtcac tcccagacag taattttatg actagtacct ttctctacca ctcccccacc      5520
agcattgttt ttggacagat taggcctttg tttgacatat atgtatgctg atacattcag      5580
ttttctttat tataacattt tccatgcatg gcaaacatta ttgaattcca tcattaggct      5640
agtggaattt atgaattctt agtcttgtgc attttccaga atttggaaat ccgtaggttt      5700
atttgtgaga cagcctacca tacacccgtt ctcagattaa tgattccgtg taaattatag      5760
tttagacatt gttctctgga gaaaacgtag gaccagataa aacattgaaa atctacagct      5820
ccttggggga aagcaaagat gctgattagg aatgctatag ggctgaggca tatatctcag      5880
ccctttatat tgtgcatgca caccaattag tttttcagta attcacagta cttaaggaaa      5940
gaatacccca gtcaggtttt catctttat tcatggtgct tctaatttcc atggttgatg       6000
ttaaagtgga taagataaaa ggaggaaaat gaaccacgta caaattagct ccgtaagtat      6060
tggctgcaaa tgaaggaaag caaaggatga aggtctcca aattaaatta aagacgcaac       6120
aggcaatctg tgttcaatta ttcctccctg gtaactggaa atggtgcttt gtcatctcat      6180
acagctaact aattttcagc ctttcctttc aactgatctg cattgccagg aaagaaatat      6240
ttgcattgaa tactcttatg ttaacagcca aatccatttg caaatgaagt ttagtgtgaa      6300
tcttagctac agaaatgggc ctgttcattg gagaaggagg tggtggggtt tttcaggttt      6360
caaaaatctc aacagctact cctcttcttc ctgtggcatt gatggggttt tgcactgtgg      6420
atcacaggta atcctgcctc cctgtgcatc ctatccatct ccctctctgg aaaagcttac      6480
ttgcaaagga tttaagctgc tttaataaaa gccacaacta cagataaatg tgactttatt      6540
tttagtcatg ttttcaataa cactattgat cagatttctg ttttttcacca gaaaaccttc      6600 aaagctttct taaatttaaa acagatgctt tcaggtgaa gttggtttca cctctggaaa       6660
tcaattgaat tgaaatacta aaaaaaaata gcactttcca agcaagaaaa aaaaaaactt      6720
tagaaatttt gaagttaatg aaataagact ggaagacagg ctggctctca gacacttaag      6780
gggttatcaa aggagtcagt gactgagatt gcatctagaa gatgtttctg gaaagcaatg      6840
aactaaagaa gccccttgct tgaatctttt gttgggtgct attcagctat ttgtgtacta      6900
ggcagataaa ggagttttga ggattaattc tgtcttgctt ttttttcaga agtatttgtg      6960
tgctttccct ctttacctgc tgcttattgg agtcataatc tgaaggatat acgagtttac      7020
aatgtttggc cctttccccc ctaaatagta cttctattta tgtttcctga aggaaacat      7080 gagatttacc ttttacccct tggtacattta ctttatttag ggtaattctt tttaaagtga     7140
aggaacctag aagattttct tgggtggaac attaaaagac catttttacct gaaatgtgcc     7200 ccttgtattt tatttctttc cctctgaaag ctattaagag tcatgccata ggtctgataa     7260
aatgtgagaa tttttatagaa atgtatatat gaaactacag ccaattttct taggctataa    7320
atgttaggtt ttctttattc tccctggggtg tacagtattt gaattatggt tcgttttttga   7380
```

-continued

```
taagagtttt ctttggagac cagtagtttt catttggatg ttgatatttt aatggaccag    7440
aaataacaat ttgggcctaa agatgttctc ccttctgcct cttcctattg tctttttcca    7500
tcattcttcc tctctcaacc tacttttcac tgatgattct gtctcgtgaa tagacatgaa    7560
aacatgttcg gattattgct tggtgcaatg aatgttgtat cttttaaaca tttaggctgt    7620
tgctgcttct tggaaaccat tgtgggtggc tccctttttt ctgtctactc tgcttgcctc    7680
taaattacaa gctggtaaat tttctcttgt gtgaacagta atggaatagt aattgctttt    7740
aaggcatgct gcaaaagcaa aatagaaaat ccaaagtcaa tggtcttatt tattaactat    7800
ttcaggtggt attcaagtag tggtaggttt tttgttgtcg tcattgtttt ttgcacagaa    7860
ttcaatattg tacagatatg tctatttaaa tgttttggac tctggaatat tcagcctgtg    7920
taagttaaca catatatatt tgattcacag tgcttgtgaa gcatgaaatt taagttttgc    7980
atggagctca aattctccca ccaaaataca aataaaattg ttataccagt acatagatag    8040
atgcataggt aggtttagaa tacatctcca aagcacagaa ataaaactaa gataaatttgt    8100 tgttcatgcc tggtaatttt tgcatacaat tttaaataaa tgttaatacc ctatatcatg    8160
gatacaagca aaatatagtt gacataaatt gagcatttac tataggcaaa gaagtaccct    8220
tagggtttta cgtgtattat ttaatcttca taacaccctg aggtaggtaa tagtactgtc    8280
tctgtttgtt tgctgttttta atactaatgc taatatttag ttatggacgc agtcccttgg    8340
tgagtacaga ggacttaaac aaatgcaacc tgacggtaat atagttgttt acctctgatc    8400
tatataatca gtatccccgt ttttaacaga agcactagga agtaacttga aaatgtcatg    8460
tagctgttat gtggcagaga tagaattttg aacccaggtg ccctggttct agcgcctgca    8520
ttgttgactg tcctgaaact catgtcattt aacacatgaa aatatgtcat cattataata    8580
agtaaagcac ctgattagca ggagccttgt gatattatta ctgtcttctg ccattttga     8640 attcaggtct ttcttcttgg ttatgtcaac tcttagcttt tcctttgac cttttgttac     8700 ttttttcctt tttgttgtta atgtattaca ttgaaaaata aaatttttt tttttgcaag     8760 aaaatgtact ttattagctt tctttgttct gtgggttgat cttcctggat atttctttat    8820
tttattttat tttattatta ttatacttta agttttaggg tacatgtgca caatgtgcag    8880
gttagttaca tatgtataca tgtgccatgc tggtgtgctg cacccattaa ctcgtctttt    8940
agcattaggt atatctccta atgctctccc tcccccccaac ccccacccca caacagtccc    9000
cagagtgtga tgttccccctt cctgtgtcca tgtgttctca ttgtnnnnnn nnnnnnnnnn    9060
nnnnnnnnnn nnnnnnnnnn nnnnnnnnnn nnnnnnnnnn nnnnnnnnnn nnnnnnnnnn    9120
nnnnnnnnnn nnnnnnnnnn nnnnnnnnnn nnnnnnnnnn nnnnnnnnnn nnnnnnnnnn    9180
nnnnnnnnnn nnnnnnnnnn nnnnnnnnnn nnnnnnnnnn nnnnnnnnnn nnnnnnnnnn    9240
nnnnnnnnnn nnnnnnnnnn nnnnnnnnnn nnnnnnnnnn nnnnnnnnnn nnnnnnnnnn    9300
nnnnnnnnnn nnnnnnnnnn nnnnnnnnnn nnnnnnnnnn nnnnnnnnnn nnnnnnnnnn    9360
nnnnnnnnnn nnnnnnnnnn nnnnnnnnnn nnnnnnnnnn nnnnnnnnnn nnnnnnnnnn    9420
nnnnnnnnnn nnnnnnnnnn nnnnnnnnnn nnnnnnnnnn nnnnnnnnnn nnnnnnnnnn    9480
nnnnnnnnnn nnnnnnnnnn nnnnnnnnnn nnnnnnnnnn nnnnnnnnnn nnnnnnnnnn    9540
nnnnnnnnnn nnnnnnnnnn nnnnnnnnnn nnnnnnnnnn nnnnnnnnnn nnnnnnnnnn    9600
nnnnnnnnnn nnnnnnnnnn nnnnnnnnnn nnnnnnnnnn nnnnnnnnnn nnnnnnnnnn    9660
nnnnnnnnnn nnnnnnnnnn nnnnnnnnnn nnnnnnnnnn nnnnnnnnnn nnnnnnnnnn    9720
nnnnnnnnnn nnnnnnnnnn nnnnnnnnnn nnnnnnnnnn nnnnnnnnnn nnnnnnnnnn    9780
```

-continued

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 9840 |
| nnnnnnnnnn | nnnnnnnnnn | nnnnnnnnnn | nnnnnnnnnn | nnnnnnnnnn | nnnnnnnnnn | 9900 |
| nnnnnnnnnn | nnnnnnnnnn | nnnnnnnnnn | nnnnnnnnnn | nnnnnnnnnn | nnnnnnnnnn | 9960 |
| nnnnnnnnnn | nnnnnnnnnn | nnnnnnnnnn | nnnnnnnnnn | nnnnnnnnnn | nnnnnnnnnn | 10020 |
| nnnnnnnnnn | nnnnnnnnnn | nnnnnnnnnn | nnnnnnnnnn | nnnnnnnnnn | nnnnnnnnnn | 10080 |
| nnnnnnnnnn | nnnnnnnnnn | nnnnnnnnnn | nnnnnnnnnn | nnnnnnnnnn | nnnnnnnnnn | 10140 |
| nnnnnnnnnn | nnnnnnnnnn | nnnnnnnnnn | nnnnnnnnnn | nnnnnnnnnn | nnnnnnnnnn | 10200 |
| nnnnnnnnnn | nnnnnnnnnn | nnnnnnnnnn | nnnnnnnnnn | nnnnnnnnnn | nnnnnnnnnn | 10260 |
| nnnnnnnnnn | nnnnnnnnnn | nnnnnnnnnn | nnnnnnnnnn | nnnnnnnnnn | nnnnnnnnnn | 10320 |
| nnnnnnnnnn | nnnnnnnnnn | nnnnnnnnnn | nnnnnnnnnn | nnnnnnnnnn | nnnnnnnnnn | 10380 |
| nnnnnnnnnn | nnnnnnnnnn | nnnnnnnnnn | nnnnnnnnnn | nnnnnnnnnn | nnnnnnnnnn | 10440 |
| nnnnnnnnnn | nnnnnnnnnn | nnnnnnnnnn | nnnnnnnnnn | nnnnnnnnnn | nnnnnnnnnn | 10500 |
| nnnnnnnnnn | nnnnnnnnnn | nnnnnnnnnn | nnnnnnnnnn | nnnnnnnnnn | nnnnnnnnnn | 10560 |
| nnnnnnnnnn | nnnnnnnnnn | nnnnnnnnnn | nnnnnnnnnn | nnnnnnnnnn | nnnnnnnnnn | 10620 |
| nnnnnnnnnn | nnnnnnnnnn | nnnnnnnnnn | nnnnnnnnnn | nnnnnnnnnn | nnnnnnnnnn | 10680 |
| nnnnnnnnnn | nnnnnnnnnn | nnnnnnnnnn | nnnnnnnnnn | nnnnnnnnnn | nnnnnnnnnn | 10740 |
| nnnnnnnnnn | nnnnnnnnnn | nnnnnnnnnn | nnnnnnnnnn | nnnnnnnnnn | nnnnnnnnnn | 10800 |
| nnnnnnnnnn | nnnnnnnnnn | nnnnnnnnnn | nnnnnnnnnn | nnnnnnnnnn | nnnnnnnnnn | 10860 |
| nnnnnnnnnn | nnnnnnnnnn | nnnnnnnnnn | nnnnnnnnnn | nnnnnnnnnn | nnnnnnnnnn | 10920 |
| nnnnnnnnnn | nnnnnnnnnn | nnnnnnnnnn | nnnnnnnnnn | nnnnnnnnnn | nnnnnnnnnn | 10980 |
| nnnnnnnnnn | nnnnnnnnnn | nnnnnnnnnn | nnnnnnnnnn | nnnnnnnnnn | nnnnnnnnnn | 11040 |
| nnnnnnnnnn | nnnnnnnnnn | nnnnnnnnnn | nnnnnnnnnn | nnnnnnnnnn | nnnnnnnnnn | 11100 |
| nnnnnnnnnn | nnnnnnnnnn | nnnnnnnnnn | nnnnnnnnnn | nnnnnnnnnn | nnnnnnnnnn | 11160 |
| nnnnnnnnnn | nnnnnnnnnn | nnnnnnnnnn | nnnnnnnnnn | nnnnnnnnnn | nnnnnnnnnn | 11220 |
| nnnnnnnnnn | nnnnnnnnnn | nnnnnnnnnn | nnnnnnnnnn | nnnnnnnnnn | nnnnnnnnnn | 11280 |
| nnnnnnnnnn | nnnnnnnnnn | nnnnnnnnnn | nnnnnnnnnn | nnnnnnnnnn | nnnnnnnnnn | 11340 |
| nnnnnnnnnn | nnnnnnnnnn | nnnnnnnnnn | nnnnnnnnnn | nnnnnnnnnn | nnnnnnnnnn | 11400 |
| nnnnnnnnnn | nnnnnnnnnn | nnnnnnnnnn | nnnnnnnnnn | nnnnnnnnnn | nnnnnnnnnn | 11460 |
| nnnnnnnnnn | nnnnnnnnnn | nnnnnnnnnn | nnnnnnnnnn | nnnnnnnnnn | nnnnnnnnnn | 11520 |
| nnnnnnnnnn | nnnnnnnnnn | nnnnnnnnnn | nnnnnnnnnn | nnnnnnnnnn | nnnnnnnnnn | 11580 |
| nnnnnnnnnn | nnnnnnnnnn | nnnnnnnnnn | nnnnnnnnnn | nnnnnnnnnn | nnnnnnnnnn | 11640 |
| nnnnnnnnnn | nnnnnnnnnn | nnnnnnnnnn | nnnnnnnnnn | nnnnnnnnnn | nnnnnnnnnn | 11700 |
| nnnnnnnnnn | nnnnnnnnnn | nnnnnnnnnn | nnnnnnnnnn | nnnnnnnnnn | nnnnnnnnnn | 11760 |
| nnnnnnnnnn | nnnnnnnnnn | nnnnnnnnnn | nnnnnnnnnn | nnnnnnnnnn | nnnnnnnnnn | 11820 |
| nnnnnnnnnn | nnnnnnnnnn | nnnnnnnnnn | nnnnnnnnnn | nnnnnnnnnn | nnnnnnnnnn | 11880 |
| nnnnnnnnnn | nnnnnnnnnn | nnnnnnnnnn | nnnnnnnnnn | nnnnnnnnnn | nnnnnnnnnn | 11940 |
| nnnnnnnnnn | nnnnnnnnnn | nnnnnnnnnn | nnnnnnnnnn | nnnnnnnnnn | nnnnnnnnnn | 12000 |
| nnnnnnnnnn | nnnnnnnnnn | nnnnnnnnnn | nnnnnnnnnn | nnnnnnnnnn | nnnnnnnnnn | 12060 |
| nnnnnnnnnn | nnnnnnnnnn | nnnnnnnnnn | nnnnnnnnnn | nnnnnnnnnn | nnnnnnnnnn | 12120 |

-continued

```
nnnnnnnnnn nnnnnnnnnn nnnnnnnnnn nnnnnnnnnn nnnnnnnnnn nnnnnnnnnn    12180
nnnnnnnnnn nnnnnnnnnn nnnnnnnnnn nnnnnnnnnn nnnnnnnnnn nnnnnnnnnn    12240
nnnnnnnnnn nnnnnnnnnn nnnnnnnnnn nnnnnnnnnn nnnnnnnnnn nnnnnnnnnn    12300
nnnnnnnnnn nnnnnnnnnn nnnnnnnnnn nnnnnnnnnn nnnnnnnnnn nnnnnnnnnn    12360
nnnnnnnnnn nnnnnnnnnn nnnnnnnnnn nnnnnnnnnn nnnnnnnnnn nnnnnnnnnn    12420
nnnnnnnnnn nnnnnnnnnn nnnnnnnnnn nnnnnnnnnn nnnnnnnnnn nnnnnnnnnn    12480
nnnnnnnnnn nnnnnnnnnn nnnnnnnnnn nnnnnnnnnn nnnnnnnnnn nnnnnnnnnn    12540
nnnnatataat nnnnctggtgc nncgtttttt aagcctgtca nnnnagtgca nnnattagggt  12600
nnnnnnnnnn nnnnnnnnnn nnnnnnnnnn nnnnnnnnnn nnnnnnnnnn nnnnnnnnnn    12660
nnnncnnnnn nnnttgcctt nnnagtgacc nnnatgcctc nnnctgcttt nnnnnnnnnn    12720
nnnnnnnnnn nnnnnnnnnn nnnnnnnnnn nnnnnnnnnn nnnnnnnnnn nnnnnnnnnn    12780
nnnnnnncag nngacnnnngc nnnnnnnnnn nnnnnnnnnn nnnnnnnnnn nnnnnnnnnn    12840
nnnnnnnnnn nnnnnnnnnn nnnnnnnnnn nnnnnnnnnn nnnnnnnnnn nnnnnnnnnn    12900
nnnnnnnnnn nnnnnnnnnn nnnnnnnnnn nnnnnnnnnn nnnnnnnnnn nnnnnnnnnn    12960
nnnnnnnnnn nnnnnnnnnn nnnnnnnnnn nnnnnnnnnn nnnnnnnnnn nnnnnnnnnn    13020
nnnnnnnnnn nnnnnnnnnn nnnnnnnnnn nnnnnnnnnn nnnnnnnnnn nnnnnnnnnn    13080
nnnnnnnnnn nnnnnnnnnn nnnnnnnnnn nnnnnnnnnn nnnnnnnnnn nnnnnnnnnn    13140
nnnnnnnnnn nnnnnnnnnn nnnnnnnnnn nnnnnnnnnn nnnnnnnnnn nnnnnnnnnn    13200
nnnnnnnnnn nnnnnnnnnn nnnnnnnnnn nnnnnnnnnn nnnnnnnnnn nnnnnnnnnn    13260
nnnnnnnnnn nnnnnnnnnn nnnnnnnnnn nnnnnnnnnn nnnnnnnnnn nnnnnnnnnn    13320
nnnnnnnnnn nnnnnnnnnn nnnnnnnnnn nnnnnnnnnn nnnnnnnnnn nnnnnnnnnn    13380
nnnnnnnnnn nnnnnnnnnn nnnnnnnnnn nnnnnnnnnn nnnnnnnnnn nnnnnnnnnn    13440
nnnnnnnnnn nnnnnnnnnn nnnnnnnnnn nnnnnnnnnn nnnnnnnnnn nnnnnnnnnn    13500
nnnnnnnnnn nnnnnnnnnn nnnnnnnnnn nnnnnnnnnn nnnnnnnnnn nnnnnnnnnn    13560
nnnnnnnnnn nnnnnnnnnn nnnnnnnnnn nnnnnnnnnn nnnnnnnnnn nnnnnnnnnn    13620
nnnnnnnnnn nnnnnnnnnn nnnnnnnnnn nnnnnnnnnn nnnnnnnnnn nnnnnnnnnn    13680
nnnnnnnnnn nnnnnnnnnn nnnnnnnnnn nnnnnnnnnn nnnnnnnnnn nnnnnnnnnn    13740
nnnnnnnnnn nnnnnnnnnn nnnnnnnnnn nnnnnnnnnn nnnnnnnnnn nnnnnnnnnn    13800
nnnnnnnnnn nnnnnnnnnn nnnnnnnnnn nnnnnnnnnn nnnnnnnnnn nnnnnnnnnn    13860
nnnnnnnnnn nnnnnnnnnn nnnnnnnnnn nnnnnnnnnn nnnnnnnnnn nnnnnnnnnn    13920
nnnnnnnnnn nnnnnnnnnn nnnnnnnnnn nnnnnnnnnn nnnnnnnnnn nnnnnnnnnn    13980
nnnnnnnnnn nnnnnnnnnn nnnnnnnnnn nnnnnnnnnn nnnnnnnnnn nnnnnnnnnn    14040
nnnnnnnnnn nnnnnnnnnn nnnnnnnnnn nnnnnnnnnn nnnnnnnnnn nnnnnnnnnn    14100
nnnnnnnnnn nnnnnnnnnn nnnnnnnnnn nnnnnnnnnn nnnnnnnnnn nnnnnntgt     14160
gggatataat ctcctggtgc gccgtttttt aagcctgtca gaaaagtgca gtattagggt     14220
gggagtgacc tgattttcca ggtgccctct gtcacccctt tctttgacta ggaaagggaa     14280
ctccctgacc ccttgcgctt cccgagtgag gcaatgcctc gccctgcttt cgcttgggca     14340
cggtgtgctg cacccactgt cctgcgccca ctgtctggca ctccctagtg agatgaaccc     14400
ggtacctcag atggaaatgc agaaatcacc catcttctgc gtcgctcacg ctgggagctg     14460
tagaccggag ctgttcctat ttggccatcg tggctgccag ctcaaaatta tatgttaata     14520
```

-continued

```
tatttgttgt gtagactata atgttttgat atagggatac attgtggaat tactaaagct   14580
aattaatata ttcattacct tacaatttta tcattttttg tgtgtgtggt gaaaacattt   14640
aaaatctcct cagcagtttg caggtgtaca atacattgtt aataactata gtcaccaatt   14700
tgtgttgcag ttgatcttct aaatgtattc tttctaactg aatttttgta tcctttgacc   14760
aaacatttcc ccaattccta cccctacctt ttttctcctg ataatatttg gtcttgtgaa   14820
aattttatct catctctcac tatctctgat ttatagacca tttgatattt attttttacaa  14880 gctagataaa aactgccaag ttagtatata aactgtagtc tttatttttt taaactacgt   14940
attcttgtga ataagaattg ataacttcta tagatattaa aattaagttt ttcctcattt   15000
gctatgtata catcaacaac tctgtctcct aggcgtgtat catgtcaggg caggcagaac   15060
tgaacggaag aataattttc agggtagaat gggagaaaat acagaattat gtgaagcagg   15120 ctcagggggtt tattattgaa acagaggaga ggagctgggg gcctgagcca atttgcgctg   15180
aagccaatgt ggctgagatg gctccttctg gaacagaga tgtgcttgga ggagccttgg    15240
ttctcctcac caatataccc cttatgttgg ctgctgcagg cagcactacc aggttcattt    15300
gactgctcac ttgttggtag aaggtttgtt aattttcttg tccgatttct tctgagatta    15360
ggaatttcct tggattaaaa acaaaataaa tcattggttg agtcttttg caggttaaaa    15420 aaaacaagaa aacttggagg tggatttgct gaggaggaca gccatgttct ctaccagaag   15480
tcagattggg tcttttttcct aaacaacta aaaacgcagt agtttgttta ctttttaaaa    15540
tccgtctcct ccacctgtgg aaagagaact ttaaacacta tttatgttac atgctgaatc   15600
taagactgtt gttccttcag cttgaactgc agatattcct aaattgtacc tgcatctcta   15660
gtgaaagctg agtgtgctaa atgctgacca ttctccatta actgagattt cagttatcta   15720
agagatttgc atcttagcag tactactgta ttactctgta agattccttc tacctacctg   15780
agctcaaact tcatcctatt cagaagatgt tttaatataa caagtcagta ggccttctct    15840
accacttaac aaatattaat tgagcaccta ctgtgtacaa ggcactgtgc ttaattaagt    15900
cagggagtat ttcagctccc tgaaacagag agcatctcag ccctcccaga ttgattctct   15960
ggactaaata tgcatggtag cttcagtgcc tgttgagaga aatgaatgtg tctgggagtg   16020
taaagcagag gtccctaatg gagttgttga ttgtaggagt aattgtggag gaagtgacat   16080
ttgagctgag aagtaaagaa caacagggcc tagtgggtga tgggacaggg atgaaggagc   16140
cctccagaga gagaaaacca tatttgtgga cctgaatact cagagacctg aaggatgttc   16200
ttgatggcaa gaggctgggt ggtgagaaga tgaggtggag aaataggcag ccactttttcc  16260 atcttctgca tgtcaaagtg ctgttctcat ctttgagaga agctgtcctg taaagaactc   16320
ttcaggttct gtgtatttgg aagtggcatc taaatcatgc ccattggaat cttcttcctg   16380
gatactatca tgtctttatg taaacttgtg aatttaaaag tatacatagc agtgtcggag   16440
caggctttcc ttttattttt tttgcatctg gttttcagaa tgcccattag gcaaattttt   16500
gacctttaac ttttttcaata ggccttggat aaggtgggtg gtaaattgat aggaaaacta   16560
tagataagta tttgtccatc tagttgtacc aaagaagtgg taatatagac ttttgtggat   16620
cctttagagc acctgatatc acattaaata atatgatacc tgaatatgta tttcagttgt   16680
ttctcccact agaataccag ggtaggaatt ttcttttgtt tactgttgta tctgtagtgt   16740
ccagagcagt gcctagcatg cagtgaatgc ttattaaata tttttttgaat gaatgaatta   16800 taagacactt ggaagctgag ggaatttatt ataaacagag tttaatccct gaaaggagtc   16860
```

```
ctgcacagag attgtcaatc aaatcatagt tttgaagtct gtgttgtatg tctaagattg    16920
tattgagccc tttaaataga aactggaaga taaacgtggt ccctactctg attctaagag    16980
cttttatact aaaaggaaag agaatgtcat gagcatttat gtatatagca aggcattacc    17040
atcaacagcc attaaaaggg gaggtttgtc aaggtggtcg tgagtcagtt gagtatttgg    17100
cctcttcaca cgtgtgagag gctggaggct gtgggggagc tcacataggc gtaacagccc    17160
atgttcaaat ccagcttcac tgcttagtgt ttgcattaca ttggcaaggg ttgactgcct    17220
cgagtgattg ttttaagtgc tctaggcaag taataaatat tagttctttt tgccttgttc    17280
tttccactat gggtgactgc cctaattgag ggtataccag ataattgcac tgtcttgatt    17340
tgttaagtgc ctcaaatgt tcttctcctg acatctggac tatgtttcta gaggcctagg    17400
gggaggagga ggtaaaggca cttgactttc ccaaattagt ctgtacccaa gtggaactgc    17460
ataaattggg taccttaatt acaccattgg gtattactag ggtgattaca gggacaagag    17520
ttaaataggg cttgtctaca aagagtcctg ggaggaagtg agatgtgaga gaactaaaag    17580
catctaaagg acattttaga tggagaggag gtgaagggtg ttctcctgtg ggttctgact    17640
tctgatgcta actcctaacg gtgaaagcta ggaagttgac ttacatgtag ctcagaggag    17700
gatgctaacc tggctcactg caacttccac ctcctggatt gaagcgattc ccctgcttca    17760
gcctcctgag tagctaggat tacaggtgca agccatcatg cctggctaat ttttgtattt    17820
ttagtaaagg tggggtttca acatgttggc caggttggtc tcaaactcct gacctcaggt    17880
gatgcaccca cctcggtttc ccaaagtgct gggattacag gtgtgagcca cggtgcctgg    17940
ccctaggtgt ggtttttaat tactatgtaa tcccagggcc cagtgtggac ctaggacata    18000
gttactacat gatacagtga ttatcgttgg cacaaatgaa tgaatcaaag agatagtatg    18060
ttacaaagga gagggcacga aatagatttt tttttttgagc acatgattag aagcagtatt    18120
ttaaggtcat ttcctgggct gggaaggtta ggaatattct tctgaccagc acctgttgga    18180
ggaggtggaa aggatcccag atgccagcct tctctgtgtc caccccttctc ccagccttgc    18240 ctggggacac tgagccccct gctgggcttc aagtgcctga tgctttttg ggaagcccca    18300 taagcttgct tctcttttg caaacattgc ttaagttttc attaataaaa acattctaaa    18360
gcttatttag tccagaatga ggaaaatgta ggagagagag agggtgtggg tgtgtgtgtg    18420
gggcgagggg gtgtctgtgt gtggttttac ctacctatgt ggttgcccct tcttacctgt    18480
gaatgcagtg gctgctttcc ttgttccttc tccacagacc ctgtaccctc catttcagtt    18540
tctggcaaga attgtggcca gacccaggga tgctgatgca gtggtcccca acattttctg    18600
gtcacataat ttctaaaaga attttgtaac attaaccctc tgggatattt tttaattgac    18660
atctacattt tattttttt attattttat tattattata cttaagtttt agggtacatg    18720
tgcacaatgt gcaggttagt tacatatgta tacatgtgcc atgctggtgt gctgcaccca    18780
ttaactagtc ttttagcatt aggtatatct cctaatgcta tccctcccccc aaccccac    18840 cccacaacag tccccagagt gtgatgttcc ccttcctgtg tctgtgttct cattgttcaa    18900
ttcccatcta tgagtgagaa catgcggtgt tggttttttg tccttgcaat agtttactga    18960
gaatgatgat ttccaattc atccatgtcc ctgcaaagga catgaactca tcattttta    19020 tggctgcata gtattccatg gtgtatatat gccacatttt cttaatccag tctatcattg    19080
ttggacattt gggttggttc caagtctttg ctattgtgaa tagtgctgca ataaacatac    19140
atgtgcatgt gtctttatag cagcatgatt tatagtcctt tgggtatata cccagtaatg    19200
ggatggctgg atcaaatggt atttctagtt ctagatccct gaggaatcgc cgcactgact    19260
```

```
tccacaatgg ttttactagt ttacagtccc accaacagtg taaaagtgtt cctatttctc    19320
cacatcctct ccagcacctg ttgtttcctg actttttaat gatcaccatt ctaactggtg    19380
tgagatggta tctcattgtg gttttgattt gcatttctct gatggccagt gatgagcgtt    19440
ttttcatatg tcttttggct gcataaatgt cttcttttga gaagtgtcta ttcatgtcct    19500
tcgcccactt gttgatgggg ttggttggtt ttttcttgta aatttgtttg agttcattgt    19560
agattctgga tattagccct ttgtcagatg agtaggttgc gaatattttc tcccatttg    19620 taggttgcct gttcactctg atggtagttt cttttgctgt gcagaagctc tttagtttaa    19680
ttagatccca tttgtcaatt ttggcttttg ttgccaatgc ttttggtgtt ttagacatga    19740
agtccttgcc catgcctatg tcctgaatgg taatgcctag gttttcttct agggttttta    19800
tggttttagg tctaacgttt aagtttccat cttgaattaa tttttgtata aggtgtaagg    19860
aagggatcca gtttcagctt tctacatatg gctagccagt tttcccagca ctatttatta    19920
aatagggaat cctttcccca ttgcttgttt ttctcaggtt tgtcaaagat cagatagttg    19980
tagatatgca gcgttatttc tgagggctct gttctgttcc attgatctat atctctgttt    20040
tggtaccagt accatgctgt tttggttact gtagccttgt agtatagttt gaagtcaggt    20100
agtgtgatgc ctccagcttt gttcttttgg cttaggattg acttgacgat gtgggctctt    20160
ttatggttcc atataaactt taaagtagtt ttttccaatt ctgtgaagaa agtcattggt    20220
agcttgatgg ggatggcatt gaatctataa attaccttgg gcagtatggc cattttcaca    20280
atattgattc ttcctaccca tgagcatgga atgttcttcc atttgtttgt atcctctttt    20340
atttcattga gcagtggttt gtagttctcc ttgaagaggt ccttcacgtc ccttgtaagt    20400
tggattccta agtattttat tatctttgaa gcaattgtgc atgggagttc actcatgatt    20460
tggctctctg tttgtctgtt attggtgtat aagaatgctt gtgatttttg tacattgatt    20520
ttgtatcctg agactttgct gaagttgctt atcagcttaa ggagattttt ggctgagaca    20580
atggggtttt gtagatatac aatcatgtcg tctgcaaaca gggacaattt gactccctct    20640
tttcctaatt gaataccctt tatgtccttc ttctgcctaa ttgccctggc cagaacttcc    20700
aacactatgt tgaataggag tggtgagaga gggcatccct gtcttgtgcc cgttttcaaa    20760
gggaatgcct ccagtttttg cccattcagt atgatattgg ctgtgggctt gtcatagata    20820
gctcttatta ttttgagata cgtcccatca atacctaatt tattgagagt ttttagcatg    20880
aagcgttgtt gaattttgtc aaaggccttt tctgcatcta ttgagataat catgtggttt    20940
ttgtctttgg ttctgtttat atgctggatt acatttattg atttgcatat attgaaccag    21000
ccttgcatcc cagggatgaa gcccacttga tcatggtgaa taagctttt gatgtgctgc    21060 tggattcggt ttgccagtat tttattgagg attttttgcat ccatgttcat caaggatatt    21120
ggtctaaaat tctctttttt ggctgtgtct ctgcccggct ttggtatcag gatgatgctg    21180
gcctcataaa atgagttagg gaggattccc tcttttttcta ttgattggaa tagtttcaga    21240
aggaatggta ccagttcctc cttgtacctc tggtagaatt cggctgtgaa tccatctggt    21300
cctggactct ttttggttgg taagctattg attattgcca caatttcaga gcctgttatt    21360
ggtctattca gagattcaac ttcttcctgg tttagtcttg ggagggtgta tgtgccgagg    21420
aatttatcca tttcttctag attttccagt ttatttgcgt agaggtgttt atagtattct    21480
ctgatggtag tttctatttc tgtgggatcg gtggtgatat cccctttatc atttttttgt    21540
gtctatttga ttttctctc ttttcttctt tattagtctt gctagtggtc tatcaattt    21600
```

```
gttgatcctt tcaaataacc agctcctgga ttcattaatt ttttgaaggg ttttttgtgt    21660
ctctatttcc ttcagttctg ctctgatttt agttatttct tgccttctgc tagcttttga    21720
atgtgtttgc tcttgcttct ttagttcttt taattgtgat gttagggtgt caattttgga    21780
tctttcctgc tttctcttgt gggcatttag tgctataaat ttccctctac acactgcttt    21840
gaatgtatcc cagagattct ggtatgttgt gtctttgttc tcgttggttt caaagaacat    21900
ctttatttct gccttcattt cgttatgtac ccagtagtca ttcaggagca ggttgttcag    21960
tttccatgta gctgagcggt tttgagtgag tttcttaatc ttgagttcta gtttgattgc    22020
actgtggtct gagagacagt ttgttataat ttctgttctt ttacatttgc tgaggagagc    22080
tttacttcca actatgtggt caattttgga ataggtgtgg tgtggtgctg aaaaaaatgt    22140
attttctgtt gatttggggt ggagagttct ttagatgtgt attaggtccg cttggtgcag    22200
agctgagttc aattcctgtg tatccttgtt aactttctgt ctcgttgatc tgtctaatgt    22260
tcacagtggg gtgttaaagt ctcccattat tattgtttgg gagtctaagt ctctttgtag    22320
gtcactcagg acttgcttta tgaatctggg tgctcctgta ttgggtgcat ttatatttag    22380
gatagttagc tcttcttgtt gaattgatcc ctttaccgtt atgtaacggc cttctttgtc    22440
tcttttgatc tttgttggtt taaagtctgt tttatcagag actaggattg caaccctgc    22500
cttttttgt tttccatttg cttggtagat cttcctccat cctttatttt tgagcctatg    22560
tgtgtctctg cacgtgtagt atgggtttcc tgaatacagc acactgatgg gtcttgactc    22620
tttatccaat ttgccagtct gtgtctttta attggagcat ttagtccatt tacatttaaa    22680
gttaatattg ttatgtgtga atttgatcct gtcattatga tgttagctgg ttattttgct    22740
cgttagttga tgcagtttct tcctagcctt gatggtctt acgttttggc atgattttgc    22800
agtggctggt accggttgtg cctttccatg tttagtgctt ccttcaggag ctcttgtaag    22860
gcaggcctgt tggtgacaaa ttctctcagc atttgcttgt ctgtagagta tttatttct    22920
ccttcactta catttaaaa atcatttaa actgttgcaa aacttttgat ttccagtgca    22980
ttataaatgt tgacatttgt aatgaaattt aaatatatcc agtagatcta taatatgtt    23040
taacagtttg atacccacca ccattcattt aataaacata cttttcaatg acatttggat    23100
ggagatatat atatacacat atatatattt tttaagtgag acaggggtct ctctctgttg    23160
cccaaactgg agtgtagtgg tgcgatcaca gcttactgca gcctccacct ccctgggtca    23220
agcaattctc ctgcctcacc ctcctgagta gctgggacta caggcacatg ccaccatacc    23280
tggctaattt ttatttttat tttttttgg tagagacagg gtcctcctat gtttccctgg    23340
ctggtctcaa gctcctggct tcaagcagtc ctaccgcctc atctttccaa agtactggta    23400
ttactggtgt gagccaccac acctggccac gtttggatat tttatattgc tctttttttt    23460
ttctatcttc attcctcctc agaattttat cttagcataa tattttgagg ttcaaagtca    23520
tctccctatt acacatatct acaatgacaa aagaatata gatagaattt aaagttttat    23580
aatcctgtgg ctatcagcct ctgtcttaga aaagcttcag gactgactta ccattacaat    23640
tagtattggt aaacaattaa tcaaacaac aataaatgtt acagggttgg gtaattaact    23700
attaaacata aaagctacat ttattagatt tcttagtgac atggatggag cattttgttg    23760
ttgattatat attctgtatt gacaaatatt acagattgct agagatagaa tttagtataa    23820
atttcattcc tattaggtca acttttttt acgtaaagaa gtaattaagg tgggaatcat    23880
tttcttacag cagtgtttct cagttttttg aactctcaag ctttaagcca aaaattacat    23940
ggtgatctga cagcaaaaac tattttaatg atttattaat gatattaggt cacctccagt    24000
```

```
tttgttgaat gcaaatagtt agaaacctct ggttgcccca aaggatttat tacccattca   24060
ttagagacat tggctttctt aataaagata gcaatatttc tgattacctt tgtttggtgc   24120
cctggaggtt atattaggtg ggacagtgca tttaataaca atacaggatg ggtgagcagt   24180
caggcccttt gtgaagtggg agaagggtga tgtgaagtgg ggtggggcgg gggtgggggg   24240
cagagcgaga gagaagcatg gagaacctgc ccctatccaa gtggatcagt tttaggaaag   24300
cttatgccgt atgtagggat gccaagggtc tgggaattta ttccctaact taaagttatc   24360
tgcattcaca tattccatgg agagttgtat gcattcaggt atcatgcact cccagtctga   24420
aaaactgctc ttttggttga aagagtataa ggacttggaa gatggggcct ctaggcctga   24480
ctgagccaaa ggctcccatg acctcaaggg aactgactag tgcttttttc attttttact   24540
gcgttctggg tcccacccct ggcattcaga tgtgtgcatg agctgctgtt taattttcat   24600
catctgcttt acaaatgagg aaaagccctg atatccagct ccctcatagg acctgataat   24660
aatacatatg gttctgagaa ttaaacgagg taataggtac gtaaagtggg taaacagagt   24720
aacttcactc tctatttgta cgtctctcag aagtctgggg caacaggagc tgtggaaggc   24780
tccagaagac aagatgtcac aaagccacct agctactgtg gctgtaccaa tcctgacagt   24840
catagcggcc ccaaggtgct gctctgttgg ctgatgggaa tgcagattta cgtatggtcc   24900
atatatggac gtgttgtttt acatctaaat aaacttggca ttgcaagatg aaaatgccag   24960
tatcattttt aaaggtcaag tgacagtttg ggaagatttt tataactttg ataagttcct   25020
cagctacatc tgttcacact ggcaagagtg ctagagacat tcttgggaag tcttttctat   25080
cagaggagct gcagccttgc tctgcagaaa agttctgatg acagtcatca gagtatttgg   25140
ggctcatgca ctaactgtta attattttca ttttttcatta atgaaaattt attttaattt   25200
ttttcattct tctttaatga atttaactat ttgcctctac ctttgcttcc tgctttgtat   25260
actgataaga caggttttgg ggttttttatg ttttctggtc ttgcttttcc cctttgtttt   25320
aggatttaaa aaacaaaaag gttaagaggg taggttgaca gtgcttgcag tttctgtttt   25380
acagcaatcc cagctgttcc tctgaaaatt ggttgattgt cctatagttt aaaatatata   25440
gatgttcatt tgattggctc ttgtaaatct agtgacattt aaaagtacat ggcagctagt   25500
catggtggct cacacttata atcccagcac tttgggaggc tcaggcagga ggatggctta   25560
gcccaggagt tcgagaccag cttgggtaac atcatgagac cccaactcta caaaaatttt   25620
taaatagttg tgagtggtgg catgtgcctg taccctcagc tacttgagag gctgaggtgg   25680
gaggattgtt tgagacctgg agtttgaggt tgtggtgctc tatgattgca ccactacact   25740
ccagcctgga tgatagactg agaccctgtc tcaaaaaaga aaagaaaaa  agttcatgtc   25800 tattctgttt tttgttatgt tactttcctc taaacatgaa gaaaagcagt gaggagaaac   25860
aaaaattgag tattcctgtg tttttttatca tagtaaaata tacatttgcc attttatatt   25920
tatcctgata accttcagtg ttgtaaaata cacattcaca attattcatt taacctgata   25980
acctctaatc tcttttccat gaatcggact aggtacctca tataagtgga atcataccat   26040
atttatactt ttgtgtctgg tttatttcac ttaatgtcct taaggttcat ccacattgta   26100
gcatgtctca gaatttaatt ccttttgggg gctgaataac attctattat atgtatattc   26160
cacattttgc ttatccattc atctcttgat aggaagttgt gttgctttca cattttacct   26220
attgtgaata atactggtac caatattagt gtacacataa tctgagtccc tgctttccgt   26280
tcttttgggt atatacacag aagtaaaatt gctagacaca atggtacttc tatgtcagtt   26340
```

```
ttttgaagaa ctaccctact gttttccata gcagttacac catttacat ttctatcacc    26400
agaccacgag ggtaacaatt tctccacacc ttagccacca cttgttattt tttgttttt    26460
gggtaatagc catgcaaaaa aatatgaagt aaagtgaaat atcattatga aagtgtgaa    26520
gtgatatgtc tttgtgattt tgatttgcat ctctcctata attagtgatg ttgaacatct    26580
tttcatgtgc ttattggcca tttgtctgtc ttctttgggg aaatatctct tcaagcctat    26640
tctgcccatt tttgaattgg gttttgttgt ttttaggaat tctttagata ttttggatat    26700
tagtcactta tcagatatgt gatttgcaaa tgaggatggc cttttttattt tgttgattgt    26760
gttctttgca caatagtttt tattttttgat gaaatataat tttctatttt gtgcttttgg    26820
tgttatatat ctaagaaatc atgccaaatt caatgtcatg aaggctttct cctgttttct    26880
tctaatagtg tgtagtttta gctcttttgt acgtggtgtt gggtaagggt tcaacttcat    26940
cctttttgcat gggaatatcc agtttttttc ccagctgcat ttgtcaaaaa gactcttctt    27000
tcttccgttg aatgatctca gtggaagtca ctgatctcat caaaaatcac tgaccatatg    27060
tgggagcata accacctgat gggttcttct tgcctgctgc ccaaatatag ctggtttatc    27120
aagatgggaa ttgcaataga gaaagagctt tacacatgta cagctggcta aatgggagac    27180
tggagcttta ttattaaata aataagcctc ccccaaaatt tggatgctag ggttttctct    27240
tttttttttct tttttttatta ttatactttta agttctaggg tacatgtgca caacgtgcag    27300
gtttgttaca tatgtatata tgtgccacgt tggtgtgctg cacccattaa ctcatcattt    27360
acattaggta ttctcctaat gctatccctt cccccctcccc ccaacccact acaggcccca    27420
gtgtgtgatg ttccccacca tgtgtccaag tgttctcatt gttcagttcc cacctatgag    27480
tgagaacatg tggtgtttgg ttttctgtgc ttgagatagt ttgctcagaa tgatggtttc    27540
cagcttcatc catgtcccta caaggacat gaactcactc tttttttatgg ctgcatagta    27600
ttccatggtg catatgtgcc acattttctt aatccaatct gtcattgatg gacatttggg    27660
ttggttccaa gtctttgcta ttgtgaatag tgccgcaata acatacgtg tgcatgtgtc    27720
tttataaatag catgatttat aatcctttgg gtatataacc agtaatggga tggctgggtc    27780
aaatggtatt tctagttcta gatccttgag gaatcaccac actgtcttcc acatggttga    27840
acgagtttac actcccacca acagtgtaaa agtgttccta tttctcccat cctctccagc    27900
acctgttgtt tcctgacttt ttaatgatcg ccattctaac tggtgtgaga tggtatctca    27960
ttgtggtttt gatttgtatt tctctgatgg ccggtgatga tgagcatttt ttcgtgtgtc    28020
tgttggctgc atgtcttttg agaagtgtct gttcatatcc ttcgcccact ttttgatggg    28080
gttgtttgat ttttttcttgt aaatttgttt aagttctttg tagattctgg atattagccc    28140
tttgtcagat gggtagattg caaaaatatt ctcccattct gtgggttgcc tattcactct    28200
gatggtagtt tcttttgctg tgcagaagct ctttagttta attagatgcc atttgtcaat    28260
tttgactttt gttgccattg cttttggtgt tttagtcatg aagtccttgc ctatgcctat    28320
gacctgaatg gtatagccta cgttttcttc tagggttctt atggttttag gtcttacatt    28380
taagtcttta atccatcttg aattaatttt tgtataaggt gtaaggaagg gatccagttt    28440
catctttcta catatggtta gccagttttc ccagcaccat ttattaagta gggaatcttt    28500
tccccatttc ttgttttttgt caggtttgtc aaagatcaga tggttgtaga tgtgtggtat    28560
tatttctgag ggctctgttc tgtgccattg gtctatatct ctgttttagt atcagtacca    28620
tgctatttgg ttactgtagc cttataatat aatttgaagt caggtagcaa gatgcctcca    28680
gctttgatct ttttgcttag gattgtcttg gcaatgtggg ctcttttttg gttccatatg    28740
```

-continued

```
aactttaaag tagttttttc caattatgtg aagaaagtca ttggtagctc aatggggatg   28800
gcagttaatc tataaattac cttgggcagt atggccattt tcacaatact gattcttcct   28860
atccataagc atggaatgtt cttccatttg tttgtcctct tttatttcat tgagcagtgg   28920
tttgtagttc tccttgaaga ggtccttcac atcccttgta agttggattc ctgggtgttt   28980
tattctcttt gaagcaattg tgaatgggag ttcactcatg atttgtctct ctgtctgttt   29040
ttggtgtata ggaaagcttg tgattttgca cattgatttt gtatcctgag actttgctga   29100
agttgcttat cagcttaagg agattttggg ctgagacgat ggggttttct aaatatacag   29160
tcatgtcatc tgcaaacaga gacaatttga cttcctgttt tcgtgattga atagctttta   29220
tttctttttt taaatatata ttttattat actttaagtt ctagggtaca tgtgcacaat   29280
gtgcaggttt ttacatatgt atacatgtgc catgttggtg tgctgcaccc attaactcgt   29340
catttacatt aggtatatct cctaatgcta tccctccccc ctctccctac cctggtgtgt   29400
gaagttcccc ttcctgtgtc caagtgttct cattgttcaa ttcccaccta tgagtgagaa   29460
catgcggtgt ttggtttttt gtccttgcga tagtttgctg agaatgatgg tttccagctt   29520
catccatgtc cctacaaagg acatgaactc atccttttt atggctgcat agtattccat   29580
ggtgtatatg tgccatgttt tcttaatcca gtctatcatt gttggacatt tggtttggtt   29640
ccaagtcttt gctattgtga atagtgcctc aataaacata catgtgcatg tgtctttata   29700
acagcatgat ttataatcct ttgggtatat acccagtaat gggatggctg ggtcaaatgg   29760
tatttctagt tctagatccc tgaggaatca ccacactgtt ttatttcttt ctcctgcctg   29820
ccagctcctc ctggtacctc tgatagaatt cagctgtgaa tatgtctggt ctgtggcttt   29880
tcttgcttgg tacactatta attattgcct caatttcaga gcctgttatt ggtctattca   29940
gggattcaac ttcttcctgg tttagtcttg ggaggttgta tgtgtccagg aattttttcta  30000 tttcttctag attttctaat ttatttgtgt agaagtgttt atagtattct ctgatggtag   30060
tttgtatttc cgtgggattg gtggtgatac cccctttatc attcttatta catctatttg   30120
attcttctct cttttcttcc ttattagtct gctagtggtc tatcaatttt gttgatcttt   30180
tcaaaaaacc aattcctaga ttcattgatt ttttgaagtt ttttttttg tgtctctgtc   30240 gccttcagtt ctggtctgat cttagttatt tcttgcgttc tgctagcttt tgaatgtgtt   30300
tgctctggct tctccagttc ttttaattgt gatgttaggg tgtcgatttt cagtcttttcc  30360 tgctttctct tgtgggcatt tagtgctata aatttccctc tacacactgc tttgaatgtg   30420
tcccagagat tctggtatgt tgtgtctttg ttctcgttgg tttcaaagaa catctttatt   30480
tctgccttca tttcattatg tacccagtag tcattcagga gcaggttgtt cagtttccat   30540
gtagttgtgc agttttgaat gagtttctta attctgagtt ccaatttgat tgcactatgg   30600
tctgagagag tttgttgtga tttctgttct tttacatttg ctgaggagtg ccttacttcc   30660
aactaagtgg ttaatttttgg agtaagtgca atgtggtgct gagaagaaag tatattctgt   30720
taattttggg tggagagttc tgtatgtgtc tattaagtcc acttggtgca gagctgagtt   30780
caagtcctgg atatccttgt taaccttctg tctcattgat ctaatattga cagtggagtg   30840
ttaaggtctc ccattattgt ctcccattat tattgtttgg gagtctaagt ctctttgtag   30900
gtttctaagg actcgcttta tggatctggg tgctcctgta ttgggtgcat atatatttag   30960
gatagttagc tcttgttgtt gaattgatcc ctttaccatt atgttaacgg ccttcttgt    31020 ctcttttgat ctttgttggt ttaaagtctg ttttagcaga gactaggata gcaaccccg    31080
```

-continued

```
gtttttttgc tttccatttg cttggtagat cttcctccat ccctttattt tgagcctatg    31140
tgtgtctctg catgtgagat gggtctcctg aatacagcac actgatgggt cttgactctt    31200
tatccaattt gccagtctgt gtcttttaat tggggctttt agcccattta cattgaaggt    31260
taatattgtt atgtgtgaat ttgatcctgt catcatgatg ttagctggtt attttgctca    31320
ttagttgatg cagtttcttc atagcatcga tggtctttac aatttggcct attttttgcag    31380
tggctggtac tggttgttcc tttccatgtt tagttcttcc ttcaggagct cttgtaaggc    31440
aggcctggtg gtgacaaaat ctctcagcat ttgcttgtct gtaaaggatt ttatttctcc    31500
ttcacttatg aagcttagtt tggctggata tgaaattctg ggttaaaaat tcttttcttt    31560
aagcatgttg aatatcggcc ccctctctct tctggcttgt agtgtttctg ctgagagatc    31620
tgctgttagt ctgatgggct tccctttgtg ggtaacccga cctttctctc tggctgccct    31680
taccatttt tccttcattt caaccttggt gaatctgaca attatgtgtc ttgggattcc    31740
ccttctggag gagtatcttt gtggcgttct gtgtatttcc tgaatttgaa tgttggcctg    31800
ccttgctagg ttggggaagt tctcctgcat aaatatcctga agagtgtttt ccaacttggt    31860
tccattctcc ccgtcacttt caggtacacc aatgaaacgt agatttggtc ttttcacata    31920
gtcccatatt tcttggagac tttgttcatt tctttttact cttttgtctc taaacttctc    31980
ttctcacttc atttcattca tttgatcttc aatctctgat accctttctt ccagttgatc    32040
gagtcagcta ctgaagcttg tgcattcgtc acgtatttct catgccatgg ttttcagctc    32100
catcaggtca tttaagatct tctctatgct ggttattgga attagccatt tgtctaatcg    32160
tttttccagg ttttttagctt cttttgagatg ggttcgaaca ccctcccttta gctcggagaa    32220
gtttggtatt accaatcttc tgaagcctac ttctgtcaac tcattaaagt cattctccat    32280
ccagctttct tcctttgctg gcgaggagct gcgatccttt ggagaagagt cgctctgatt    32340
tttaaattt ttggctttc tactctgttt tctccgcatc tttgtggttt tatcaaactt    32400
tggtctttga tgatggtgac ctacagatgg ggttttggtg tggatgtcct ttttgttgat    32460
gttgatgcta gttttgttga tgctttgtta gttttccttc taacattcag gaccctcagc    32520
tgcaggtctt ttggagtttg ctggaggtct actccagacg ctgtttgcct gggtgtcacc    32580
agcagaggct gcagaacaac aaatattgca gaacggcaaa tgttgctgcc tgatccttcc    32640
tctggaacct tcatctcaga ggggcacctg gctgtatgac gtgtcagtcg gcccctactg    32700
ggaggtgtct cccactgggc tactcagggg tcagggaccc acttgaggag gcagtctgtc    32760
cattcccaga tctcagactc tgtgctggga ggaccactgc tctcttcaaa gctgtcagac    32820
agggacgttt aagtctgcag gtttctgctg ccttttgtta agttatgccc tgcccccaga    32880
agtggagtct acagaggcag gcaggcctgg ttgagctctg gtgggctcca cccagtttga    32940
gctttctggc cgcttcgttt acctagtcaa gcctcagcaa tggcagacgc cctcccccca    33000
gtcttgggc cgtcttgcag tttgatctcg gactgctgtg ctagcagtaa gcaaggctcc    33060
ataggtgtgg gaaccgccga gccaggcacg ggttataatc tcctggtgtg ccgtttgcta    33120
agaccattgg aaaagcgcag tattagggcg ggagtgtccc gagtttccag gtaccatctg    33180
tcacggcttc ccttggctag gaaagggaat tccctgaccc cttgtgcttc cagggtgagg    33240
tgatgccccg ccctactttg gctcacactc catggcctgc acccactgtc caacaagtcc    33300
cagtaagatg aacccagtac cttagttgga aatgcagaaa tctcctgtct tctgcgtcac    33360
tcacgcagat gcatgagctg tagactagag ctgttcctct tcggccatct tgtaacgatc    33420
ctgctagggt ttttttcaagg atagtttggc agggagagag atgacaaagg aatgagtgct    33480
```

```
gctgattggt tggcggtgca atcacagagg tgtgggaaat gatccttatg ctgagtccac   33540
ttctgggcga aggccgcagg actggttggc aggtcaggtg gtgccatctg gttgtcagaa   33600
ttgcaaaagc ctgaaaagac atctcaaaag gccaacctca ggatctataa tagtgatatt   33660
acctgcagga gtaattgagg aagttgcgaa tcttgtgatt tgcagaataa tgactggtaa   33720
ttgttcacat ctatgtctta gtagaattga ggctcctctc attctcccat tctggtggtc   33780
tttcattagt tttacgaaag tagtttagtt tgggggaagg gctattatca tttaaactac   33840
aaactaaatt tcttccaaag ttagcttgac ccaatcccag gaatgactaa gggcatttgg   33900
agggtaaagg caagatgcag gctggttgga tcagatctcc ttcactgtca taattttctc   33960
actgttttaa gttttgcaag ggtggttgca tagggtttat ttctgggctc tctattctag   34020
tccattggtc tatatttctg tctttatgcc agtaccacat tgctttgatt aatgtagctt   34080
tgttataagt tttgaaattg gaaagtgtga cttacttatt cttttcaaga ttcttttggc   34140
tattcagggt gccttgagat tccatgtgaa ttttaagatg tattattatt ctgttactgc   34200
aaaaaacatc attgggattt tgatagagat tgcattgact ctgtagatct tctttagtag   34260
ttttgacatt tagcaatatt aactcttcca atccataaat atggaatttt gttccattta   34320
tctttgtggt ctttaatttc tttcaccagt gtttcatagt ttttagtgta tatggttttt   34380
gcctccttgg ttaagtttat ttatgatttt ttatgctggt aggttttatt ttttaaattt   34440
tgggggaagt gttttattaa tacaaatgta tgggttacaa gtgcaatttt gttacatgta   34500
tagattgtat agtggtgatg tcaggacttt tatggtatcc atcactcaaa taacttccat   34560
tgtacccatt aagtacaccc cactcccacc tgttaagttt taataagttg gtttagtctc   34620
tgttctgtct ctgaaaaatg tcagatacta ctaacagaac taaaaaatcc aggactgaga   34680
gaaactttaa gtacatacaa caatataaac agatcttaaa aatatgatac agcatagaaa   34740
aatggaaacc aaacatattc cacaatgtca ttcagtactt ttaaattact acacagaaag   34800
tgttatacat ttcacaaaaa tgtataagaa tagcacacac aaattatcaa caaaataata   34860
cagggttttc tgaattgtct acctgtgaga tgtttctaag cagggttttta ttattgattg   34920 attgattgag acagggtctg actctgtcgc ccagattgga gtacagtggt gcaatcctgg   34980
cttgacctcc tggctcaagt aatccttcca cctcagcatc ccaagcagct gggactatag   35040
gttcacacaa ccatgcctgg ctacttcttt aaaaaaattt ttgtagagag tctcactaca   35100
ctgctcaggt ggtctcaagc tcttgggctc aagcaattct gacacctcag cctcccaaag   35160
tgcagggatt acgggtgtga gccgttgcac ctggactaag cagggtttta agtgacttgg   35220
ttcttgttta tgttgacact aaacatgcat caaagattaa ccttctaaat tctggaacac   35280
agaaagaagg gcagcccctta tttcagggct gggctgatga tagaatttac ttgatgcagt   35340
ttttcataga aagatatgtg tcttttttgtt ttaaacatat aagaaaagag tttccactgt   35400
ttacctggta ctaggtccca atgtctaaac caagtttgga gaatcacatc ctctgagcag   35460
cctatgttga tgatgatgct gatgacaatg atgacagaag acacttatat ggtacttatt   35520
tatgtagcag aaccatagtc ctttatatgt tttaactcat ttaatattca aaacaaccct   35580
atgacatggt acattgatgt tgttataccc atttatatgt gtggaaatgg tcatacagtg   35640
tcttattaat ttgcctgagg ccacacagct aattagtggt ggatctgagg ttggatttct   35700
aggagccaga ttcacaaatc caacactgca ctttgctttt tctctattgt ctatcgctca   35760
ttgatttttt tattctcaat tttatttcct tcctttattt ttggtttaat tttctcttct   35820
```

```
tttttttagtt tcttgagatg aaaacttaga tctttgattt ttctacctct cttcttttca    35880
atatttatta tgcttaaagc tttacacttc accctaggca ttgttttgt tgcatcccac      35940 atattttgat gctgtatttt tatattcaga atattttcta atttatattt atttgttcat    36000
tttaaaaata attttactaa ataatataaa atgctaattt tgaaatactt aggattttct    36060
tacatttggt tttgatttct aatttaattc tatgtggttt taaaatatag tttcactcaa    36120
ttgaaattta ttgatttact ttatattcct gcatatggtt gatactggtg catgttgcat    36180
gtacacttaa ataacattta ttctgcgatt gttggataca gtgttctata tttgtcaatt    36240
agattgagtg ctgctcagat gttctatatt cctacagata tttcatgtgc ttattctata    36300
aaatacaaat tgttaatgtt tctgattagg actagaagac ttttctttta cctttaaat     36360 atatttttta ttttatgtat tttgaaacta tgttatttgg tgcctataca cttagatttt    36420
tttcttgagg aattgatcct ttatcattat gaaatatcct tcaggcaccc cgctcccaca    36480
gatgtatgca tcttgctgta cccctgcttc tgctggcaca aatgcacagg catggatcct    36540
gctgccacca ccttgatgaa gtgtgtggcc agcaccccca tcagagtact gttaccagca    36600
tactgggaat accttgcccc cagagtgcag cagctttcta acctctatgg ggcagagaac    36660
aaagttgggg ggcccagtac cagcccatca gcgttacatc acatagccca tgagtgatga    36720
gctgagcctt ggtgccctga agcatccag aatgaagcca gtcaactgaa ccgacattat     36780
accacaatca aaccctcaag aatatcaaag aatataaaag taaaaagccc tatccaaagg    36840
atagcaactt caaagattaa aggaatgtca gcccacacag atgagaaaga atcaatgcaa    36900
gaactctggc aattcaaaaa actagagtgc cttcttacct ccagacaacc ccactggttc    36960
cctagcaatg gttcttaaca aaactgaaat gacagagata gaattgagaa tctggataga    37020
aaaaagatca ttgagattca ggagaaagtt gaaacccaat ccaaggaatc taaggaatcc    37080
aataaaacaa tacaagagat gaaacgaaat agccatttta agaagaacc aaactgaact     37140 gatagagctg aaaaactcac tacaagaatt tcataatgca atcacaagca ttgttaacat    37200
cagaatagac tactaacatc agaatagacc aagctgagga agaatctca gagcttgaag     37260 actggttcct caaatcaact cagacaaaaa taatgaacaa ataattaaaa agagtgaaca    37320
aaaccactga gaaatatgag attaggtaga gaccaaatct gtgactcatt gacatccctg    37380
aaagagagag agaaaaagca attttttccag ccttgctaga gaggccaaaa ttcaaattca    37440
ggaaatgcag aaaaccccctg tgagatacta tacaagacaa ccatccccaa gacatgtagg    37500
catcagattc tccaacgtca acatcaaaga aaaaatacta aggcagctag agaaaagggg    37560
caggtcacct acaaagggat tccgatgagg ctaacgaaag acctttcagc aaaagcacta    37620
caagccagga gagatttgga gacctatgtt cagcaaaaaa aattccaacc aagtatttcc    37680
tgtgcagcaa gactaagctt aataagcaaa ggagaaacaa gatcctttc agacaagcaa     37740 atgctaagag aattcattac caccagacat gccttacaag aggtccttaa gtgagtgcca    37800
aatatggaaa caaagactg ttactggcca ccacaaaaat atacttaagg actagacctc      37860
tgaacactat aaagcaatta cgctatcaag tctgcataat atccagctga catcatgatg    37920
acaggatcaa atcaacacat ataagtatta tccttaaaag taaacatgca aaatgcctga    37980
cttaaaaagt acagaatggc aaatttgata agaaataag acacatggag agttgctcca    38040
aatggcagga taggaacagt tctggtctac agctcccagc aagatcaatg cagaagacag    38100
gtaatttctg catttccaac tgaggtacct ggttcatctc attgggattg gttggacagt    38160
gggtgcagcc catggagggc aagccgaagc agggcggtgc atccctcacc gaggaagtgc    38220
```

```
aagggtcag gggatttccc tttcctatcc aagggaagcc atgagtgact gtacctagag    38280
gaaaagtaca ctcctgctca aatactgcac ttttcccacg gtattcgcaa caggcagacc    38340
ggaagattcc ctcccatgcc tgctcggtgg gtcccacgct catggtgcct tgctcactgc    38400
tagcacagca gtctgagatc gacctgggat gctggagctt ggtgggtggg gagcggcgtc    38460
caccattgct gaggcttgag taagcggttc tatgctcaca gcgtaaacaa agcagcaggg    38520
aagcttgaac tgcacggagc ccactgcagc tcagcaaggc ctactgcctc tgtagattct    38580
acctcggggg cagggcatat ctgaaaaaaa tgccgcagac agcttctgca gacttaaaca    38640
tccctgcctg acagctctga agaaagcagt ggttctccca gcacgggggc gttcaagctc    38700
tgataacgga cagactacct cctcaagtgg gtccctgacc cctgtgtagc ctgattgggg    38760
gatacctccc agtaggggcc aacagacatc tcatacaggc gggtgcccct ctaggacgaa    38820
gcttccagag gaaggatcag gcagcaatat ctgctgttct gcagcctcca ttggtgatac    38880
cgaggcaaac ggtctggagt ggaactccag caaactccaa cagacctgca gctgagggga    38940
ctgtctgtta gaaggaaaac taacaaagag gaatagcatc aacatcagca aaaaggacat    39000
ccacacgaaa accccatccg taggtcacca acatcaaaga ccaaaggtag ataaaaccac    39060
aaagatgggg agaaaccaga gaagaaaggc tgaaaattcc aaaaccagaa cgcctttctt    39120
ctccaaggat cacaactcct cgccagcaag ggaacaaaac tggacagaga atgaatttga    39180
tgagttgaca gaagtaggct tcagaaggtc ggtaataaca aacttctcca gctaaagga    39240 gcatgttcta accaatcgcg aggaagctaa aaaccttgaa aaaatgctag atgaatggct    39300
aactagaata caataaccag tgtagagaag aatataaatg acatgataga gcttaaaacc    39360
atagtacaag aactttatga aacatacaca agcttcaata gctgattcaa tcaagcgaaa    39420
gaaaggatat cagtgattga agatcaaatt aatgaaataa agcaagaaga caagattaga    39480 gaaaaagag tgaaaagaaa cgaataaagc ctccaagaaa tacgggacta tgtgaaaaga    39540
ccaaatctac gtttgattgg tgtacctgaa agtgacaggg agaatggaac caggttataa    39600
aacactttca ggatattatg caggagaact tccccaacct agcaaggcag gccaacattc    39660
aaattcagga aagacagaga acaccacaaa gatactcctc gagaagagca accccaagac    39720
acataattgt cagattcacc aaggttgaaa tgaaggaaaa aatgttaagg gcagccagag    39780
agaaaggtcg ggttacccac aaagggaagc ccatcagact aacagcagat ctctcagcag    39840
aaacactaca agccagaaga gagaggggc cgatattcaa catgcttaaa gaaagaatt    39900 tttaacccag aatttcatat ccagccaaac taagcttcat aagtgaagga gaataaaat    39960 cctttacaga caagcaaatg ctgagagatt ttgtcaccac caggcctgcc ttacaaaagc    40020
tcctgaagga agaactaaac atggaaagga acaaccggta ccagccacta caaaaacatg    40080
acaaattgta aagaccatcg atgctatgaa gaactgcat caattgatgg gcaaaataac    40140
cagctaacat cataatgaca ggatcaaatt cacacataac aatattaacc ttcaatgtaa    40200
gtgggctaaa tgcccccaatt aaaagacaca gactggcaaa ttggataaag agtcaagacc    40260
cttgactgta ttcaggagac ctatctcaca tgcaaagaca cacataggct caaataaagt    40320
gatggaagaa gatctaccaa gcaaatggaa agcaaaaaa agggtttgcc atcctggtct    40380
ctgatgaaac agactttaaa gcaacaaaga tcaaaagaga caagaaggc cgttaacata    40440 atggtaaagg gatcaattca acaagaagag ctaactatcc taaatatata tgcacccaat    40500
acaggagcac ccagattcat aaagcaagtt cttagagact aagtctacaa agagacttag    40560
```

```
actcccacac aataataatg ggagacttta acaccccact gtcaatatta gatggatcaa    40620
cgagacagaa agttaacaag gatatccagg acttgaactc agctctagag caagcagaac    40680
taatagacat ctacagaact cttcttccca aatcaacaga atatacattc tcctcagccc    40740
cacatcacac ttattctaaa attgaccaca taattggaag caaaacactg ctcagcaaat    40800
ataaaagaac agaaattaca tcaaactgtc tctcagaccg caatgcaatc aaattagaac    40860
tcaggattaa gaaactcact caaaactgca caactgcatg gaaactgaac aacctgctcc    40920
tgaatgacta ctgggtaaat aacgaaatga aggcataaat aacaatgttc tgtgaagcca    40980
ataagaacaa agatacaacg ttcaagaatc tctgagaaac atttaaagca gtgtgtagag    41040
agaaatttac agcactaagt gtccacagga gaaaacagga aagatctaaa atcgacaccc    41100
taacattgca attataaaag aactacagaa gcaagagcaa atgaattcaa aagctagcag    41160
aagacaagaa ataatcaga gcagaactaa aggagagaga gacacaaaaa accctaaaa     41220 aaaatcaatg aacccaggag ctggttttct gaaaagagca acaaaataat tacatgacaa    41280
gcaagactaa taaggaagaa aagagagaag aatcaaatag acgcaataaa aaatgataaa    41340
ggggatatca ccaccgatcc cacggaaata caaactatca tcagacaata ctataaacac    41400
ctctacgcaa ataaaataga aaatctagaa gaaatggaaa aattccttga cacatacacc    41460
ctcccaagac taaaccagga agaagttgaa tctctaaata gttcagtgac agcttctgaa    41520
attgaggcaa taattaatag ccaaccaacc aaaaaaagtc caggaccaga cagactcaca    41580
gccaaattct accaggggca caaagaggag ctagtaccat tccttctgaa actattccaa    41640
tcaatagaaa aagagggaat cttccctaac tcatttata aggccaacat catcctgata    41700
acaaagcctc acagagacac aacaaaaaaa gataatttta ggccaacatc cctgatgaac    41760
atcgatatga aattttcaa aaaaaaatac tggcaaaccg aatccagcag cccatcaaaa    41820
agcttatcca ctacgatcaa gtcgacttca tccctgggat ggaaggctgg ttcaacatag    41880
gcaaatcaat aaatgtaatc catcacataa acagaaccaa cgacaaaaac cacatgatta    41940
tctcaataca tgcagcaaag gccttcaaca aaattcaaca gcctttcatg ctaaaaactc    42000
tcaataaact aggtattgat agaatgtatc tcaaaacagt aagagttatt tatgacacac    42060
ccacagccaa tatactgaat gggcaaaaac tggaagcatt ccctttgaaa actggcacaa    42120
gacaaggatg ctctctctca ccactcctat tcaacatcgt gttggaagtt ctggccaggg    42180
caataaggca agagaaataa ataaatggta ttcaattagg aaaagaggaa gtcaaatagt    42240
ctgtttgtag atgacatgat tatatatgta gaaaacctca tcgtctcagc tccaaatctc    42300
cttaagctga taaacaactt cagcaaagta tcaggataca aaatcaatgt acaaaaatca    42360
caagcattcc tatccaccaa gaacagacaa acagagagcc aaatcatgag tgaactccca    42420
ttcccaactg cctcaaagag aataaaatac ctaggaatcc aacttacaag ggatgtgaag    42480
gacctcttca aggagaacta caaaccactg ctcaatgaaa taaagagga tacaaacaaa    42540 tggaagaaca ttccatgctc atggataggg agaatcacta tcatgaaaat ggccatactg    42600
cccaaggtaa tttaaagatt caatgctatc cctatcaagc tatcactgac ttcacagaat    42660 tgaaaaaaa ctactttaaa gctcatatgg aaccaaaaaa gagcccacat agccaagaca    42720
atcctgggca aaaagaacaa agctggaggc atcacactac ctgacttcaa actacactac    42780
aaggctacag taaccaaaac agcatgttac tggtaccaaa acagacatgt agaccaacgg    42840
aatagaacag aggcctcaga ataaaccca cacatctaca accatctgat atttgacaaa    42900
cctgacaaaa acaaatcggg aaaggattcc ctatttaata aatggtgctg ggaaaacagg    42960
```

```
ctagccatat gtagaaagct gaaactggat cccttcctta caccttatac aaaaattaac    43020
tcaagatgga taaaagactt gaatgtaata cctaaaacca taaaaccct acaaaaaaac    43080 ctaggcaata cccttcagtg cataggcatg ggcaaagact ttatgactaa aacaccaaaa    43140
gcagtggcaa caaaagccaa aattgacaaa tggcatctaa ttaaactaaa cagcttctgc    43200
acagcaaaat aaactaccat cagagtgaat aggcaaccta cagaatggga gaaaatttt    43260 tcaatctatc catctgacaa agggctaata ttcagaatgt acaaagaacc taaacaaatt    43320
tacaagaaaa aaaaaaccac tgcatcaaaa agtgggcaaa ggatatgaac agacacttct    43380
caaaagaaga cagttatgca gccaacagac atatgaaaaa atgtccatca tcactggtca    43440
tcagagaaat gcaagtcaaa accacaatga gataccatct catgccagtt agaatggcga    43500
tcattaaaaa gccaggaaac cacagatgct ggagaggatg tggagaaata ggaacacttt    43560
tacactgttg gtgggagtgt aaattagtgc aaccattgtg gaagacagtg tggcgattcc    43620
tcaaggatct acaactataa ataccatttg acccagcaat cccatttgtg ggtatatacc    43680
caaaggatta taaagcattc tactataagg acacatgcac acatatgttt attgcagcac    43740
tatttacaat agcaaagact tggaaccaac ccagatgtcc atcaataata gactggatat    43800
atagtattct atgtctggtt aaaaaaaaag ttattcaatt ttatggattt ggattaggat    43860
cattcccatt tctgtaaata tttacaccta taaggatatc aagaaggaat gtcaggcagt    43920
ttactagtaa ctttttcaaag tcttagaaaa gttgcatttt ttgctggcac caagagggga    43980
aaacatcata aaaatagttt caaaatctac aatcaatgct ttctccaaaa taaatgtctt    44040
tgttaaaaaa aataataata atagactgga taaagaaaat gtggcacata taccatggg    44100 aatactatgc agccataaaa aaggatgagt tcatatcctt tgtaggtaca tggatgaagc    44160
tggaaatcat cgttctcagc aaactatcac aaggacagaa aaccaaacac cgcatgttct    44220
cactcataag tgggagctga actatgggaa cacgtggaca cagagagggg aacatcacac    44280
accggggcct gtcagagggt gggggactgg gggagaggta gtgttaggag aaatacctaa    44340
tgtaaatgac gagttgatgg gtgcagcata ccagcatggc acatgtataa ccacgtaaca    44400
aacctgcatg ttgtgcacat gtacccttga atttaaagta taatttaaaa aaagaagaag    44460
aaataagtca caattgtatg ctgtcttcaa gagacccatc tcatgcagag ctacccatag    44520
gctcaaaata aaggtttaaa gaaaaatcta ccaagtaaat gggaaaagaa acaggagtt    44580 actattctaa ttttagacaa agcagacttt aaagcaacaa tgatcaaaaa agacaagcgc    44640
atgacataat cataaagggt tcaattcaac aagaagactt aaatatccta aatatatgta    44700
cccaacacag gagcttgcag attcatagaa caaattctta gagacctaca aagagacatg    44760
gataaccaca cggtaatatt gggagacttc agcaccccac taacagtatt caatcatcaa    44820
ggcagaacac taacaaagat acttgggacc tgaactcagt atttgactaa atggacccaa    44880
cagacatcta cagaactctg cactccaaaa caacagaata tacattcttc tcatcgccac    44940
atggcacata ctctaaagtc gaccacacaa tcggccataa gtcaattctt agcaaattaa    45000
aaacacaaga atcacactaa ccacactctt ggaccatggc gcaacaaaag tagaaatcag    45060
ccccaagaag atcattcaaa acatacagct acatgcaaat caaacaaccct gctcctgaat    45120 gacttttggg taaacaatga aattaaggca gaaatcaaga cattttttga aactattgaa    45180
aataaagata aaatatacga aaatatctga gacacagcta aaataaagat aaaatatacc    45240
aaaatctctg cgacacagct aaagcagtat taagagggaa gtttatagca ctaaacaccc    45300
```

```
ctatcaaaaa gttagaaaga tctcaaatta acagcctaac attgcaccta gaggaactag   45360
aaaaacaaga gcaaaccaac tgcaaagcta gcagaagaaa agaaccaaaa caagaactga   45420
actgaatgaa attgagacag gaaaatgata taaaagacca gtgaaaccag aagctggttc   45480
tttgaaacaa taaataagat ggatagacca ctgattatac taatcaaaaa acagagcaga   45540
tccaaataaa cttaatcaga aatgacaaag aggacattac catcaaccca acagaaatat   45600
aaaaaacctt aaaagactat tacaaacacc tctatgcaga caaactaaaa aacctacaag   45660
aaacgataaa ttcttggaaa catacagtct cccaagactg aacaaggaag aaattgaaac   45720
cctgaacaga ccaataacaa gttccaaaat tgaatcagta gtaaaaagcc taccaaccaa   45780
aaaagccctg gaccagatgg atccacaacc aaattctgcc agatgtataa agaagagctg   45840
gtaccattcc tactgaaact attccaaaaa attaaggagg agggacccct ccctaactca   45900
ttctataagg ccagcatcat cctgatataa ggccagcatc atcctgatat aaggccagct   45960
tcatcctgat aacgaaaact gggagagaca acataaaaag aaaacctcaa gtcaatatcc   46020
tggacaaaca tagatgcaaa aattctcaat aaaatactag caatctgaat tcagcagcac   46080
atcaaaaaac taatccacca tgatccaagt aggctttata cttggcatgt gagattggtt   46140
caccatatac aaatcaataa atatgattca tcacatgaac agaactaaaa agaaaaacca   46200
aatgataatc tcaatagatg cagatacatc tattgaatgc aaaattcagt accccttcat   46260
gttagaaacc ctcaacaaac taggcatcaa aggaacatac ctcaaaataa taagagctat   46320
ctgtgaaaaa atcacagcca gcatcatact gaaagagcaa aagctggaag cattcccctt   46380
gtggaataag acaaggatgc ccactatcac cactcatatt caatatacta ctggaagtcc   46440
taggcagagc agtcaagcaa gacaaataaa gaaaaggcat ccaaataggra agagaggaag   46500 tcagacaata tgattttata cctagaaaat tccatagtgt ctgcccaaaa gctcctagat   46560
ctgacaaaca acttcagcaa agttgcagtg tacaaaatca ctgtgcaaaa ataagttgca   46620
ttcctttaca ctaacaacat ccaagctgag agccaatcaa ggacacaatc ccattcataa   46680
tagccacaca aaaaataaaa tacctacgca tacagctaac cagagaggca aaatatttct   46740
agattgagaa ttacaaaaca gtgctgaaag aaatcagaca acacaaacaa acgagaaaac   46800
attcattcca tgctcgtgga taggaagaat caatgttgtt aaagtggcca tactgcccaa   46860
agcaatttac agattcaatg ctattccttt caaactacca gtgatatttt tcacagaatt   46920
agaaaaaact attctaaaat tcaggtggaa ccaaaaaaga gcctgaatag ccaaatcaat   46980
cctgagcaaa aagaacaaaa ctggaggcat cacattacca aaattcaaac tgtactgcaa   47040
gcttacagta acaaaaacag catggtactt gtacaaaaac agacacataa accaatggaa   47100
tagagagccc agaaataaag ctgtgtactc agaaccatct gatctttgac aaaattgaca   47160
aaaacaaaca atggggaaag gacctgctag tcaataagtg attcgggatg gatcgctacc   47220
catatgcaga agattaaaac tagaccactt cctatcacca tatataaaat caactcaagg   47280
atgtattaaa gacttaactg taaaaactat aaaaccctag aggaaaacct aggaaatacc   47340
attctggaca tagtccctgg caaagatttc atgatgaaga tgccaaaagc aattgcaaca   47400
aaaaaacggc aagtgggacc taattaaaga tcttctgcac aacaaaaaga aactatcaag   47460
agagtaaaca gacaacctat agaatgggag aaagtatttg taaagtatgc atctgacaaa   47520
ggtctaatat ccagaatcta taggaacttt aaacaagttt acaagaaaaa aaattttta   47580 aagtagctaa agtaaatgaa cagacacttt tcaaaagatg acatacatgt gaccaacaag   47640
catatgaaaa aatgcccaac atcactaatc attagagaaa tacaaattaa aaccacagtg   47700
```

```
agataccatc tcacaccagt cagaatgggt attattaaaa agttataaaa tagcagatgt    47760
tgacgaggtt atggagaaaa gggaatgcct atacgctgct ggtggaaatg taaattagtt    47820
cagccattgt ggaaaacagg gtggcaattt ctcaaagtac ttaaaacaga actaccattt    47880
tacccagcca tccacttatt gggtatatgc ccaaaggaat agaaatcatt ctaccataaa    47940
gacacatgca cacacacgtt catcgcagca ctattcacag taggaaagac atggaaccaa    48000
cttaaatttc catcactggt agattggata aagaaaatgt ggtacatata caccatgtaa    48060
tactacgtaa ccataaaaaa agaataagat gatgtccttt gcagcaacat ggatagtgct    48120
ggaggtcaat actctaagcg aactaatgta ggaacagaaa accaaatgct gcatgttcta    48180
acttataagt ggaagctaaa cattgagaac acatggatac aaagaaggga ataatggaca    48240
ctggacctac ttgagggtgg agggtaggag gaggatgagg agagaaaaaa tgacctaata    48300
tgcttattac ctgggtgatg aaaatctgta caccaaaccc ccacaacatg caatttattg    48360
ataacaaacc tgcacatgga ccctgaacc taaaataaag tcttaaaaaa agaagagggg    48420
ccgggcacag tggctcacgc ctgtaatccc agcactttgg aaggctgagg cggtggatc    48480 aggaggtcag gagattgaga ccatcctggc caacacggtg aaaccccatc tctactaaaa    48540
atacaaaaaa ttagccgggt gtggtggtgg gcttttgcag tcccagctac tcgggagact    48600
gaggcaggag aatggcatga actcgggagg tggagcttgc agtgagctga gatcatgcca    48660
ctgcactcca gcctgggcaa caaagcaaga ctccgtctca aaacaaaag aaaaacaaaa    48720 aaacaaagag gaggaagagg aaaataaggc ccatggtgct taaagtcaca catgtgccaa    48780
agccagctag taaacaaagc aaagatctga attcagatat ttgtttaact gctgtggttc    48840
taattatatc acgcaccttg gactcaaagc aggatagaga aggttgggca gtggatcaca    48900
aaagatatca gcataaatac acatcattta ttctgtatta tctgatgcca agcagtgtgc    48960
taagcacttt acatacatca tcttatttgt acatcccaat taccttctga tacagctgtc    49020
aattcccact tttatcagga aactgaggat caaagagggt aagtaataca tccagagtta    49080
caaagctgtt aaaaatatta gagggtctga ctccagtgta tatattttta aaagccctt    49140 attatctctg gtaatcactg tcttgaaaac tactttgtct gatattaata aagccacagt    49200
agctttcata caccttcttg tttacatatg atttcccata ttcttttatc ccatctatgt    49260
tattaaaatg tgtcttgtca atagtatata gtttgttctt gtttctttat tcattttgtt    49320
ttcctgatac tcttttccca attaaggagg taataatctg taagcaaagc cttatttaca    49380
taaacactgc tgtgatctta taccaaataa acagccctag catgtgtgtg tgtgtgtgag    49440
agagagagag tgtgtgaatg tgtgtgtgtt tgggctttct gaattagatt ttcttttcaag   49500 atccacctac atctttactt ttggcctaag taatggttgg tcatgttaac tgtgtaaaat    49560
attaatcttt ttctgaagct acaaagagtc catgtctact tactgttcta ggaaaagttt    49620
tttcaaattt gggaagtgtc taccttttaa aatattttct gagagtgttt aattacttct    49680
atgatcttaa aaggttctct ccattttact tttatccagc tgtcacatat tctgagtatg    49740
ttttccacca ggagaacctg agaattttttt tttctcttag attttgagta tagagataag    49800
attttatcct gcatccagtt ccaacctgtt aatataattc tatgcaagtt tcctctcttg    49860
ttgtgtttat ttcccttttat ccttatcctt agtcatctat tccaatgttt atgctgtgca    49920
ttattatatt tcatgtatc cttgtgaaat gtagagtgct ttatgtgcaa tatttttaaat    49980 gtacataaat ggcattatag attaaaacat tttttcatgt tgtaccatgt ttttgaggtt    50040
```

```
tatttatatt gctatgtata cctctagtct actgcttcta actgtgaaac attttttca       50100
aattcaaatt ctcataaatg ctgtacttat tttggaaatt agaattcagc acaaggtact      50160
tctctgtatt caacaccata gcattttagc gctttactaa tgggtggaaa aattaaactt      50220
cagtcctact gttcaaagag cctatttagt caaagatggc caagatggaa agcttccact      50280
ttcctgtgag tcaggtccta gtaaatgtga atcttacaca gagatgatta gttatagctc      50340
ctagcactaa ctccctggag gcaatgtcct tggtgcccct gactctcttc catttaggca      50400
ctcatctttg ttagatgcct taggtttatt tacgtaaaat catgctgcac ttctccctga      50460
tactgtggtt aaagttttta tggccttgca ccaaaccaac agcccagaat agctacatgc      50520
cagggagata ttgtcagcaa ggtttgggca ttaatatgaa gaatcttgta tattgttgaa      50580
acttctggtc caacagaatg gaaagtgtgc caaataggaa gcttttgggt acaggtgaca      50640
aaaccccaa ctcaaactgg cttcaacgct aagcacatat attatctcac tatattagca       50700
gaataactaa atattggcag ctgcagaggc aaaccctgac tactgagagg cttgatacag      50760
taaaagctta ttgcttggtc tcacaaagtt tgccaggggt tggtgactct cctgggcagt      50820
tagtgactca gatatgtcgc tttataagca acacatgact tgtaaagtca cccctgcaag      50880
ggaagaggac tggtggatca catagattgt ttttaaggac caggctggaa attgacttat      50940
atgaattttg cccatgctcc agtgtgcata atccgtcat cagtcatatg accccatcct       51000
aactgcaaag gatgcagaaa catggagtct tcctgtgaac ttaggaagag gaaaagtgtt      51060
gagcaagaag ccacattcca taacaggaag tccagatata cagcaggttt tagggatgga      51120
tgacttagtg actcagtggt gtcatcaccg tcctgaagtc tttccaatgc tctccaccct      51180
gccgtcctca caatgtcagc tttgtcttca ggctggttct cttcctggtt gcaaggtggc      51240
tgctgtagtt cagccatcac aaccagacat ggcaatgtgc tgggacagaa agggaccatc      51300
cttaggagtg agggcacttt tcccagaagc agcccagcac acttcctctg atggccagga      51360
ctgccaggcc caaactaatc actgacaact caagatttat ccctggcatt gagagaccat      51420
caccctcttg gcagtcatgt gggggaaggg ctggttacca tttgaaccaa aatgaagctt      51480
agccaataag gaagagaaga aagtagatgt tgagtaggca acgaacagta tctgctatag      51540
cccatccctg gactcgctga ggtttcatgg taaagtttgt ggttttcatc atgttcctgc      51600
accattctca gtaagttgat gcctagcatt gcatattttc ttttgctatt gtaatgctgt      51660
ttccatgata gttgcttgtg tataggattg tcattgattt ttcactcacc tttgttcagt      51720
tttctttat ctatgtgtct gtgtaattgc cttaaattct tttttcaagc agtattagat       51780
gttaattaga gactgagaaa cccagaggtg gaaggatctt aagtggagca ggggatcgga      51840
ttaaagaata agaaagcaaa gaatactgta tttcatttct gtgaaaagag aggttacatt      51900
tccttgcatg aggaaaaagt aggagtgtgt gcttttctca aaacttgcta taaggctggg      51960
tgcagtggct catgcctata atcagcactt taggtggcca aggcaggagg attgcttgag      52020
cccaggagtt tgagaccagc ctgggaaatc tagtaaagcc ctgtatctac aaaaaataaa      52080
aaattagctg agagtggtgg tgcacgcctg cagtccccag ctagctggga ggctgaggca      52140
ggaggattgc ttgagcccag gaggaggtca agcttgcagt gagctgtgat catgccactg      52200
aactccagtc tgggtgacag agtgagactc tgtcttaaaa aaaaattgct atgagagaat      52260
gctctaggta tgtgtgtggt cgtggtagag tataggggtg tacgatcact gtaatgtgct      52320
ggaatagtac ctaattttga aactgcatgg ttaataacat cttttaagaa tgtctaagtg      52380
ctttagagac ttctttttccc ccattctccg tgagaagaat aggagataga tcgttggttt     52440
```

```
tcgtgtggaa aaattaagaa agagaaatga agcagtttaa atttcctcac attatcatgg   52500
tattaagtaa actagagcag aggtctttgg gttagaactc atttgggaaa atagattgag   52560
tgtggccaag gcaaccattc ctgtagtgaa ctcagctccc ttttatgtag tgaagataaa   52620
tagttgaaca atccaataca tgccccagtc cctctctctc tacacacact gcacacacac   52680
acacatacac acacacacac acacagtgcc aggagacatt ccgggaccat attttttttaa  52740 gaagaaaaag tattattatg ctttcaagtc agttatgtta atttattcct tttttgagat   52800
gtagagtagc tcctttgtat ctgagtttgc ctattacatg aaaagactag tggataatga   52860
taccagctat cctatgttac aaaaagctgc agatccccat gccaagtgga ctatacagct   52920
acacaaacct tctgttacct gttggacaca ctgccacaga ggcgagcaac atgctgtctg   52980
ccattaaaga actcgggacc cttgaaaccc attttgggga atatatgtag caaataatcc   53040
aattttaaaa ggggcaaaaa cgtaggttat cggagtacat tagacatgct aatctgcagc   53100
agttttgtgc aaacctaagt ataatttaat tttgtattaa gttttccttt tgatatccag   53160
ataaagatta acatagtcat tggcaattat atttgtattt tcaataaaca tcacatttta   53220
ctgaagtata cagatctatg caagggatag tgaaatagac aaagctcatt tgacttttcc   53280
agaaggaatg catttttaaca ttggtggctc ctgtggttag ggggacttcc aaagcagtaa   53340
ctcttgcgtt tcctcagcag catcatcata attacaccac tatacacaat aattatactc   53400
ctagctgtgg ttctattcta cagcagttgc tgctttcctg gaaaccttgg ggaaaataga   53460
aatttaaata gctcatagat ttggctatga taagttcaca caaagacaaa attgcatttg   53520
gcagtttagt ttccccaacc tttatttgtt tcctgataac tatatttagt ctgaacctct   53580
ttgtcaagga caccacatag gttatattgt cttcctcttt gcatccaatg aagcagcata   53640
tattgccagg tcatttttttt ttatggtgat gccaaacttg accacttggc caagggagtg   53700
actgccatac ctcttattgt gaaggcacat tttcctcctg taattaacaa gtaaccccag   53760
gggtgatacc ttgagacaat gagaatattt tgttttccaa taactttttac ccaagaatag   53820 ctacacacac cccctgtaat tatagactta tgggtcagtt tttctcacca tgtgttttaa   53880
tccatcgatg tcattctttc tgatatttaa aatcgttcac agattggcca ggaacccttc   53940
agaccagctt ctgtcttcat tgaacttgtc cttgtttagc tttgagcact tcttggcgtt   54000
tttggcccaa gatatcttag gcttatctcg tactttcagt actctggacg tgtgtcagac   54060
ctgaaatcag cctcttctcc aaggagacct gtttcccttt agtggaaaat aatatttaca   54120
aaccaagagt tgggtgtttg tgttttactg ctactgggt gttaattttt ctaggctctt   54180
taatcgtgag ttcatattga aaccacctaa ttattttgtt tttattttga attacctttc   54240
ttgaggtata gtttacctaa acgaaagtgt actcatttga agtgctgagt ttgcttcatg   54300
ttagcaaatt catataccct gaactgtcac cctgtcacct atgaccttttt gcagtcagcc   54360 ctctttcagc ctctgacctg ctttgtgtca ctgtagatta gtgtacctat tctagaattt   54420
catgtaagtg gaataacact atatgaggcc ttttctctgg ctacttttac tcagcattat   54480
gttttggaaa ttggtacatg gtattatgca taccaattat tcattactgt ctcttactga   54540
atagcagtcc attgtatgta tgttttgctt atctatttgt ttatctatttt acaagttgat   54600 gaacatttgg accatttcca gcttatggat attatgagtg aaactgtttg aacattcagg   54660
cacaaggttt tgtatggaca tgagctttca tttctctgca gtaaatacct aggaaaggaa   54720
ttgctgtgtc atgtttttta actttatagg aaactaccaa tttttttttcc caagtagttg   54780
```

```
ttaccatttt ttactaccac caagaatgta tatgagacct aattattcca cattgtcatc   54840
agctcttggt attgccaatc ttttcatttt agccattctg gtgggtcagt agtggcttta   54900
atttctgttt tttaattttg tttaatttct gaaattttaa ttttattgtg gttttaattt   54960
ccatttctgt aatgggtgat gacacagagc atctttttgt gtgataattg gtcattcata   55020
tatcttgatg aaatgtccat tcatatcttt cactgacttt tttaattggg ttgtcttttt   55080
tcttgagcta tgaagttcta tgcattctga atactagtgt tttgtcagat gtatgtatta   55140
ggatatgttc tcccagtcta cagattactt taaaattttt cctaatagta tcttttggag   55200
agtagaaaat tttaattttg atgaagtcca atttatagat ttatttaagg ttcctattat   55260
ttatgtcgtg tttaaggaag ttttgcctac cctaagacct caaagatttt ctcctgtatt   55320
ttcttctaga agtttgtaaa cttaaaaact ttagcttttg tgtttgggtt catggtccca   55380
ttttaattta atttttatga attttgtgag atataggtgt tgttcttttt ctttcttttt   55440
taatttttta gttaataaaa atggtatata tttatattgt ataacatgat gatttgatac   55500
atgtatacat tgtggaatac atattacctc acatggttat catttttttg tgataagaac   55560
acttaaaaat ctgtctcagc aatttttaac tatataatat attaactata gtcaccatga   55620

tatacaatag atctcttgaa cttattcctt ctaagtaaaa atttgtcctt tgaccaccag   55680

cccccctgcc acccctcact ccctgtccaa cctctgatac caccatttta ctttctgttt   55740

ctatgagttt gactttttaa gattccattt atcagtgaga ccattggtat tgtgttttct   55800

tagcctggtg aattttactt agcataatgt cttcccagtt tttttatgtt gttgcaaatt   55860

acaggatttc cttcttttct aaggcagaat agtaccctat tgtgtttatg tgtatatata   55920

tatatgtgtg tgtgtgtgtg tgtgtgtgtg tgtatatata tatatatata tccsttttc   55980 ttaatccatt catctgttga taggcactta ggttgatttt gtatcttggc tattgtgaat   56040
agtgctgcaa taaacatggg cattctcttt gacatactga tttcatatcc tttggatata   56100
tatgttcaat aatggaattg ctgcatcatt tggtagctct atttttaata ttttgaagag   56160

cstccatact gttctctaca atggctatgc caatttacat ttctaccaac catgtacaag   56220
ggtccctctt tctccacatc tacttttttt ttttagcatg gatgtccatt cattccagcc   56280
ctgattgctg aagagactgt ccttttcccc cattgaactg ccttggcatc ttagccagaa   56340
atcgactgac tatatgtagg aggaactatt tctaaattct ctagtctctt ccatttatct   56400
atgtatttat ccttacacta atgccacatt gtcttgattt atatagcttt ataataagca   56460
gagcccagtc aggcccctcc tagacagtcc ataccagaat tcacaaatac atatgaccta   56520
aagcaagtaa cataattaag tgaagctgtt cttgtataag cagtattact ttatttatat   56580

taaaatctaa cgggctaaaa tttcaacgtg gttcattttc atttattaat gttttgagtc   56640
atgtcccttt ctcacatgtc tcatggttct tattatggtt tatttctaat gatatcttta   56700
tacacatact tttcacacta aatatttagg aacattccct gttttcatac atagaacaat   56760
actgcctcca tacatttttg aaatgcgtgg cccatttgat ctgtttttca gtttcccact   56820
tcaaagagag gaatacagta tctcccatga cagcatcagc tggttaatga atggtgattg   56880
gcatgcagac tcagcattga gactgcagtg gggaatgatg gggacactgt ggcaaacggg   56940
ggagggctgg cactgctgag aggggcacag ccactctacg ccactttcat aacatcatgt   57000
caaatgtaca caaattcacc attatttatt ttgttgctca attattcca gctttgtcca   57060 ctaggagctg tttcaattgg ctatgtccct ttgacacaca caccaatgtg ggtttgttcg   57120
gttttttgtc ttatttgaat gcttctttcc tttctggctc ctccaggctt atcttgtgta   57180
```

-continued

```
tttcccatcc cagtcctaga atcagccatt tctctaagaa tccctggttt cttttataag    57240
agaatggcat tagaaaatgc cacagaggtt aagtgtcatt cccatcacat catagcaagg    57300
gtacatacta tcaacacgat ttatgactat cgatgttacc cttaatcatc tagccaagat    57360
ggatggtgaa atcattagga gggggatgca ataaagagga agaaaagcag actttatgtt    57420
cattttcaag cttgttccaa aggaaagtta taggtgtatt tgatcatata aatatcgttt    57480
tgttttggaa aatcacgttt agggacaata aaattggaaa gaatccttgc ttccaaatca    57540
cctctgtgtt caaatcttca tcatatttgc actgcccttt cctttgtgtt cttagttcat    57600
gggtcccatt ggatttgatg ggtttcgttt acttttttgct actgaaattg ttagtttaaa    57660
aaaacaggat acagagtgtc acatttttta ttgtaactcc actttcttga agttgcctat    57720
agcattttaa atttcagaag atcgataact ttattcattt cccttttggaa aaaataaaac    57780 aagattttaa ctagtggcat gtcttcaagg aagctaaaga catttaactt tttctgtttt    57840
gctctaaggg cattctgatg attgcctgaa tgtgatcttc tgagtgttcc agtccctgga    57900
gctggctgtt agccatctcc caaggagggt cgaaaagaac gtagcagaaa gctgcagaaa    57960
gaaaagctgg ctaaagaaac aggagctgcc agccagggca acatagtgag accccaactc    58020
tatagaaaat ttaaaaagct gtcctggcat ggcatgcctg taatcttagc tactcagaag    58080
gctgaggtgg gaggatcact tgatcccagg agttggggc tgcagtgagt acttccagcc    58140
tgggtgacag aggagaccct gactcaaaaa aaaaaaaaag agccggttgt tgttaagggc    58200
caccagactg gagtgcatgg tagtcacctg cctccctcct ttcctggaga agatgacaac    58260
gtgatgaaca agcaccacta ccctggaata gtttaaatgg cattcagcct ggaggagtgt    58320
gcacatgcac caaatatatc ttgtgtgtcc tttgtagcca ttgggtctat ggagattact    58380
ctggctgtga gtttggttga ttaacattgc tatgcaagcc ctgtccattt agctggaggt    58440
tatcacagga ggaataaacc acagaatatg actttggcat tgaataaatg ggaagagagt    58500
gcttttgggg gccagaactg tttgtaatat tataactcct ataaatacat gaattgctgc    58560 cccttttatca taatatccat tgctttaatg ctctgtttta gattggagtt cacaccagac    58620
acctgagatt gtgtttgtta tgtaactgct atttcatgtt gagaaagtag caaagctttt    58680
aaatactgag aatatttttag ttacatgaag atacttttag tagtcactgt tgttgttaca    58740 ttcccccctac ccctcagaaa ataacagggc tgttaaggaa tcctcaaaga gcatagattg    58800
agtgaaaatg acacagaaca aaggacagat cccaggagtg aaatgaagaa gttctgtaaa    58860
tagctgtgcc gttttccttt gaaatgtctg gcacactcta tatagtatag tggtcgagga    58920 tagagggct aattctgtga tgaagcattc tgcatggaat ttcagcaggg catagatggt    58980
gagggcatct ggatctgttt gagttttttaa actaattata tgacaaactt tttaaaatgt    59040
agcatacctg gaaacatcat cccgccacgt catctgcatt taaataatca ttgcctcacc    59100
tttaacaccc agcctctaga aaaataaagc atgaacaaat gttagctctg agctgctctc    59160
agtaatttgg agtgtgctaa gcaaaaccta cattttctag catgaaattg gcacaggaat    59220
gcatgcaaag ttttgcttct ttgattcatc tggttaccta gaacctgagg ccattctgta    59280
ttctgtggac aaaaccctat ataccttttca tgacccagct taaatgaaaa gtctaatgca    59340
aaacatgctg aatttctgtg gccatattta attgttctag tggtcccaca ggtatagttt    59400
attattcttt ttaattcccc tttaatggca atttctcttt tcctttttta aaaatgtctt    59460
ttgccttctg ttcatttatt acctgtctcc cttttttatt gtgagcatgt ctcttgcaca    59520
```

```
gcacagacac atagtgattt cttgttacat gtgggcccac atttattttt tatttctatt   59580
tgtttttcat tcctatttat ttatttattt atttatttat ttattttgag ccagggtctt   59640
gcttcattgt ccaggccaga gtgcagtggt gcaatcacat ctcactgcaa cctctacttc   59700
ccgggctcaa gcaatcctcc cgcctcagcc tcccaagtag ctggaactac aggcacacac   59760
caccaaccac acctggctaa tgggcccata tgtaaatgac taattagtat ttaaacactt   59820
gccaagagtt gtttaatacc tgctgtgtgc agggcacaat cttatacatt cttaagggag   59880
cacagaggtg tcagatgggg tctgcccacc agttttcac agatttgaat atttagcgtt    59940
ctgggcaaaa gcagtttagg agctgaaaaa tcatggccat tttaagaaga ttatcttacc   60000
caaaaaccca cagtactatt gttattgcct tatatataaa gccattctgt taatttttta   60060
aaagtatgta ttaggtttaa cctggtttct ctgtgtttgc catgtttaac atctaaggcc   60120
aaaaatttga aatatttta ctttctgagt atgtcaggaa agaggagtct gaagctggag     60180
tgagttgggg aggtgggggg gactatattt ttatgaaaat tttagtaaat ttcctgggtt   60240
tttgtcccac ctatggggaa gatctaggat acaaaagcat taaatgttaa tattgattca   60300
agaattaaat catcaaaaca ttgctgggag aaattaaaga cctaaataaa tgtagagaga   60360
tcatgtttat gggctagaaa actcaatatt gttaagatgt caccaaatta atatatagat   60420
tcaatgcaat ctctatcgga atttgctgaa attgaccaac tgactctgaa attcatgtgg   60480
aaataaaaag gatctataac agtcaaaaca accttgaaaa tgaaggataa agttggagga   60540
gtaatactat ctgattataa gacttattat aaagctatgg taaatcagga tattgtggca   60600
ttggtattaa gatcactgaa gagaccaatg gaccagatta gagcatccag aaataaaccc   60660
atacatatat gcatagctga tttttgaaaa agttgtaatg gcggctcagt tgttccagga    60720
caattagata tagttggaac aattagttat ccatatacaa aaaagaaaa gaacttcaat    60780 cagttcctca taccatatat aaaaattaac tgaaaatgga tcatagtcta aatatattac   60840
ctaaaactat aatacttgta gaaggagga gaaaacccctt gtaaccttga attaggcaaa    60900
tatatatata tatattttt ttttttttcaa gcagttctca tgcctcaccc tcctgaatag   60960
ctgttgttac aggtgttccc caccacacct ggctaatttt tgtatttta gtagagacgg    61020 ggttctcacca tgttggccag gctggtctcg aactcctgac ctcaagtgat ccgcccacct   61080
cgacctccca agtgtgctg gaattacagg catgagccac cgtgcagagc cacaaaaata    61140
ttttaagtag aacatcaaaa gcatgatcca taaaataaca aatagatgaa ttggacttca   61200
ttaagattaa aacttctgtt tttcaaaaga cactgttata agaatgaaaa gatgagccac   61260
ggagtgggag aaaatattta tacatcatat aaaagatttg tgtgcagaat atataaataa   61320
ctctcaaaag tcaatgtaag aaaacctttt ttttttttgaa tgtgcgaaag atttgaactg   61380 acttttttgcc aaggaagaga tacagatagc agtaagcata ttagtcatta aaataatgca   61440
aattaaaact ataatgggat accactatta gtagtatgta ttagaattac tgaaattgaa   61500
gatcgacaat accaagtgtt ggtgaggatg tggaggaact agacgtctct tacactgctg   61560
atgagaatgt aaaatggcag aagcactttg gaaaataatc tgacagtttc tgaaaaagtt   61620
aaatgtatac ctagtgcatg atccagccat tccacttcta tgtatttatc ttaaaaaaaa   61680
gagaaagaaa ttcgcataaa cttgtaaaca cgtatttagt ttgtagcagc ttcatctgta   61740
atagccaaaa gcttgaaaca acccaaatgt ccctcagcag gtgaatgtgt aaactgtggt   61800
atgaactacg caatagaata ccatccagta aaataaagga gggaactatt aatgtacatt   61860
acaagtagat gaatctcttt ataactatgc caaatgaaag aagctatatt tacacataca   61920
```

-continued

```
cacattcaca tacaccccac atgctgaatt attacattca tacaaaattc tagaggatgc    61980
aaactaatgt atagttatag aaaggagatt ggggtttcct ggcgatgggt gatataaaaa    62040
gggattggag aaatggatta aaagcacaag gaaattttg ggggtgctgg gtgtgttaat     62100
tatattcatt gtggtgatgg cttcatggct atatacatat gtcaaaatgt gtctaatttt    62160
agactttaaa aagcgcattt tattctatat tagtatttca gggatcccaa gacaaccctg    62220
tttggtggtt tactaggacc tgtagcactc agcatatagt cgttcttagg gctaagactt    62280
attacactga cgtagaagga tacacaggtg gatcagtaag gggaaatgac atcaggcagg    62340
gtccagagga atccatgtgt gggttttctg tgttccctcc ctccctctga gatcacacac    62400
agcataccac ctctccagta gtgaaaatgt agtcacaggc gtacaatgat tatacccagg    62460
gaaacccact taagattcaa gagttcaggg tttttgttca gggcttgtca cataggcact    62520 cttgccacc aatatttcat attcctgaaa ggaaagcagt tgttcagtgc cccagacaga     62580
taaaataacc ttataagggt aggaaatgtt tcaaaagctg tgttcccgga cactagccaa    62640
gggcaagcct tgcaagcaga cctttctaaa gataaggctt tagataaagt ctcaggcttg    62700
ttaacacttt tctgcagtca cttataccctc agcttgttaa aaaaaaaaa agttgtaaaa    62760 gttagtgtga gttagcacaa gacagttgca gttcatttat tgaaaaaatg ataagagatt    62820
ataaaaaata gtaactttag atttgaggca gaccaatgca gtgagaacct cattacctgg    62880
aatgcttcat acccttaaat cccctctttg gaattagcca ggagtgttgg tgggtggctg    62940
taatcgagct actcaggagg ctgaggcagg agaattactt gaacccggga ggcagagatt    63000
gcagtgagcc aagatcacac cactgcactc cagcctgggc aacagagtga gactctgact    63060
ccaaaaaaaa aaaaaaaaa aaaaaaaat cccctttttg gaacaaggta ggataataat     63120
aagtaaaacc aggaagcttg gctaatggga gcttctaatt attttttactc tttaatattg    63180 tgactttcat ttctattgta tttgaaaatc tttccaaggt atatcatttt tttcctttca     63240
taaaaaattc cttggttgat gttcattatt taaccactgg ttaactgatt atgacccagt    63300
tcagttctat agcaaataaa agataaagca ctgctgttga aattataatt acctcaacaa    63360
caagaccacc tcatgcagtt gtgcaggtta tacctcgtcc aaggcacacc cagctgtgag    63420
ggtgcgtgga gcttaagtcc agcttgtact ttgccaagct atgggctcca gcatgggtg     63480 tgtctgcccg agaaaggggc accttttttct agtttatgct aagatgcctt ttgagctgtt    63540
cagcatgagc cctggaaaaa ggtggtggta gcgatttcct cctacagtgc tgcctaatat    63600
cagcaagctt tcttgtgggc atctcttttcc ccttaaagaa atccagctag taacttttcag   63660 ttgagcgtca tgtttaacca ggattccact gtgtgtaaca aggacaagcg attccaacgg    63720
tctctagttt ggcccaattg cccttaaaag gcaggcaaat gtttagggta tgtgtttctt    63780
tttatcactc tggaagaagc caggttcagg tctgtatctg gatcccatta ttaatgtccc    63840
cagccaagaa ttctgtgtat gtatagcaat agaaagtca gagaaaggac gctcctgtga     63900
cttctctgaa gttttttgttc ttcctgagta atgaagtttc ctaaagggga attaaacttt    63960
ctcacctcgg aagatagaag tattgtttaa agattcaact ttgaaacaaa taggaaaata   64020
tctgatagtt gcaacttagc ttcaaatcag cgatgtccag atattgacaa ccattttatt    64080
tctcctaaac cttgagccct agcccaattt atgaccgagt agagatcatg gcacagcagc    64140
cagcctaaca gatgggggcc atactctagc agcagaagga ttctgttttg aaaccttcag    64200
cttttgaaat cttacaccac taccagccct acttcttcta catgatcac attcatttcc       64260
```

-continued

| | | | | | |
|---|---|---|---|---|---|
| tccctcttt | tcctaaggaa | acttaaaaca | catgtcttt | cccttttat | agatgcgaac | 64320 |
| cacccgcaag | gtctccgtct | ggcctgtggg | cctggttggt | gggcggcgct | acgaacgtcc | 64380 |
| gctggtggaa | aacggcaaag | ttgttggctg | gtacaccggc | tggagagcag | acaggccttt | 64440 |
| tgccatcgac | atggcaggtg | agcagtgtgg | gtgatgacat | ttgttcctgc | tggactgttc | 64500 |
| ttatgctctt | gtttataacg | atgcactaga | tgaaggaagc | tttaaaagac | aaatttggat | 64560 |
| aaaaccctac | atcatatcat | attcaggaga | tgaaatattt | aaaccttcaa | aataggctct | 64620 |
| ttggttagat | caagtggaaa | ttgatttgga | gggtgattag | aaaatgccct | ttctgttcca | 64680 |
| ttttgtcccc | tgtctgtgcc | tttatcccac | aagcgtctac | atggcagcta | ctgggttggc | 64740 |
| cactggggat | tcggtggtga | gagctagacc | tggctcctgc | cttccagggg | tctgttagct | 64800 |
| ggaacctttt | gactcccttt | tctagaagac | tgatatatta | aaatatatca | tgtttattga | 64860 |
| taaatttaac | aatgatataa | aaattgacaa | gtcatttaa | tgcttattga | taggtttagt | 64920 |
| gctttattga | tatatttaat | actaaaatat | aaacttagat | ttctggtatt | tcaagaattt | 64980 |
| attgagtata | actgtcttaa | agttttatt | ccctgaacaa | ccaactgaat | tgaattagcc | 65040 |
| ctgcagtagg | accacacgtt | ctaaaatgct | actttatcat | aaaacaactc | attttctatg | 65100 |
| ggttatagaa | aatgatgcct | gtgataactg | tggaaggatg | gagtttgaaa | catgaggctc | 65160 |
| agaggcaaaa | aaaaaaaaaa | ttcggtgaca | tctatactct | taaaaatgaa | ggcagaaagg | 65220 |
| cttcaaaatt | gatctcatca | atcttgagct | ctgaagcaca | gctctgtcgg | gctgccagcc | 65280 |
| tgtgcttgcc | ccatcttctg | tgcatatttc | ccagccgtag | tcaagatctc | cgcgttcaga | 65340 |
| attctgatgg | gatggaggct | gtcttctgaa | ctggattcat | cactttatt | ctgacaatac | 65400 |
| tataaatctg | agggagccag | aggacgaaga | ataccaggag | tcatctgagg | ggcacagcgc | 65460 |
| tcatggacag | ctgtgtggtg | ggtcttgtca | catggcatcg | tgggagagga | caaataggag | 65520 |
| attttactc | aacatttaac | acacatctcc | acagcaccag | ccctcagcca | ggccatgtct | 65580 |
| caggcccctg | acctctccat | ccctctgtta | ctccagctgt | ttgctttggt | cttcagttct | 65640 |
| tgcagctcca | gaactgagct | ggcatctcag | tctaggtctc | cacctggagg | cagaaggaga | 65700 |
| ggcagctgag | ccatcttgga | cggtcctgag | gaccctcgaa | agaggcctgc | cctcgacccg | 65760 |
| ctcagagtgc | atggccctga | aaacatgggg | catagtgtat | cttttgaaaa | tcgggcttct | 65820 |
| tgctgaccag | aagtgtacct | tagagcagaa | aatttagaca | acattaggga | aagtccttct | 65880 |
| gcttctctgg | gatgtagttt | tcttgtgtaa | agtgaggcag | ctgccggaga | tgaccaccag | 65940 |
| ggccctccag | tgcagccctc | ctttcctggc | ctcccacctt | ggaactctca | agtaagagcc | 66000 |
| caagcttggg | cttctaagtg | aggattgtga | ctgctcaagc | agccgcagac | agacttttgc | 66060 |
| ttcagatttt | cccagagcct | tgtttcaaca | cggacttccc | agacatatct | ccttaacacg | 66120 |
| tgggatgtct | gcccatttcc | ttgcatggat | catgcaaggt | gagggcaact | tgggtaactc | 66180 |
| ttcctggatt | ttaatctagg | aactttatgt | agatgatcac | gtatcaaata | gacttgttga | 66240 |
| atatttgcat | tggttcccct | agaatttggg | tcacattgat | atttctaaaa | ttaaagatgt | 66300 |
| atgtgtttgt | gcattagggc | tggcctatct | aggactgcca | aattctgtgg | gaattctttt | 66360 |
| ttccatgaca | agaccaatgt | ttggattttt | ctaagcattt | cagtatattt | tcaaagcata | 66420 |
| ttaaaaacac | ccatcataat | aagatatgaa | ttatttcctt | gctctgtatt | cattatcatg | 66480 |
| gtttttaaaat | aggaataaag | tgtctctaag | gagacaactt | ttgtcacact | aaataatttt | 66540 |
| tttcacttca | cacatgaact | tgctttgcat | cttagctttc | agtaaattat | tgatatttt | 66600 |
| ggaagtcttt | aagtgtaagt | aatttggtcg | ataggatagt | tattctgttt | ttgaggcagt | 66660 |

-continued

```
ttgttctaat tctaacttaa aaatttgtgg ctttgtttag attccacata caattcattt    66720
attctctggg aagagggaaa agaccttttta ggccttcatg ttcaattggt gcttcccgcc    66780
tcatttccaa gttacatgta cacacacaca cacacacaca cacacacaca cacacaatct    66840
gagctctgag gagctctact ttgaaaatgc tctgtgatag tcaagtgaga gcaccatatt    66900
ggagcctggg tctgtcttgc atttgcaaag cggattaaga gcccaaatgg aacatttgtg    66960
ggtttgagca cattcagtag aagcccctca gagcctgtcc tgtttgtatc tctgtgaggt    67020
catcacatag cccatcactg gaaactcatt tgagtatcaa acattgaaac tgcgatgttt    67080
catgtcattc tagtagttct tacactgtca ttttattgcc atgttgaact tgcctgatac    67140
tgaaattttg ctctcaggtg acatgaaaca ttgttcttga aataatctta tgtttacaac    67200
cataatggca gaattaagat tatttctgtt ccattggagg atatttttta aaataatgat    67260
tactacttaa aaaaattaat atgcctgccc acaagatgga agaaaacac tggaggcagc     67320 cccactggtg gtgtgcagtt ggcttcaaag ctgaccagta gccacatagc tctgccaagc    67380
cagtgaggcc ctgggggtt tctactgttc tgtgcctcag aattcaattc ttacacctca     67440
ggaatctgag gattggctaa aagtgaggaa gtccaccaaa ggttttagct ctgttttgaa    67500
gggaggcagt taatttcaag tgacagactc acttcagcca cttccaggga ggtgtcagta    67560
agaacgactg cttgaaagaa ctgagcttaa atcaatcttc accctcacca ggaggtgtag    67620
atttgttcaa gttgagaact taaaacagat atttattagg aattttcaac attggcatgt    67680
gccttattat taattctagg atgtggcccg tgggacacgg tgctccatta atgacagtat    67740
atgcagttcc cagttgagtt gctggcacac agtaggtact ttattctgct aaaaacacaa    67800
ctaggtgtac tgcaattaga ttctgacacc acctggagtt ggtgcagacc ccacaggtta    67860
gagggcacag tctccaacaa gactgcccctt atttcacatg ccccccacgc gctggagagt    67920
cccaggccac ctgcacttct gatcaactga ctgcactgga tgtttcccac aatctcctca    67980
ggtttgctaa tttgctagaa tgactcacag aactcaggag agtgctgtaa ttatacaaat    68040
tatcattgta atcagtgtta taaagaatac aagtcaggac cagccaaatg aagtgacaca    68100
caggccagca gagccaggtg gaaggagcag gctgggagca tacaggtctt ctgtgccttt    68160
tcctcataca ggtgaagtct aggaaagctt agttttctgg tctggagtcc tgtggaccag    68220
ggtgtgtcga agccctgggg atggatgtgc tcccacaggg agactctgtg gcagcctcgg    68280
attgcatcct gggggcaggc atttaaagtg actgcagggg gggagccagg gaaagagaca    68340
aggcccagca agagggtgtt agggtggaca gtggcgaggt cactggagag aaggggtgga    68400
tgaatgatga attccgttat tggatgtggg aagaggagga cccttggtga gtatgggaga    68460
aagaccgctg gaagcagaat ggtctgagca aagttaggtt tctggacggg catggtagct    68520
aacacctata atctcggcac tttgggaggc tgaggcaggt gaatcacctg aggtcaggag    68580
ttcaagacca gcctggccaa catggtgaaa ccccgtctct actacaaata caaaaattag    68640
ctgggcgtgg tggcaaatgc ctataatccc agctactcag gaggctgaga catgagaatc    68700
acttgaacca ggaggtggag gttgcagtga gccgagattg cacctctgca ctccagcctg    68760
ggagacacag ggagactgtt tcaaaaaaaa aaaaaaatt aggtttctaa tggagcagag    68820
ggggagagat ttgatctggg aaaggcttgg ggaggttctg tcttggctgg acagggattt    68880
gaaaggatgt tgtgatgatg agtggccagg aggtatgggt taggaagagg aagggtgcaa    68940
tggccactga ggtcccctcc aactcgaggg ttgtgtgatt ttgacaagtt ctgattctaa    69000
```

-continued

```
ggactgaggt tgtgtaaggc ggtgcacctg gttatacttg tcttctgtcg gcagccaact   69060
cctcctcgcc tacggcctat caccagcttt ccagctggtg gtagttttat tcaatggagg   69120
cttaaaagcc ctgacttttg tggcgagtgg gtggacagtg gggtggggga gcatgactag   69180
gaggcaggag ggccaggaga caactcttaa gaaatgcggc agcaaatgag taggaaagac   69240
agatggtggc agtttcaagg ggtataacag cttttttcctc tttctttaat gatggagggg   69300
gagaaattga agtttaaga agtgataagt gttgaaagtc ccaaaggaga ggaaatgagg   69360
ggagatcaag accttagatg gacaggttca cctagataga gtcacctctg actcccagaa   69420
aaaaggtgag ataagtaagg aagccaaggg ctgggaaggt ggaggggcca gttgttggaa   69480
ttgaccgtcc gccaaatgtt aatagaggga gaagtgacat ttggctgaat ccacacaca   69540
ctgaatgtag cagcccctcg cctcaaggag ttttgtatct agcagagaga gaatgtctac   69600
aagagcatgg cagatacatc gtggggtcga aaatgagtac aagtggaatg attgggggtt   69660
acatttaaag agaaaaccac agccactggg ggagtttcgg gaaaggtctt gggaagaggt   69720
gacatctgag aggcaccttc cgtgctaggc ccaggccagg gtaggaggg atcatgggca   69780
gggtgtgttt ttggaacaag ttatcccagg gtatgtgtag ctcttgggaa gggcaagctg   69840
gggtcagata gtgaggactg agtgctaaga tgagaagttt ttcttcattt ctgtggacat   69900
tggagagtct gacattttc aagtagggga ctgatgtgat tagaaataca gtttgagaac   69960
cacatgttgg cagtgtggga tgaatgggg aggagggctg ggcctggagg ctcaggcagc   70020
catctgggta atgagccggt agcgggctgg gaggtgagag gaggtcttaa ataccacagc   70080
tattggggac ttataaaatt ttaacagcct tttcagatta tactctaaat cagcagacac   70140
ttagatcttt ttaacacctt tttctgttgt atggtatggt gataaatgat gtattaaatt   70200
taagtttggt taattttaat tggtgtaatt tgtattatcc tttgagtcgt aatttatgtg   70260
tagaaaatac agtgatgttg ggtaattaaa acattctttt aaccagaaca cctattttgt   70320
gtaaaatagg agtctgcata ttaggaaaaa aaaaaaaaat cacatcacct gactgaagtt   70380
ttcaagctca ggattcactg tgggtgtgtt gtcccagtgg agggtgtcga ggctgaaagt   70440
gaggaagaca gtgatcacgc ctggctgggc ctcctgtatc catacctgcc ctctcccgtg   70500
tccactccac ctcgaagcag gaggaatctt tcaggaatgc aaaccagatt cttggcagtc   70560
ccttgctcat agctcttcag gggctactca tgctcttgga ataaacaatt ccttgtcact   70620
ggcacctgcc aggccctgcc cggcccaccc ctgcccacct tactattctt gttccctct   70680
actcaatctt tgcgggcaga gatcacttcc tccagcacat tctacccttc cctttgggc   70740
ctgcactgat gcccctgcct ggaaatgctc cttcctcgtt cagccctact catccttcaa   70800
atctcagctt aaaggctgcc ttcttgggga aggttttgct gatgcttcaa ttaagatagc   70860
tcctcccgtg ttataatgtg ctgttctctc agcctcccat acctctgcac cttgtcacag   70920
tggttgtaca tctctcatta taattgttga ggctccgcca ccccgactcc cagaatgcat   70980
ccttcctgta ggcagaagcc ggactatcct gccctccact ccttgcccaa tcccagcccc   71040
aggtttcccc tagccccagc ctgtgagtgg ggctgagtga cggcactatc ccagagcagc   71100
tgtccccgct acaagtttac caggcaaacc tttaaaaaat tattataaat gatgaccatg   71160
aaactggagg gggtcgaggg atcactctgg gcaggttgct gaagcctgct ttctgtgggc   71220
tctctgcagg gacatgggaa tgacagttat tctgggtctc cttcatctca atgtttgtca   71280
acaaggaatt ttgcctgggt taattttattt ggcagacctt ttctcagtag ataatgctgt   71340
gatcagcttc agcccagccc ggatcagatg atcatcaaag ccaaatgagc agtcaaaatt   71400
```

-continued

```
aatgacgttt tgctttgctt catgaatata aatactgcaa gaaaatggag ggaattgtct    71460
tcctgccact ttggagtcat tcgtgattta agtgtgctgt tttccatgca tgaatgtttt    71520
ctatgagaac tataaagtta ctgaatgttc tcagtagagt gacttgatgt gtcatgtggt    71580 acctttagt gcaggatcta gggaccagct tgggactttg tccttgggtt ggtacagtgt     71640
gattgtcacc gggagaggac tgcagctgcc aggggtggt aattctgtcc caacaactta    71700
tagaaccaca gggacaggtg gcagagtgtt ggggcaatag gcagcctgcc actcagtttt    71760
taatctattt ctagaacatg gtgcagtcta gagacttgca gggatttgat gcccacagta    71820
ctgtgtctgg tcctgtctgc atgtgctgtg gccagggctg tgctgggtag aggtgggcgt    71880
gtggggcaag gagcacatgt gcatctgtgt gctcatactc agggtgcttg ctctggagca    71940
gctggtagtg gggtcaggtg gggtggacgt ggagagggag ggctctgcag aggcctttca    72000
gggctgaagg ggaagtgggg agacgggttt ccaggcctct gtccacctca attctagcag    72060
ctctgcattt acatattgga gatcccctca agatttcaat ggaataaaac attcattcca    72120
ggactaaaaa ttttgaaaac ctgaagtttt cctttctatc aggatgtcca gcagactcaa    72180
taattatata ttgtttgctt agcatttacc aagcatcagg catttggaag cattctgtgt    72240
tctttcttca tgaatcctca cttagctgtg caagggatat gctagtttta ttatccccac    72300
ttacatataa ggagcccgag gcctaggtat gctaagtgag ttgtctggga ttcagagtca    72360
ggccagtgtg tctacagaga tggtctccaa ctcacccacc tacagccaag tcactgagtt    72420
cttggtctct gagcctgcag aacagtttct tggtttcttc atctgcagaa cagggaaaat    72480 gaaattttc acaaaatcag acatcacgtg caaagcagcc aggagtagaa cattgtagac    72540
acttggtgaa tgtcactctt aaccaagaaa caagactgtg cctttgggtt cagctggctc    72600
acacatttat tttgatgaat taggtcagtg ttttgtttga ttatcacagt ggtgaggtcc    72660
atgcaggtag ctgtagggtg gaagaatcac tcatccttgg gtcctgctct gacacctaca    72720
ggctgtgcag cctgaagatc tagggggaata tctgtttctt cctaatacct gtagattagg    72780
gatcattgct tcttcctaat acctgtagat tagggatcat tgcaccagct ttctgggttg    72840
tgttgaggtt gaagtaaaac gaatacatac agaagttcct gctgttctgt gaatatttga    72900
atctgcaccc acttgtagct ttgtgagatc actcttaacg gtagtattta agaacatttg    72960
aactccgctg tgggctcatg atgaacttca tttctcttct ggcgggtgga cctgtgctca    73020
ttatcattca atgaattggc tcagcatgca ggatggcatg ctgagataaa cgctagccct    73080
tactttagat taaataccc caaaagagag tgatcaacag gagaaaatcg aagccaaaaa     73140
agatcattaa agagttgttt aggagcagat acgtgttcat tgttaaaatt tcccagctga    73200
aaatctaaac aaacagcact tgagctttca gaagaaaatg ccatttgtaa cattgagatt    73260
tgcaaggcat ttggtgccat gtgagtgccg cttgccctg taggtgagtc tatgtagacc       73320
acgagacaag tattcaatat gcaaattcct gatggcacat agggaaggat ttaaaagaat    73380
gattctcatg ctttctaatc aagtcacaag ggggcaaaat gtccttttc accacctcga     73440 ctttcctaag agtccctagg agagcatctg taggtaatag ttttcatcta gaatctgtta    73500
aataggtatt atttatttta ctcatatataa tagttaggat taagggttgt tgccctgcac   73560
tgctaacgtg ggggccgggg tgcagaccac ttctctcttt ggcatgcagg ttgtttgctg    73620
tgactactac acattttct gcactggctt cagaagttaa gccttgcagg cattcttcct     73680 gggctcccctg agcagctgta atcaccctga ccccaaacac tctgcacatc agttcacctc   73740
```

```
aattttaaat ccctcaggcc aaccgctgtg gtcagtcggc attgccctaa gctgatgggc    73800
ctgattaaac caagagtggc acacactgcc ctccagccta ggatatgcaa tgtcactttt    73860
cttctcacgt ttgcctagct aatttccagt tactcttcca gactcattga tgaggcagga    73920 atcgctttt  ctgggaagtt tttcctgatt ttccatcaca cgtggatgcc cctttctacc    73980
tttcccctag aatgccttgg cttatgcagt tatgaatatt tccacaaggt ggcgctcatg    74040
tcagtgtcct ccctgcccct ggccgccttg ctagcccgg  agtacactag gagggcgctc    74100
gggtctgcct gcatctccag gccgggcaca gtctctgatg gtaatagctt gaacaaatgt    74160
ttgctgaatt catgaatttt aacatgtttt cctttctag  tgtaaggatt atcaaaatta    74220
agatttaaag cttctcgctt ctgagacaac attgccatta tttaatggtg gaggtgtaaa    74280
gggggatgcc gagctgtata ctccagagct ctctgaggag ggtctaattc agcgggtctc    74340
cccatggctt cgcatcaaaa tggcaagggg cttttgaaaaa acacccacac ttgagctcca    74400
cctaggagca aagagaccat atagtctctg agggtgaggc ctggtatttg tgtggttgcg    74460 ggttttttt  gtttttttt  tttttttga  gtcttgaggt gatcccgaag tgcacccagg    74520
agtaagagag gcgggcgaaa gtgatcagaa gcgactccta tttccttcct gtggctcgtt    74580
atcgtctctc agtggtcaca gtcctttccc aggccacccc ctgtgtccat ctcaggtggg    74640
ataacctcat gacagagttt gggaacgctc aatagagtca cttccataga aaatacgtct    74700
tccattgctc aagcaagaag agaatttgag cataggacag gaatatttta atcataataa    74760
ctgaaaaaca ccagcaacaa tataaacaaa aagattgcct gtattcattg ggaatgcaag    74820
ttttatctgt gttttgattg tggtgaaata tacgtaacat aaaatttacc atttaacca    74880 ttttgaagtg gacagttcag tggtattcaa ttcattcaca ttgttgtgca accataacca    74940
ctgtccaact ccacccttt  tccatcactg aaccaaaatt ctatgctcac taaacaataa    75000
ctcctgactt gccctcccc  tcagccctg  gttaccacaa ttctactttc tgtctcgatt    75060
aattagacta ttctaggtac ctcatataag tggaatcata tttgtcct  ttttttttt    75120 tttgctttatt gagcataata tctttaaggt tcattcatat tatattatgt atcagaattt    75180
cattcctttt taaggctact aatattccat tgttacgtat agtccacatt tcgtttatcc    75240
atgcatacag ccatggacgt ttgggttgtt tccacctttt ggctactgtg aataatgttg    75300
ctataaacat tggtgcacag atatctgttc gagtccctgc tttagattct tttggatgtc    75360
caaagtagaa ctgttggatc acaggtaatt ttttgtttga attttttgaa gaatcaccat    75420
actattttct acagcagctg catcattta  cactctccac agcaatgcag gaaggttcca    75480
gattctccat atcctcacta atacttattt gcttctgttt tgttgtatta gttttttaa    75540 taatagccac ctaatgggga tgaagtggta tctcattctg gttttgattt gcacttcatg    75600
tgcttcgtgg ccatttgtac ttccttctta gagaaatgtc tattcaagtc ctttatttct    75660
ataaaatgtt tatgtattta tttgacttca ccaacagaaa tggattttct cacagttctg    75720
gaggctggag gtccaaggtc agggtgtcag catgtgagtt cccttgaggc ctctccttgc    75780
tcacagatgg cctttcctct gcggcatgca ttctccactc tctcctcttt ttatatcagt    75840
catattggac tttgcccatt tttgaattga gttgtttggt ttattcttgc tgagctgtag    75900
aaattcttta tattttgggt attaatcctt tatcagatat gctatttaca aatattttc    75960 ccattctatg ggttaccttt cccactctgt taatactgtt ctttaatgca ctaatgcttt    76020
agttttggaa gaagtctagt ttatctattt gatttatta  tttttatttt ttatttttg    76080 agatgtagtc tcgctctgtc ccccaggctg gagtgcagtg gcatgatctc ggctcactgc    76140
```

```
aagctctacc tcccgggttc acactttct cctgcctcag cctcctgagt agctgggact    76200
acaggcaccc gccaccatgc ccagctaatt ttttgtattt ttagtagaga cggggtttca    76260
ccatgttagc cagtatggtc tggatctcct gacctcgtga tctgcccgcc ttaacctccc    76320
aaagtgctgg gattacaggt gtgagccacc acacccagcg tacctatttg atcttttgtc    76380
gtctgtgctt ttggtgtcat atctaagaag tcactgctga atccaatctc atgaagcttt    76440
cctcgttgtc ttccaagagt tttatagttt gagttcttta gctttagtct gctgttagag    76500
aaagaataac aaaccttcat ttatccagaa tggttgaggg ttggggggcag agtatggtct    76560
tttttataat taactgtaat aaattttacc atttctacat tcctccatcc attaaaaaga    76620
tcaggattag aaagtaggaa aatatctaaa accatgctgg aaaacagaaa aggacatgta    76680
caatgaagct tctgggagaa atgtgaggct aagtttggat ggacagacag acagaggagg    76740
gggatcatat gagaagtaag aggatggtgt cctcatggga gcccctggac accctattc    76800
tcagagtgca gagatccagt gggctgaagg gggccgtgcc tcagacacat gccatcaagc    76860
ccctacacag cttcctcgca tggcagagaa tgccccaca tcaggtgggg gttgtgtggt    76920
aagctcctgg ttctgcctga cttctgggca gtttcctccc attaacatgg agggaaaggc    76980
tctatcacag cccactggtg aagccgcctc tgaagtgttg agtttccctg agtaactccc    77040
tggttttct gtggaaaccg ctcaaagtgg ccacaggtgt acctaaaata aagcctctca    77100
caattgctaa caaagaccaa tacaagccat caatgctgtt cagccttgac ttctgtttgc    77160
aaatatgagt agataattaa aaaagtaaaa ccaagacaca ggagttccca ctgaaagagt    77220
ataggaatca agagagggct tttaaaattt ctagagttca ttctcagatt ttaaaagatg    77280
tggcatcata aaacaagagc cagcagctgt gaggaaagag tcattggaga gcaaggattc    77340
ctgtaaataa aaggcatgac tgctggaata acctcatgtg agagggtgac agcatcgagg    77400
ctctaagtgt cagtgatact gttagggttg caatgcagag gagtggatcc caaagccctc    77460
ctggaagaat cctccaggaa ttcttccaaa ataggagcaa aagtacaaag aaatagaaat    77520
gtcagtggaa ggagacttat aaatccagca tgttcagtaa gagtttcaga attagaaaat    77580
aactatatat gaaatatcaa gaaagaaaca gggctggttg tggtggctca catctgtaat    77640
cccagcactt tggaaggcga aggcaggaga atcgtttgag gccaggagtt tgagaccacc    77700
agcctggcca acatggtaaa accccatctc tactaaaaat ataaaaattg gctgggcatg    77760
gtggtgcacg cctgtgatcc cagttactcg ggaggctgag gcaggaggat tgtttgaacc    77820
cgggaggcag aggttacagt gagctgagat catcccactg cactccagcc tgggtgacag    77880
agcaagactc acagagcaag actctgtttc aaaaaaaaaa aaaattagc cagctgtggt    77940
ggtgcacgct gtagtcctag ctacttggga ggctcagcca gaaggatcac ttgagcccag    78000
gggattcgag gctatagtca tgccactgca ctccagcctg ggtgacagag tgagactctg    78060
tctctaaaaa tcagaaagaa acaggataca agttcctata atacttgagt tttgagagtg    78120
attccattgc caggttgaa tttgggctct gctacttcct cagagtaagc ttttaagcaa    78180
gttacttagc ctctctgtgc ctccatttct tcatttgtaa attatggtag taatagtatc    78240
tacctagtgg ggtcactgtg aggattaagc aggttaatac agacagagca cctaggacaa    78300
ggcctggttc actgtgaatg tttcctaaaa tgtagctgct gttaagccaa ccgtcactgc    78360
caccactact cttagttctt agaatgtaca ggtatgcggc tgccctgtga aagcttcaca    78420
gtcggtccgg tttaccactc cagtctctct ctctacctcc tctgccgcat tgccacctcc    78480
```

-continued

```
acccccaccc ccacccacac gccccggcat ctcttacctg gaccagcagt aacctcctaa  78540
ctagctccac agcttcattt cttatcccca ataatatgct ccctgacccg ttaggctcca  78600
ggttaaaaca tttctgcagc tccccttgca cttcgtttct ccatggcctc ccaggccctg  78660
catggttggg catccccacc cccgagcctc gctcaagtta ttttccttgt gttctctgtg  78720
cactcagctt cagtggcttg ctgtcccatc tcacaatccc gccatcacgt gtacttgtct  78780
ctgcctggaa ggctctttcc tcaacccacc tgcctctccc acaccatcct tcagagtcca  78840
gcttaatcat ccttggtcca ccctggaggg tcagatttct tcacatagca cccgcaccct  78900
tccttcatag cactcaccac cgtgtgtgca cctgcactat tagccaacat tccacctccc  78960
tgacaagcct gcacctgggc tataatgact ctaagatgca gatcatgact gattttgctt  79020
accaccttct ccccagtccc tggcagtttg cctggtatgt atgtttttgt tgaatgaatg  79080
aatgaatgaa tgaatgaatc ctaagtttag aacaactgtg ccaggattta ataataaaac  79140
aatcccaagg gtattcacag ggggtcaggg ggaaaactgc ttctctatga aggagggaaa  79200
aatcagacta gcatcaggtt ttttttctgta acactgaatg atacagaata atggagaaag  79260
gtgtttagag ttctgaagaa aagaaatgga tcctaggatt ttttgtaccc cgtgaaatca  79320
ttatgtctgt gtgagggcaa aagagacatt tcaaatattt ttctcaaaaa acaaacaaca  79380
acaacaacaa caaaaacaaa gtcacttaag gaaagcgctt tagccaaagt gaattagaat  79440
aagaaactaa aaaataggaa gattgctgta ccagataaaa tagtaagcaa caaaagtggc  79500
aattttaaca attaaaagtg gatagtaact aacatgactg tgaagtttaa agctgtttgt  79560
tggaatctgg aaataggaga agcaaagtga aaatgaagtt ttcaaataaa aacgttggta  79620
tatttgaatg cctgctggtg acggagagga taggaaatgg gagaataggt gcccactagc  79680
agatgtagtc tcattcaaaa aggtaagggg gaggggggc agagagaggc tttaattcat  79740
gatgataaga gaaatatcag ttccttaaaa gctccttaaa cagttaaaaa tattttaaat  79800
aaggaatttt aaaggtaacc acagtagaat acatataaaa caaaaccttt tcaacaatta  79860
gaggaagaag agaaaccaaa atgaattcaa aagaagaag gaaaaaaagc aaaaaaaaaa  79920
aagtatgtaa tgcacctaag ataaaaccaa acatgataac cacactaagt gtgaaaaaaa  79980
ttaaattgct ctaaataaaa cacagcagca aagctctatc tcatataaaa gacatgtaaa  80040
aatgtgatgg agatggacaa taaagagata aactatagta tcctaaggaa ggacagacaa  80100
caaaagagca ggagtgttca cattcgtgtt gaacaaggca gaagtcaagg acaaaaatat  80160
tgaatgagaa ggagaggaac attttgtatt gacggaaact atgtatacta caaaagtaca  80220
gcattcatca gccattgtgt atgagttatc aatgagtcca aaaactaaag gcagacatag  80280
ataaaaatag aaaatttgac aaaaccataa tcatagtaga catgtttaac acacttatct  80340
aaatctgaca gatttaagta gacaaaaggc tgtagaaaat ggaatatata aaaaacttga  80400
tctaataatt atatataaaa cactgtactc aatagacaca gaatataccct ttatttcaag  80460 tgttcatgaa acatttataa aaattgaaac tgtatcaggc cataaaacct taaaaaagtg  80520
cttgtatagg ctcaaagcac tacactagaa actaacaaat aataaattac ataataatga  80580
taattaaaaa gtggagttag atctgttgac aagtagatga ccagaggtaa actgacagca  80640
gggctggaga agcatggatg gtttgatcct tgctcagaag cctggtccct ggccagtctc  80700
tccctgtgct tccccatcag catttgcagg gaggaacaca ggattacaaa ggtcatggct  80760
ggcttatgga aacacaagct gaaattgaat ctcaggtatc tatgcctttg taccttagga  80820
cagtgtgttt tacccacagt tcttttttaaa gtggggaagc gtggacagtc ttacaggcag  80880
```

```
gtgccttgag cagctccacc cccgccgcca ccacattcat gtcagtcttg gcctgaacat    80940
atcttcaggc tacaccaagg ttcaaagcca atgtaaggta agatttggct acaggatttt    81000
gcatgcagaa accatcagcg ctgttagaag cccctttgaa ggagtgagaa ggagaaaaac    81060
ctgtacagag gagagcgtac aggttactct aggtacttaa gaccaggact tgatggtaag    81120
agagcctaca ggaaatgtcc aggaagaacc catagctctg cagaagaggc agagggtcgg    81180
gggaaaactg cctggccatg gagtgagagt tggaccaccc caatcctgct ccttctcttt    81240
tgtgtcttgg gtgaaagagt gaaatgcctt ccaggttctg atgtaagctc cttctttgtc    81300
ccagtgtcca ggcctgcact ggtgaccttc tccagcactc tctgtacctg tgctgaacac    81360
ccccggtggg gcccatctgt ctgctcttac ctgaaccatc tagtgcagca gacactttgc    81420
tggtctctct acctcaggca gttaccatac tgctgccaga gaaattttcc taaaattgac    81480
ttttgattac aatctggagc caaggttgcc tgccacagat agggtgcag agtcctgggc    81540 acaagcaact tgacagcctt gtcacccatc attgctgctc cagcctaaga cttggcctca    81600
caggtctccc ttcctctaca tggatgcttc aaagtccctc tcagatttca gtgtctccaa    81660
agcccttact cattctagtc agatagcatt tgcttctcca actcctgtgc tcccaaagct    81720
ctctacttac accttttata gcatctgtgg cacagctgtg cccatatctg ttcttctaat    81780
taaactagga gttgccagag ggcagagacc acattcagta ttgtgttacc aatactgaaa    81840
accagcaatg ggccctaaa gagcttctga atgagtgaat aatatcaaaa ggaagatgaa    81900
aaatgaaaga taacatcctt tagattggtg aataagaatg ctcttttta atgattatgc    81960 ttaacaaaga atgcttacta tgtttccagg taaatatttg tttacatata ttcatttaag    82020
atttacaata accgtataag atgatagcta tctgcatttt acatttgtgt aaaccaaggc    82080
acagaacagt gaaagtacct tcctgagtca ctttaatagt agatggcaga gtaaggattt    82140
gaattcaagc cctccaagtt acaagccttt actcaactac cgtccttccc cgccacacta    82200
tttcattaaa ataggtcttt aggaaactct gaagatttcc agtcagaaac caacatagct    82260
tccatgtgaa actaggaggt gatgtaatag cttcattagt gaatccctga agagctacca    82320
tttaaaaaat tatttcacta ggattgggga ataagtacct tcttcaccat gctctgctat    82380
attttctggg ttggactaga gtggcttagt ttgaccaatt cagtagtacc atggcctctt    82440
acccaggcca tgtcaagcat gttgactctg ccatgcccag catatacaag taaactctga    82500
agggtttatt tcccatcaga gtcttttttgg ttctaaactt cagtgttagt tgtgcccact    82560
aaaaaataat tcatggatat tttccgtatt cagttaatta acccctttta tattatgttt    82620
ggttattagg atcagatttt ccatccttgc tcagcatcct gattgtttcc ttagaagatt    82680
cagttttcta tgatggtttt ttcagagtag agatttaaat gaattgttta tagattaaat    82740
aaagaacact tcttggaaat gcagagtgtt tcactttttt ccatggaaaa taatgactgc    82800 taaataccctt ttgaggaatt tttaaaatta gacttttact taagtttcac cttgaagcaa    82860
ttataaagtt tcagtcagta gtcagcagat taacagacct gtttaacaac caaggcatgc    82920
tttttcattc ttcttccaca ccagaagaaa ataattctaa attataattg gaagtaaatg    82980
cgggaagcta tggttctgtt tactcagtag gaaagggtag atttggaaga aaatctatca    83040
tggctgtgaa agaacacttc atgacatatg agcattcagt cttagagcca tgaaaattat    83100
aaaggaacac ttgcaggaaa cagtggcaat ttgggatagt aaataagcaa aggaaacatt    83160
cctttatata gccttctttt ctgctttcta tatttgattt aaatctagtg gaaatgattc    83220
```

```
ctaaatcaat tttactaaca catttgtttc tcacttggat agtttgaga tgccagggct    83280 ggaaagtaca gggccagggg aaaaaaaagt agttaagtag cagttttctg ttttcaatca    83340 tcaaaccta cattacagta ttttgttttt cttctatact tacctataat gtggtactgg    83400 gatttgggt tgcaaaaaga gtaatgtcat tgggaatgac agagtaagga cttctgaata    83460
ttctcatcca taaaaacagt gagaacactg gcaaaatttg tcaaagtcaa cttcttaaga    83520
actatggaaa ttagctaaaa gtatgcaaga atctggggag ttttgttttt tttttttaaa    83580
aaaaggctaa atcttggtaa gagcagtatt gtagtatatc aatttgccct atttccatcc    83640
ccttctctcc atttcctcca tggtagcttt gaaaaccaac agccctgtaa ttgtggtgaa    83700
aaccagcagc atagcagtta ctagaagggc agaacagggt tggaactcat tcagagctcc    83760
attttaagag aattgtcatt atgtgatctg tccagcaatt ccctagaaaa ccctgttcac    83820
aaggcttgtc tttatttgac ctcattcact agagcaaaca ggcttttccc tgggggcgtt    83880
tgtcaaaaac agcttgtggt gattgtttac catcacagct ccctgaggca ataacagttg    83940
tggcaaacaa gctaagcaaa aaacttcatt ccgtaggggc atttgaaaag ctctgacata    84000
tttctggaag gccttgtgga tgtgtaggac tatatgcatg cccagggcta tgtgcttgtt    84060
caagaaaatc cttacaaagt cctcagtctt ccccctctta gtactgtgag cccctgtgca    84120
atcaagaagt gaaaactaaa gcagttgtac attgcctggc tgagtgttga aagcatgccc    84180
aaatggacac agagcatctt ggcaaagact gagagactct ggttccaggc atttaaggaa    84240
atctgtgtcc aatatttagt tgacctctta agctaactga acacagactt cattgcccac    84300
actcagcaaa gaacacagac ttacaaagt tagttcaagg aagtcactaa aacgataatg    84360
acaacaataa aagaacaact aaccttagag catctgattt ccagagttgt cacattatat    84420
tatttcaaat gttcagtttt cagcaaaaga gtacaagaca tgcaaataaa caagaaagca    84480
taaccaatac acaaaaaaga aagcagttga tagaaactgt ccctgaaaat gtctggacat    84540
tatatttggt aggtaaaaac tttaaatcag atattttaaa tatatggagt ccactaaaga    84600
taaccatgtc taaatagcta agaaaaatg ggagaatgat gtctcacaaa tagagatcaa    84660
taaagagata gaaattatat attttttaaaa aagaaccaaa tagaaatgct ggagttgaaa    84720
tgtacactaa taaaaacaaa aaattcaata gagggctca aagcagtttc agcaggcaga    84780
agaattagtg aatttgaaac atagataaat tgatatgatc cagtttaagg aacagaaaaa    84840
agaatgacga aaaatgaaca ggacctcata gtcttattat tcacatatac taatatacat    84900
attatgagtc gtagaaaaag agagaaaaag ggacaaaaag aatatttgaa aaaaaatgtt    84960
agaacttccc aaatctgtat gaaaaacatt aaacatcgag gaagctcagt ggattccaag    85020
taggataaac tcagagattc atacctagac acatcataat cagttgaaaa ccaaacatga    85080
agagaatctt gagagtaaca aaagaaaact gaatatgatt aacaaaggct ctttaataag    85140
ccattgttta ttaacaaaga ctgatttctt atcagaaacc acagaagcta gaaggcagtg    85200
ggatgacaga ttcaaagtac tggaaggaaa aaagaaaga tcaaccaaga attctgtatc    85260
cagcaaaact atccttcaaa aatgaaggag aaatgaaaat attcccaatt aacaaacacc    85320
atgaaaattc attgctagca catgtgccct acaagaaata ctcaaaggag tcctttaggc    85380
aaaagtgaaa ggatgctaga cgggaactgt aatccacatg aacaaataag aacactagta    85440
aaagtaacta cataggtaat tttgaaaggc agtataaatg taatctttat agctcttttc    85500
tcctgttttg aaaacagct acataaacca gtcatcagaa atctggtttg aggagcacaa    85560
aatgtataaa gatataattt ttatgacaat aatagcccaa atgaggggca agaatggat    85620
```

```
ctgtgtaggg gcaaagtttt tttatcctgt tgaaattaag ttggtattaa tctgaactaa   85680
actgttagaa attgaaatgt taattataat ccccatggca acctctaaga aaataactca   85740
aatgataaat gacaagagaa ttaaaatcat acactaggaa atatttgttt aataataaag   85800
aaggcagtaa tagagaaata gaggaataaa ataacattag acatgtagaa aacaaacttc   85860
aaaaagacaa atgtaaatca atttattggt aattacatta aacgtaactg gataaaaaac   85920
ccaatcaaaa ggcagatgga caggatgtat aaaaatgatc caactatatg ctgtctacaa   85980
gacaaacatg ttagattcaa agacacaaat aaattgaaag caagagaaga gaaaaagta   86040 tatatcatgc taacaggaac caaaaaaaaa aaaaaaaaga acgggaatga ttatatgaac   86100
accagacaaa atagacttta agacgaactg ttactagaga ccaaaaaaaa gttataatga   86160
gaaaagggtc actctgtcaa gaagatataa ctataaacat atacgtgact tacagcagag   86220
ctccaaaata cacaaagtaa aaatgacaaa actgaaggaa aaaataattc atcaataatc   86280
attgcaacta tcaacatccc actttcaata ctagacagaa caactagata gatcaactgg   86340
gatagaagac ttgaaaaaca ctgtaaatca attagatgta acaaacatct atagaacact   86400
ccacccaaca agaatggaat acgctttctt ctcaaaggca caatggaaca ttctccaaga   86460
ttatatacca tcttaggcca taaagcagga cacaatttaa aataactaaa attacacaaa   86520
gtatggtctt ggtttatact ggaataaaat cagaaattaa taccagaaag gagtttgtga   86580
aattcacaaa tatatggaaa ttatacacac actcctaaaa aaaatcaatt tgttaagaaa   86640
tcacagggaa aattgggaaa tattttgaag agaatgaaaa tggaaaaaca acatatgaaa   86700
acctatgggg gtacagccag agtagtgctt agcaggacta ttatagcttc acatacctcc   86760
attaaaaaga agaaagatct caaatcaata acctaacctt ctgccataaa aaacagaaa    86820 aagaagagta aactcaaaat aagcagaagg aagttattag attagagaaa aatacagaat   86880
ataaaaacaa tataagaaaa tccataaaaa tgtttttaa aaaccaacaa attgggaaac    86940
ctttacttag actgtcaaga aaaggagag aagcctcaca ttactaaaat caggaatgaa    87000
agcacgaata ttaataccaa ccttacataa atttatgag aatactttaa aaaattgtat    87060
tgcaacaaat tagataacct atatgaaaat ggacaaatta ttggaatgac tattaaaact   87120
gtctcaaaaa aatctaaata ggcctataac agagagattg aattaataat caacaaaact   87180
tccctcagag aaaagcccat tttcagatgg ctttactggt gacttctacc aaacatttaa   87240
agaattacca attcttcaca aatcctccaa aaaatagaag ggaacacttt tgaaggaatt   87300
ctaccaagcc aatgttaccc tgataccaaa accaagaca tcacgaagaa aaaaaaaaa    87360 aaaaaaaaca gacagaccta tatcccttttt gaatacagat gcaaaatcc ttaaaaaaaa    87420 aatactagta aagtgaattg agcaacatat agaaaggatt atacaccatg agcaggtaag   87480
atttatccct ggaatataag attatttcaa atataaaagt aaatcaatgt aacacaccat   87540
atcaatacaa taaagaacaa aagctgcaca attatatcag tagatgcaga aaaagcacct   87600
gacaaaattc agcattcttt catgataaaa acactagaga gaagatcaat aaactaggaa   87660
taggagggaa cttcatttat ttgataaagc atatctatga aaaattcaca gctaacattt   87720
ttaatagttg aatgccgaaa gctttttccc taagatcaag aataagacaa gatgacccct   87780
ctacccattt gtatacacca ttgcactata gcttataaaa ggcatccaga ttgtaaaggc   87840
attagtaaaa ctatctccat ttatcaatga catgatcttt tacatagaaa aatcctaagg   87900
aacacacaca cataactgtt tttttgtttg tttgtttgtt tgtttttaag agattttctt   87960
```

```
gagggtttat ttacatggct gtttggacat ctctgttgaa aaggaaaact cttttttttt    88020 cttttttta ttattattat actttaagtt ttagggtaca tgtgcacaac gtgcaggttt     88080
gttacatatg tatacatgtg ccatgctggt gtgctgcacc cattaactcg tcatttagca    88140
ttagggtata tctcctaaat gctatccctc ccccctcccc ccaccccaca acagtccctg    88200
gtgtgtgatg ttccccttcc tgtgtccatg tgttctcatc gttcaattcc cacctatgag    88260
tgagaacatg cggtgtttgg ttctttgtcc ttgcgatagt ttgctgagta atgatggttt    88320
ccagcttcat ccatgtccct acaaaggaca tgaactcatc attttttgatg gctgcatagt   88380 attccatggt gtatatgtgc cacatttctt taatccagtc tatcgttgtt ggatatttgg    88440
gttggttcca agtctttgct attgtgaata gtgccgcaat aaacatacgt gtgcatgtgt    88500 cttttctagca gcatgattta taatcctttg ggtatatacc cagtaatggg atggctgggt   88560
caaatggtat ttctagttct agatccctga ggaatcgcca cactgacttc cacaatggtt    88620
ttactagttt acagtcccac caacagtgta aaagtgttcc tatttctcca catcctctcc    88680
agcacctgtt gtttcctgac tttttaatga tcaccattct aactggtgtg agatggtatc    88740
tcattgtggt tttgatttgc atttctctga tggccagtga tgaacacaca caactgttaa    88800
tgctaattaa atgagtttag caagactgca ttgatacaaa atcaatatat gaaaatcaat    88860
tgtatttata tacactagca atgaacaatc tgaaaattaa actaagaaaa tttcattcac    88920
aatagtgtca gaaataataa aatgcttagt aataaagtat gacttacaca ggaaactata    88980
aaatatcact gaaatgaaga actaaataag tggaaagata tgttcatgga ttagaagact    89040
taatattgtt atgggtcaga agacttaata ttgctaaaat ggcaatattc ccccaattaa    89100
tctacagatt caatgcaatc tttatcaaaa ttctggctgc ccttttttgta aaaattgaca    89160 aggtatttgt ttctaaaatt gatatggaaa gtgatgaact cagaaagaag ttagggatt    89220 tatacttccc aatttgaaaa cttataaaac tacaataatg ccatcaccag atggagcgac    89280
atgcacctta tagtcccagc tactcaggag gctgaggcag gagcatccct cgagcccagg    89340
agtttgagac cagcctggac aacataggaa gaccctgtct caacttaaag aaagcaaact    89400
acagtaatac agtgtggtac tgacataagg atagccatat agattaatga aatagaactg    89460
acagtgtaga aataaatcat ttatggtcag ttgattttttg ccaaaggttc taagacagtt    89520
caatgggaaa aaaagtcttc tcaaaaattg gttcccagag ttatgaatat gctaaaaccg    89580
cccttaatca taccatataa aaggacaagt tttaatatat gtgaattata tctcaataag    89640 gagggtggt gggcaggaaa ggtggaaaca cacaacattc caaaaggcag tgtatgcttt     89700
gctgggaaga ggtatgaaag gagagttggc cggctcagaa ttgaggagg tcccacacat     89760 atctttcttt ctccagcaag ttccatgact gcactgtgtg tatatacttt ttaatatgaa    89820
agttgaaatc tcttttttctt attgtttaac gtgggggggg aaagagaggc ttttgaaatt    89880
acctgatagc tattggtaac actaaacatg tgtcaagagc ccaatactct aggacaacta    89940
cccagagtga ttattacaca gaaaaagctg ttagtatctt tcttgtggcc aaactataaa    90000
agtcttgttg ccaaaagtca tcgtttagaa actggaacta gttcttattt gtaacagcct    90060
tgctgagatt agatgatgta tagttggaga agagagaatg tggcagtggg atgagcctat    90120
ggaggtgagg ctaaattgat acttacacaa tagaagaact gagaagcact attgatactg    90180
ttaactgtgg ctgaaggaag aagaggaggc ttgctgtact tcttcctttc caatatttct    90240
gccttttttg tggggggtggg agccttattt aaatggccag gatctccagg actttgttga    90300
ataaaagtca agagcagcca tccttgcctc attccaatct tcagggattt aacactcagt    90360
```

```
cttttcaccaa ttaagtataa tgttggcatt aggtattttt gtagatgccc ttattaagtt    90420
gagaaagttc acttctagtc ttagtttgct gagaggcttt tatttcttct tttcattatt    90480
actagatgtt agattttgtc aaagcatttt ctccagctat tgtgatagtc agattttttt    90540
ttttagtctg ctaatatggt gaattacatt gattgatttt gaaattttaa accaacattg    90600
caatctggag ataatcctca agtggtcatg atttattgtc tttttattgt tgaatttgat    90660
ttgctaaaat tttgagaatt tttctgtgat catgaggatt attagtctgt agttttcttg    90720
taatgttttt gtctggtttt ggtatcaggg caatgctggc cttacaggat aacttgagaa    90780
agatttcctc cttttctatt ttctagaaaa attcatgtag aattgctgtc atttcttcct    90840
taaatgcttg gtagaattta ccagtgaagc tctctggtcc tggagggttg tgtgtatgtg    90900
tgtggaagat tttaattata aacttaattt atttgataca gggctatttc acattatcta    90960
tttcttcatg agtgagcctt gtagcttgtc tttcaaggac tttttctatt ttgatctaag    91020
ttgtcaaatt tactatcata aaagttgcta tataatagcc ccatattatc attttaaggt    91080
ttgtagaacc tatctctttc atttctgagg ctggtaattt atatcttctc ttttttcctga   91140 taagcatggg tagagtttat caatttttatt aacttttttt tcctaaatga ctaggttttt    91200
atttcactta tcttctcaat tgttttctat ttctacttta gtcgtttctg ctctcatatc    91260
tattagtata gtcgttttct ccatttactt tgggcttcat ttgctttctt tttctaattt    91320 ataaggtag gagcttaggt tattgaattc agacctttct tatccagtaa gtgcttaatg    91380
ttttctaaaa actagtttcc catctaaaca ctcctttaga tgtatcctac acattttgat    91440
atgtcttgtt ttcattttca ttcagttaac cactttatca tttcccttttt gatttcttct    91500 ttggtttgta ttttgcttag aattatattg tttagtttcc aaatatttgg gatattttcc    91560
aggtatcttt gtatttactg atatctattt taattccact gtagtcagaa aacatatttt    91620
gtacaattta aattatttta aatgtattga gacagattta tggcccagac tatggtctaa    91680
ctatcgtgat aatgttccca tgtgtacttt aaaagattgt attctgctgt tgttgggtgg    91740
agtgttctat aaatgtcatt taggtgtagt tgaaaatgtt atttaagtct tacatatctt    91800
tcctgagttt tcaagtttgt aaattttttca gtcgtcattt cttcaaattt ttttcccctgt   91860 ctccctcatt cattcacctt tgactctgtt cctgtgactc tgtacggtgt gtgtgtgttg    91920
gtcttgcctt ttctgtttca ttttggtagt ttctgtcatt atgtgttcga gtttactcaa    91980
cttttattct gcagtgtctc ctctgctgct aatcccatcc aatgtatttt tcatctcaga    92040
cattgtattt ttcatcactg aggtgtcttg ggcatcaggc attttgaatt ttatgttgct    92100
agatactgga tgagagagac atatatgtat acacacaacc atacataaaa acacatatat    92160
atgtaatgtt atactatatt ataaatacat atgtattctt gagctttgta ctgggacaca    92220
actgagttaa cttggaaaca ttttgatcct ttccaggctt gcttttgaag tttgttaggc    92280
aaaaccatct cagcctctag tttagggcta atcaatttga ccttacaaca ggcacgataa    92340
ccttccaagt tctcctccag gtgctccagc tgttactagg tagctccact ctggctactg    92400
agaatgggaa ctagtcccct ccagtaattg attcacctgc tccttgccag tggttctgta    92460
cctggcctga ggtagttgtg tgagcatttg ctcttcatac tcagttgaag agttgaggag    92520
agctgtctac agatcagcag agttcttcct tctctagtac tccaccctgc atatcctagt    92580
tgtcttggcc tcctcaaaatt ctcagttgtt tcctcaattc aaggggactg cagagctttc    92640
cgggttcccc tccctgtggt gtagcctgaa aacatacttc aggcaggaag ctgggcagt    92700
```

```
tgtagggtc acatttctct tttctcagag atctctgtct catgtgcctc ttttccaatg   92760
tctggaaact tttttcaatc attttgtctg ccttttcgtt atttaaaaca agtgaggaaa   92820
aaccagtccc tattgcaatt ttgtccagaa atgtaaatag cttgttggac ttttaaagtc   92880
ttacaaattt tctactcagt aatcagtaat catatatgga ggtaggccct atccctctgc   92940
ctgagaggga atagttattc ctgagtatcc atagggaatt ggtttcagga ctgctactca   93000
taccaaaatc catggacgct caagtccctg atatagtgtt tacatataac ctaggcagat   93060
cctcctgtat actttaaatc atctctagat tacttaccta atacaatgca aatgccatgc   93120
aaattgttgt tatactatat agctttaaaa cttgtattat tttgactggc tgctgtagct   93180
cacgcctgta atcccagcac tttaggaggc cgagggggc agataacttg aagtcaggag    93240
ttcaagacca gcctggccga catagtgaaa ccccgtctct gctaaaaata caaaattagc   93300
caggcccacg tctgtagtcc cagctactcg ggaggctgag gcaggagaat cacttgaacc   93360
caggaggcag aggttgcagt gagccgagat tgtgccactg cactccagcc tgggcaacaa   93420
gagtgaaact ctgtccaaaa acaaaaaagc cctattattt cttgttgtat tgtcattttt   93480
ttgttttatt ttcagatatt tttaatctga ggttagttgg atctgcagat gcatctgcag   93540
atacagaggg tgactgtgta tcctccccac ctagctctgc tgaagaagtc aggaaatcct   93600
gccttctcag tgaacaatca tttttatttg cattttttt tttactcagc tgaccagggc    93660
agaaaatcct actcccatga ctttcgtaag catctccaaa gtaaccaaca tctttaaaga   93720
taacgaatct cactaaaaaa ggaaagatat aatacttgaa gtataaatac ttggaattac   93780
ccaagaaaac atcttaggtt ggaaatcaat ggtttaggat tccctttact gtgatttcag   93840
aggggagaac tctttaactc tgcccccagc ttcacagcgg gtcagattcc ccaaaagtaa   93900
cccaggggtt gacctagtta acatgcagtc tctcctgcca gctgtgacct gcttcctttc   93960
aagagatcac tgagcaaagg aaattgcgtt agctgattgt ggggcatctg aattgtgctc   94020
ctccacccct ttgtattaga gaatagaaaa acacttgggt actgtggaga gccacaggct   94080
aacatgtctc cagggtgctg gcctttcagg tgcgcaccat tctctagtga caccaggaaa   94140
ggagaccttg ctgcaaaatg atgtatagct tcacaactgg ctgttaactt tacataaatt   94200
gtagattttg ccatgtcatt ctgtgtgaag cgctggaagg atattcctgt gctaaggaaa   94260
gcaacaaaag aatctgaatc cttcagtggt cgtgatggtt aatgtgttaa agtcttaggg   94320
gaaaatgaag gaaatcagat ccaggtggct ccatatcatt tccagaaatc acctctgcac   94380
aatttggatc ccatgttttt gagagaatgg ggaaatacaa ccagtatcct gaagccatgt   94440
gaagaatgta tcaggagttt cagtatgact gagaagggta ggctctcatc tgaatttaaa   94500 aaaaaaaaa aaaaaaaag gataaagctt atttataagc atgtgggaaa aagcaagaaa     94560
tcttttaaca ctaaaatctg atctgacctg ttggaaagga cactacgtta tcaatttgaa   94620
cctctggctt ttgttgaggt gtctggtggt tgtcctagtt gtgtctaagg aaggctgtgg   94680
acttgttacc agagttgcta tcacatgtag gtgtcctggc tttgctacct ggaactttcc   94740 caaaccttt acatctgtca accagtattc tttcagccat aaatggtggc tggcatcacc     94800 tgccctcat gatcacactg acaatagtat tttatttat atattgcagt atcttttgaa     94860
cagtgctttg cagtcagtgg agtctttcca tacctcaatt tttcatcaaa cattgagttg   94920
aagtgttaca cttctctcgc aaataaagaa atggggaagt tagaaaatca agaaggtta    94980 aatgagttgg ccagtgtccc aggggcaggg acctaggcaa aaacaaaagg cttctaattc   95040
caaatccagt attctctgct aaaatgtgcc acctccctcc ctttagggtt ggtggaggta   95100
```

```
tcgatactgg ggctagtcct acagctaatg ctttatgatt ctttgttctg cttcactcag    95160
cacctgctgt accatgttat gtttgtaagt ggcttagtgt taacttttct ccaaaaggca    95220
gcagggtctg gaacaggaga ctggcccagt ctggcatctg gagaggatgg tggttgtggt    95280
gttttcacag ctcctccatt accacctggt atcatttagt attactttgc aaactgaatc    95340
ataaatcaac tcatttaatg tagagaaggg caaaagttgc tgagaaatgt tttgtgggtt    95400
ggtgcccgga gcttcaactc tgggagggtg cctgacttga cagtatcacc ttagtcacta    95460
aggaaaaaga gatccagggc ttcagacctt caaaacaatt attacttgct gagatggcaa    95520
aaacaattgt agagtgcttc aatggctgag ctttaaacag tttgttaaac tacagattaa    95580
atacgaatga ttcttttttc tttgagacag ggcctcattc tgttgcccag ctggagttg     95640 cagtggcaca gtcatagctc acagcagcca caacctcata ggctcaggca atcctcccac    95700
ctcagcctcc taagtagctg ggactacagg cacgcaccac gtgccacaac cccagctaa     95760 tttttgtatt ttttgtagag acagggtctc attatgctgc ccaggctggt cttgaactcc    95820
tgggctcaag agatccttct gccttggcct cccaaagtgc tgagattaca gatgtgagac    95880
actgtgccca gccagtaatg ttttttcgta tgaccaaacc attgaagaaa atttacactt    95940 attttggta aatgaaatac caaaaaaaaa ctttatcaga tgatggcctg atatctcctg     96000
cactgatttc tgccccacat accctttta gattgaacca aattagaaat ataaaccaga     96060
tgattaaaaa ttaggtatga ttcatttcc agctaatcgg cttactttct gttgctccct     96120
cttctaaatg caaaatgaat ccaagcagtg ctggatttaa ggaagcatac ataattaata    96180
ttacagggca ggcaggagag ctgggcatgt ggtctcatac cccacatgta gttaggtaag    96240
catgtatgtt tttcagctgc atttatttct tagttattcc tagtggcaaa tgtgggggt     96300 tgatgatcac tgtgaaacag cagcttataa aattcaccct ttattatcaa cagactaaac    96360
ttcctatttt gcgtagatgc tcctgtgcac gcctttattt tacacggaat gtaaatatt     96420 gtaatgactg attttccttt gagactgtaa tacaggtaat gttcctattc aactttgtaa    96480
accaagacct gacacacagt aggtatttta aaaactgttt tgatgtgacc aaaattatac    96540
agaaaaaaag agaagtacac caggatttta aagtctcttt ttttttttta ttttcacaa     96600 aggatttgct gtaagtcttc aagtcatttt gtccaatcca aaagctgtat ttaagcgtcg    96660
tggatcccag ccagggatgc aagaatctga ctttctcaaa cagataacaa cagtcgaaga    96720
actggaaccg aaagcaaata actgcactaa ggtattcatt acacttgtgc tgcccgacct    96780
cgagtgtcac catgaagagt gcgctaccca agctatttcc ttccccttca ggttctcgtg    96840
tggcacactc ggacagagaa ggttaatcta gccaacgagc caaagtacca cctggacaca    96900
gtgaaaattg aggtataaat tgaagcagca actggtgcag tttgtccagc cagtggatcc    96960
atatggaaga ggatgtttgg agtttaggct acagagcatt caggtattgt ttgtttact     97020 tcagtacagc agccttttctt gtcatctgat ggacatctgt ttaaatggag cttgtcagtt    97080
aacataagct aattggatgg ttggtacaaa atgtatgttt tgtcttcatt tgttctgcat    97140
gttttctcta caacaactaa attggaagat tttttgtac agtgccgata ctgcaagata    97200
ccactcttga gtatatattt tttctttttc tccaatttgc ccttataatt ggtagacttg    97260
aacaggttgg tagacttgaa caggttttta aaacagacaa gtattttgtc agctaaacgt    97320
tcctgatgat tcctgacttt gcaatactaa gtaattttg gaaggttagt ggcagtatac     97380
atcataggaa ataaaaaccc acaaatgaaa aggtctatgg agtcatgttt aatgtaggga    97440
```

```
aataacattt tgtcaatact aggcaccata aaatgtaaac acaattactg tcataaacct   97500
agatatacct tcaaggattg aagattgaaa gtggctttgt tttagttagt taccctgttt   97560
gcatatagtg cagaaaaagg tcttcatgtt agcactatgt acattaagaa gagatccaaa   97620
ttacaagaga ggcagataaa atttgaattc tttaagcatt cattaaacga agttttggag   97680
taacatccac gtttatcttc ctttcactaa tcacgttccc tgttaagcac atcataacaa   97740
cagcacagtg aagtgaatga tgaaataaga gcattttgat acactagaaa acagtgctca   97800
gtgagacatt tacattctat ttatatgatt aaacatttga tcatacagta ccttcctaca   97860
ggattactgg ctaattttgg ggtggggttt atactattag aggtattact aacatgataa   97920
ctacttccct tatatgcaaa cattagagct ataattttat tgagaggaaa actgattttg   97980
caagttgagc agcttctcaa ataatgcagt acatgaaatc atgggaaata tgagcaaagc   98040
tgcccttgac ataaaatgat ttatcaacct gcttttcacc acatcaaatt gaatcagtac   98100
agaccaacac ggtcaatcag atcattctta atatgaacaa atgggtaaaa agaaaaaaaa   98160
tatgcatatg aataaacagg ggaactagat gcgtttcagc aaggaatgtc aggtggtagt   98220
tctggatgaa acttgtattg cagttttcat ttccacagtt gtgtgctgag agtctgacct   98280
gatgagcttc cagaccatcc tgctgttgtg ctggagggct ggccaaaacc tgcagtaggg   98340
gttgcactac tgatactcat gccagccatc tgctgattca tctgtgaaac atataaaagg   98400
cttagttcaa gaggcttact tcacttttaa ttcttgtttc tttagccaca cagttggtca   98460 tttttttcatt aatgtgacaa ctagtccaag cactggaata aaaacagagt accatacaaa   98520
tatttcttaa agcaaatagc tactttgttc ccttctttat ctactttcta gatacagttt   98580
ccccaaagat taaccacaac ttacttaaaa aaaaatacca aagcaatctt gggattttaa   98640
tgagtccgct actctaacta actttcacct acactaggat attgtgcttt aactactaag   98700
gagtaagaaa attttaggaa gtaaaatagt ctaaaattat cctataaact ttgtatgata   98760
gatattattc tctattaaaa tcttatatac ttcctaaata tttttaaagt ggtcataaag   98820
catttatttc tctcgctgat ctaacaacat aaacatctaa aatttatttt cattgtatgc   98880
aataaagcat aagattacat gtattttttct tcaagactgg agtcaaatat atatatatat   98940
aagcatctta accctgtgat tctcttactt ccaaaattgg tgataagaga aggaaaggca   99000
agatttacca tatagtgagt gggtttaaaa cttacactca gagttagact gtgttcttaa   99060
tttaatacat ttgacttgac ttatttacag tttcaaagac actaacataa actacatcac   99120
taatcaggca taagtgtctg aagaagcaga tcacgtcttc atacctacta aaggacattt   99180
taaccacctt gtcgttggcc agtagattgc actgatggag tgctggagaa cagcatcacc   99240
cttctgcatt atctggaagt aagagccagt attaactcct tcctggttca tctagcacct   99300
taacctgagc tgggtgtgct tcagcatgtt gaccatgtga ctgacactta gcacataaa   99360 ttttttagat tcccagcggg tagagaccaa tgttttacct atattcttgt aaatggtggt   99420
agcaaaatta actgtgatat atagtgattg tgctaatgtt agaaatcact ctagactatt   99480
ccctgaatgc tctaaaggta aaacaagtga ccaaacagaa accaagattg ccaaaatgct   99540
ggaggaacat caatgggaag tgtaaaagga agaagagtgg gagcatgaac ctctctaaga   99600
gcctttgtct gtgcagctag agaaaagtca gaacacagca cctgaaatag aaatgttcta   99660
tctcagctct aacttaggta gaaataggat tttataatat gaggggatgt ctggttcaca   99720
ccttatggga attgaatctt tttgtactct ttttaaacat aaaagtcatt ataggtatg   99780 taaaagaaa atacaacttt acaaggtttt ctcaacaaaa agaattttta cagagccatg   99840
```

```
gggcagtaat catccgacct gaaaaacagc cttagatccc tcataaaata gtgctttgag    99900
aatatgaggc tagatt                                                    99916
```

<210> SEQ ID NO 4
<211> LENGTH: 324
<212> TYPE: PRT
<213> ORGANISM: Rattus norvegicus

<400> SEQUENCE: 4

```
Met Lys Ser Ala Leu Cys Asn Arg Phe Phe Ile Leu Leu Pro Trp Ile
 1               5                  10                  15
Leu Ile Val Ile Ile Met Leu Asp Val Asp Pro Arg Arg Pro Ala Pro
            20                  25                  30
Gln Leu Thr Ser Arg Pro Tyr Phe Ser Pro His Thr Val Gly Cys Gly
        35                  40                  45
Gly Ser Arg Val Pro Leu Arg Arg Ser Ser Pro Gly Arg Asp Ala Ala
    50                  55                  60
Glu Lys Arg Asn Glu Ser Arg Pro Gln Leu Gln Pro Glu Pro Arg Leu
65                  70                  75                  80
Pro Thr Ile Tyr Ala Ile Thr Pro Thr Tyr Ser Arg Pro Val Gln Lys
                85                  90                  95
Ala Glu Leu Thr Arg Leu Ala Asn Thr Phe Arg Gln Val Ala Gln Leu
            100                 105                 110
His Trp Ile Leu Val Glu Asp Arg Ala Thr Arg Ser Glu Leu Val Ser
        115                 120                 125
Ser Phe Leu Ala Arg Ala Gly Leu Pro Asn Thr His Leu His Val Pro
    130                 135                 140
Thr Pro Arg Arg Tyr Lys Arg Pro Trp Leu Pro Arg Ala Thr Glu Gln
145                 150                 155                 160
Arg Asn Ala Gly Leu Ala Trp Leu Arg Gln Arg His Gln His Gln Ser
                165                 170                 175
Ala Gln Pro Gly Val Leu Phe Phe Ala Asp Asp Asp Asn Thr Tyr Ser
            180                 185                 190
Leu Glu Leu Phe Gln Glu Met Arg Thr Thr Arg Lys Val Ser Val Trp
        195                 200                 205
Pro Val Gly Leu Val Gly Gly Arg Arg Tyr Glu Arg Pro Leu Val Lys
    210                 215                 220
Asn Gly Lys Val Val Gly Trp Tyr Thr Gly Trp Arg Glu Asp Arg Pro
225                 230                 235                 240
Phe Ala Ile Asp Met Ala Gly Phe Ala Val Ser Leu Gln Val Ile Leu
                245                 250                 255
Ser Asn Pro Lys Ala Val Phe Lys Arg Arg Gly Ser Gln Pro Gly Met
            260                 265                 270
Gln Glu Ser Asp Phe Leu Lys Gln Ile Thr Thr Val Asp Glu Leu Glu
        275                 280                 285
Pro Lys Ala Asn Asn Cys Thr Lys Val Leu Val Trp His Thr Arg Thr
    290                 295                 300
Glu Lys Val Asn Leu Ala Asn Glu Pro Lys Tyr His Met Asp Thr Val
305                 310                 315                 320
Asn Ile Glu Val
```

<210> SEQ ID NO 5
<211> LENGTH: 197
<212> TYPE: PRT

-continued

```
<213> ORGANISM: Human

<400> SEQUENCE: 5

Met Lys Ser Ala Leu Phe Thr Arg Phe Phe Ile Leu Leu Pro Trp Ile
 1               5                  10                  15

Leu Ile Val Ile Ile Met Leu Asp Val Asp Thr Arg Arg Pro Val Pro
                20                  25                  30

Pro Leu Thr Pro Arg Pro Tyr Phe Ser Pro Tyr Ala Val Gly Arg Gly
            35                  40                  45

Gly Ala Arg Leu Pro Leu Arg Arg Gly Gly Pro Ala His Gly Thr Gln
        50                  55                  60

Lys Arg Asn Gln Ser Arg Pro Gln Pro Gln Pro Glu Pro Gln Leu Pro
65                  70                  75                  80

Thr Ile Tyr Ala Ile Thr Pro Thr Tyr Ser Arg Pro Val Gln Lys Ala
                85                  90                  95

Glu Leu Thr Arg Leu Ala Asn Thr Phe Arg Gln Val Ala Gln Leu His
            100                 105                 110

Trp Ile Leu Val Glu Asp Ala Ala Arg Ser Glu Leu Val Ser Arg
            115                 120                 125

Phe Leu Ala Arg Ala Gly Leu Pro Ser Thr His Leu His Val Pro Thr
    130                 135                 140

Pro Arg Arg Tyr Lys Arg Pro Gly Leu Pro Arg Ala Thr Glu Gln Arg
145                 150                 155                 160

Asn Ala Gly Leu Ala Trp Leu Arg Gln Arg His Gln His Gln Arg Ala
                165                 170                 175

Gln Pro Gly Val Leu Phe Phe Ala Asp Asp Asp Asn Thr Tyr Ser Leu
            180                 185                 190

Glu Leu Phe Gln Glu
            195
```